US010556898B2

(12) United States Patent
Aicher et al.

(10) Patent No.: US 10,556,898 B2
(45) Date of Patent: Feb. 11, 2020

(54) INDAZOLYL-1,2,4-THIADIAZOLAMINES AND RELATED COMPOUNDS FOR INHIBITION OF RHO-ASSOCIATED PROTEIN KINASE AND THE TREATMENT OF DISEASE

(71) Applicant: Lycera Corporation, Ann Arbor, MI (US)

(72) Inventors: Thomas D. Aicher, Ann Arbor, MI (US); Fernando Padilla, Ann Arbor, MI (US); Donald J. Skalitzky, Saline, MI (US); Peter L. Toogood, Ann Arbor, MI (US); Chad A. VanHuis, Hartland, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 16/275,426

(22) Filed: Feb. 14, 2019

(65) Prior Publication Data
US 2019/0276447 A1 Sep. 12, 2019

Related U.S. Application Data

(63) Continuation of application No. PCT/US2017/048575, filed on Aug. 25, 2017.

(60) Provisional application No. 62/379,831, filed on Aug. 26, 2016.

(51) Int. Cl.
*C07D 417/12* (2006.01)
*C07D 417/14* (2006.01)
*C07F 9/6558* (2006.01)
*C07D 471/04* (2006.01)

(52) U.S. Cl.
CPC ......... *C07D 417/14* (2013.01); *C07D 417/12* (2013.01); *C07D 471/04* (2013.01); *C07F 9/65583* (2013.01)

(58) Field of Classification Search
CPC .......................... C07D 417/12; C07D 417/14
See application file for complete search history.

(56) References Cited

U.S. PATENT DOCUMENTS

| 10,112,935 B2 | 10/2018 | Aicher et al. |
| 2004/0102437 A1 | 5/2004 | Takami et al. |
| 2009/0093452 A1 | 4/2009 | Huang et al. |
| 2011/0190355 A1 | 8/2011 | Klein et al. |

FOREIGN PATENT DOCUMENTS

| KR | 2013/0100587 A2 | 9/2013 |
| WO | WO-2006/058120 A1 | 6/2006 |
| WO | WO-2007/076161 A2 | 7/2007 |
| WO | WO-2008/093674 A1 | 8/2008 |
| WO | WO-2008/138448 A2 | 11/2008 |
| WO | WO-2012/040499 A2 | 3/2012 |
| WO | WO-2012/049161 A1 | 4/2012 |
| WO | WO-2014/055996 A2 | 4/2014 |
| WO | WO-2014/055999 A2 | 4/2014 |
| WO | WO-2016/138335 A1 | 9/2016 |

OTHER PUBLICATIONS

International Search Report and Written Opinion for PCT/US2016/019678 dated May 31, 2016, (9 pages).
Barbuceanu, S.-F. et al. "New heterocyclic compounds from 1,2,4-triazole and 1,3,4-thiadiazole class bearing diphenylsulfone moieties. Synthesis, characterization and antimicrobial activity evaluation," *Eur. J. Med. Chem.* (2012) vol. 49, pp. 417-423.
Khan, I. et al. "Synthesis, antioxidant activities and urease inhibition of some new 1,2,4-triazole and 1,3,4-thiadiazole derivatives," *Eur. J. Med. Chem.* (2010) vol. 45, pp. 5200-5207.
SciFinder Database Record for KR2013-0100587, (1 page). , 2013.
Yang, S.-J. et al. "Regioselective Synthesis of 2-Amino-Substituted 1,3,4-Oxadiazole and 1,3,4-Thiadiazole Derivatives via Reagent-Based Cyclization of Thiosemicarbazide Intermediate," *J. Org. Chem.* (2013) vol. 78, pp. 438-444.
International Search Report and Written Opinion for PCT/US2017/048575 dated Dec. 5, 2017 (13 pages).
Akhmetshina A, Dees C, Pileckyte M, Szucs G, Spriewald BM, Zwerina J, Distler O, Schett G, Distler JH. In "Rho-associated kinases are crucial for myofibroblast differentiation and production of extracellular matrix in scleroderma fibroblasts," Arthritis Rheum. (2008) 58(8): 2553-64.
Bei Y, Hua-Huy T, Nicco C, Duong-Quy S, Le-Dong NN, Tiev KP, Chéreau C, Batteux F, Dinh-Xuan AT. in "RhoA/Rho-kinase activation promotes lung fibrosis in an animal model of systemic sclerosis." Exp Lung Res. (2016) 42(1): 44-55.
Yiu ZZ, Warren RB. in "Novel Oral Therapies for Psoriasis and Psoriatic Arthritis," Am J Clin Dermatol. (2016) 17(3): 191-200.
Van den Bogaard EH, Rodijk-Olthuis D, Jansen PA, van Vlijmen-Willems IM, van Erp PE, Joosten I, Zeeuwen PL, Schalkwijk J. in "Rho kinase inhibitor Y-27632 prolongs the life span of adult human keratinocytes, enhances skin equivalent development, and facilitates lentiviral transduction," Tissue Eng Part A. (2012) 17-18: 1827-36.
Feng Y, LoGrasso PV, Defert O, Li R. in "Rho Kinase (ROCK) Inhibitors and Their Therapeutic Potential," J Med Chem. (2016) 59(6): 2269-300.
Ma Z, Chu L, Liu H, Li J, Zhang Y, Liu W, Dai J, Yi J, Gao Y. in "Paeoniflorin alleviates non-alcoholic steatohepatitis in rats: Involvement with the ROCK/NF-κb pathway," Int Immunopharmacol. (2016) 38: 377-84. (Abstract only).
Lally L, Pernis A, Narula N, Huang WT, Spiera R. in "Increased rho kinase activity in temporal artery biopsies from patients with giant cell arteritis," Rheumatology (Oxford) (2015) 54(3): 554-8.

(Continued)

*Primary Examiner* — Laura L Stockton
(74) *Attorney, Agent, or Firm* — Dechert LLP

(57) ABSTRACT

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. An exemplary indazolyl thiadiazolamine compound is an N-(3-(5-((1H-indazol-5-yl)amino)-1,2,4-thiadiazol-3-yl)phenyl)-heteroaryl-carboxamide compound.

31 Claims, No Drawings

(56) References Cited

OTHER PUBLICATIONS

Pernis AB, Ricker E, Weng CH, Rozo C, Yi W. in "Rho Kinases in Autoimmune Diseases," Annu Rev Med. (2016) 67: 355-74.
Du L, Kim JJ, Shen J, Dai N. in "Crosstalk between Inflammation and ROCK/MLCK Signaling Pathways in Gastrointestinal Disorders with Intestinal Hyperpermeability," Gastroenterol Res Pract. (2016) 2016: 7374197.
Chen C, Yu JZ, Zhang Q, Zhao YF, Liu CY, Li YH, Yang WF, Ma CG, Xiao BG. In "Role of Rho Kinase and Fasudil on Synaptic Plasticity in Multiple Sclerosis," Neuromolecular Med. (2015) 17(4): 454-65.
Isgro J, Gupta S, Jacek E, Pavri T, Duculan R, Kim M, Kirou KA, Salmon JE, Pernis AB. In "Enhanced rho-associated protein kinase activation in patients with systemic lupus erythematosus," Arthritis Rheum. (2013) 65(6): 1592-602.
Paz Z, Tsokos GC. in "New therapeutics in systemic lupus erythematosus," Curr Opin Rheumatol. (2013) 25(3): 297-303.
Stirzaker RA, Biswas PS, Gupta S, Song L, Bhagat G, Pernis AB. In "Administration of fasudil, a ROCK inhibitor, attenuates disease in lupus-prone NZB/W F1 female mice," Lupus (2012) 21(6):656-61.
Li H, Zhang M, Wang CC, Li XL, Zhang P, Yue LT, Miao S, Dou YC, Li YB, Duan RS. in "ROCK inhibitor abolishes the antibody response in experimental autoimmune myasthenia gravis," Mol Cell Neurosci. (2016) 74: 106-13. (Abstract only).
Xie T, Luo G, Zhang Y, Wang X, Wang X, Wu M, Li G. in "Rho-kinase inhibitor fasudil reduces allergic airway inflammation and mucus hypersecretion by regulating STAT6 and NFκB," Clin Exp Allergy. (2015) 45(12): 1812-22.
Righetti RF, Pigati PA, Possa SS, Habrum FC, Xisto DG, Antunes MA, Leick EA, Prado CM, Martins Mde A, Rocco PR, Tibério Ide F. in "Effects of Rho-kinase inhibition in lung tissue with chronic inflammation," Respir Physiol Neurobiol. (2014) 192: 134-46.
Gerthoffer WT, Solway J, Camoretti-Mercado B. in "Emerging targets for novel therapy of asthma," Curr Opin Pharmacol. (2013) 13(3): 324-30.
Zanin-Zhorov A, Weiss JM, Nyuydzefe MS, Chen W, Scher JU, Mo R, Depoil D, Rao N, Liu B, Wei J, Lucas S, Koslow M, Roche M, Schueller O, Weiss S, Poyurovsky MV, Tonra J, Hippen KL, Dustin ML, Blazar BR, Liu CJ, Waksal SD. in "Selective oral ROCK2 inhibitor down-regulates IL-21 and IL-17 secretion in human T cells via STAT3-dependent mechanism," Proc Natl Acad Sci U S A. (2014) 111(47): 16814-9.
Fava A, Wung PK, Wigley FM, Hummers LK, Daya NR, Ghazarian SR, Boin F. in "Efficacy of Rho kinase inhibitor fasudil in secondary Raynaud's phenomenon." Arthritis Care Res (Hoboken) (2012) 64(6): 925-9.
Takeshita N, Yoshimi E, Hatori C, Kumakura F, Seki N, Shimizu Y. in „Alleviating effects of AS1892802, a Rho kinase inhibitor, on osteoarthritic disorders in rodents, J Pharmacol Sci. (2011) 115(4): 481-9.

INDAZOLYL-1,2,4-THIADIAZOLAMINES AND RELATED COMPOUNDS FOR INHIBITION OF RHO-ASSOCIATED PROTEIN KINASE AND THE TREATMENT OF DISEASE

CROSS REFERENCE TO RELATED APPLICATIONS

This application is a continuation of International (PCT) Patent Application serial number PCT/US2017/048575, filed Aug. 25, 2017, which claims the benefit of and priority to U.S. Provisional Patent Application Ser. No. 62/379,831, filed Aug. 26, 2016; the contents of each of which are hereby incorporated by reference.

FIELD OF THE INVENTION

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds.

BACKGROUND

Rho-associated protein kinase (ROCK) is a member of the serine-threonine protein kinase family. ROCK, which exists in two isoforms, ROCK1 and ROCK2, is an effector molecule of RhoA, and the RhoA/ROCK signaling pathway is involved in a number of cellular functions, which include, for example, actin organization, cell adhesion, cell migration, and cytokinesis. In addition, the RhoA/ROCK signaling pathway is involved in regulating smooth muscle contraction. Inhibitors of ROCK have been reported to be useful for treating multiple medical disorders, such as fibrosis, inflammatory disorders, autoimmune disorders, and cardiovascular disorders.

Fibrosis is a condition featuring excess fibrotic connective tissue, which may form in numerous types of bodily tissues, including, for example, skin, lung, kidney, heart, liver, and gastrointestinal tract. Exemplary fibrotic disorders include scleroderma, kidney fibrosis, pulmonary fibrosis, liver fibrosis, cardiac fibrosis, and skin fibrosis. Scleroderma is frequently characterized as featuring increased synthesis of collagen, and the disease typically features hardening of the skin, and in more severe forms of the disease may also affect internal organs. Pulmonary fibrosis involves scarring of lung tissue, which can occur when alveoli and interstitial tissue of the lungs become inflamed and develop scars in an attempt to repair themselves. Pulmonary fibrosis can be caused by various conditions which include chronic inflammatory processes, infections, environmental agents (e.g., asbestos or silica), exposure to ionizing radiation, and even certain medications (e.g., pingyangmycin, busulfan, methotrexate, and nitrofurantoin). Cystic fibrosis is a type of pulmonary fibrosis. Liver fibrosis typically involves excessive accumulation of extracellular matrix proteins in the liver, and the subsequent scarring process. Over time, advanced liver fibrosis can result in cirrhosis of the liver. Cardiac fibrosis can involve a disproportionate accumulation of fibrillated collagen that can occur after myocyte death, inflammation, enhanced workload, hypertrophy, and/or stimulation by a number of hormones, cytokines, and growth factors. Cardiac fibrosis may contribute to sudden cardiac death, ventricular tachyarrhythmia, left ventricular (LV) dysfunction, and heart failure.

Inflammatory disorders that continue to afflict a significant number of people include psoriasis and nonalcoholic steatohepatitis. Psoriasis is a chronic, inflammatory, hyperproliferative skin condition. It has been reported that approximately 150,000 new cases of psoriasis and approximately 400 deaths from psoriasis are reported each year. See Stern, R. S. (1995) Dermatol. Clin. 13:717-722. Typical symptoms of psoriasis include skin lesions, redness, inflammation, or patches of skin that become dry, red, covered with silvery scales, cracked, and/or painful. Psoriasis can affect all parts of the skin, but it is more commonly seen on the skin of the trunk, scalp, elbows, knees, or in the fingernails or toenails. The symptoms of psoriasis may become worse in response to cuts, burns, insect bites or other skin injuries. The symptoms of psoriasis can also be more severe in patients having a deficient immune system, such as patients afflicted with AIDS or receiving cancer chemotherapy. Amongst the several types of psoriasis, the most common type of psoriasis is chronic plaque syndrome. This type of psoriasis consists of periods of remission and relapse during the course of the condition. If left untreated, plaque psoriasis can evolve into a more severe condition, such as pustular psoriasis or erythrodermic psoriasis. Current treatment options for psoriasis include acitretin, cyclosporine, methotrexate, apremilast, phototherapy, and biologics such as anti-TNF antibodies adalimumab, etanercept, and the anti-IL12/IL23 antibody ustekinumab. However, these treatments do not meet the needs of all patients suffering from psoriasis, and thus the need exists for new therapeutic agents for treating psoriasis and other inflammatory disorders.

Nonalcoholic steatohepatitis (NASH) is a liver disorder featuring inflammation and damage associated with buildup of fat in the liver. A significant percentage of patients suffering from NASH are approximately forty to fifty years old and also suffer from obesity, insulin resistance, high cholesterol, and/or metabolic syndrome. Diagnostic tests for identifying NASH include histological evaluation of a liver biopsy, and patients suffering from NASH may experience right upper quadrant pain, hepatomegaly, or non-specific symptoms such as abdominal discomfort, weakness, fatigue, and/or malaise. Treatment options for NASH are quite limited and new therapeutic agents are needed.

Accordingly, a need exists for improved treatments for inflammatory and other medical disorders. The present invention addresses this need and provides other related advantages.

SUMMARY

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. In particular, one aspect of the invention provides a collection of indazolyl thiadiazolamines and related compounds, such as a compound represented by Formula I:

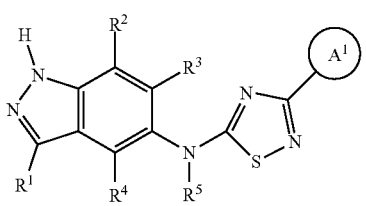

(I)

or a pharmaceutically acceptable salt thereof, or a solvate of the foregoing, where the variables are as defined in the detailed description. Further description of additional collections of indazolyl thiadiazolamines and related compounds are described in the detailed description. The compounds may be part of a pharmaceutical composition comprising a pharmaceutically acceptable carrier.

Another aspect of the invention provides a method of treating a patient suffering from a medical disorder. The method comprises administering to the patient a therapeutically effective amount of one or more indazolyl thiadiazolamine or related compounds described herein, e.g., a compound of Formula I, I-A, I-B, I-C, or II, to treat the disorder. A large number of disorders can be treated using the indazolyl thiadiazolamine and related compounds described herein. For example, the compounds described herein can be used to treat an inflammatory disorder, immune disorder, fibrotic disorder, or cardiovascular disorder. In certain embodiments, the disorder is scleroderma, psoriasis, nonalcoholic steatohepatitis, giant cell arteritis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, ulcerative colitis, asthma, uveitis, rheumatoid arthritis, or epidermal hyperplasia. In yet other embodiments, the disorder is cystic fibrosis or idiopathic pulmonary fibrosis.

Another aspect of the invention provides a method of inhibiting Rho-associated protein kinase isoform 2. The method comprises exposing a Rho-associated protein kinase isoform 2 to an effective amount of one or more indazolyl thiadiazolamine or related compounds described herein, e.g., a compound of Formula I, I-A, I-B, I-C, or II, to inhibit said Rho-associated protein kinase isoform 2.

DETAILED DESCRIPTION

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. Certain embodiments utilize compounds described herein that are highly selective for inhibiting ROCK2, while having little inhibitory activity towards ROCK1. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —$CH_2$—, —$CH_2CH_2$—, and —$CH_2C(H)(CH_3)CH_2$—.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl group. Exemplary hydroxyalkyl groups include —$CH_2C(H_2)OH$, —$CH_2C(H)(OH)CH_3$, and the like.

The term "hydroxyalkylene" refers to a diradical of a hydroxyalkyl group. Exemplary hydroxyalkylene groups include —$CH_2C(H)(OH)$—, —$CH_2C(H)(OH)CH_2$—, and the like.

The term "aralkyl" refers to an alkyl group substituted with an aryl group. Exemplary aralkyl groups include

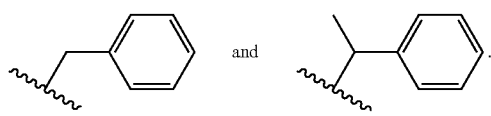

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group. The aryl group may be a 6-14 membered carbocyclic aromatic group, or a 6-10 membered carbocyclic aromatic group. In certain embodiments, the aryl group is not substituted (i.e., it is unsubstituted). In certain embodiments, unless specified otherwise, the aryl group is substitituted with 1, 2, or 3 substituents.

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocylic ring or a 9-10 membered bicyclic ring. In certain embodiments, the heteroaryl is not substituted, i.e., it is unsubstituted. In certain embodiments, unless specified otherwise, the heteroaryl group is substituted with 1, 2, or 3 substituents The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. The nonaromatic ring may be a saturated ring, or it may be a partially saturated ring (i.e., it contains one or more double bonds between ring atoms, but does not contain enough double bonds between ring atoms to qualify as aromatic). Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, oxo, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted. In certain embodiments, the heterocyclyl is not substituted, i.e., it is unsubstituted.

The term "heterocycloalkyl" refers to a saturated heterocyclyl group having, for example, 3-7 ring atoms (which may be C and one or more of O, N, and S). In certain embodiments, the heterocycloalkyl is not substituted, i.e., it is unsubstituted.

The term "oxo-heterocycloalkyl" refers to a heterocycloalkyl group substituted by an oxo group (i.e., =O).

The terms "amine" and "amino" are art-recognized and refer to both unsubstituted and substituted amines, e.g., a moiety that may be represented by the general formulas:

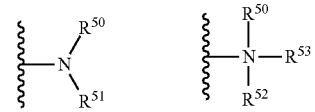

wherein $R^{50}$, $R^{51}$, $R^{52}$ and $R^{53}$ each independently represent a hydrogen, an alkyl, an alkenyl, —(CH$_2$)$_m$—R$^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—R$^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—R$^{61}$, wherein m and R$^{61}$ are described above.

The term "oxo" is art-recognized and refers to a "=O" substituent. For example, a cyclopentane susbstituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is H$_2$O.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "IC$_{50}$" is art-recognized and refers to the concentration of a compound that is required for 50% inhibition of its target.

The term "EC$_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to N,N-dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid. The abbreviation "Ts" is art-recognized and refers to tosylate. The abbreviation "TBS" is art-recognized and refers to tert-butyldimethylsilyl. The abbreviation "DMSO" is art-recognized and refers to dimethylsulfoxide. The abbreviation "ACN" is art-recognized and refers to acetonitrile.

As a general matter, compositions specifying a percentage are by weight unless otherwise specified.

I. Indazolyl Thiadiazolamines and Related Compounds

The invention provides indazolyl thiadiazolamines and related compounds.

Exemplary compounds are described in the following sections, along with exemplary procedures for making the compounds. Additional exemplary compounds and synthetic procedures are described in the Examples.

One aspect of the invention provides a compound represented by Formula I:

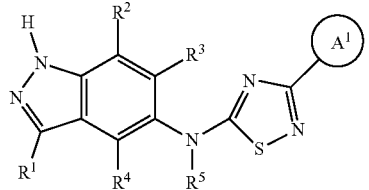

or a pharmaceutically acceptable salt thereof, or a solvate of the foregoing; wherein:
$R^1$ is hydrogen, halogen, $C_1$-$C_3$ alkyl, $C_1$-$C_3$ haloalkyl, cyclopropyl, $C_2$-$C_4$ alkenyl, cyano, or —N($R^6$)($R^7$);
$R^2$, $R^3$, and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;
$R^5$ is hydrogen, $C_1$-$C_6$ alkyl, $C_1$-$C_6$ hydroxyalkyl, or —$CO_2R^{12}$;
$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 occurrences of $R^{12}$;
$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, 3-7 membered heterocycloalkyl, —($C_1$-$C_6$ alkylene)-O—($C_1$-$C_6$ alkyl), or —($C_1$-$C_6$ alkylene)-N($R^6$)($R^7$); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;
$R^{10}$ represents independently for each occurrence $C_1$-$C_6$ alkyl, $C_1$-$C_6$ haloalkyl, $C_3$-$C_6$ cycloalkyl, —($C_1$-$C_6$ alkylene)-($C_3$-$C_6$ cycloalkyl), $C_1$-$C_6$ hydroxyalkyl, —($C_1$-$C_6$ alkylene)-O—($C_1$-$C_6$ alkyl), —($C_1$-$C_6$alkylene)-N($R^8$)($R^9$), —($C_1$-$C_6$ alkylene)-$CO_2R^6$, —($C_1$-$C_6$ alkylene)-(3-7 membered heterocycloalkyl), 3-7 membered heterocyclyl, phenyl, or aralkyl; wherein said cycloalkyl, heterocyclyl, phenyl, and aralkyl are optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, and hydroxyl;
$R^{11}$ represents independently for each occurrence a 5-6 membered heteroaryl, 3-7 membered heterocycloalkyl, or phenyl, each of which is optionally substituted with 1 or 2 occurrences of $Y^1$;
$R^{12}$ represents independently for each occurrence $C_1$-$C_6$ alkyl or $C_3$-$C_6$ cycloalkyl;
$R^{13}$ represents independently for each occurrence $C_1$-$C_6$ alkyl, $C_3$-$C_6$ cycloalkyl, —($C_1$-$C_6$ alkylene)-($C_3$-$C_6$ cycloalkyl), or aralkyl;
$A^1$ is a cyclic group selected from:
(a) phenyl, $C_3$-$C_7$ cycloalkyl, $C_3$-$C_7$ oxocycloalkyl, 5-10 membered heterocyclyl, 5-10 membered oxoheterocyclyl, aralkyl, or heteroaralkyl, each being substituted by $X^1$ and 0, 1, 2, or 3 occurrences of $Y^1$; and
(b) 8-10 membered bicyclic heterocyclyl optionally substituted by $C_6$ aryl and 0, 1, 2, or 3 occurrences of $Y^1$;
$X^1$ represents independently for each occurrence:
—N($R^6$)C(O)-(3-7 membered heterocyclyl), —N($R^6$)C(O)-(3-7 membered oxo-heterocyclyl), —N($R^6$)C(O)-phenyl, —N($R^6$)C(O)-aralkyl, or —N($R^6$)C(O)-heteroaralkyl; each of which is optionally substituted by 1, 2, or 3 occurrences of $Y^1$;
—$CO_2R^8$, —C(O)N($R^8$)($R^9$), —C(O)$R^{11}$, —C(O)$R^{12}$, —C(O)-(3-7 membered heterocyclyl), —C(O)N($R^8$)($R^{10}$), —N($R^6$)C(O)$R^{10}$, —N($R^{10}$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), —N($R^6$)C(O)N($R^6$)($R^7$), —N($R^6$)C(O)N($R^6$)($R^{10}$), —N($R^6$)($R^7$), or —$NO_2$;
—O—($C_1$-$C_6$alkylene)-$CO_2R^8$, —OC(O)$R^{12}$, —O—($C_1$-$C_6$ alkylene)-C(O)N($R^8$)($R^9$), —O—($C_1$-$C_6$ alkylene)-N($R^8$)($R^9$), —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;
$SO_2R^{10}$, —$SO_2N(R^8)$-heteroaryl, cyano, —P(O)(O$R^8$)$_2$, or —P(O)($R^{12}$)($R^{13}$);
5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl); or
—($C_1$-$C_6$ alkylene)-aryl, —($C_1$-$C_6$ alkylene)-heterocyclyl, —($C_1$-$C_6$ alkylene)-$COR^{12}$, —($C_1$-$C_6$ alkylene)-N($R^6$)C(O)$R^{10}$, or —($C_1$-$C_6$)alkylene)-C(O)N($R^8$)($R^{10}$); and
$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —C(O)N($R^8$)($R^9$), —N($R^6$)C(O)$R^{10}$, —N($R^6$)C(O)N($R^6$)($R^7$), —N($R^6$)($R^7$), —($C_1$-$C_6$ alkylene)-$CO_2R^8$, —($C_1$-$C_6$ alkylene)-O—($C_1$-$C_6$ alkyl), —($C_1$-$C_6$alkylene)-N($R^6$)($R^7$), —($C_1$-$C_6$ alkylene)-N($R^6$)S(O)$_2R^{12}$, —($C_1$-$C_6$alkylene)-S—C(O)$R^{12}$, —S—$R^{12}$, 3-7 membered heterocycloalkyl, or —($C_1$-$C_6$ alkylene)-(3-7 membered heterocycloalkyl).

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is phenyl substituted by $X^1$, $X^1$ is —N($R^6$)C(O)-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I or a pharmaceutically acceptable salt thereof. In certain other embodiments, the compound is a compound of Formula I. In yet other embodiments, the compound is a compound of Formula I or a solvate thereof, such as $C_1$-$C_3$ haloalkanoic acid solvate.

The compound can be further characterized according to the definition of variables $R^1$ through $R^{10}$. Accordingly, in certain embodiments, R', $R^2$, and $R^3$ are hydrogen. In certain embodiments, $R^1$ is $C_1$-$C_3$ alkyl, and $R^2$ and $R^3$ are hydrogen. In certain embodiments, $R^4$ is hydrogen. In certain other embodiments, $R^4$ is chloro. In certain embodiments, $R^5$ is hydrogen. In certain embodiments, $R^6$ and $R^7$ each represent independently for each occurrence hydrogen or $C_1$-$C_6$ alkyl. In certain embodiments, $R^8$ and $R^9$ each represent independently for each occurrence hydrogen or $C_1$-$C_6$ alkyl. In certain embodiments, $R^8$ and $R^9$ each represent independently for each occurrence $C_1$-$C_6$ alkyl. In certain embodiments, $R^8$ and $R^9$ each represent independently for each occurrence hydrogen, $C_1$-$C_6$ alkyl, $C_1$-$C_6$ hydroxyalkyl, or $C_3$-$C_6$ cycloalkyl. In certain embodiments, $R^{10}$ is $C_1$-$C_6$ alkyl, $C_1$-$C_6$haloalkyl, $C_3$-$C_6$ cycloalkyl, or $C_1$-$C_6$hydroxyalkyl. In certain embodiments, $R^{10}$ is $C_1$-$C_6$ alkyl.

The compound can be further characterized according to the definition of variable $A^1$. Accordingly, in certain embodiments, $A^1$ is phenyl or a 5-6 membered heteroaryl, each being substituted by $X^1$ and 0, 1, 2, or 3 occurrences of $Y^1$. In certain embodiments, $A^1$ is phenyl substituted by $X^1$ and 0, 1, 2, or 3 occurrences of $Y^1$. In certain embodiments, $A^1$ is phenyl substituted by $X^1$. In certain embodiments, $A^1$ is a 6-membered heteroaryl substituted by $X^1$ and 0, 1, 2, or 3 occurrences of $Y^1$. In certain embodiments, $A^1$ is a 6-membered heteroaryl substituted by $X^1$. In certain embodiments, $A^1$ is

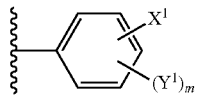

wherein m is 0, 1, 2, or 3. In certain embodiments, $A^1$ is

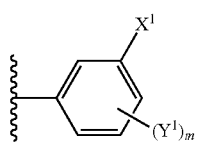

wherein m is 0, 1, 2, or 3. In certain embodiments, $A^1$ is

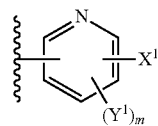

wherein m is 0, 1, 2, or 3. In certain embodiments, $A^1$ is

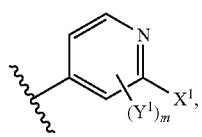 or 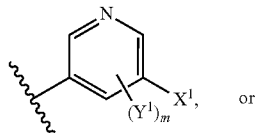

wherein m is 0, 1, 2, or 3. In certain embodiments, $A^1$ is

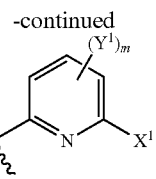

wherein m is 0, 1, 2, or 3. In certain embodiments, $A^1$ is

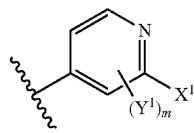

wherein m is 0, 1, 2, or 3. In certain embodiments, $A^1$ is

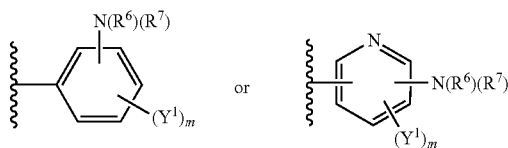

wherein m is 0, 1, 2, or 3. In certain embodiments, $A^1$ is

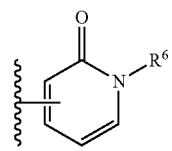

optionally substituted by $X^1$ and 0, 1, 2, or 3 occurrences of $Y^1$. In certain embodiments, m is 0 or 1. In certain embodiments, m is 0.

In certain embodiments, $A^1$ is a 5-10 membered heterocyclyl, 5-10 membered oxo-heterocyclyl, aralkyl, or heteroaralkyl, each being substituted by $X^1$ and 0, 1, 2, or 3 occurrences of $Y^1$. In certain embodiments, $A^1$ is a heteroaryl selected from the group consisting of an 8-10 membered bicyclic heteroaryl, a 5-membered heteroaryl, and a 6-membered heteroaryl containing at least two ring nitrogen atoms; wherein said heteroaryl is substituted by $X^1$ and 0, 1, 2, or 3 occurrences of $Y^1$. In certain embodiments, $A^1$ is an 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by $X^1$ and 0, 1, 2, or 3 occurrences of $Y^1$. In certain embodiments, $A^1$ is an 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo oxazolyl, 1H-indazolyl, and oxazolo[5,4-b]pyridinyl, each being optionally substituted by $X^1$ and 0, 1, 2, or 3 occurrences of $Y^1$. In certain embodiments, $A^1$ is a 3-7 membered heterocycloalkyl substituted by $X^1$ and 0, 1, 2, or 3 occurrences of $Y^1$.

In certain embodiments, $A^1$ is an 8-10 membered bicyclic heterocyclyl substituted by 0, 1, 2, or 3 occurrences of $Y^1$.

The compound can be further characterized according to the definition of variable $X^1$. Accordingly, in certain embodiments, $X^1$ is —N($R^6$)C(O)-(3-7 membered heterocyclyl) optionally substituted by 1, 2, or 3 occurrences of $Y^1$. In certain embodiments, $X^1$ is —N($R^6$)C(O)-(5-6 membered heteroaryl) substituted by 1, 2, or 3 occurrences of $Y^1$. In certain embodiments, $X^1$ is —N($R^6$)C(O)-(5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl) substituted by 1, 2, or 3 occurrences of $Y^1$. In certain embodiments, $X^1$ is —N($R^6$)C(O)-phenyl, —N($R^6$)C(O)-aralkyl, or —N($R^6$)C(O)-heteroaralkyl; each of which is optionally substituted by 1, 2, or 3 occurrences of $Y^1$. In certain embodiments, $X^1$ is —C(O)-(5 or 6-membered heteroaryl optionally substituted with 1 or 2 occurrences of $Y^1$). In certain embodiments, $X^1$ is —C(O)-phenyl optionally substituted by 1, 2, or 3 occurrences of $Y^1$.

In certain embodiments, $X^1$ is —$CO_2R^8$, —C(O)N($R^8$)($R^9$), —C(O)$R^{11}$, —C(O)$R^{12}$, —C(O)-(3-7 membered heterocyclyl), —C(O)N($R^8$)($R^{10}$), —N($R^6$)C(O)$R^{10}$, —N($R^{10}$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), —N($R^6$)C(O)N($R^6$)($R^7$), or —$NO_2$. In certain embodiments, $X^1$ is —$CO_2R^8$ or —C(O)N($R^8$)($R^9$). In certain embodiments, $X^1$ is —N($R^6$)C(O)$R^{10}$, —N($R^{10}$)C(O)$R^{10}$, —N($R^6$)$CO_2R^{10}$, or —N($R^8$)$SO_2R^{10}$. In certain embodiments, $X^1$ is —N($R^6$)$CO_2R^{10}$. In certain embodiments, $X^1$ is —N($R^6$)—($C_1$-$C_6$ alkylene)-C(O)N($R^8$)($R^9$), —N($R^6$)—C(O)—($C_1$-$C_6$ hydroxy alkylene)-N($R^8$)($R^9$), —N($R^6$)—C(O)-(2-6 membered heteroalkyl), or —N($R^6$)C(O)N($R^6$)($R^7$).

In certain embodiments, $X^1$ is —O—($C_1$-$C_6$alkylene)-$CO_2R^8$, —OC(O)$R^{12}$, —O—($C_1$-$C_6$ alkylene)-C(O)N($R^8$)($R^9$), —O—($C_1$-$C_6$ alkylene)-N($R^8$)($R^9$), —O—($C_1$-$C_6$alkyl), —O-(3-7 membered heterocyclyl), —O—($C_1$-$C_6$ alkylene)-aryl, or —O—($C_1$-$C_6$ alkylene)-heteroaryl. In certain embodiments, $X^1$ is $SO_2R^{10}$, —$SO_2$N($R^8$)-heteroaryl, cyano, or —P(O)(O$R^8$)$_2$.

In certain embodiments, $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl). In certain embodiments, $X^1$ is a 5-6 membered heteroaryl optionally substituted with 1, 2, or 3 substituents independently selected from the group consisting of $Y^1$ and phenyl. In certain embodiments, $X^1$ is a 5-6 membered heteroaryl optionally substituted with 1, 2, or 3 occurrences of $Y^1$. In certain embodiments, $X^1$ is a 5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl, each being optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$haloalkyl, $C_1$-$C_6$ hydroxyalkyl, —$CO_2R^8$, hydroxyl, or —($C_1$-$C_6$ alkylene)-N($R^6$)($R^7$). In certain embodiments, $Y^1$ represents independently for each occurrence halogen, $C_1$-$C_6$ alkyl, $C_1$-$C_6$haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

In certain embodiments, the compound is not any of compounds IV-91 through IV-106.

The description above describes multiple embodiments relating to compounds of Formula I. The patent application specifically contemplates all combinations of the embodiments. For example, the invention contemplates a compound of Formula I wherein $A^1$ is phenyl substituted by $X^1$ and 0, 1, 2, or 3 occurrences of $Y^1$, and $X^1$ is —C(O)-(5-membered heteroaryl optionally substituted with 1 or 2 occurrences of $Y^1$).

Another aspect of the invention provides a compound represented by Formula I-A:

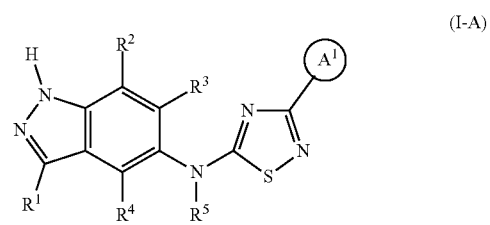

(I-A)

or a pharmaceutically acceptable salt thereof, or a solvate of the foregoing; wherein:
$R^1$ is hydrogen or $C_1$-$C_3$ alkyl;
$R^2$, $R^3$, and $R^5$ are hydrogen;
$R^4$ is hydrogen, chloro, or fluoro;
$R^6$ and $R^7$ each represent independently for each occurrence hydrogen or $C_1$-$C_3$ alkyl;
$R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, —$CO_2R^6$, —N($R^6$)$_2$, and hydroxyl;
$R^{10}$ is $C_1$-$C_6$ alkyl, $C_1$-$C_6$ haloalkyl, $C_3$-$C_6$ cycloalkyl, or $C_1$-$C_6$ hydroxyalkyl;
$A^1$ is phenyl or a 6-membered heteroaryl, each being substituted by $X^1$ and 0, 1, 2, or 3 occurrences of $Y^1$.
$X^1$ represents independently for each occurrence:
—N($R^6$)C(O)-(3-7 membered heterocyclyl) or —N($R^6$)C(O)-phenyl, each of which is optionally substituted by 1, 2, or 3 occurrences of $Y^1$;
—C(O)N($R^8$)($R^9$), —N($R^6$)C(O)$R^{10}$, —N($R^{10}$)C(O)$R^{10}$, —N($R^6$)$CO_2R^{10}$, or —N($R^8$)$SO_2R^{10}$; or
5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl); and
$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$alkylene)-N($R^6$)($R^7$).

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is phenyl substituted by $X^1$ and 0, 1, 2, or 3 occurrences of $X^1$ is —N($R^6$)C(O)-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I-A or a pharmaceutically acceptable salt thereof. In certain other embodiments, the compound is a compound of Formula I-A. In yet other embodiments, the compound is a compound of Formula I-A or a solvate thereof, such as $C_1$-$C_3$ haloalkanoic acid solvate.

The compound can be further characterized according to the definition of variables $R^1$ through $R^{10}$. Accordingly, in certain embodiments, $R^1$ is hydrogen. In certain embodiments, $R^4$ is chloro. In certain embodiments, $R^6$ and $R^7$ each represent independently for each occurrence hydrogen or $C_1$-$C_2$ alkyl. In certain embodiments, $R^8$ and $R^9$ each represent independently for each occurrence hydrogen or $C_1$-$C_3$ alkyl. In certain embodiments, $R^6$ and $R^7$ each represent independently for each occurrence hydrogen or $C_1$-$C_2$ alkyl; and $R^8$ and $R^9$ each represent independently for each occurrence hydrogen or $C_1$-$C_3$ alkyl. In certain embodiments, $R^{10}$ is $C_1$-$C_6$ alkyl.

The compound can be further characterized according to the definition of variable $A^1$. Accordingly, in certain embodiments, $A^1$ is phenyl substituted by $X^1$ and 0, 1, 2, or 3 occurrences of $Y^1$. In certain embodiments, $A^1$ is a 6-membered heteroaryl substituted by $X^1$ and 0, 1, 2, or 3 occurrences of $Y^1$. In certain embodiments, $A^1$ is

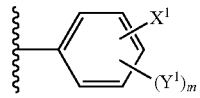

wherein m is 0, 1, 2, or 3. In certain embodiments, $A^1$ is

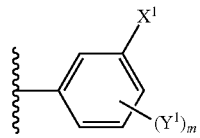

wherein m is 0, 1, 2, or 3. In certain embodiments, $A^1$ is

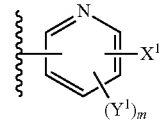

wherein m is 0, 1, 2, or 3. In certain embodiments, $A^1$ is

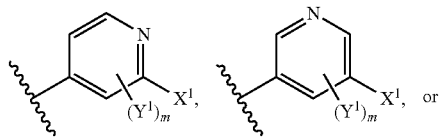

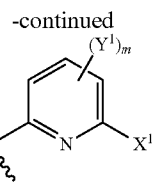

wherein m is 0, 1, 2, or 3. In certain embodiments, $A^1$ is

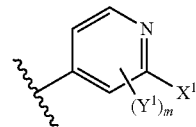

wherein m is 0, 1, 2, or 3. In certain embodiments, m is 0 or 1. In certain embodiments, m is 0.

In certain embodiments, $A^1$ is

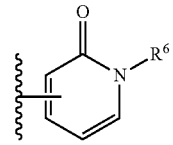

optionally substituted by $X^1$ and 0, 1, 2, or 3 occurrences of $Y^1$.

The compound can be further characterized according to the definition of variable $X^1$. Accordingly, in certain embodiments, $X^1$ is —N($R^6$)C(O)-(3-7 membered heterocyclyl) optionally substituted by 1, 2, or 3 occurrences of $Y^1$. In certain embodiments, $X^1$ is —N($R^6$)C(O)-(5-6 membered heteroaryl) substituted by 1, 2, or 3 occurrences of $Y^1$. In certain embodiments, $X^1$ is —N($R^6$)C(O)-(5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl) substituted by 1, 2, or 3 occurrences of $Y^1$. In certain embodiments, $X^1$ is —$CO_2R^8$ or —C(O)N($R^8$)($R^9$). In certain embodiments, $X^1$ is —C(O)N($R^8$)($R^9$). In certain embodiments, $X^1$ is —N($R^6$)C(O)$R^{10}$, —N($R^{10}$)C(O)$R^{10}$, —N($R^6$)$CO_2R^{10}$, or —N($R^8$)$SO_2R^{10}$. In certain embodiments, $X^1$ is —N($R^6$)$CO_2R^{10}$.

In certain embodiments, $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl). In certain embodiments, $X^1$ is a 5-6 membered heteroaryl optionally substituted with 1, 2, or 3 substituents independently selected from the group consisting of $Y^1$, $C_6$ aryl, and —C(O)—($C_6$ aryl). In certain embodiments, $X^1$ is a 5-6 membered heteroaryl optionally substituted with 1, 2, or 3 occurrences of $Y^1$. In certain embodiments, $X^1$ is a 5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl, each being optionally substituted with 1, 2, or 3 occurrences of $Y^1$.

The compound can be further characterized according to the definition of variable $Y^1$. Accordingly, in certain embodiments, Y¹ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain embodiments, Y¹ represents independently for each occurrence halogen or $C_1$-$C_6$ alkyl.

The description above describes multiple embodiments relating to compounds of Formula I-A. The patent application specifically contemplates all combinations of the embodiments. For example, the invention contemplates a compound of Formula I-A wherein A¹ is phenyl substituted by X¹ and 0 occurrences of Y¹, and X¹ is —$N(R^6)C(O)$-(5-membered heteroaryl optionally substituted with 1 or 2 occurrences of Y¹).

Another aspect of the invention provides a compound represented by Formula I-B:

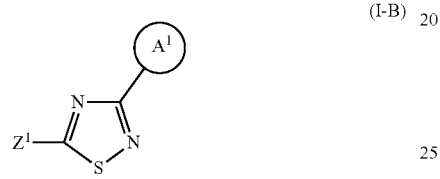

(I-B)

or a pharmaceutically acceptable salt thereof, or a solvate of the foregoing; wherein:

Z¹ is one of the following:

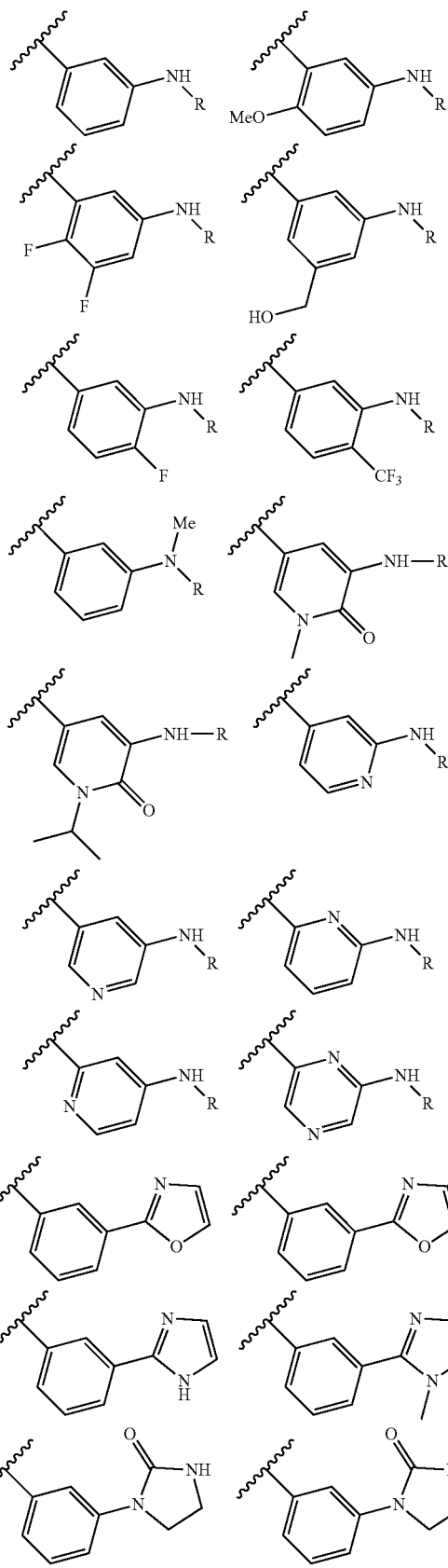

A¹ is one of the following:

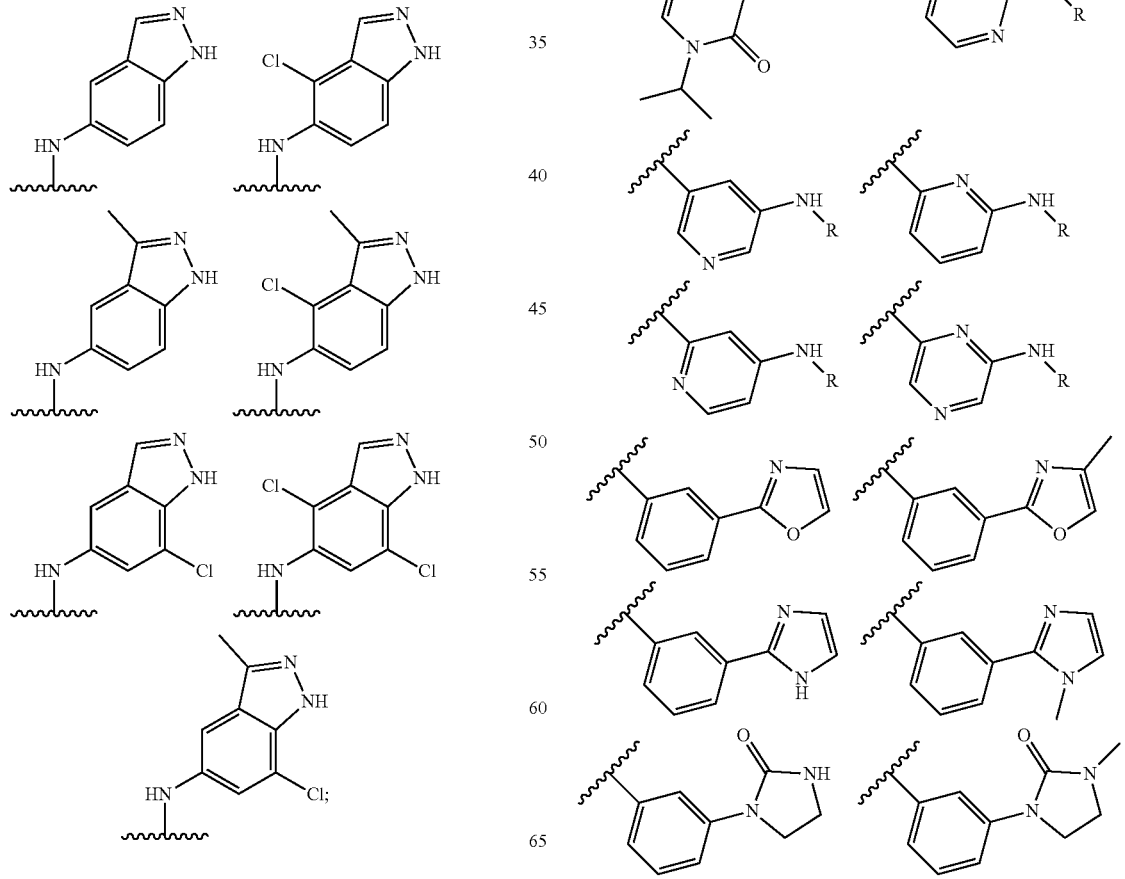

-continued
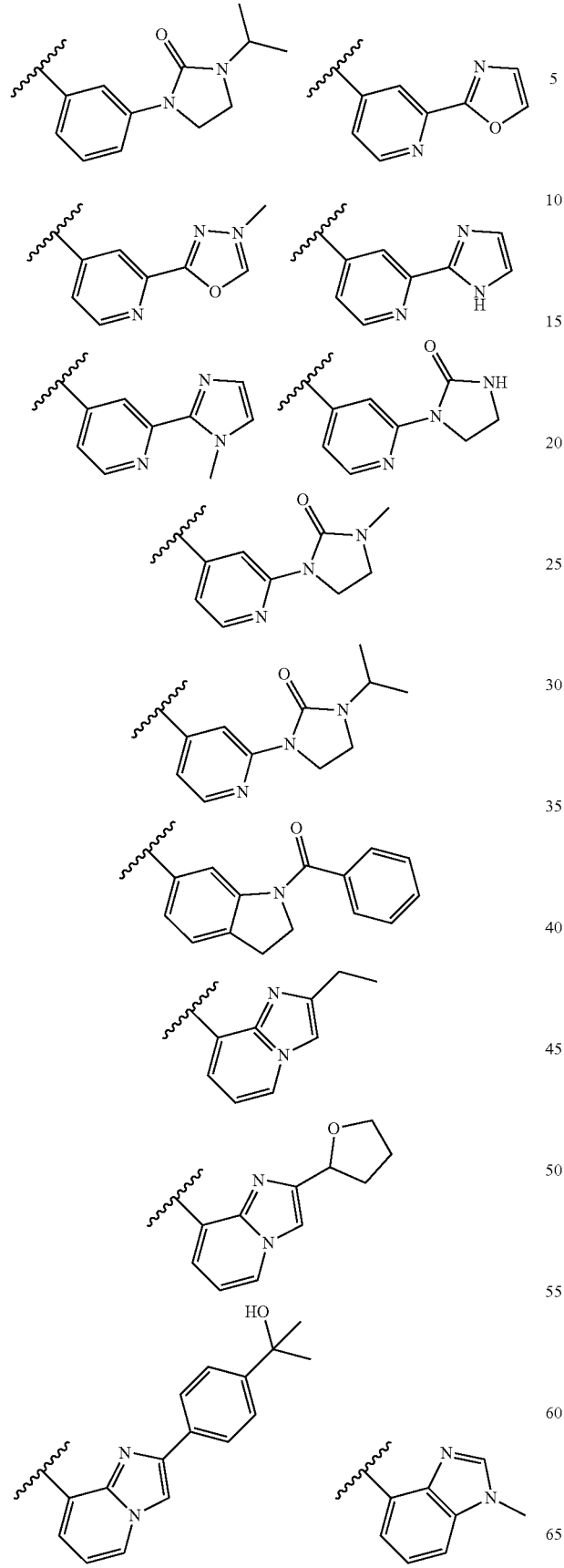
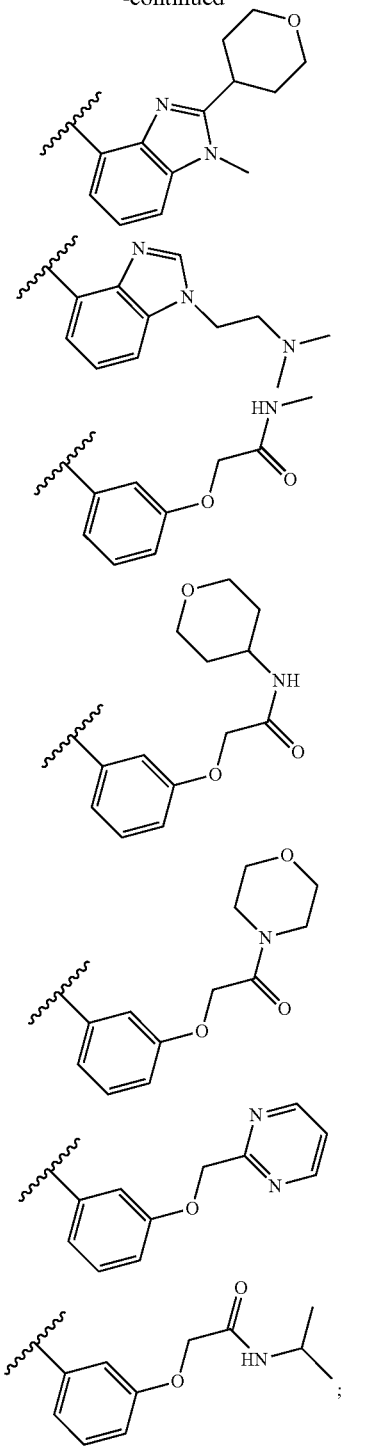
and
R is one of the following:
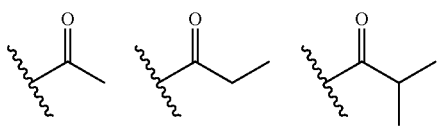

-continued
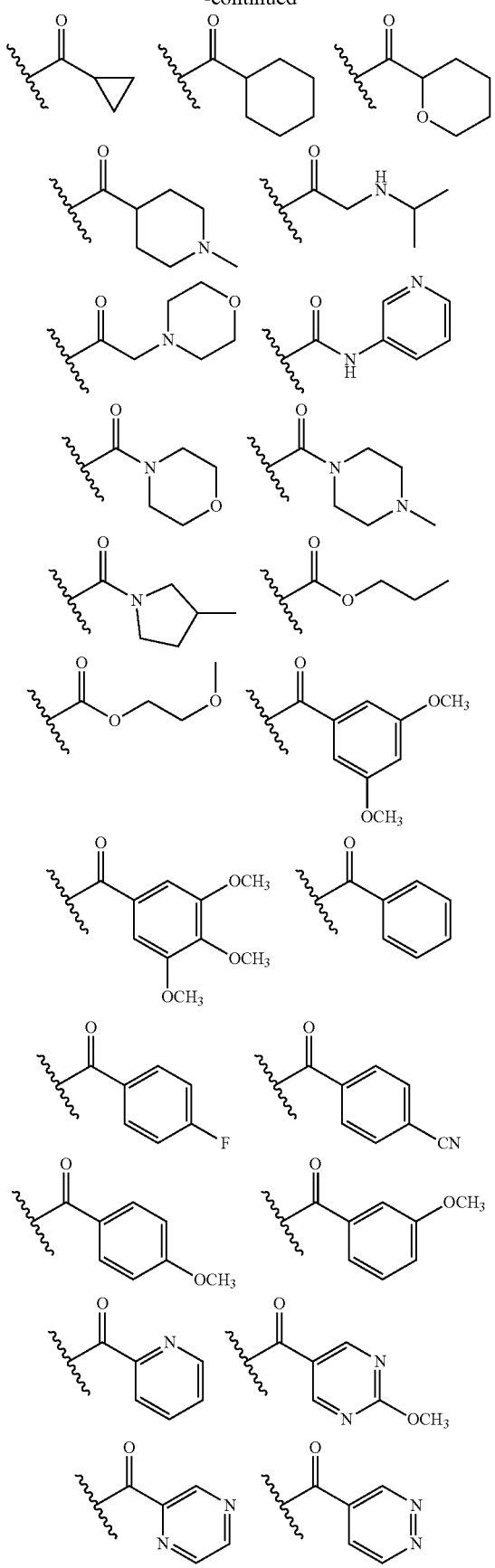
-continued
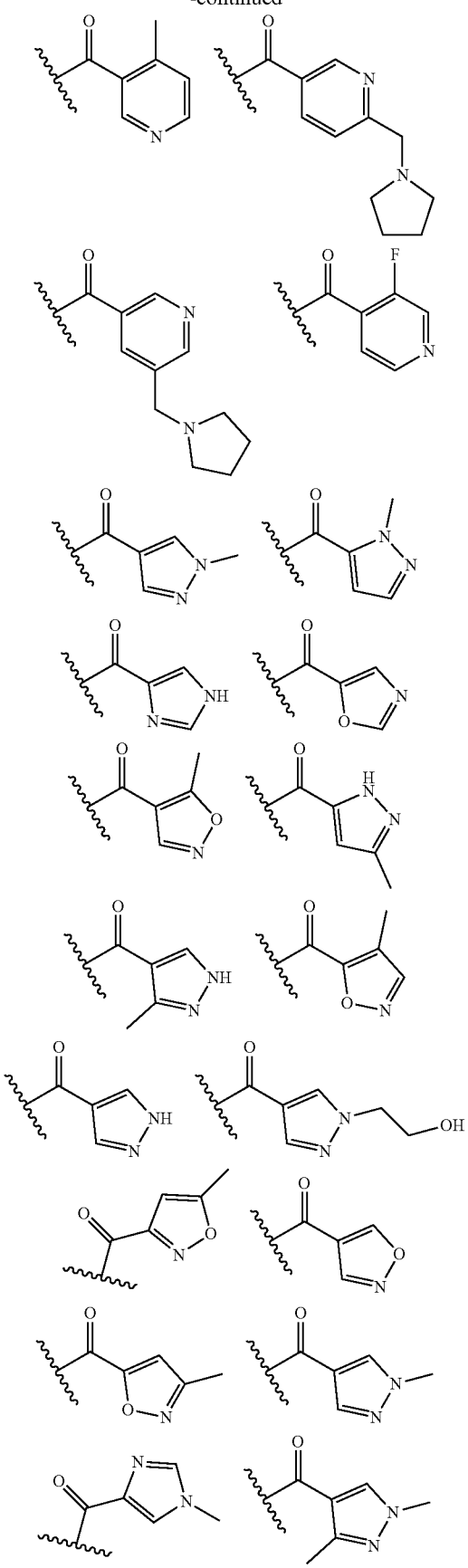

-continued

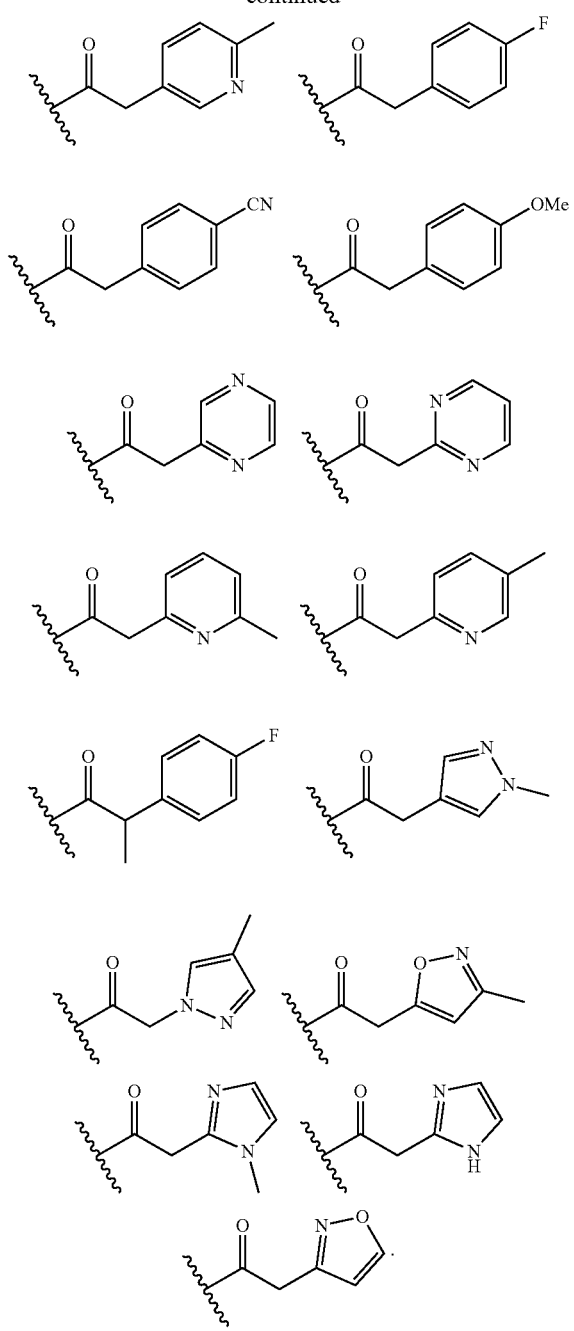

In certain embodiments, the compound is a compound of Formula I-B or a pharmaceutically acceptable salt thereof. In certain other embodiments, the compound is a compound of Formula I-B. In yet other embodiments, the compound is a compound of Formula I-B or a solvate thereof, such as $C_1$-$C_3$ haloalkanoic acid solvate.

In another embodiment, the invention provides a compound of Formula I-B as described above, but now further substituted with 1, 2, or 3 substituents independently selected from the group consisting of halogen, hydroxyl, amino, $C_1$-$C_6$ alkyl, $C_1$-$C_6$ haloalkyl, and $C_1$-$C_6$ alkoxyl.

Another aspect of the invention provides a compound represented by Formula I-C:

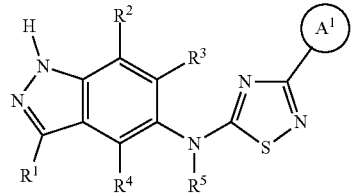

(I-C)

or a pharmaceutically acceptable salt thereof, or a solvate of the foregoing; wherein:

$R^1$ is hydrogen or $C_1$-$C_3$ alkyl;
$R^2$, $R^3$, and $R^5$ are hydrogen;
$R^4$ is hydrogen, chloro, or fluoro;
$R^6$ represents independently for each occurrence hydrogen or $C_1$-$C_3$ alkyl;
$R^8$ represents independently for each occurrence hydrogen or $C_1$-$C_3$ alkyl;
$A^1$ is

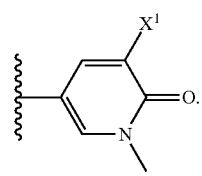

$X^1$ is —N($R^6$)C(O)-(5-6 membered heteroaryl) or —N($R^6$)C(O)-phenyl, each of which is optionally substituted by 1, 2, or 3 occurrences of $Y^1$; and
$Y^1$ represents independently for each occurrence halogen, $C_1$-$C_6$ alkyl, $C_1$-$C_6$ haloalkyl, $C_1$-$C_6$hydroxyalkyl, —$CO_2R^8$, or hydroxyl.

The definitions of variables in Formula I-C above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I-C or a pharmaceutically acceptable salt thereof. In certain other embodiments, the compound is a compound of Formula I-C. In yet other embodiments, the compound is a compound of Formula I-C or a solvate thereof, such as $C_1$-$C_3$ haloalkanoic acid solvate.

The compound can be further characterized according to the definition of variables $R^1$ through $R^8$. Accordingly, in certain embodiments, $R^1$ is hydrogen. In certain embodiments, $R^4$ is chloro. In certain embodiments, $R^6$ is hydrogen. In certain embodiments, $R^8$ is hydrogen.

The compound can be further characterized according to the definition of variable $X^1$. Accordingly, in certain embodiments, $X^1$ is —N($R^6$)C(O)-(5-6 membered heteroaryl) optionally substituted by 1, 2, or 3 occurrences of $Y^1$. In certain embodiments, $X^1$ is —N($R^6$)C(O)-(5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl) optionally substituted by 1, 2, or 3 occurrences of Y¹. In certain embodiments, X¹ is —N(R⁶)C(O)-phenyl optionally substituted by 1, 2, or 3 occurrences of Y¹.

The compound can be further characterized according to the definition of variable Y¹. Accordingly, in certain embodiments, Y¹ represents independently for each occurrence halogen, $C_1$-$C_6$ alkyl, or $C_1$-$C_6$ haloalkyl. In certain embodiments, Y¹ represents independently for each occurrence halogen or $C_1$-$C_6$ alkyl.

The description above describes multiple embodiments relating to compounds of Formula I-C. The patent application specifically contemplates all combinations of the embodiments.

Another aspect of the invention provides a compound represented by Formula II:

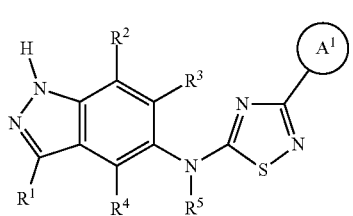

(II)

or a pharmaceutically acceptable salt thereof, or a solvate of the foregoing; wherein:

$R^1$ is hydrogen, halogen, $C_1$-$C_3$ alkyl, $C_1$-$C_3$ haloalkyl, cyclopropyl, $C_2$-$C_4$ alkenyl, cyano, or —N(R⁶)(R⁷);

$R^2$, $R^3$, and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;

$R^5$ is hydrogen, $C_1$-$C_6$ alkyl, or $C_1$-$C_6$ hydroxyalkyl;

$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 substituents selected from the group consisting of $C_1$-$C_6$ alkyl and $C_3$-$C_6$ cycloalkyl;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, 3-7 membered heterocycloalkyl, —($C_1$-$C_6$ alkylene)-O—($C_1$-$C_6$ alkyl), or —($C_1$-$C_6$ alkylene)-N(R⁶)(R⁷); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —CO₂R⁶, —C(O)N(R⁶)(R⁷), —N(R⁶)C(O)R⁶, —N(R⁶)₂, and —($C_1$-$C_6$ alkylene)-CO₂R⁶;

A¹ is a cyclic group selected from:
(a) phenyl, $C_3$-$C_7$ cycloalkyl, $C_3$-$C_7$ oxocycloalkyl, 5-10 membered heterocyclyl, 5-10 membered oxoheterocyclyl, aralkyl, or heteroaralkyl, each being substituted by X¹ and 0, 1, 2, or 3 occurrences of Y¹; and
(b) 3-7 membered heterocycloalkyl substituted by —($C_1$-$C_6$alkylene)-N(R⁶)(R⁷) and 0, 1, 2, or 3 occurrences of Y¹;

X¹ represents independently for each occurrence:
—C(O)-(8-10 membered heterocyclyl containing a ring nitrogen atom bonded to the carbon atom of the attached —C(O)— group); or 5-10 membered oxo-heterocyclyl that is partially unsaturated and optionally substituted with 1, 2, or 3 occurrences of Y¹; and Y¹ represents independently for each occurrence halogen, $C_1$-$C_6$ alkyl, $C_1$-$C_6$ haloalkyl, $C_1$-$C_6$hydroxyalkyl, $C_3$-$C_6$ cycloalkyl, $C_1$-$C_6$ alkoxyl, $C_2$-$C_6$ alkenyl, cyano, hydroxyl, —CO₂R⁸, —C(O)N(R⁸)(R⁹), —N(R⁶)C(O)N(R⁶)(R⁷), —N(R⁶)(R⁷), —($C_1$-$C_6$ alkylene)-CO₂R⁸, —($C_1$-$C_6$ alkylene)-O—($C_1$-$C_6$ alkyl), or —($C_1$-$C_6$alkylene)-N(R⁶)(R⁷).

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A¹ is phenyl substituted by X¹, X¹ is 5-10 membered oxoheterocyclyl that is partially unsaturated and optionally substituted with 1, 2, or 3 occurrences of Y¹, and Y¹ represents independently for each occurrence halogen, $C_1$-$C_6$ alkyl, $C_1$-$C_6$ haloalkyl, or $C_1$-$C_6$hydroxyalkyl.

In certain embodiments, the compound is a compound of Formula II or a pharmaceutically acceptable salt thereof. In certain other embodiments, the compound is a compound of Formula II. In yet other embodiments, the compound is a compound of Formula II or a solvate thereof, such as $C_1$-$C_3$ haloalkanoic acid solvate.

The compound can be further characterized according to the definition of variables $R^1$ through $R^9$. Accordingly, in certain embodiments, $R^1$, $R^2$, and $R^3$ are hydrogen. In certain embodiments, $R^1$ is $C_1$-$C_3$ alkyl, and $R^2$ and $R^3$ are hydrogen.

In certain embodiments, $R^4$ is hydrogen. In certain embodiments, $R^4$ is chloro.

In certain embodiments, $R^5$ is hydrogen.

In certain embodiments, $R^6$ and $R^7$ are independently hydrogen or $C_1$-$C_6$ alkyl.

In certain embodiments, $R^8$ and $R^9$ each represent independently for each occurrence hydrogen, $C_1$-$C_6$ alkyl, $C_1$-$C_6$ hydroxyalkyl, or $C_3$-$C_6$ cycloalkyl.

In certain embodiments, A¹ is phenyl substituted by X¹ and 0, 1, 2, or 3 occurrences of Y¹.

In certain embodiments, X¹ is —C(O)-(8-10 membered heterocyclyl containing a ring nitrogen atom bonded to the carbon atom of the attached —C(O)— group).

In certain embodiments, Y¹ represents independently for each occurrence halogen, $C_1$-$C_6$ alkyl, $C_1$-$C_6$ haloalkyl, $C_1$-$C_6$ hydroxyalkyl, —CO₂R⁸, hydroxyl, or —($C_1$-$C_6$ alkylene)-N(R⁶)(R⁷). In certain embodiments, Y¹ represents independently for each occurrence halogen or $C_1$-$C_6$ alkyl.

The description above describes multiple embodiments relating to compounds of Formula II. The patent application specifically contemplates all combinations of the embodiments.

In certain other embodiments, the compound is a compound in Table 1, or a pharmaceutically acceptable salt thereof TABLE 1
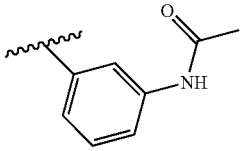 [SMILES: *c1cccc(NC(C)=O)c1]
| No. | R^I | R^II | R^III | A^1 |
|---|---|---|---|---|
| I-1 | H | Cl | H | 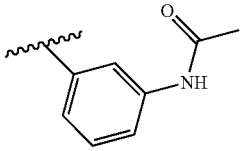 [SMILES: *c1cccc(NC(C)=O)c1] |
| I-2 | CH₃ | Cl | H | 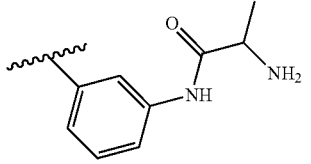 [SMILES: *c1cccc(NC(=O)C(C)N)c1] |
| I-3 | CH₃ | H | H | 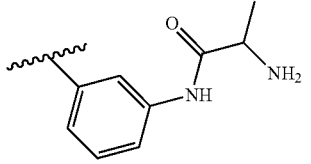 [SMILES: *c1cccc(NC(=O)C(C)N)c1] |
| I-4 | H | Cl | H | 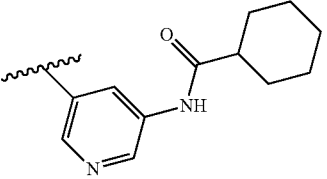 [SMILES: *c1cncc(NC(=O)C2CCCCC2)c1] |
| I-5 | CH₃ | H | Cl | 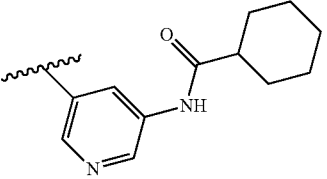 [SMILES: *c1cncc(NC(=O)C2CCCCC2)c1] |
| I-6 | H | Cl | H | 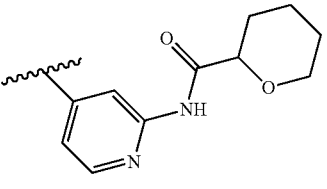 [SMILES: *c1ccnc(NC(=O)C2CCCCO2)c1] |
| I-7 | H | Cl | H | 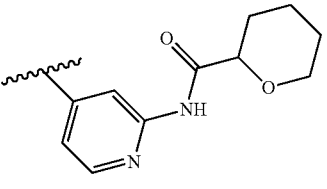 [SMILES: *c1ccnc(NC(=O)C2CCCCO2)c1] |

TABLE 1-continued

| No. | $R^I$ | $R^{II}$ | $R^{III}$ | $A^1$ |
|---|---|---|---|---|
| I-8 | H | Cl | H | 3-(3-pyridyl-ureido)phenyl |
| I-9 | H | Cl | H | 2-[(3-methylpyrrolidin-1-yl)carbonylamino]pyridin-4-yl |
| I-10 | H | Cl | H | 3-(ethoxycarbonylamino)phenyl |
| I-11 | H | Cl | H | 3-(2-methoxyethoxycarbonylamino)phenyl |
| I-12 | CH$_3$ | H | H | 3-(2-methoxyethoxycarbonylamino)phenyl |
| I-13 | H | Cl | H | 2-(2-methoxyethoxycarbonylamino)pyridin-4-yl |

TABLE 1-continued
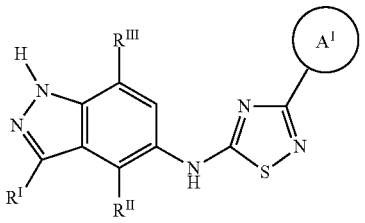
| No. | R$^I$ | R$^{II}$ | R$^{III}$ | A$^1$ |
|---|---|---|---|---|
| I-14 | H | Cl | H | |
| I-15 | H | Cl | H | |
| I-16 | H | Cl | H | |
| I-17 | H | Cl | H | |
| I-18 | CH$_3$ | Cl | H | |
| I-19 | H | Cl | H | |

TABLE 1-continued
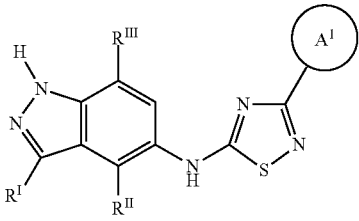
| No. | R^I | R^II | R^III | A^1 |
|---|---|---|---|---|
| I-20 | H | Cl | H | 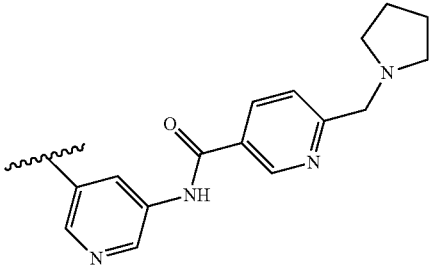 [SMILES: *c1cncc(NC(=O)c2ccc(CN3CCCC3)nc2)c1] |
| I-21 | H | Cl | H | 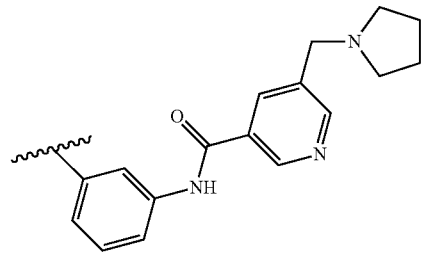 [SMILES: *c1cccc(NC(=O)c2cncc(CN3CCCC3)c2)c1] |
| I-22 | CH₃ | H | H |  |
| I-23 | H | Cl | H | 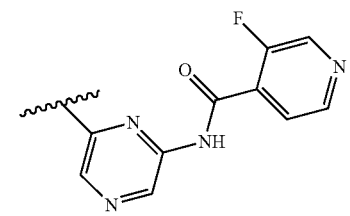 [SMILES: *c1cncc(NC(=O)c2ccncc2F)n1] |
| I-24 | H | Cl | H | 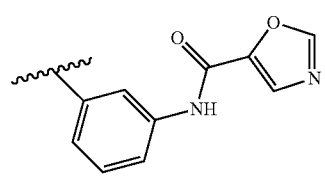 [SMILES: *c1cccc(NC(=O)c2cnco2)c1] |
| I-25 | H | Cl | H | 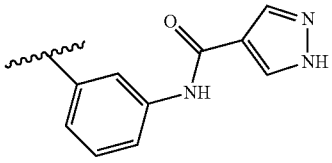 [SMILES: *c1cccc(NC(=O)c2cn[nH]c2)c1] |

TABLE 1-continued
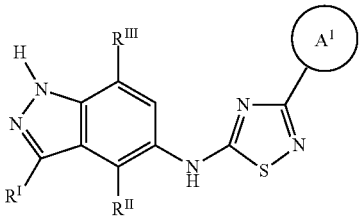
| No. | R^I | R^II | R^III | A^1 |
|---|---|---|---|---|
| I-26 | H | Cl | H | 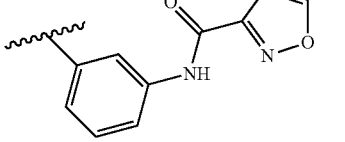 |
| I-27 | H | Cl | H | 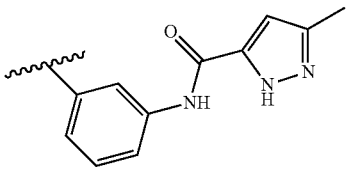 [SMILES: *c1cccc(NC(=O)c2cc(C)n[nH]2)c1] |
| I-28 | CH₃ | Cl | H | 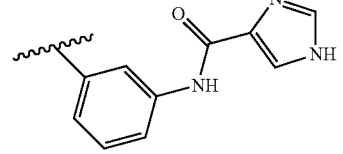 |
| I-29 | H | Cl | H | 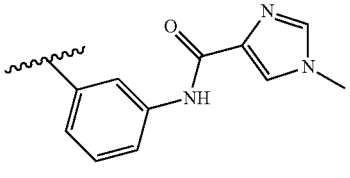 [SMILES: *c1cccc(NC(=O)c2cn(C)cn2)c1] |
| I-30 | CH₃ | H | H | 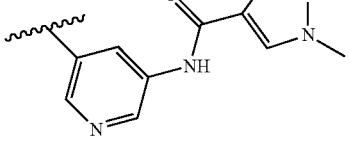 |
| I-31 | H | Cl | H | 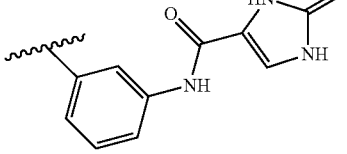 |
| I-32 | H | Cl | H | 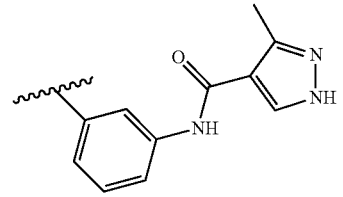 [SMILES: *c1cccc(NC(=O)c2c[nH]nc2C)c1] |

TABLE 1-continued
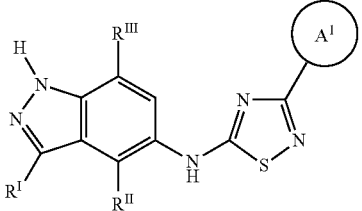
| No. | $R^I$ | $R^{II}$ | $R^{III}$ | $A^1$ |
|---|---|---|---|---|
| I-33 | H | Cl | H | 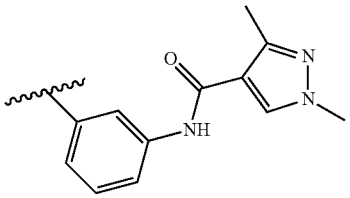 [SMILES: *c1cccc(NC(=O)c2cn(C)nc2C)c1] |
| I-34 | H | Cl | H | 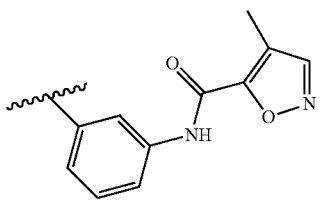 [SMILES: *c1cccc(NC(=O)c2oncc2C)c1] |
| I-35 | H | Cl | H | 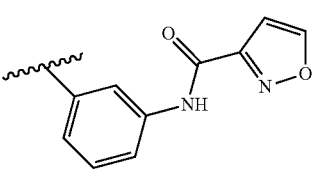 [SMILES: *c1cccc(NC(=O)c2ccon2)c1] |
| I-36 | H | Cl | H | 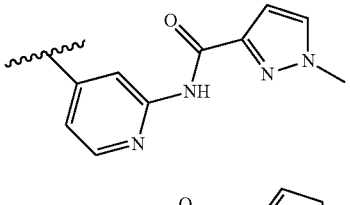 |
| I-37 | H | Cl | H | 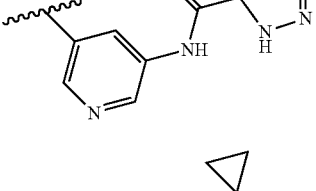 |
| I-38 | H | Cl | H | 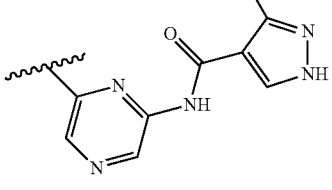 |
| I-39 | CH$_3$ | H | H | 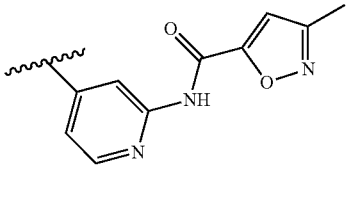 [SMILES: *c1ccnc(NC(=O)c2cc(C)no2)c1] |

TABLE 1-continued
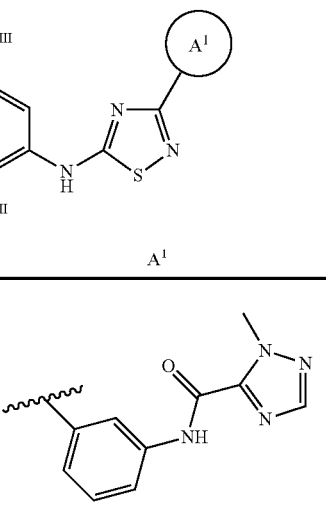
| No. | $R^I$ | $R^{II}$ | $R^{III}$ | $A^1$ |
|---|---|---|---|---|
| I-40 | H | Cl | H | 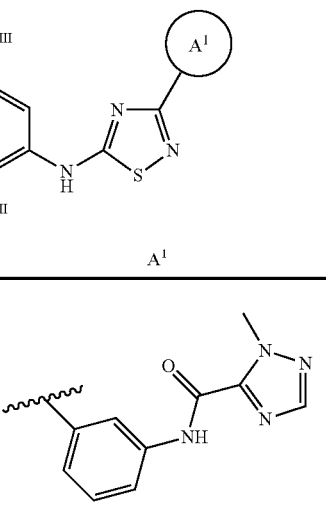 |
| I-41 | H | Cl | H | 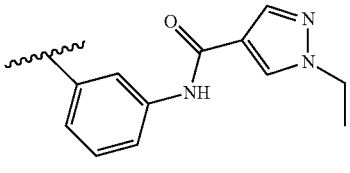 [SMILES: *c1cccc(NC(=O)c2cnn(CC)c2)c1] |
| I-42 | H | Cl | H | 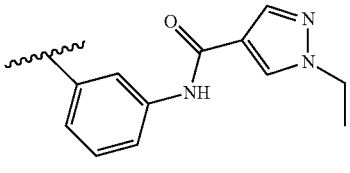 [SMILES: *c1cccc(NC(=O)c2cnn(CC)c2)c1] |
| I-43 | H | Cl | H | 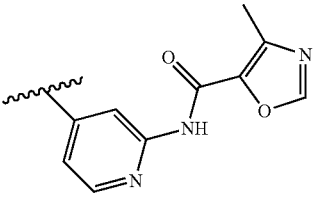 [SMILES: *c1ccnc(NC(=O)c2ocnc2C)c1] |
| I-44 | H | Cl | H | 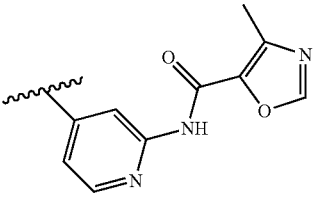 [SMILES: *c1ccnc(NC(=O)c2ocnc2C)c1] |
| I-45 | H | Cl | H | 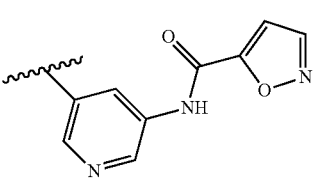 [SMILES: *c1cncc(NC(=O)c2ccno2)c1] |
| I-46 | CH$_3$ | Cl | H | 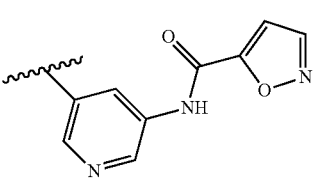 [SMILES: *c1cncc(NC(=O)c2ccno2)c1] |

TABLE 1-continued
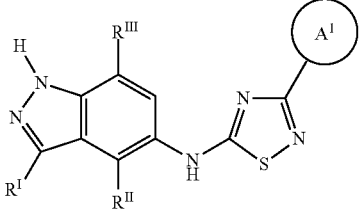
| No. | R$^I$ | R$^{II}$ | R$^{III}$ | A$^1$ |
|---|---|---|---|---|
| I-47 | H | Cl | H | 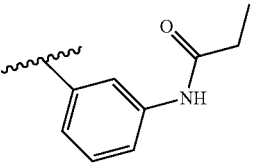 [SMILES: *c1cccc(NC(=O)CC)c1] |
| I-48 | H | Cl | H | 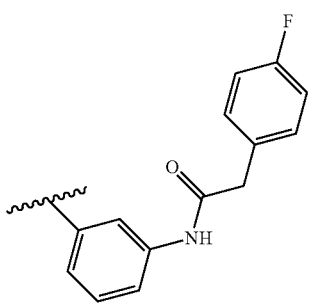 [SMILES: *c1cccc(NC(=O)Cc2ccc(F)cc2)c1] |
| I-49 | H | Cl | H | 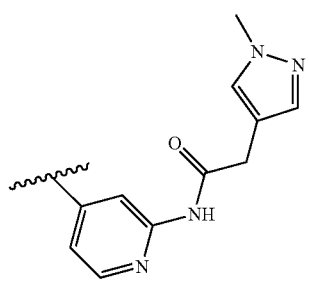 [SMILES: *c1ccnc(NC(=O)Cc2cnn(C)c2)c1] |
| I-50 | CH$_3$ | H | H | 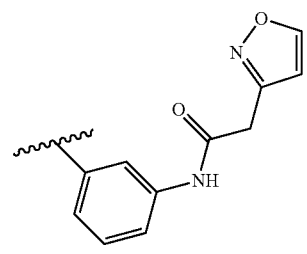 [SMILES: *c1cccc(NC(=O)Cc2ccon2)c1] |
| I-51 | H | Cl | H | 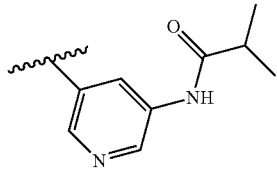 [SMILES: *c1cncc(NC(=O)C(C)C)c1] |

TABLE 1-continued
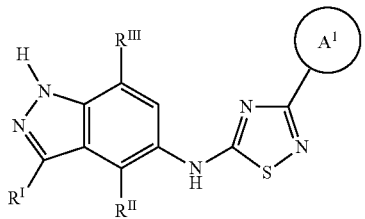
| No. | $R^I$ | $R^{II}$ | $R^{III}$ | $A^1$ |
|---|---|---|---|---|
| I-52 | H | Cl | Cl | |
| I-53 | H | Cl | H | |
| I-54 | CH$_3$ | Cl | H | |
| I-55 | H | H | H | |
| I-56 | CH$_3$ | H | H | |

TABLE 1-continued
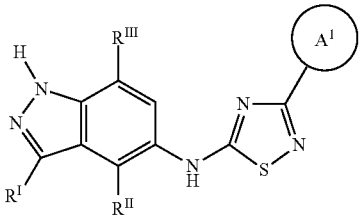
| No. | R<sup>I</sup> | R<sup>II</sup> | R<sup>III</sup> | A<sup>1</sup> |
|---|---|---|---|---|
| I-57 | H | H | Cl | 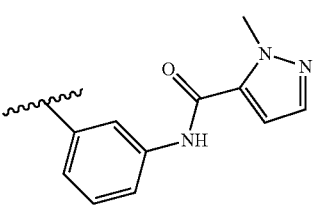 [SMILES: *c1cccc(NC(=O)c2ccnn2C)c1] |
| I-58 | CH₃ | Cl | H | 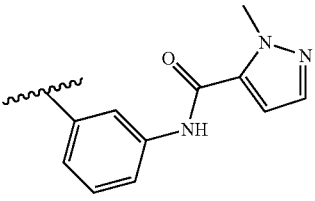 [SMILES: *c1cccc(NC(=O)c2ccnn2C)c1] |
| I-59 | H | Cl | Cl | 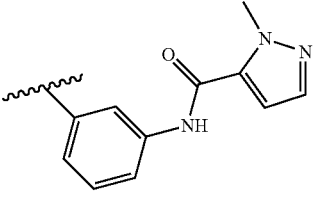 [SMILES: *c1cccc(NC(=O)c2ccnn2C)c1] |
| I-60 | CH₃ | H | Cl | 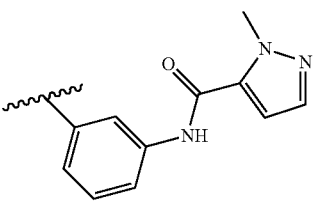 [SMILES: *c1cccc(NC(=O)c2ccnn2C)c1] |
| I-61 | H | Cl | H | 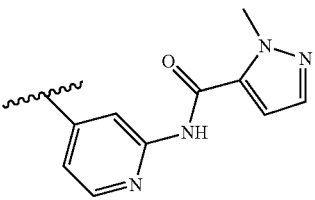 [SMILES: *c1ccnc(NC(=O)c2ccnn2C)c1] |
| I-62 | H | Cl | H | 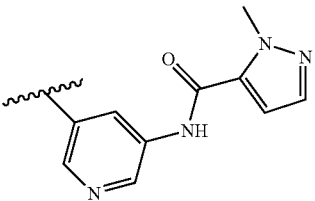 [SMILES: *c1cncc(NC(=O)c2ccnn2C)c1] |

TABLE 1-continued

| No. | R^I | R^II | R^III | A^1 |
|---|---|---|---|---|
| I-63 | H | Cl | H | (2,6-dimethylpyridin-4-yl)-NH-C(O)-(1-methyl-1H-pyrazol-5-yl) |
| I-64 | H | Cl | H | 3-(4-methyloxazol-2-yl)phenyl |
| I-65 | H | Cl | H | 2-(5-methyloxazol-2-yl)pyridin-4-yl |
| I-66 | CH₃ | H | H | 2-(1-methyl-1H-imidazol-2-yl)pyridin-4-yl |
| I-67 | H | Cl | H | 2-(3-isopropyl-2-oxoimidazolidin-1-yl)pyridin-4-yl |
| I-68 | H | Cl | Cl | 3-(3-methyl-2-oxoimidazolidin-1-yl)phenyl |
| I-69 | H | Cl | H | 2-ethylimidazo[1,2-a]pyridin-8-yl |
| I-70 | CH₃ | H | H | 2-(tetrahydrofuran-2-yl)imidazo[1,2-a]pyridin-8-yl |

TABLE 1-continued
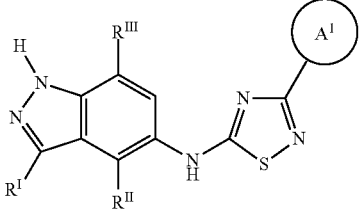
| No. | R^I | R^II | R^III | A^1 |
|---|---|---|---|---|
| I-71 | CH₃ | Cl | H | 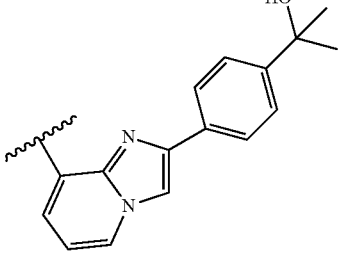 |
| I-72 | H | Cl | H | 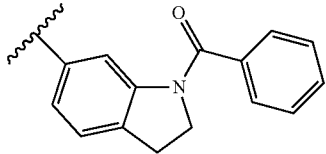 [SMILES: *c1ccc2c(c1)N(C(=O)c1ccccc1)CC2] |
| I-73 | H | Cl | H | 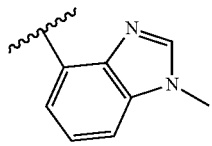 [SMILES: *c1cccc2c1ncn2C] |
| I-74 | CH₃ | Cl | H | 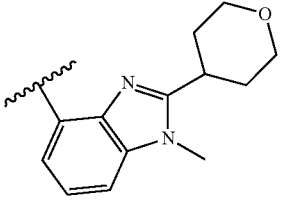 [SMILES: *c1cccc2c1nc(C1CCOCC1)n2C] |
| I-75 | H | H | Cl | 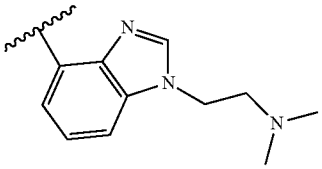 [SMILES: *c1cccc2c1ncn2CCN(C)C] |
| I-76 | H | Cl | H | 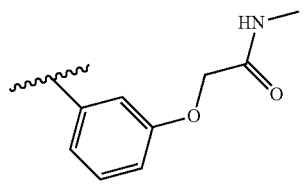 [SMILES: *c1cccc(OCC(=O)NC)c1] |

TABLE 1-continued
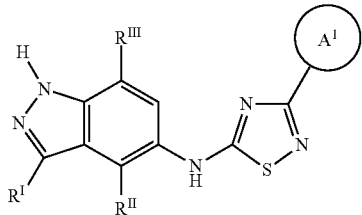
| No. | R<sup>I</sup> | R<sup>II</sup> | R<sup>III</sup> | A<sup>1</sup> |
|---|---|---|---|---|
| I-77 | CH₃ | H | H | 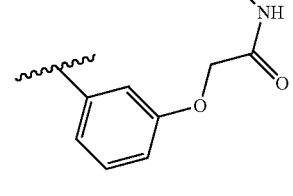 |
| I-78 | H | Cl | H | 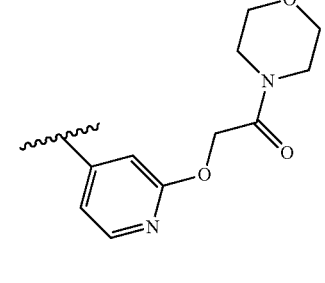 |
| I-79 | CH₃ | Cl | H | 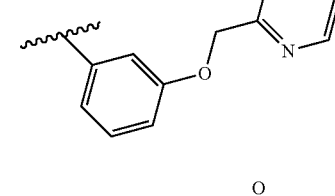 |
| I-80 | H | Cl | H | 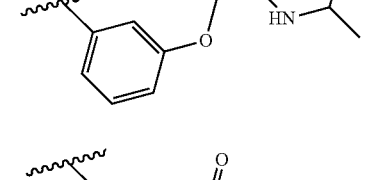 |
| I-81 | H | Cl | H | 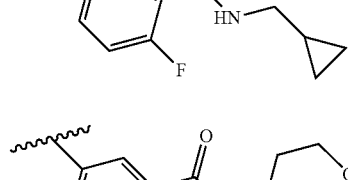 |
| I-82 | H | Cl | H | 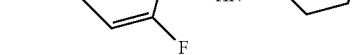 |

TABLE 1-continued

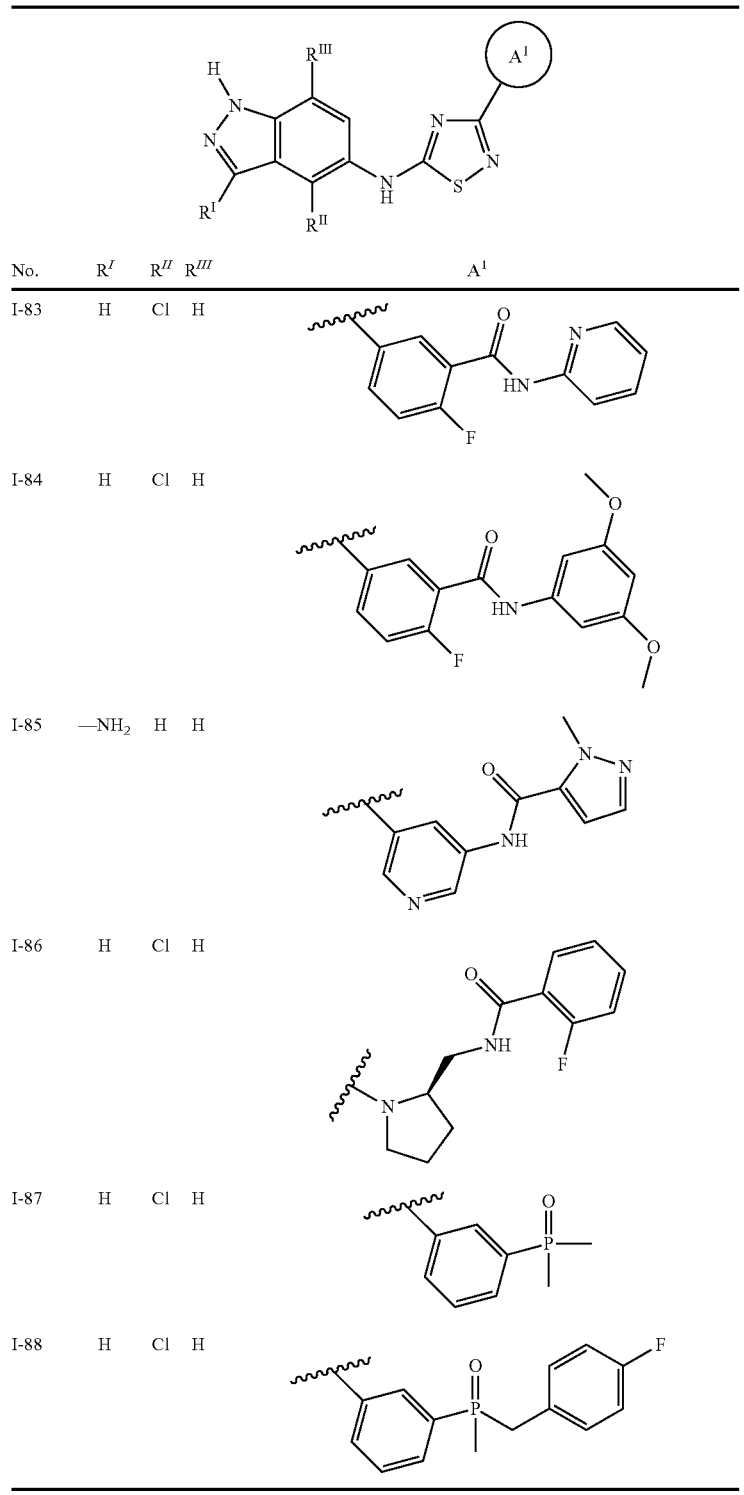

| No. | $R^I$ | $R^{II}$ | $R^{III}$ | $A^1$ |
|---|---|---|---|---|
| I-83 | H | Cl | H | |
| I-84 | H | Cl | H | |
| I-85 | —NH$_2$ | H | H | |
| I-86 | H | Cl | H | |
| I-87 | H | Cl | H | |
| I-88 | H | Cl | H | |

In other embodiments, the compound is a compound in any one of Tables 1, 2, 3, or 4 herein, or a pharmaceutically acceptable salt thereof. In other embodiments, the compound is a compound in any one of Tables 1, 2, 3, or 4 herein, a pharmaceutically acceptable salt thereof, or a solvate (e.g., a haloalkanoic acid solvate, such as fluoroalkanoic acid solvate) of the foregoing. In other embodiments, the compound is a compound in any one of Tables 1, 2, 3, or 4 herein, wherein the compound is in solvated form, non-solvated form, or a pharmaceutically acceptable salt of any of the foregoing. In other embodiments, the compound is a compound in Table 3-1 or 5 herein, or a pharmaceutically acceptable salt thereof. In other embodiments, the compound is a compound in Table 3-1 or 5 herein, a pharmaceutically acceptable salt thereof, or a solvate (e.g., a haloalkanoic acid solvate, such as fluoroalkanoic acid solvate) of the foregoing. In other embodiments, the compound is a compound in Table 3-1 or 5 herein, wherein the compound is in solvated form, non-solvated form, or a pharmaceutically acceptable salt of any of the foregoing.

In embodiments where a compound is described as a solvate (e.g., trifluoroacetic acid solvate), the invention includes the free base form of such compounds.

Compounds described herein can also be characterized according to their ability to inhibit ROCK1 and/or ROCK2. In certain embodiments, the compound has an $IC_{50}$ towards ROCK1 of less than about 10 μM, 1 μM, 0.1 μM, or 0.01 μM. In certain embodiments, the compound has an $IC_{50}$ towards ROCK2 of less than about 10 μM, 1 μM, 0.1 μM, or 0.01 μM. In certain embodiments, the compounds are characterized according to their ability to selectively inhibit ROCK2 vs. ROCK1. For example, in certain embodiments, the ratio of $IC_{50}$ of ROCK2 to ROCK1 for the compound is at least 5, 10, 25, 50, 100, 250, 500, 750, or 1000. In yet other embodiments, the compound is at least a five-fold more potent inhibitor of Rho-associated protein kinase isoform 2 than Rho-associated protein kinase isoform 1.

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing indazolyl thiadiazolamine compounds. Chloro-imidate B is prepared, such as by conversion of aldehyde A to chloro-imidate B (where Ms refers to mesylate in Scheme 1). Reaction of chloro-imidate B with a thiocyanate under basic conditions (e.g., pyridine in acetonitrile) followed by protected amine C provides 1,2,4-thiadiazole D. Removal of the protecting group (Pg) from the indazolyl nitrogen atom in D may be achieved using standard procedures described in the literature for removal of a protecting group. See, for example, "Comprehensive Organic Synthesis" (B. M. Trost & I. Fleming, eds., 1991-1992). If a functional group that is part of aldehyde A or chloro-imidate B would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis,* 2nd ed.; Wiley: New York, 1991, for further description of protecting chemistry and strategies.

Scheme 1.

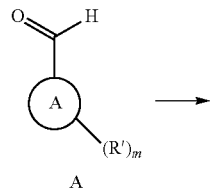

A

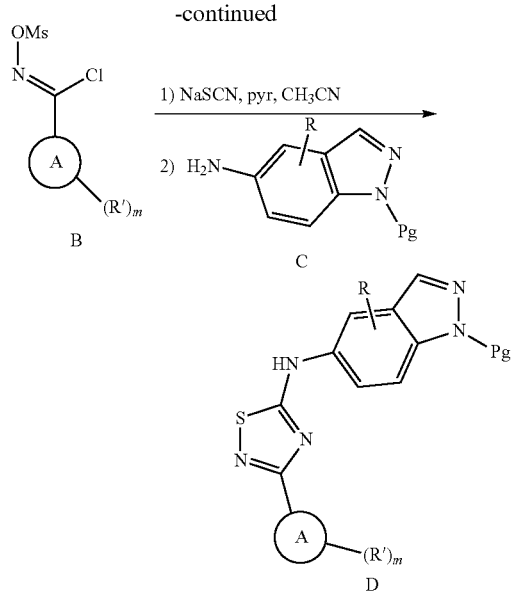

Scheme 2 depicts an alternative approach for preparing indazolyl thiadiazolamine compounds. In this approach, reaction of amidine A with indazolyl isothiocyanate B in the presence of an azodicarboxylate coupling reagent (such as di-tert-butyl azodicarboxylate) and a base (e.g., DBU) in a polar solvent provides thiadiazole C. Various amidino compounds are available commercially and contemplated for use in the synthetic procedure. In addition, various amidino compounds may be prepared based on procedures described in the literature (such as preparation from nitriles using an aluminum amide (Garigipati, R. S., *Tetrahedron Lett.* (1990) vol. 31, 1969-1972) or lithium hexamethyldisilazide). Alternatively, amidino compounds can be prepared from ethyl imidate compounds via displacement of the ethoxy group by ammonia.

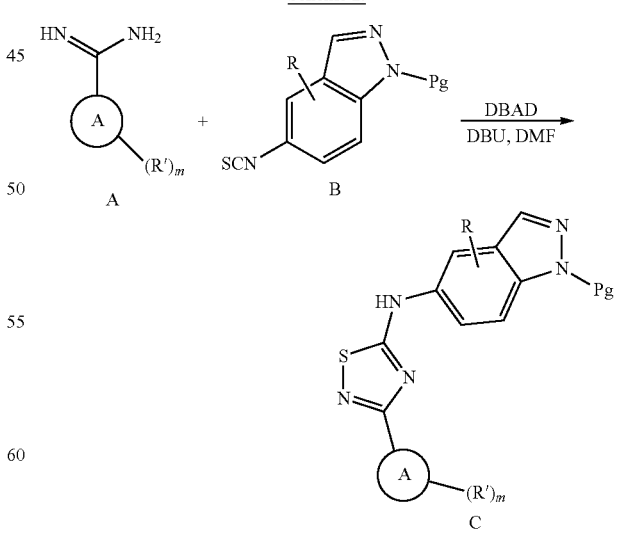

Subsequent to formation of thiadiazole C, further functional group manipulation may be performed to achieve a final target molecule. For example, a nitro-aryl ring may be subjected to reduction and acylation to form an amide functional group. A bromoaryl ring may be employed in a palladium-mediated cross-coupling reaction to install an alkenyl, alkyl, aryl or heteroaryl ring, or to install a nitrogen containing substituent. If a functional group that is part of amidine A or indazolyl thiocyanate B would not be amenable to a reaction condition described in Scheme 2, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, $2^{nd}$ ed.; Wiley: New York, 1991, for further description of protecting chemistry and strategies.

II. Therapeutic Applications of Indazolyl Thiadiazolamine and Related Compounds It is contemplated that the indazolyl thiadiazolamine and related compounds described herein, such as a compound of Formula I, I-A, I-B, I-C, or II, or other compounds in Section I, provide therapeutic benefits to patients suffering from an inflammatory disorder, immune disorder, fibrotic disorder, or cardiovascular disorder. Accordingly, one aspect of the invention provides a method of treating a disorder selected from the group consisting of an inflammatory disorder, immune disorder, fibrotic disorder, and cardiovascular disorder. The method comprises administering a therapeutically effective amount of an indazolyl thiadiazolamine or related compound described herein, such as a compound of Formula I, I-A, I-B, I-C, or II, or other compounds in Section I, to a patient in need thereof to treat the disorder. In certain embodiments, the particular compound of Formula I, I-A, I-B, I-C, or II, is a compound defined by one of the embodiments described above.

In certain embodiments, the disorder is scleroderma, psoriasis, nonalcoholic steatohepatitis, giant cell arteritis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, ulcerative colitis, asthma, uveitis, rheumatoid arthritis, or epidermal hyperplasia.

In certain embodiments, the disorder is scleroderma or psoriasis.

In certain embodiments, the disorder is nonalcoholic steatohepatitis or giant cell arteritis.

In certain embodiments, the disorder is a fibrotic disorder. In certain embodiments, the fibrotic disorder is liver cirrhosis, renal fibrosis, cardiac fibrosis, pulmonary fibrosis, idiopathic pulmonary fibrosis, hypersensitivity pneumonitis, chronic obstructive pulmonary disease, sarcoidosis, Wegener's granulomatosis, cirrhosis, systemic sclerosis, scleroderma, dermatofibroma, keloids, peyronie's disease, dupuytren's contracture, endomyocardial fibrosis, atrial fibrosis, mediastinal fibrosis, myelofibrosis, retroperitoneal fibrosis, nephrogenic systemic fibrosis, nephrogenic fibrosing dermopathy, mixed connective tissue disease, scleromyxederma, eosinophilic fasciitis, glomerular sclerodis, pancreatitis, or arthrofibrosis. In certain embodiments, the fibrotic disorder is liver cirrhosis, pulmonary fibrosis, systemic sclerosis, endomyocardial fibrosis, atrial fibrosis, mediastinal fibrosis, myelofibrosis, retroperitoneal fibrosis, nephrogenic systemic fibrosis, or arthrofibrosis. In certain embodiments, the fibrotic disorder is cystic fibrosis or idiopathic pulmonary fibrosis. In certain embodiments, the fibrotic disorder is caused by infection, environmental agents, certain medications, chronic inflammatory disease, autoimmune disease, or radiation.

In certain embodiments, the disorder is an inflammatory disorder. In certain embodiments, the disorder is an immune disorder. In certain embodiments, the inflammatory disorder is arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costostemal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, *piriformis* syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, or yersinial arthritis.

In certain embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, or autoimmune hepatitis. In yet other embodiments, the disorder is linear scleroderma.

It has been reported that small molecule inhibitors of Rho kinase are capable of inhibiting MCP-1 mediated chemotaxis in vitro (H. Iijima, *Biorganic and Medicinal Chemistry*, 2007, vol. 15, pages 1022-1033). Due to the dependence of immune cell migration upon the RhoA/ROCK signaling pathway, inhibition of Rho kinase is understood to provide a therapeutic benefit for treating diseases such as rheumatoid arthritis, psoriasis, and inflammatory bowel disease.

In certain embodiments, the disorder is a cardiovascular disorder. In certain embodiments, the cardiovascular disorder is angina, atherosclerosis, stroke, cerebrovascular disease, congestive heart failure, coronary artery disease, myocardial infarction, peripheral vascular disease, stenosis, vasospasm, hypertension, cerebral thrombosis, cerebral embolism, or cerebral hemorrhage. In certain embodiments, the stenosis is coronary artery stenosis, aortic stenosis, restenosis, or pulmonary stenosis.

A link between inhibition of ROCK and treatment of cardiovascular disorders has been described in the literature. For example, the RhoA/ROCK signaling pathway has been reported to have an important role in signal transduction initiated by vasoactive factors such as angiotensin II (T. Yamakawa et al., Hypertension, 2000, 35, 313-318), urotension II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Additional studies in the literature, some using the known ROCK inhibitor fasudil (T. Asano et al., J. Pharmacol. Exp. Ther., 1987, 241, 1033-1040) or Y-27632 (M. Uehata et al., Nature, 1997, 389, 990-994), further illustrate the link between ROCK and cardiovascular disease. For example, ROCK expression and activity have been shown to be elevated in spontaneously hypertensive rats, indicating a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats.

Other studies illustrate a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 inhibited neointimal formation in rats (N. Sawada et al., Circulation, 2000, 101, 2030-2033). In a porcine model of IL-1 beta-induced coronary stenosis, treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional reports indicate that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy, fibrosis and function in a model of congestive heart failure in Dahl salt-sensitive rats (N. Kobayashi et al. Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In certain embodiments, the patient is a human.

Another aspect of the invention provides for the use of a compound described herein (such as a compound of Formula I, I-A, I-B, I-C, or II, or other compounds in Section I) in the manufacture of a medicament. In certain embodiments, the medicament is for treating a disorder described herein, such as an inflammatory disorder.

Another aspect of the invention provides for the use of a compound described herein (such as a compound of Formula I, I-A, I-B, I-C, or II, or other compounds in Section I) for treating a medical disorder, such a medical disorder described herein (e.g., inflammatory disorder).

Another aspect of the invention provides a method of inhibiting a Rho-associated protein kinase. The method comprises exposing a Rho-associated protein kinase to an effective amount of an indazolyl thiadiazolamine or related compound described herein, e.g., a compound of Formula I, I-A, I-B, I-C, or II, to inhibit said Rho-associated protein kinase.

In certain embodiments, the Rho-associated protein kinase is the Rho-associated protein kinase isoform 2. In such embodiments, the method is to inhibiting a Rho-associated protein kinase isoform 2, which method comprises exposing a Rho-associated protein kinase isoform 2 to a compound described herein, e.g., a compound of Formula I, I-A, I-B, I-C, or II, to inhibit said Rho-associated protein kinase isoform 2.

The description above describes multiple embodiments providing definitions for variables used herein. The application specifically contemplates all combinations of such variables.

III. Combination Therapy

Another aspect of the invention provides for combination therapy. Indazolyl thiadiazolamine and related compounds (e.g., a compound of Formula I, I-A, I-B, I-C, or II, or other compounds in Section I) or their pharmaceutically acceptable salts may be used in combination with additional therapeutic agents to treat medical disorders, such as inflammatory disorder, immune disorder, fibrotic disorder, and cardiovascular disorder.

The amount of indazolyl thiadiazolamine or related compound (e.g., a compound of Formula I, I-A, I-B, I-C, or II, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, an indazolyl thiadiazolamine or related compound (e.g., a compound of any one of Formula I, I-A, I-B, I-C, or II, or other compounds in Section I) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the indazolyl thiadiazolamine or related compound (e.g., a compound of any one of I, I-A, I-B, I-C, or II, or other compounds in Section I) and the additional therapeutic agent(s) are administered in doses commonly employed when such agents are used as monotherapy for treating the disorder. In other embodiments, the indazolyl thiadiazolamine or related compound (e.g., a compound of any one of Formula I, I-A, I-B, I-C, or II, or other compounds in Section I) and the additional therapeutic agent(s) are administered in doses lower than the doses commonly employed when such agents are used as monotherapy for treating the disorder. In certain embodiments, the indazolyl thiadiazolamine or related compound (e.g., a compound of any one of Formula I, I-A, I-B, I-C, or II, or other compounds in Section I) and the additional therapeutic agent(s) are present in the same composition, which is suitable for oral administration.

In certain embodiments, the indazolyl thiadiazolamine or related compound (e.g., a compound of any one of Formula I, I-A, I-B, I-C, or II, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the indazolyl thiadiazolamine or related compound (e.g., a compound of any one of Formula I, I-A, I-B, I-C, or II, or other compounds in Section I), a pharmaceutically acceptable carrier, vehicle or diluent, and optionally at least one additional therapeutic agent.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising an indazolyl thiadiazolamine or related compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art. The phrase "MeCN (0.05% TFA)" is art-recognized and refers to acetonitrile containing 0.05% v/v trifluoroacetic acid. The phrase "H$_2$O (0.1% TFA)" is art-recognized and refers to water containing 0.1% v/v trifluoroacetic acid. MTBE stands for methyl tert-butyl ether. ACN stands for acetonitrile. DMSO stands for dimethylsulfoxide. TFA stands for trifluoroacetic acid.

Example 1—Synthesis of N-(4-Chloro-1H-indazol-5-yl)-3-(3-nitrophenyl)-1,2,4-thiadiazol-5-amine

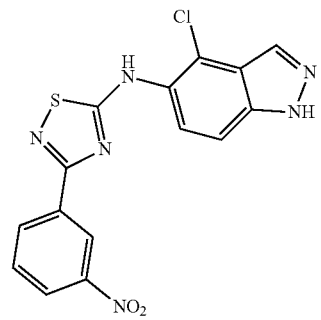 [SMILES: O=[N+]([O-])c1cccc(-c2nsc(Nc3ccc4[nH]ncc4c3Cl)n2)c1]

Part 1—Synthesis of 3-nitrobenzaldehyde oxime

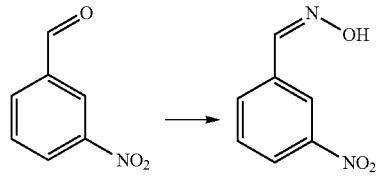 [SMILES: O=Cc1cccc([N+](=O)[O-])c1 ; O=[N+]([O-])c1cccc(/C=N\O)c1]

A 100 mL round bottom flask was charged with a solution of potassium carbonate (4.57 g, 33.09 mmol) in water (20 mL), then hydroxylamine hydrochloride (4.98 g, 66.17 mmol) was added. The reaction mixture was stirred for 5 minutes at room temperature, then 3-nitrobenzaldehyde (10 g, 66.17 mmol) was added and the mixture was stirred at ambient temperature overnight. The reaction mixture was poured into MTBE (150 mL) and the layers were separated. The combined organic layers were washed with brine, dried over MgSO$_4$ and concentrated in vacuo to afford crude 3-nitrobenzaldehyde oxime (10.95 g, 99.6% yield) as a white solid which was used in the next step without further purification. $^1$H NMR (CHLOROFORM-d, 400 MHz, ppm) δ: 8.44 (t, J=1.8 Hz, 1H), 8.23 (d, J=7.7 Hz, 1H), 8.20 (s, 1H), 7.91 (dt, J=7.7, 1.2 Hz, 1H), 7.48-7.68 (m, 1H), 1.63 (br s, 1H).

Part 2—Synthesis of N-hydroxy-3-nitro-benzimidoyl chloride

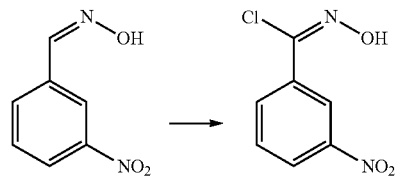 [SMILES: O=[N+]([O-])c1cccc(/C=N\O)c1 ; O=[N+]([O-])c1cccc(/C(Cl)=N\O)c1]

A 100 mL round bottom flask was charged with a solution of 3-nitrobenzaldehyde oxime (10.95 g, 65.9 mmol) in DMF (20 mL) at 0° C., then N-chlorosuccinimide (8.801 g, 65.91 mmol) was added and the reaction mixture was stirred at ambient temperature overnight. Then, the reaction mixture was poured into water and the product was extracted with MTBE. The combined organic layers were washed with brine, dried over MgSO$_4$, and concentrated in vacuo to afford crude N-hydroxy-3-nitro-benzimidoyl chloride which was used immediately in the next step without further treatment. (MS, m/z): [M+H]$^+$ 201.0, 203.1. $^1$H NMR (CHLOROFORM-d, 400 MHz, ppm) δ: 9.47 (br s, 1H), 8.73 (t, J=2.0 Hz, 1H), 8.29 (ddd, J=8.2, 2.2, 1.1 Hz, 1H), 8.21 (d, J=7.4 Hz, 1H), 7.61 (t, J=8.1 Hz, 1H).

Part 3—Synthesis of [[chloro-(3-nitrophenyl)methylene]amino] methanesulfonate

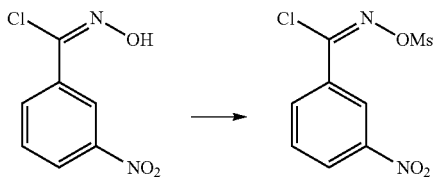 [SMILES: O=[N+]([O-])c1cccc(/C(Cl)=N\O)c1 ; CS(=O)(=O)O/N=C(/Cl)c1cccc([N+](=O)[O-])c1]

A 250 mL round bottom flask was charged with a solution of N-hydroxy-3-nitro-benzimidoyl chloride (13.22 g, 65.91 mmol) in dichloromethane (150 mL) at 0° C., then methane sulfonyl chloride (7.55 g, 65.9 mmol) was added. The reaction mixture was stirred for 5 minutes, then N,N-diisopropylethylamine (17.04 g, 131.8 mmol) was added drop-wise keeping the reaction mixture in the ice bath for an additional 2 h. Then, the reaction mixture was concentrated in vacuo, MTBE was added to the residue, and the slurry was stirred at ambient temperature for 30 min. The suspension was filtered and the solid washed with MTBE. The filtrate was concentrated, and the resulting residue was dissolved in dichloromethane and purified by silica gel chromatography eluting with 0 to 30% hexanes/EtOAc. The product was dissolved in dichloromethane then cyclohexane was added to promote solid formation, the formed solid was separated by filtration and dried under vacuum to yield [[chloro-(3-nitrophenyl)methylene]amino] methanesulfonate as a white solid. $^1$H NMR (CHLOROFORM-d, 400 MHz, ppm): δ: 8.78 (t, J=2.0 Hz, 1H), 8.43 (ddd, J=8.2, 2.2, 1.1 Hz, 1H), 8.30 (d, J=8.2 Hz, 1H), 7.71 (t, J=8.1 Hz, 1H), 3.32 (s, 3H).

Part 4—Synthesis of N-(4-Chloro-1H-indazol-5-yl)-3-(3-nitrophenyl)-1,2,4-thiadiazol-5-amine

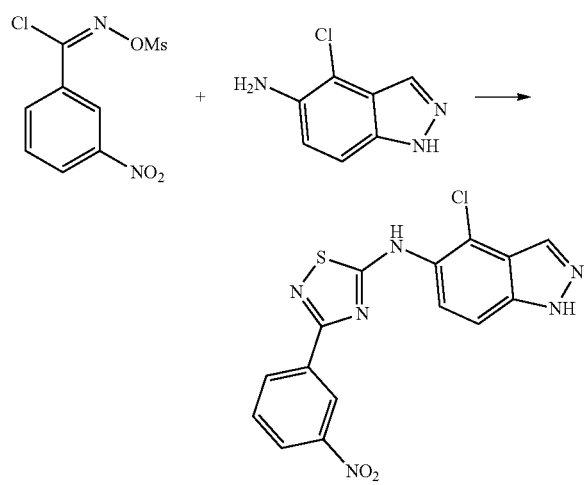

A 100 mL round bottom flask was charged with a solution of [[chloro-(3-nitrophenyl)methylene]amino] methanesulfonate (2.49 g, 8.93 mmol) in acetonitrile (10 mL) and the mixture was heated to 40° C. with stirring. Pyridine (2.12 g, 26.8 mmol) was added drop-wise over 5 min. Then, a solution of sodium thiocyanate (0.724 g, 8.93 mmol) in acetonitrile (8 mL) was added dropwise at 40° C. over the course of 60 min. Stirring was continued at 40° C. for an additional 30 min and then the mixture was cooled to 0° C. using an ice bath and 4-chloro-1H-indazol-5-amine (1.496 g, 8.928 mmol) was added slowly portion-wise at 0° C. An abundant solid was formed. Additional acetonitrile (12 mL) was added to allow stirring and the stirring was continued at room temperature overnight. The pink solid formed was collected by filtration, washed with acetonitrile, dried by suction, and then under high vacuum to yield N-(4-chloro-1H-indazol-5-yl)-3-(3-nitrophenyl)-1,2,4-thiadiazol-5-amine (3.32 g, 100% yield). (MS, m/z): [M+H]$^+$ 373.02, 374.96. $^1$H NMR (DMSO-d$_6$, 400 MHz, ppm) δ: 13.58 (br s, 1H), 10.78 (s, 1H), 8.64-8.91 (m, 1H), 8.47 (dt, J=7.9, 1.1 Hz, 1H), 8.31 (ddd, J=8.2, 2.3, 1.0 Hz, 1H), 8.16 (s, 1H), 7.93 (d, J=8.8 Hz, 1H), 7.78 (t, J=7.9 Hz, 1H), 7.65 (d, J=9.4 Hz, 1H).

Example 2—Synthesis of N-(3-[5-[(1H-indazol-5-yl)amino]-1,2,4-thiadiazol-3-yl]phenyl)pyridine-3-carboxamide 2,2,2-trifluoroacetic acid solvate

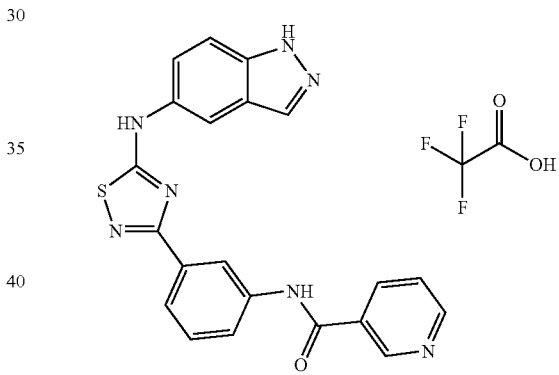

Part 1—Synthesis of tert-butyl 5-isothiocyanato-1H-indazole-1-carboxylate

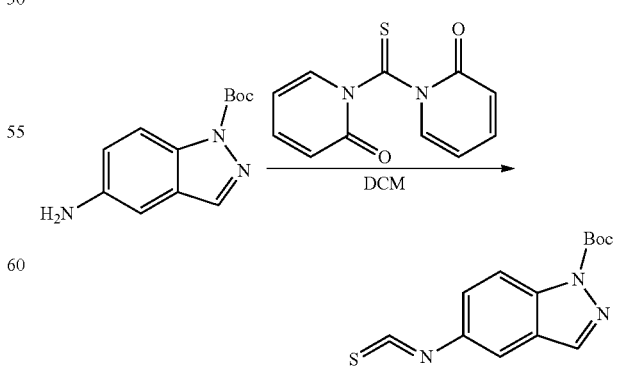

Into a 250-mL round-bottom flask, was placed tert-butyl 5-amino-1H-indazole-1-carboxylate (2 g, 8.57 mmol, 1.00 equiv), 1-[(2-oxo-1,2-dihydropyridin-1-yl)carbothioyl]-1,2-dihydropyridin-2-one (2 g, 8.61 mmol, 1.00 equiv), and dichloromethane (75 mL). The resulting solution was stirred overnight at room temperature. The resulting mixture was washed with 2×50 mL of sat. sodium bicarbonate and 1×50 mL of brine. The organic mixture was dried over anhydrous sodium sulfate. The solids were removed by filtration. The resulting mixture was concentrated under vacuum. This resulted in 1.5 g (64%) of tert-butyl 5-isothiocyanato-1H-indazole-1-carboxylate as a yellow solid.

Part 2—Synthesis of tert-butyl 5-[[3-(3-nitrophenyl)-1,2,4-thiadiazol-5-yl]amino]-1H-indazole-1-carboxylate

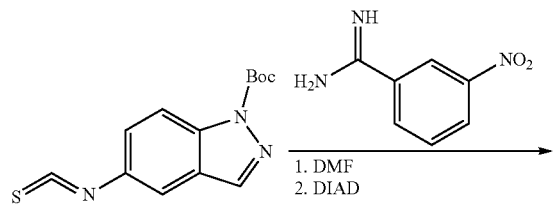

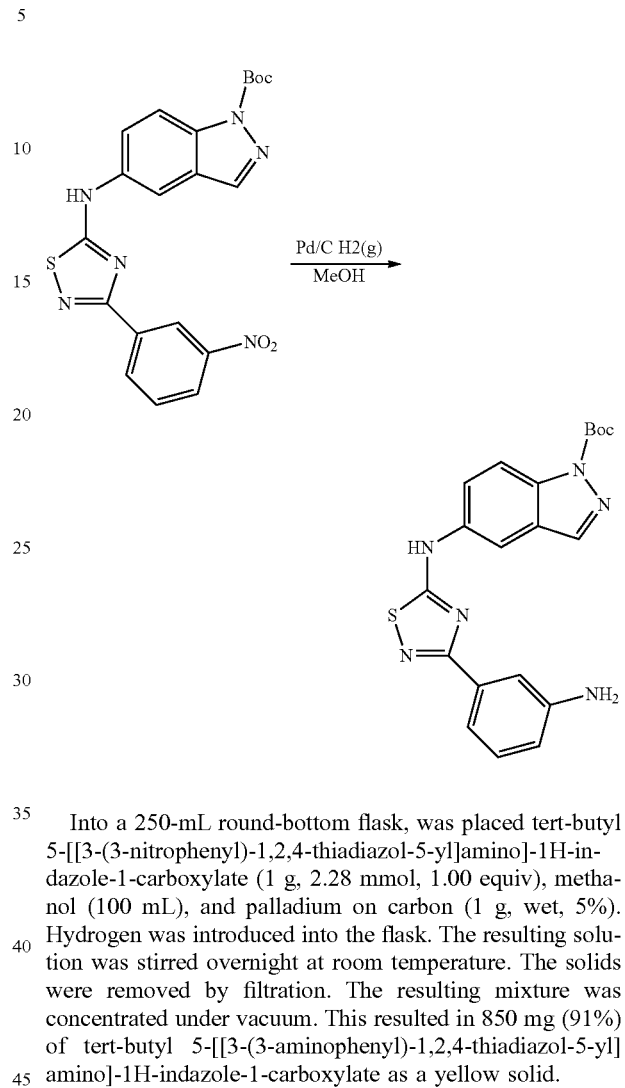

Into a 250-mL round-bottom flask was placed tert-butyl 5-isothiocyanato-1H-indazole-1-carboxylate (950 mg, 3.45 mmol, 1.00 equiv), N,N-dimethylformamide (100 mL), and 3-nitrobenzene-1-carboximidamide (570 mg, 3.45 mmol, 1.00 equiv). The resulting solution was stirred for 4 h at room temperature, DIAD (1174 mg, 5.81 mmol, 1.7 equiv) was added. The resulting solution was allowed to react, with stirring, for an additional 3 h at room temperature. The resulting mixture was concentrated under vacuum. The residue was applied onto a silica gel column with ethyl acetate/petroleum ether (7:3). This resulted in 1 g (66%) of tert-butyl 5-[[3-(3-nitrophenyl)-1,2,4-thiadiazol-5-yl]amino]-1H-indazole-1-carboxylate as a yellow solid. Reference: JP 2001081084.

Part 3—Synthesis of tert-butyl 5-[[3-(3-aminophenyl)-1,2,4-thiadiazol-5-yl]amino]-1H-indazole-1-carboxylate Into a 250-mL round-bottom flask, was placed tert-butyl 5-[[3-(3-nitrophenyl)-1,2,4-thiadiazol-5-yl]amino]-1H-indazole-1-carboxylate (1 g, 2.28 mmol, 1.00 equiv), methanol (100 mL), and palladium on carbon (1 g, wet, 5%). Hydrogen was introduced into the flask. The resulting solution was stirred overnight at room temperature. The solids were removed by filtration. The resulting mixture was concentrated under vacuum. This resulted in 850 mg (91%) of tert-butyl 5-[[3-(3-aminophenyl)-1,2,4-thiadiazol-5-yl]amino]-1H-indazole-1-carboxylate as a yellow solid.

Part 4—Synthesis of tert-butyl 5-([3-[3-(pyridine-3-amido)phenyl]-1,2,4-thiadiazol-5-yl]amino)-1H-indazole-1-carboxylate -continued

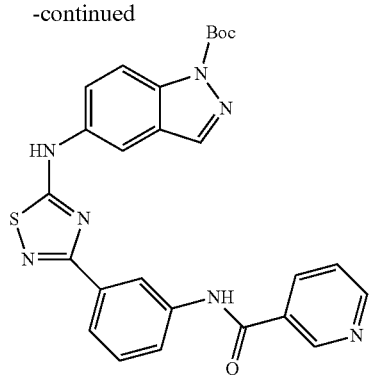

Into a 100-mL round-bottom flask, was placed tert-butyl 5-[[3-(3-aminophenyl)-1,2,4-thiadiazol-5-yl]amino]-1H-indazole-1-carboxylate (200 mg, 0.49 mmol, 1.00 equiv), HATU (280 mg, 0.74 mmol, 1.30 equiv), N,N-dimethylformamide (30 mL), DIEA (190 mg, 1.47 mmol, 3.00 equiv), and pyridine-3-carboxylic acid (60 mg, 0.49 mmol, 0.90 equiv). The resulting solution was stirred for 2 h at room temperature. The resulting mixture was concentrated under vacuum. The residue was purified by silica gel column chromatograph using dichloromethane/methanol (10:1) as eluant. This resulted in 110 mg (44%) of tert-butyl 5-([3-[3-(pyridine-3-amido)phenyl]-1,2,4-thiadiazol-5-yl]amino)-1H-indazole-1-carboxylate as a yellow solid.

Part 5—Synthesis of N-(3-[5-[(1H-indazol-5-yl)amino]-1,2,4-thiadiazol-3-yl]phenyl)pyridine-3-carboxamide 2,2,2-trifluoroacetic acid solvate

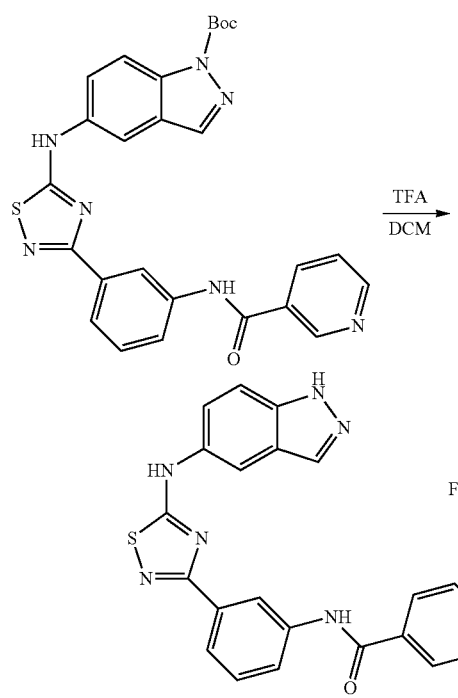

Into a 100-mL round-bottom flask, was placed tert-butyl 5-([3-[3-(pyridine-3-amido)phenyl]-1,2,4-thiadiazol-5-yl] amino)-1H-indazole-1-carboxylate (110 mg, 0.21 mmol, 1.00 equiv), dichloromethane (10 mL), and trifluoroacetic acid (3 mL). The resulting solution was stirred for 2 h at room temperature. The resulting mixture was concentrated under vacuum. The crude product was purified by Prep-HPLC with the following conditions: Column, Gemini-NX C18, 21.2*150 mm 5 nm; mobile phase, water with 0.05% TFA and ACN (30.0% ACN up to 80.0% in 10 min); Detector, 254 nm. This resulted in 40 mg (35%) of N-(3-[5-[(1H-indazol-5-yl)amino]-1,2,4-thiadiazol-3-yl]phenyl) pyridine-3-carboxamide trifluoroacetic acid solvate as a light yellow solid. (ES, m/z): [M+H]$^+$ 414.00. $^1$H NMR (DMSO, 300 MHz, ppm): δ: 9.18 (s, 1H), 8.83-8.82 (d, J=3.9 Hz, 1H), 8.71 (s, 1H), 8.45 (m, 1H), 8.21 (s, 1H), 8.15 (s, 1H), 8.01-8.99 (d, J=7.5 Hz, 1H), 7.86 (m, 1H), 7.66 (m, 2H), 7.55 (m, 2H).

Example 3—Synthesis of N-(3-[5-[(1H-indazol-5-yl)amino]-1,2,4-thiadiazol-3-yl]phenyl)-1H-imidazole-4-carboxamide 2,2,2-trifluoroacetic acid solvate

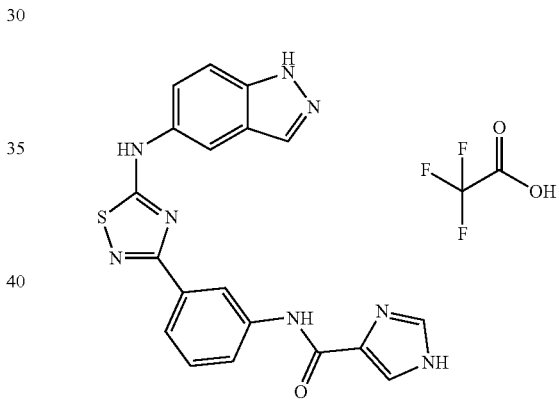

Part 1—Synthesis of tert-butyl 5-([3-[3-(1H-imidazole-4-amido)phenyl]-1,2,4-thiadiazol-5-yl]amino)-1H-indazole-1-carboxylate

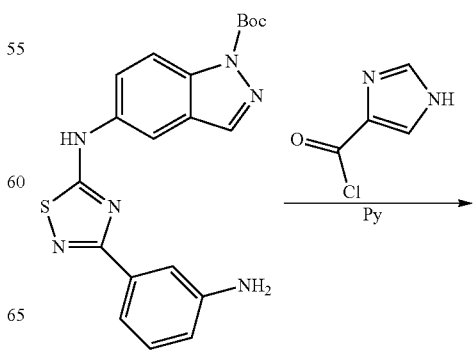

-continued

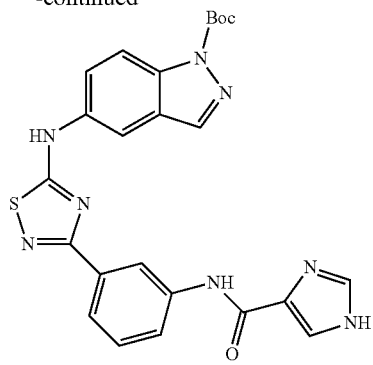

Into a 50-mL round-bottom flask, was placed tert-butyl 5-[[3-(3-aminophenyl)-1,2,4-thiadiazol-5-yl]amino]-1H-indazole-1-carboxylate (150 mg, 0.37 mmol, 1.00 equiv), 1H-imidazole-4-carbonyl chloride (48 mg, 0.37 mmol, 1.00 equiv), and pyridine (50 mL). The resulting solution was stirred for 3 h at room temperature. The resulting mixture was concentrated under vacuum. The residue was purified by silica gel column chromatograph with dichloromethane/methanol (10:1) as eluant. This resulted in 95 mg (51%) of tert-butyl 5-([3-[3-(1H-imidazole-4-amido)phenyl]-1,2,4-thiadiazol-5-yl]amino)-1H-indazole-1-carboxylate as a yellow solid.

Part 2—Synthesis of N-(3-[5-[(1H-indazol-5-yl)amino]-1,2,4-thiadiazol-3-yl]phenyl)-1H-imidazole-4-carboxamide 2,2,2-trifluoroacetic acid solvate

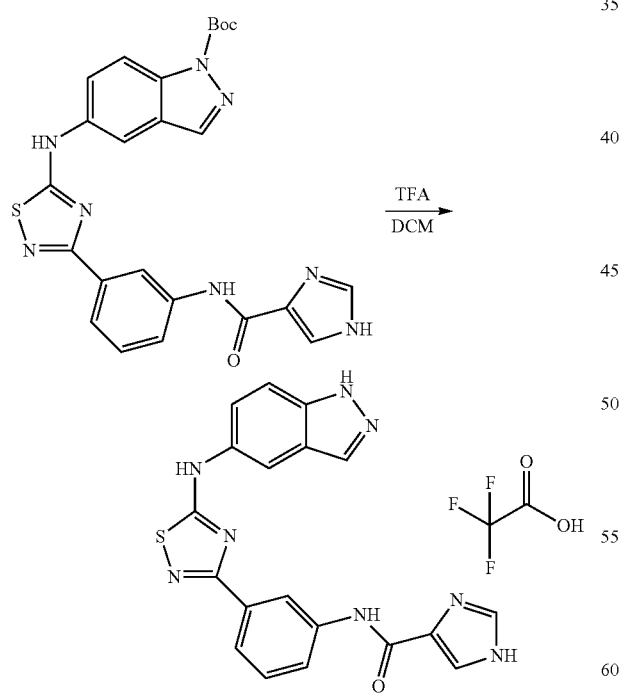

Into a 50-mL round-bottom flask, was placed tert-butyl 5-([3-[3-(1H-imidazole-4-amido)phenyl]-1,2,4-thiadiazol-5-yl]amino)-1H-indazole-1-carboxylate (95 mg, 0.19 mmol, 1.00 equiv), dichloromethane (10 mL), and trifluoroacetic acid (3 mL). The resulting solution was stirred for 2 h at room temperature. The resulting mixture was concentrated under vacuum. The crude product was purified by Prep-HPLC with the following conditions: Column, Gemini-NX C18, 21.2*150 mm 5 µm; mobile phase, water with 0.05% TFA and ACN (60.0% ACN up to 85.0% in 10 min); Detector, 254 nm. This resulted in 25 mg (33%) of N-(3-[5-[(1H-indazol-5-yl)amino]-1,2,4-thiadiazol-3-yl]phenyl)-1H-imidazole-4-carboxamide 2,2,2-trifluoroacetic acid solvate as a yellow solid. (ES, m/z): 403.0 [M+H]+. $^1$H NMR (DMSO; 300 MHz, ppm): δ: 8.67 (s, 1H), 8.39 (s, 1H), 8.22 (s, 1H), 8.18 (s, 1H), 8.09 (s, 1H), 8.00-7.97 (d, J=6.9 Hz, 1H), 7.81 (m, 1H), 7.69-7.66 (d, J=9.3 Hz, 1H), 7.56-7.53 (d, J=9.9 Hz, 1H), 7.52 (m, 2H).

Example 4—Synthesis of N-(3-(5-((4-chloro-1H-indazol-5-yl)amino)-1,2,4-thiadiazol-3-yl)phenyl)-1-methyl-1H-pyrazole-5-carboxamide 2,2,2-trifluoroacetic acid solvate Part 1—Synthesis of tert-butyl 5-((tert-butoxycarbonyl)(3-(3-nitrophenyl)-1,2,4-thiadiazol-5-yl)amino)-4-chloro-1H-indazole-1-carboxylate

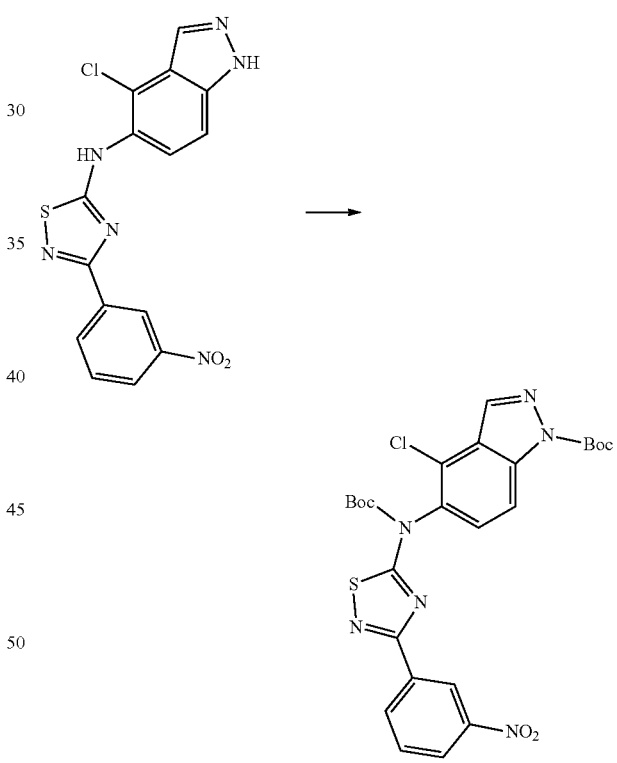

A 100 mL round bottom flask was charged with a solution of N-(4-chloro-1H-indazol-5-yl)-3-(3-nitrophenyl)-1,2,4-thiadiazol-5-amine (3.328 g, 8.9273 mmol), N,N-diisopropylethylamine (2.5383 g, 19.64 mmol), 4-pyrrolidinopyridine (0.1323 g, 0.8927 mmol) and Boc anhydride (3.8968 g, 17.855 mmol) in DMF (5 mL) and the mixture was heated at 45° C. for 72 h. Next, solvents were removed under high vacuum and the resulting residue purified by silica gel chromatography (120 g column, 40-63 uM 60 A flash cartridge from Silicycle) eluting with 0 to 50% hexanes/EtOAc to yield tert-butyl 5-[tert-butoxycarbonyl-[3-(3-nitrophenyl)-1,2,4-thiadiazol-5-yl]amino]-4-chloro-indazole-1-carboxylate (3.127 g, 61.1% yield).

Part 2—Synthesis of tert-butyl 5-((3-(3-aminophenyl)-1,2,4-thiadiazol-5-yl)(tert-butoxycarbonyl)amino)-4-chloro-1H-indazole-1-carboxylate

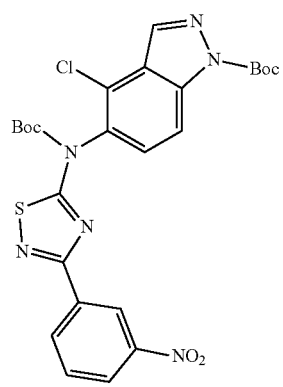

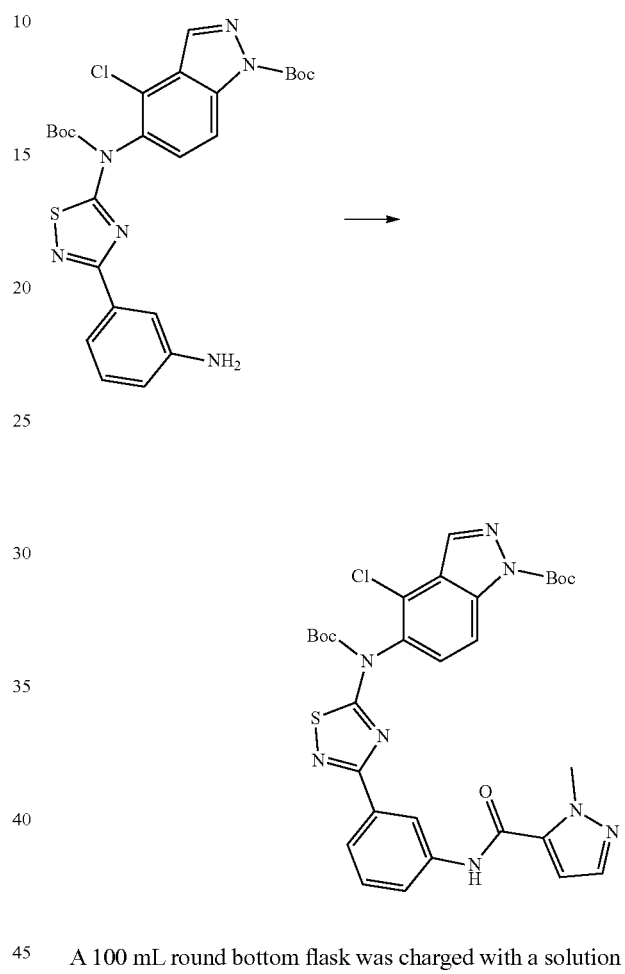

A 250 mL round bottom flask was charged with a solution of tert-butyl 5-[tert-butoxycarbonyl-[3-(3-nitrophenyl)-1,2,4-thiadiazol-5-yl]amino]-4-chloro-indazole-1-carboxylate (1.1 g, 1.9197 mmol) in THF (100 mL), then was added 5% Rhodium on carbon (0.5926 g, 0.2879 mmol) (pre-suspended under nitrogen in 5 mL of THF) and the reaction mixture was evacuated and back filled with hydrogen. Then, the reaction mixture was stirred under a hydrogen filled balloon for 18 hours. Next, catalyst was removed by filtration over celite, rinsed with THF and the solvent evaporated to yield tert-butyl 5-[[3-(3-aminophenyl)-1,2,4-thiadiazol-5-yl]-tert-butoxycarbonyl-amino]-4-chloro-indazole-1-carboxylate (1.042 g, 99.9% yield) as a beige foam which was used directly in the next step without further purification.

Part 3—Synthesis of tert-butyl 5-((tert-butoxycarbonyl)(3-(3-(1-methyl-1H-pyrazole-5-carboxamido)phenyl)-1,2,4-thiadiazol-5-yl)amino)-4-chloro-1H-indazole-1-carboxylate A 100 mL round bottom flask was charged with a solution of 2-methylpyrazole-3-carboxylic acid (0.2662 g, 2.1107 mmol), EDC HCL (0.5634 g, 2.8782 mmol) and HOBt (0.389 g, 2.8782 mmol) in DMF (5 mL) and the reaction mixture stirred for 5 min at rt then N,N-diisopropylethylamine (0.7440 g, 5.7565 mmol) was added and the mixture stirred for 5 min. Then was added a solution of tert-butyl 5-[[3-(3-aminophenyl)-1,2,4-thiadiazol-5-yl]-tert-butoxycarbonyl-amino]-4-chloro-indazole-1-carboxylate (1.042 g, 1.9188 mmol) in DMF (5 mL) and the solution stirred at room temperature for 24 h. Then, solvents were removed under vacuum and the resulting residue was purified by silica gel chromatography (40 g column, HP 15-40 uM 60 A flash cartridge from Silicycle) eluting with 0 to 50% hexanes/EtOAc to yield the title compound (0.717 g, 57.386% yield) as a light yellow foam.

Part 4—Synthesis of N-(3-(5-((4-chloro-1H-indazol-5-yl)amino)-1,2,4-thiadiazol-3-yl)phenyl)-1-methyl-1H-pyrazole-5-carboxamide 2,2,2-trifluoroacetic acid solvate

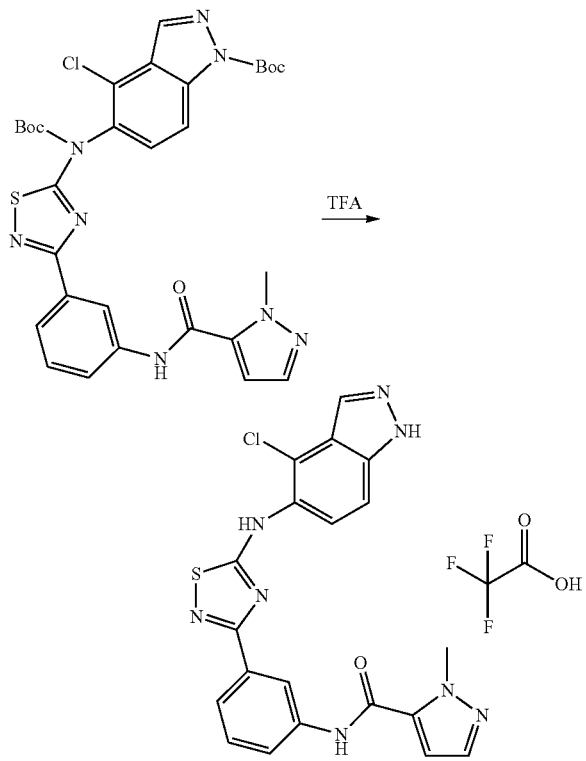

A 100 mL round bottom flask was charged with a solution of tert-butyl 5-((tert-butoxycarbonyl)(3-(3-(1-methyl-1H-pyrazole-5-carboxamido)phenyl)-1,2,4-thiadiazol-5-yl)amino)-4-chloro-1H-indazole-1-carboxylate (0.7170 g, 1.1011 mmol) in dichloromethane (10 mL), TFA (12.555 g, 110.11 mmol) was added and the solution stirred at room temperature for 18 h. Solvents were removed under vacuum and the residue was purified by silica gel chromatography (40 g column, HP 15-40 uM 60 A flash cartridge from Silicycle) eluting with 0 to 15% dcm/(MeOH containing 10% NH$_4$OH) to yield the title compound (0.3437 g, 69.2% yield) as a white solid. (MS, m/z): [M+H]$^+$ 451.03, 452.98. $^1$H NMR (DMSO-d$_6$, 400 MHz): δ: 13.49 (br s, 1H), 10.53-10.71 (m, 1H), 10.33 (s, 1H), 8.52 (t, J=1.8 Hz, 1H), 8.15 (s, 1H), 7.96 (s, 1H), 7.75-7.91 (m, 2H), 7.64 (d, J=8.8 Hz, 1H), 7.52 (d, J=2.2 Hz, 1H), 7.28-7.50 (m, 1H), 7.09 (d, J=2.2 Hz, 1H), 4.09 ppm (s, 3H).

Example 5—Preparation of Additional Indazol-5-yl-amino-1,2,4-thiadiazol-3-yl Compounds Compounds in Table 2 below were prepared based on procedures described in Example 2.

TABLE 2

| No. | Chemical Structure [name] | Physical Characterization Data |
|---|---|---|
| II-1 | [structure of N-(4-(5-((4-chloro-1H-indazol-5-yl)amino)-1,2,4-thiadiazol-3-yl)pyridin-2-yl)morpholine-4-carboxamide 2,2,2-trifluoroacetic acid solvate] | MS (ES, m/z): [M + H]$^+$ 457.3. $^1$H NMR (400 MHz, DMSO-d$_6$, ppm): δ: 13.55 (s, 1H), 10.75 (s, 1H), 9.38 (s, 1H), 8.59-8.45 (m, 1H), 8.40-8.29 (m, 1H), 8.19 (s, 1H), 7.94 (d, J = 8.8 Hz, 1H), 7.65 (dd, J = 8.8, 1.0 Hz, 1H), 7.59 (dd, J = 5.2, 1.5 Hz, 1H), 3.60 (dd, J = 5.7, 3.7 Hz, 4H), 3.48 (dd, J = 5.7, 3.7 Hz, 4H). |

TABLE 2-continued

| No. | Chemical Structure [name] | Physical Characterization Data |
|---|---|---|
| II-2 | 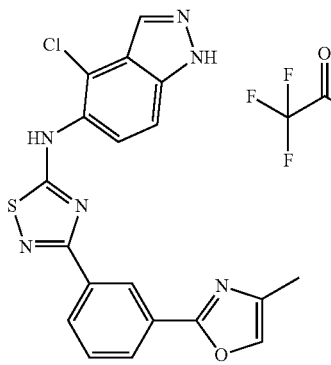<br>[N-(4-chloro-1H-indazol-5-yl)-3-(3-(4-methyloxazol-2-yl)phenyl)-1,2,4-thiadiazol-5-amine 2,2,2-trifluoroacetic acid solvate] | MS (ES, m/z): [M + H]⁺ 409. ¹H NMR (400 MHz, DMSO-d₆, ppm): δ: 13.53 (s, 1H), 10.68 (s, 1H), 8.68 (d, J = 1.6 Hz, 1H), 8.19 (t, J = 14.4 Hz, 2H), 8.03 (d, J = 8.0 Hz , 1H), 7.95 (d, J = 8.4 Hz, 2H), 7.67-7.62 (m, 2H), 2.18 (d, J = 0.8 Hz, 3H). |
| II-3 | 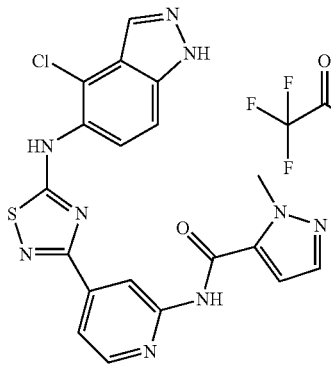<br>[N-(4-(5-((4-chloro-1H-indazol-5-yl)amino)-1,2,4-thiadiazol-3-yl)pyridin-2-yl)-1-methyl-1H-pyrazole-5-carboxamide 2,2,2-trifluoroacetic acid solvate] | MS (ES, m/z): [M + H] 452. ¹H NMR (400 MHz, DMSO-d₆, ppm): δ: 13.52 (s, 1H), 10.93 (s, 1H), 10.71 (s, 1H), 8.92-8.83 (m, 1H), 8.48 (dd, J = 5.2, 0.9 Hz, 1H), 8.16 (s, 1H), 7.91 (d, J = 8.9 Hz, 1H), 7.75 (dd, J = 5.2, 1.5 Hz, 1H), 7.63 (dd, J = 8.9, 1.0 Hz, 1H), 7.50 (d, J = 2.1 Hz, 1H), 7.29 (d, J = 2.1 Hz, 1H), 4.10 (s, 3H). |
| II-4 | 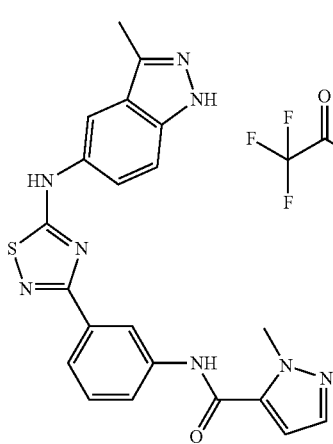<br>[1-methyl-N-(3-(5-((3-methyl-1H-indazol-5-yl)amino)-1,2,4-thiadiazol-3-yl)phenyl)-1H-pyrazole-5-carboxamide 2,2,2-trifluoroacetic acid solvate] | MS (ES, m/z): [M + H]⁺: 431. ¹H NMR (400 MHz, DMSO-d₆, ppm): δ: 12.71 (s, 1H), 10.99 (s, 1H), 10.37 (s, 1H), 8.73 (t, J = 1.8 Hz, 1H), 8.13-8.08 (m, 1H), 7.94 (dt, J = 7.7, 1.3 Hz, 1H), 7.80 (ddd, J = 8.2, 2.2, 1.1 Hz, 1H), 7.59-7.46 (m, 3H), 7.41 (dd, J = 8.8, 2.0 Hz, 1H), 7.13 (d, J = 2.1 Hz, 1H), 4.12 (s, 3H), 2.52 (s, 3H). |

TABLE 2-continued

| No. | Chemical Structure [name] | Physical Characterization Data |
|---|---|---|
| II-5 | 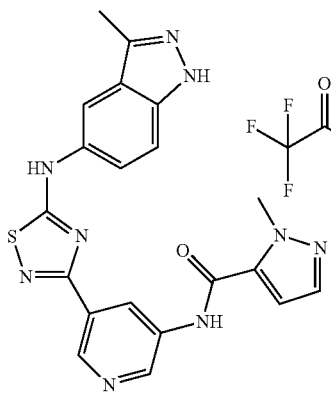 [1-methyl-N-(5-(5-((3-methyl-1H-indazol-5-yl)amino)-1,2,4-thiadiazol-3-yl)pyridin-3-yl)-1H-pyrazole-5-carboxamide 2,2,2-trifluoroacetic acid solvate] | MS (ES, m/z): [M + H] = 432. $^1$H NMR (400 MHz, DMSO-$d_6$, ppm): δ: 12.70 (s, 1H), 11.14 (s, 1H), 10.61 (s, 1H), 9.09 (d, J = 2.1 Hz, 2H), 8.97 (d, J = 2.1 Hz, 1H), 8.14 (s, 1H), 7.59 (d, J = 2.1 Hz, 1H), 7.53 (d, J = 8.8 Hz, 1H), 7.47-7.38 (m, 1H), 7.18 (d, J = 2.1 Hz, 1H), 4.14 (s, 3H), 2.55 (s, 3H). |
| II-6 | 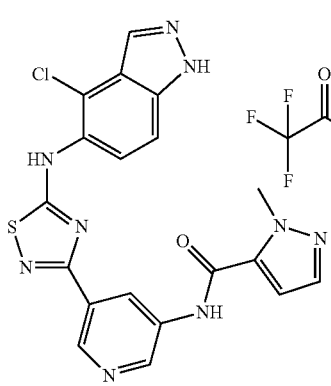 [N-(5-(5-((4-chloro-1H-indazol-5-yl)amino)-1,2,4-thiadiazol-3-yl)pyridin-3-yl)-1-methyl-1H-pyrazole-5-carboxamide 2,2,2-trifluoroacetic acid solvate] | MS (ES, m/z): [M + H] = 451. $^1$H NMR (400 MHz, DMSO-$d_6$, ppm): δ: 10.76 (s, 1H), 10.57 (s, 1H), 9.02 (dd, J = 6.1, 2.2 Hz, 2H), 8.88 (t, J = 2.2 Hz, 1H), 8.19 (s, 1H), 8.00 (d, J = 8.9 Hz, 1H), 7.67 (dd, J = 8.8, 1.0 Hz, 1H), 7.58 (d, J = 2.1 Hz, 1H), 7.14 (d, J = 2.1 Hz, 1H), 4.12 (s, 3H). |
| II-7 | 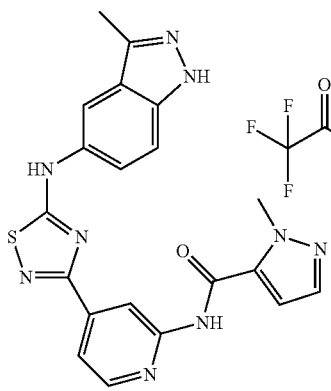 [1-methyl-N-(4-(5-((3-methyl-1H-indazol-5-yl)amino)-1,2,4-thiadiazol-3-yl)pyridin-2-yl)-1H-pyrazole-5-carboxamide 2,2,2-trifluoroacetic acid solvate] | MS (ES, m/z): [M − TFA + H] = 432. $^1$H NMR (400 MHz, DMSO-$d_6$, ppm): δ: 12.70 (s, 1H), 11.17 (s, 1H), 11.00 (s, 1H), 9.15-8.99 (m, 1H), 8.62-8.54 (m, 1H), 8.22 (s, 1H), 7.88 (dd, J = 5.1, 1.5 Hz, 1H), 7.61-7.50 (m, 2H), 7.35 (dd, J = 8.5, 2.1 Hz, 2H), 7.25-6.94 (m, 0.28H), 4.16 (s, 3H), 2.57 (s, 3H). |

Example 6—Preparation of Additional Indazol-5-yl-amino-1,2,4-thiadiazol-3-yl Compounds Compounds in Table 3 below were prepared based on procedures described in Example 4.

TABLE 3

| No. | Chemical Structure [name] | Physical Characterization Data |
| --- | --- | --- |
| III-1 | 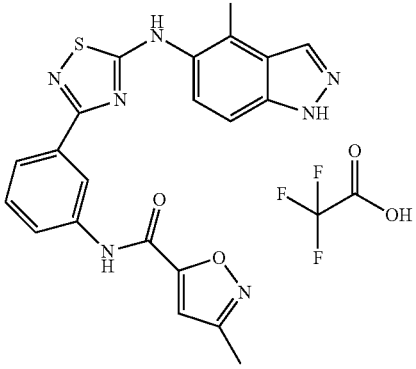 [N-(3-(5-((4-Chloro-1H-indazol-5-yl)amino)-1,2,4-thiadiazol-3-yl)phenyl)-3-methylisoxazole-5-carboxamide 2,2,2-trifluoroacetic acid solvate] | (MS, m/z): [M + H]$^+$ 452.0, 454.0. $^1$H NMR (DMSO-d6, 400 MHz, ppm) 13.49 (brs, 1H), 10.81 (s, 1H), 10.59 (s, 1H), 8.51-8.58 (m, 1H), 8.05-8.27 (m, 2H), 7.98 (br d, J = 8.6 Hz, 1H). 7.87 (br dd, J = 8.4, 2.2 Hz, 1H), 7.64 (br d, J = 8.8 Hz, 1H), 7.47 (br t, J = 7.9 Hz, 1H), 7.13 (s, 1H), 2.33 (s, 3H). |
| III-2 | 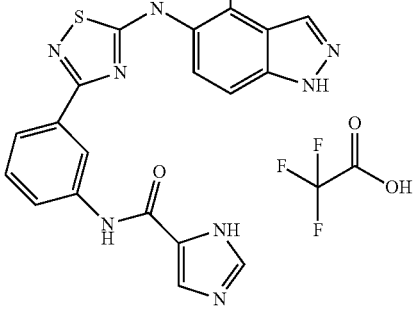 [N-(3-(5-((4-Chloro-1H-indazol-5-yl)amino)-1,2,4-thiadiazol-3-yl)phenyl)-1H-imidazole-5-carboxamide 2,2,2-trifluoroacetic acid solvate] | (MS, m/z): [M + H]$^+$ 437.06, 439.01. $^1$H NMR (DMSO-d$_6$, 400 MHz, ppm): δ: 13.40-13.58 (m, 1H), 10.58 (s, 1H), 10.23 (br s, 1H), 8.50-8.58 (m, 1H), 8.54 (s, 1H), 8.34 (br s, 1H), 8.16 (s, 1H), 7.95-8.06 (m. 2H), 7.84 (ddd, J = 15.4, 8.0, 1.3 Hz, 2H), 7.58-7.68 (m, 1H), 7.44 (br t, J = 8.0 Hz, 1H). |
| III-3 | 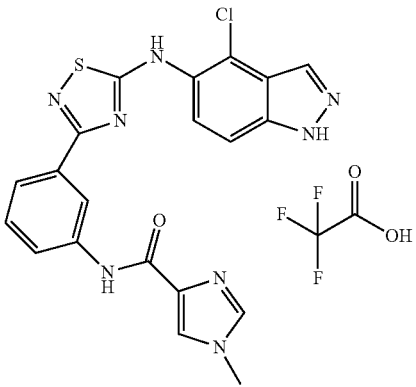 [SMILES: Cn1cnc(C(=O)Nc2cccc(-c3nsc(Nc4ccc5[nH]ncc5c4Cl)n3)c2)c1 ; O=C(O)C(F)(F)F] [N-[3-[5-[(4-chloro-1H-indazol-5-yl)amino]-1,2,4-thiadiazol-3- | (MS, m/z): [M + H]$^+$ 450.99, 452.96. $^1$H NMR (DMSO-d$_6$, 400 MHz, ppm): δ: 13.35-13.60 (br s, 1H), 10.60 (s, 1H), 10.45 (s, 1H), 8.52-8.64 (m, 1H), 8.48 (t, J = 1.8 Hz, 1H), 8.14 (d, J = 16.0 Hz, 2H), 7.92-8.02 (m, 1H), 7.73-7.88 (m, 2H), 7.59-7.70 (m, 1H), 7.38-7.53 (m, 1H), 3.96 (s, 3H) |

| No. | Chemical Structure [name] | Physical Characterization Data |
|---|---|---|
| | yl]phenyl]-1-methyl-imidazole-4-carboxamide 2,2,2-trifluoroacetic acid solvate] | |
| III-4 | 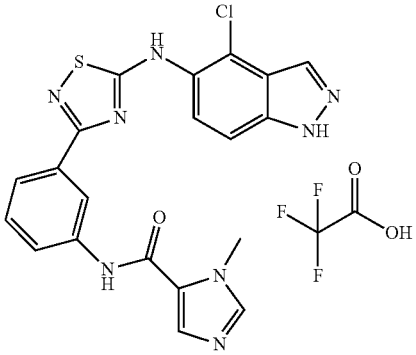<br>[of N-(3-(5-((4-Chloro-1H-indazol-5-yl)amino)-1,2,4-thiadiazol-3-yl)phenyl)-1-methyl-1H-imidazole-4-carboxamide 2,2,2-trifluoroacetic acid solvate] | (MS, m/z): [M + H]⁺ 450.99, 452.96. ¹H NMR (DMSO-d₆, 400 MHz, ppm): δ:13.38-13.62 (br s, 1H), 10.52-10.68 (m, 1H), 9.97-10.18 (m, 1H), 8.61 (s, 1H), 8.16 (br s, 2H), 7.96-8.06 (m, 2H), 7.74-7.88 (m, 1H), 7.54-7.70 (m, 2H), 7.41 (br t, J = 7.9 Hz, 1H), 3.76 (s, 3H). |
| III-5 | 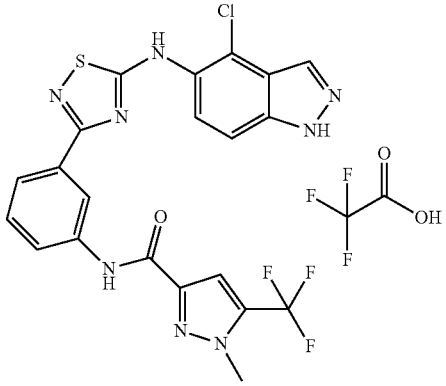<br>[N-(3-(5-((4-Chloro-1H-indazol-5-yl)amino)-1,2,4-thiadiazol-3-yl)phenyl)-1-methyl-5-(trifluoromethyl)-1H-pyrazole-3-carboxamide 2,2,2-trifluoroacetic acid solvate] | (MS, m/z): [M + H]⁺ 519.01, 521.01. ¹H NMR (DMSO-d₆, 400 MHz, ppm): δ: 13.37-13.59 (m, 1H), 10.59 (s, 1H), 10.36-10.48 (m, 1H), 8.54-8.64 (m, 1H), 8.15 (s, 1H), 7.98 (br d, J = 8.8 Hz, 1H), 7.78-7.90 (m, 2H), 7.64 (br d, J = 8.8 Hz, 1H), 7.36-7.50 (m, 2H), 4.08 (s, 3H). |
| III-6 | 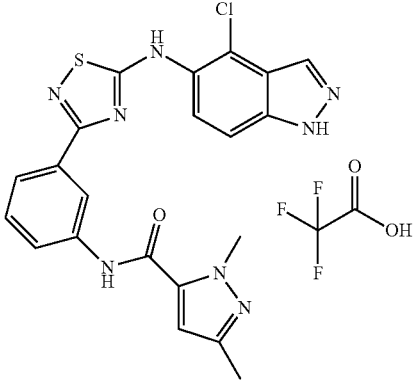<br>[N-(3-(5-((4-Chloro-1H-indazol-5-yl)amino)-1,2,4-thiadiazol-3-yl)phenyl)-1,3-dimethyl-1H-pyrazole-5-carboxamide 2,2,2-trifluoroacetic acid solvate] | (MS, m/z): [M + H]⁺ 465.0, 467.0. ¹H NMR (DMSO-d₆, 400 MHz, ppm): δ: 13.50 (br s, 1H), 10.58 (s, 1H), 9.79 (s, 1H), 8.41-8.50 (m, 1H), 8.30 (s, 1H), 8.09-8.19 (m, 1H), 7.89-8.02 (m, 1H), 7.79-7.86 (m, 1H), 7.71-7.79 (m, 1H), 7.64 (br d, J = 9.0 Hz, 1H), 7.32-7.44 (m, 1H), 3.80 (s, 3H). |

TABLE 3-continued

| No. | Chemical Structure [name] | Physical Characterization Data |
|---|---|---|
| III-7 | 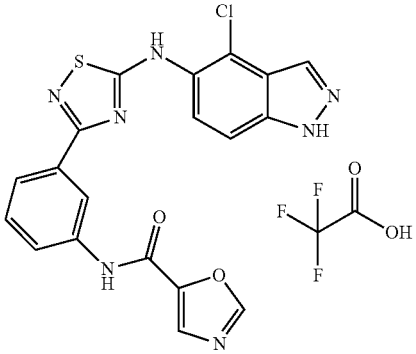<br>[N-(3-(5-((4-Chloro-1H-indazol-5-yl)amino)-1,2,4-thiadiazol-3-yl)phenyl)oxazole-5-carboxamide 2,2,2-trifluoroacetic acid solvate] | (MS, m/z): [M + Na]⁺ 459.93, 461.94. ¹H NMR (DMSO-d₆, 400 MHz, ppm): δ: 13.49 (b rs, 1H), 10.59 (m, 1H), 10.57 (m, 1H), 10.53-10.57 (m, 1H), 8.65 (s, 1H), 8.42-8.51 (m, 1H), 8.15 (s, 1H), 7.94-8.04 (m, 2H), 7.80-7.91 (m, 2H), 7.59-7.68 (m, 1H), 7.39-7.51 (m, 1H). |
| III-8 | 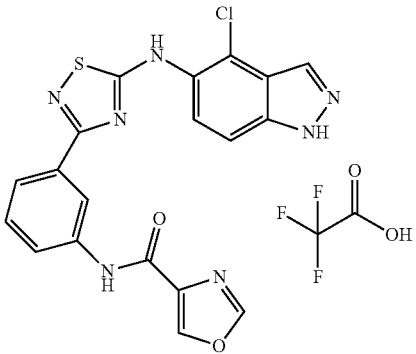 [SMILES: O=C(Nc1cccc(-c2nsc(Nc3ccc4[nH]ncc4c3Cl)n2)c1)c1cocn1 ; O=C(O)C(F)(F)F]<br>[N-(3-(5-((4-Chloro-1H-indazol-5-yl)amino)-1,2,4-thiadiazol-3-yl)phenyl)oxazole-4-carboxamide 2,2,2-trifluoroacetic acid solvate] | (MS, m/z): [M + H]⁺ 437.99, 439.96. ¹H NMR (DMSO-d6, 400 MHz, ppm): δ: 13.38-13.63 (m, 1H), 10.53-10.70 (m, 1H), 10.24-10.38 (m, 1H), 8.80 (d, J = 1.0 Hz, 1H), 8.54-8.69 (m, 1H), 8.03-8.32 (m, 2H), 7.99 (br d, J = 9.0 Hz, 1H), 7.75-7.87 (m, 2H), 7.64 (br d, J = 8.8 Hz, 1H), 7.43 (br t, J = 7.9 Hz, 1H). |
| III-9 | 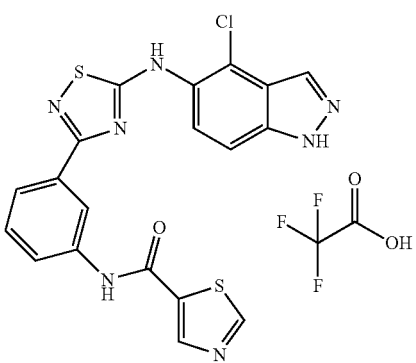 [SMILES: O=C(Nc1cccc(-c2nsc(Nc3ccc4[nH]ncc4c3Cl)n2)c1)c1cncs1 ; O=C(O)C(F)(F)F]<br>[N-(3-(5-((4-Chloro-1H-indazol-5-yl)amino)-1,2,4-thiadiazol-3-yl)phenyl)thiazole-5-carboxamide 2,2,2-trifluoroacetic acid solvate] | (MS, m/z): [M + H]⁺ 453.95, 455.97. ¹H NMR (DMSO-d6, 400 MHz, ppm): δ: 13.43-13.54 (m, 1H), 10.54-10.63 (m, 2H), 9.28-9.34 (m, 1H), 8.71 (s, 1H), 8.41-8.49 (m, 1H), 8.10-8.19 (m, 1H), 7.93-8.01 (m, 1H), 7.78-7.93 (m, 2H), 7.58-7.70 (m, 1H), 7.40-7.53 (m, 1H). |

TABLE 3-continued

| No. | Chemical Structure [name] | Physical Characterization Data |
|---|---|---|
| III-10 | 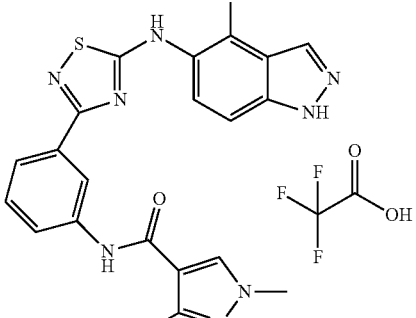<br>[N-(3-(5-((4-Chloro-1H-indazol-5-yl)amino)-1,2,4-thiadiazol-3-yl)phenyl)-1,3-dimethyl-1H-pyrazole-4-carboxamide 2,2,2-trifluoroacetic acid solvate] | (MS, m/z): [M + Na]⁺ 486.96, 488.98. ¹H NMR (DMSO-d6, 400 MHz, ppm): δ: 13.46-13.55 (m, 1H), 10.55-10.64 (m, 1H), 10.22-10.30 (m, 1H), 8.48-8.57 (m, 1H), 8.15 (s, 1H), 7.97 (br d, J = 8.8 Hz, 1H), 7.82 (br dd, J = 8.9, 1.7 Hz, 2H), 7.64 (br d, J = 8.8 Hz, 1H), 7.44 (br t, J = 8.0 Hz, 1H), 6.86 (s, 1H), 4.00 (s, 3H), 2.19 (s, 3H). |
| III-11 | 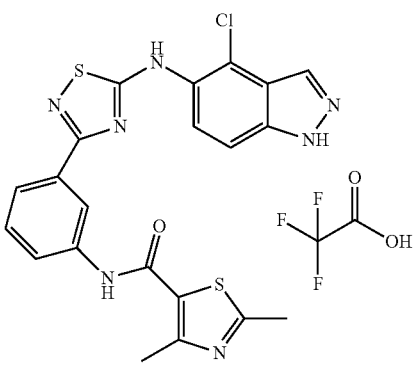<br>[N-(3-(5-((4-Chloro-1H-indazol-5-yl)amino)-1,2,4-thiadiazol-3-yl)phenyl)-2,4-dimethylthiazole-5-carboxamide 2,2,2-trifluoroacetic acid solvate] | (MS, m/z): [M + Na]⁺ 503.93, 505.94. ¹H NMR (DMSO-d₆, 400 MHz, ppm): δ: 13.43-13.56 (m, 1H), 10.55-10.61 (m, 1H), 10.16-10.25 (m, 1H), 8.40-8.48 (m, 1H), 8.14-8.18 (m, 1H), 7.93-8.00 (m, 1H), 7.82 (br d, J-7.8 Hz, 1H), 7.76 (br dd, J = 8.0, 1.2 Hz, 1H), 7.59-7.67 (m, 1H), 7.37-7.48 (m, 1H), 2.65 (s, 3H), 2.54 ppm (s, 3H). |
| III-12 | 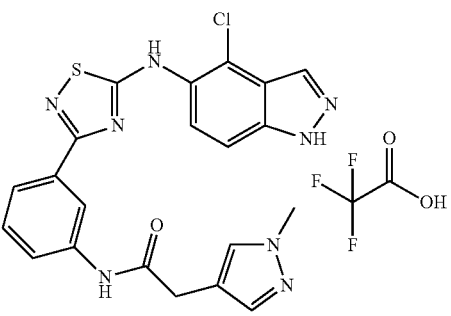<br>[N-(3-(5-((4-Chloro-1H-indazol-5-yl)amino)-1,2,4-thiadiazol-3-yl)phenyl)-2-(1-methyl-1H-pyrazol-4-yl)acetamide 2,2,2-trifluoroacetic acid solvate] | (MS, m/z): [M + H]⁺ 465.01, 466.98. ¹H NMR (DMSO-d₆, 400 MHz, ppm): δ: 13.49 (br s, 1H), 10.56 (s, 1H), 10.17 (s, 1H), 8.33 (s, 1H), 8.15 (s, 1H), 7.96 (br d, J = 8.8 Hz, 1H), 7.67-7.85 (m, 2H), 7.49-7.67 (m, 2H), 7.23-7.48 (m, 2H), 3.77 (s, 3H), 3.45 (s, 2H). |

Example 7—Synthesis of 3-(5-((4-chloro-1H-indazol-5-yl)amino)-1,2,4-thiadiazol-3-yl)-N-methylbenzamide

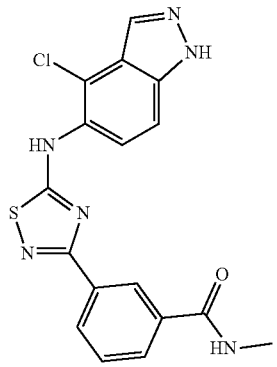 [SMILES: CNC(=O)c1cccc(-c2nsc(Nc3ccc4[nH]ncc4c3Cl)n2)c1]

Part 1—Synthesis of methyl (Z)-3-(N'-hydroxycarbamimidoyl)benzoate

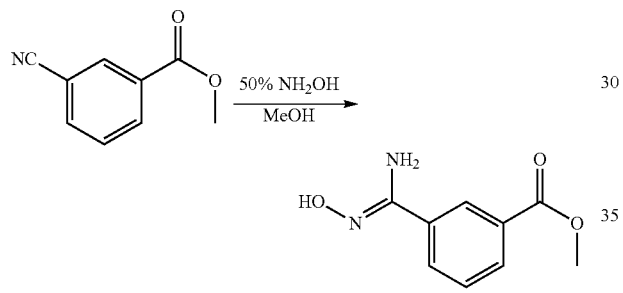

Into a 1000-mL round-bottom flask, was placed methyl 3-cyanobenzoate (20 g, 124.10 mmol, 1.00 equiv), methanol (200 mL), and 50% NH$_2$OH (10 mL). The resulting solution was stirred for 1.5 h at 70° C. in an oil bath. The resulting mixture was concentrated under vacuum. This resulted in 24 g (100%) of methyl (Z)-3-(N'-hydroxycarbamimidoyl)benzoate as a tan solid.

Part 2—Synthesis of methyl 3-carbamimidoylbenzoate

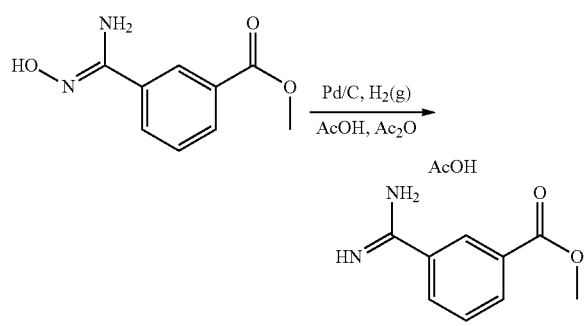

Into a 500-mL round-bottom flask, was placed methyl (Z)-3-(N'-hydroxycarbamimidoyl)benzoate (24 g, 123.59 mmol, 1.00 equiv) and AcOH (200 mL). This was followed by the addition of acetic anhydride (25 g, 2.00 equiv). The reaction was stirred for 1 h at room temperature. To this was added palladium on carbon (12 g, 0.50 equiv). To the above hydrogen was introduced in. The resulting solution was stirred for 1 h at room temperature. The solids were filtered out. The resulting mixture was concentrated under vacuum. This resulted in 30 g (crude) of methyl 3-carbamimidoylbenzoate acetic acid solvate as a gray solid.

Part 3—Synthesis of methyl 3-(5-((4-chloro-1H-indazol-5-yl)amino)-1,2,4-thiadiazol-3-yl)benzoate

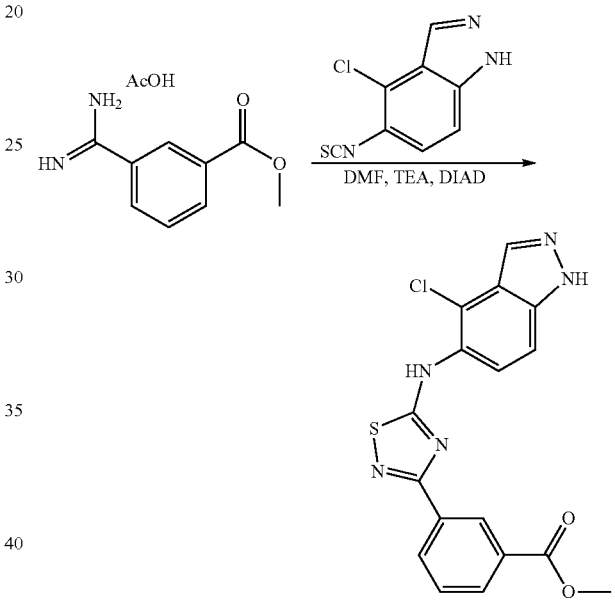

Into a 250-mL round-bottom flask, was placed methyl 3-carbamimidoylbenzoate acetic acid solvate (1.76 g, 7.38 mmol, 2.00 equiv), N,N-dimethylformamide (80 mL), and TEA (4.0 g, 39.53 mmol, 10.00 equiv). This was followed by the addition of 4-chloro-5-isothiocyanato-1H-indazole (800 mg, 3.82 mmol, 1.00 equiv). The reaction was stirred overnight at room temperature. To this was added DIAD (2.2 g, 10.88 mmol, 3.00 equiv). The resulting solution was stirred for 2 h at room temperature. The resulting solution was diluted with 700 mL of EtOAc. The resulting mixture was washed with 3×100 mL of brine. The mixture was dried over anhydrous sodium sulfate and concentrated under vacuum. The residue was applied onto a silica gel column with 0 to 30% ethyl acetate/petroleum ether. This resulted in 530 mg (36%) of methyl 3-(5-((4-chloro-1H-indazol-5-yl)amino)-1,2,4-thiadiazol-3-yl)benzoate as a light brown solid.

Part 4—Synthesis of methyl 3-(5-((4-chloro-1-(tetrahydro-2H-pyran-2-yl)-1H-indazol-5-yl)amino)-1,2,4-thiadiazol-3-yl)benzoate Part 5—Synthesis of 3-(5-((4-chloro-1-(tetrahydro-2H-pyran-2-yl)-1H-indazol-5-yl)amino)-1,2,4-thiadiazol-3-yl)benzoic acid

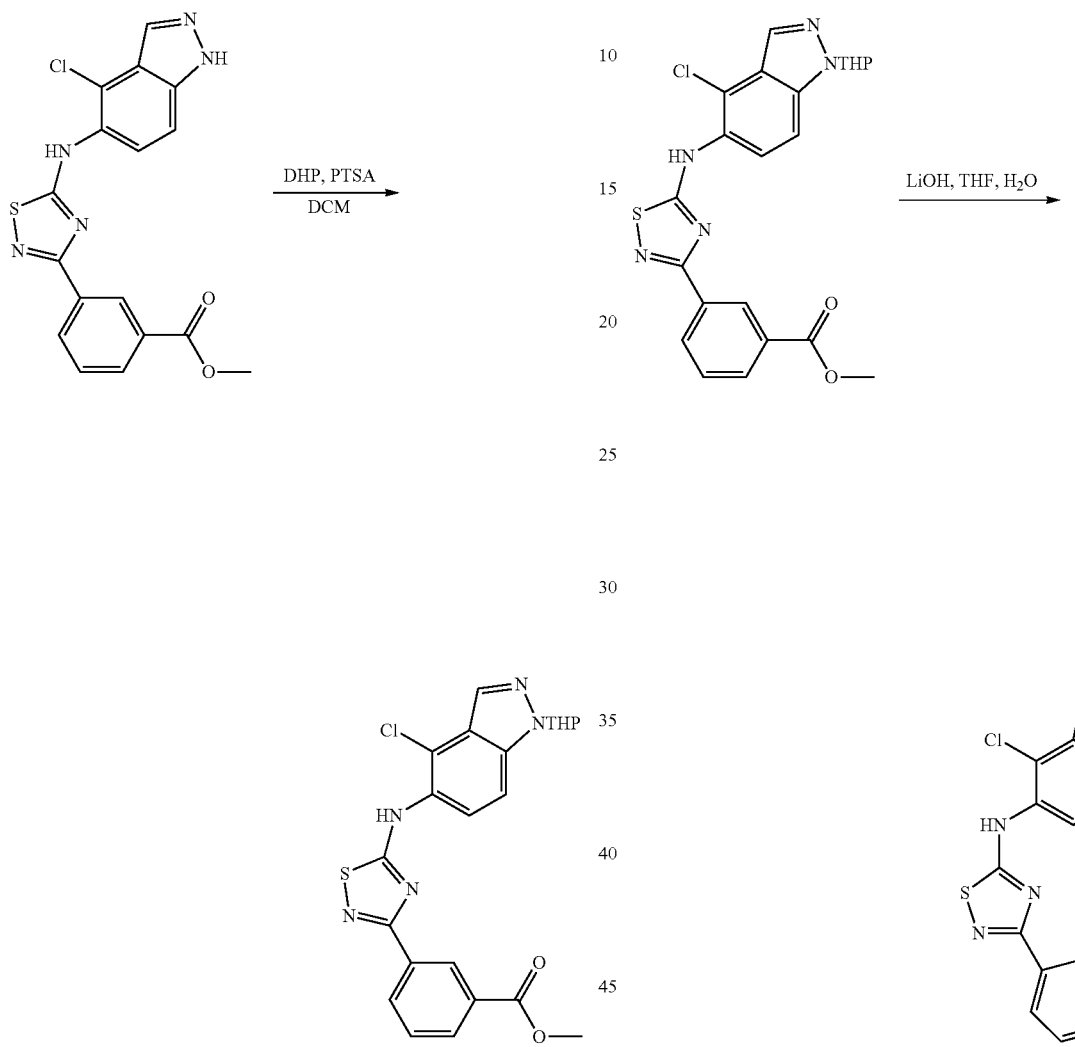

Into a 100-mL round-bottom flask, was placed methyl 3-(5-((4-chloro-1H-indazol-5-yl)amino)-1,2,4-thiadiazol-3-yl)benzoate (800 mg, 2.07 mmol, 1.00 equiv), dichloromethane (50 mL), p-toluenesulfonic acid (PTSA, 200 mg, 1.16 mmol, 0.50 equiv), and dihydropyran (DHP, 720 mg, 8.56 mmol, 4.00 equiv). The resulting solution was stirred overnight at room temperature. The resulting mixture was concentrated under vacuum. The residue was applied onto a silica gel column with 0 to 40% ethyl acetate/petroleum ether. This resulted in 530 mg (54%) of methyl 3-(5-((4-chloro-1-(tetrahydro-2H-pyran-2-yl)-1H-indazol-5-yl)amino)-1,2,4-thiadiazol-3-yl)benzoate as a light yellow solid.

Into a 100-mL round-bottom flask, was placed methyl 3-(5-((4-chloro-1-(tetrahydro-2H-pyran-2-yl)-1H-indazol-5-yl)amino)-1,2,4-thiadiazol-3-yl)benzoate (530 mg, 1.13 mmol, 1.00 equiv), tetrahydrofuran (50 mL), water (5 mL), LiOH (280 mg, 11.69 mmol, 10.00 equiv). The resulting solution was stirred overnight at room temperature. The resulting mixture was concentrated under vacuum. The residue was dissolved in 20 mL of H$_2$O. The pH value of the solution was adjusted to 6 with hydrogen chloride (1 mol/L). The solids were filtered out. The solid was dried in an oven. This resulted in 450 mg (crude) of 3-(5-((4-chloro-1-(tetrahydro-2H-pyran-2-yl)-1H-indazol-5-yl)amino)-1,2,4-thiadiazol-3-yl)benzoic acid as an off-white solid.

Part 6—Synthesis of 3-(5-((4-chloro-1-(tetrahydro-2H-pyran-2-yl)-1H-indazol-5-yl)amino)-1,2,4-thiadiazol-3-yl)-N-methylbenzamide Part 7—Synthesis of 3-(5-((4-chloro-1H-indazol-5-yl)amino)-1,2,4-thiadiazol-3-yl)-N-methylbenzamide

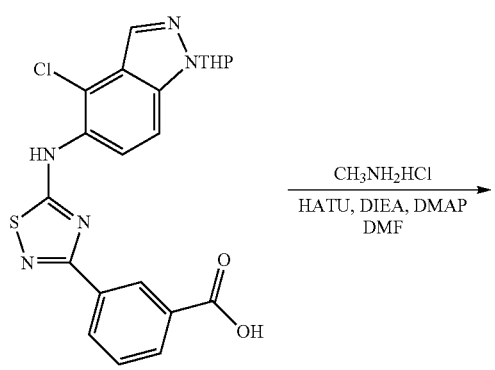

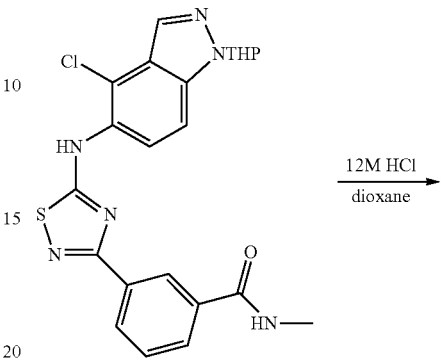

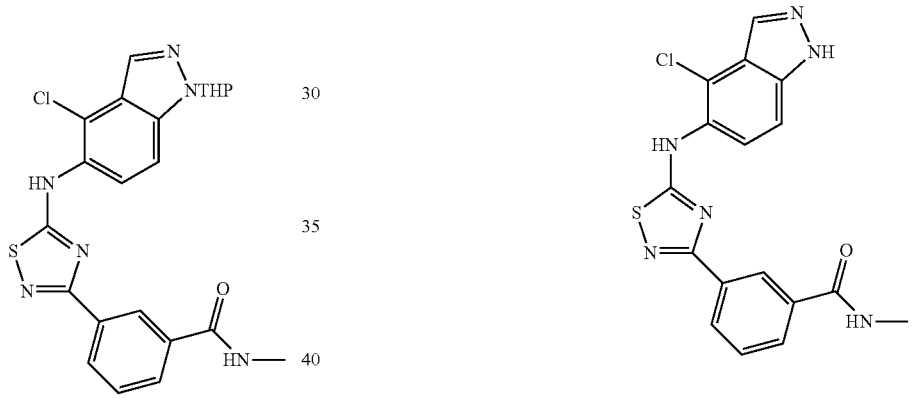

Into a 25-mL round-bottom flask, was placed 3-(5-((4-chloro-1-(tetrahydro-2H-pyran-2-yl)-1H-indazol-5-yl)amino)-1,2,4-thiadiazol-3-yl)benzoic acid (200 mg, 0.44 mmol, 1.00 equiv), N,N-dimethylformamide (10 mL), HATU (320 mg, 0.84 mmol, 2.00 equiv), DIEA (226 mg, 1.75 mmol, 4.00 equiv), 4-dimethylaminopyridine (5 mg, 0.04 mmol, 0.10 equiv), and methylamine hydrochloride (100 mg, 1.48 mmol, 3.37 equiv). The resulting solution was stirred overnight at room temperature. The resulting solution was diluted with 100 mL of EtOAc. The resulting mixture was washed with 3×50 mL of brine. The mixture was dried over anhydrous sodium sulfate and concentrated under vacuum. The residue was applied onto a silica gel column with ethyl acetate/petroleum ether (1:1). This resulted in 100 mg (49%) of 3-(5-((4-chloro-1-(tetrahydro-2H-pyran-2-yl)-1H-indazol-5-yl)amino)-1,2,4-thiadiazol-3-yl)-N-methylbenzamide as a light yellow solid. 1.48 mmol, 3.37 equiv Into a 25-mL round-bottom flask, was placed 3-(5-((4-chloro-1-(tetrahydro-2H-pyran-2-yl)-1H-indazol-5-yl)amino)-1,2,4-thiadiazol-3-yl)-N-methylbenzamide (100 mg, 0.21 mmol, 1.00 equiv), dioxane (2 mL), and 12M hydrogen chloride (2 mL). The resulting solution was stirred for 1 h at room temperature. The resulting mixture was concentrated under vacuum. The crude product was purified by Prep-HPLC with the following conditions: Column, XBridge Prep C18 OBD Column, 19*150 mm 5 μm; mobile phase, Water (0.1% TFA) and ACN (33.0% ACN up to 46.0% in 11 min); Detector, UV 254 nm. This resulted in 18.6 mg (23%) of 3-(5-((4-chloro-1H-indazol-5-yl)amino)-1,2,4-thiadiazol-3-yl)-N-methylbenzamide as a white solid. (ES, m/z): [M+H]$^+$ 385.0. $^1$H NMR (300 MHz, DMSO-d6, ppm): δ 13.82-13.03 (m, 1H), 10.39 (s, 1H), 8.65-8.44 (m, 2H), 8.18 (dt, J=7.8, 1.4 Hz, 1H), 8.14 (s, 1H), 7.95 (d, J=8.9 Hz, 1H), 7.88 (dt, J=7.8, 1.5 Hz, 1H), 7.63 (dd, J=8.9, 1.0 Hz, 1H), 7.53 (t, J=7.7 Hz, 1H), 2.77 (d, J=4.4 Hz, 3H).

Example 8—Synthesis of N-(4-(5-((4-chloro-1H-indazol-5-yl)amino)-1,2,4-thiadiazol-3-yl)pyridin-2-yl)-4-methoxybenzamide

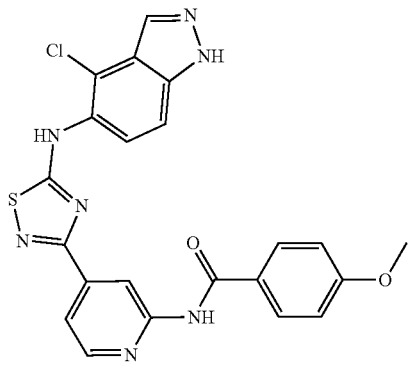 [SMILES: COc1ccc(C(=O)Nc2cc(-c3nsc(Nc4ccc5[nH]ncc5c4Cl)n3)ccn2)cc1]

Part 1—Synthesis of 4-methoxybenzamide

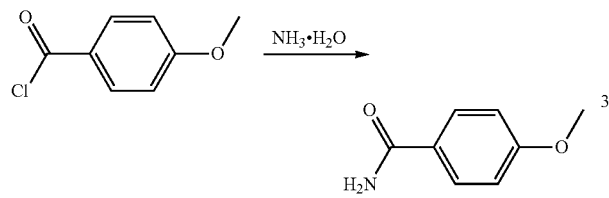

Into a 100-mL round-bottom flask, was placed concentrated ammonia in water (30 mL). This was followed by the addition of 4-methoxybenzoyl chloride (3 g, 17.59 mmol, 1.00 equiv) dropwise with stirring. The resulting solution was stirred for 1 h at room temperature. The solids were collected by filtration. This resulted in 2.1 g (79%) of 4-methoxybenzamide as a white solid.

Part 2—Synthesis of tert-butyl 5-((tert-butoxycarbonyl)(3-(2-(4-methoxybenzamido)pyridin-4-yl)-1,2,4-thiadiazol-5-yl)amino)-4-chloro-1H-indazole-1-carboxylate

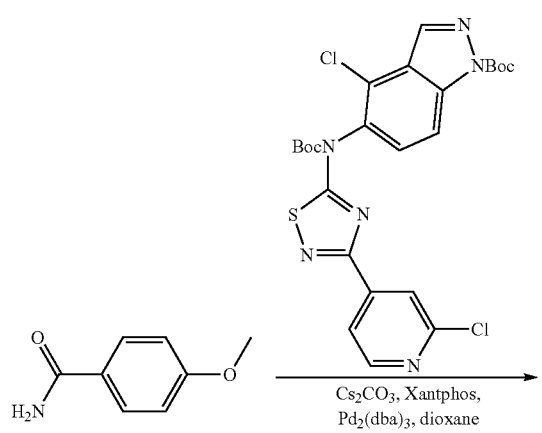

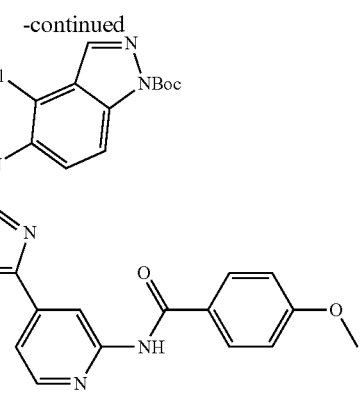

Into a 50-mL round-bottom flask purged and maintained with an inert atmosphere of nitrogen, was placed 4-methoxybenzamide (30.2 mg, 0.20 mmol, 1.00 equiv), tert-butyl 5-(((tert-butoxycarbonyl)(3-(2-chloropyridin-4-yl)-1,2,4-thiadiazol-5-yl)amino)-4-chloro-1H-indazole-1-carboxylate (113 mg, 0.20 mmol, 1.00 equiv), $Cs_2CO_3$ (78 mg, 0.24 mmol, 1.20 equiv), Xantphos (46.2 mg, 0.08 mmol, 0.40 equiv), dioxane (10 mL), and $Pd_2(dba)_3$ (21 mg, 0.02 mmol, 0.10 equiv). The resulting solution was stirred overnight at 105° C. in an oil bath. The resulting mixture was concentrated under vacuum. The residue was applied onto a silica gel column eluting with ethyl acetate/petroleum ether (1:5-1:2). This resulted in 120 mg (88%) of tert-butyl 5-(((tert-butoxycarbonyl)(3-(2-(4-methoxybenzamido)pyridin-4-yl)-1,2,4-thiadiazol-5-yl)amino)-4-chloro-1H-indazole-1-carboxylate as yellow oil.

Part 3—Synthesis of N-(4-(5-((4-chloro-1H-indazol-5-yl)amino)-1,2,4-thiadiazol-3-yl)pyridin-2-yl)-4-methoxybenzamide

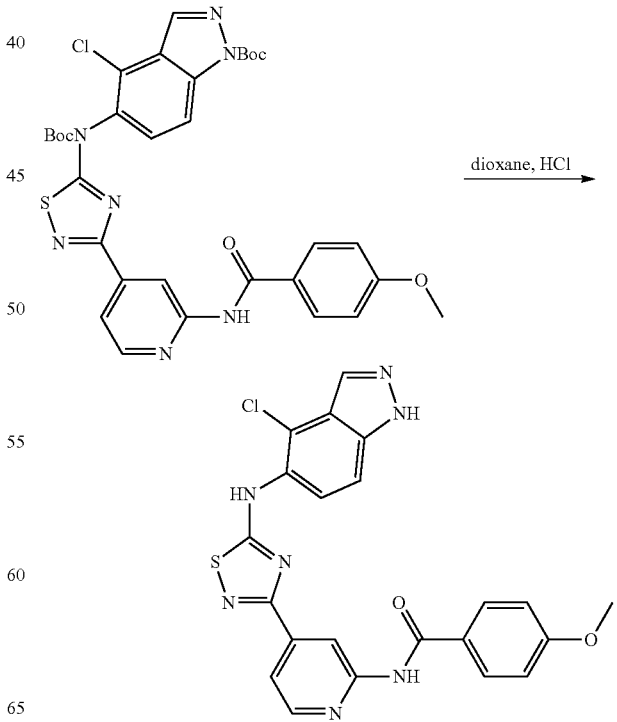

Into a 25-mL round-bottom flask, was placed tert-butyl 5-((tert-butoxycarbonyl)(3-(2-(4-methoxybenzamido)pyridin-4-yl)-1,2,4-thiadiazol-5-yl)amino)-4-chloro-1H-indazole-1-carboxylate (120 mg, 0.18 mmol, 1.00 equiv), 1,4-dioxane (4 mL), and concentrated hydrochloric acid (2 mL). The resulting solution was stirred for 2 h at room temperature. The resulting mixture was concentrated under vacuum. The crude product was purified by Prep-HPLC with the following conditions: Column, XBridge Shield RP18 OBD Column, 5 um, 19*150 mm; mobile phase, Water (0.05% aqueous NH$_3$) and ACN (5.0% ACN up to 50.0% in 1 min, up to 67.0% in 8 min); Detector, uv 254 nm. This resulted in 21.7 mg (26%) of N-(4-(5-((4-chloro-1H-indazol-5-yl)amino)-1,2,4-thiadiazol-3-yl)pyridin-2-yl)-4-methoxybenzamide. (ES, m/z): [M+H]$^+$ 478.0. $^1$H NMR (300 MHz, DMSO-d6, ppm): δ13.53 (s, 1H), 10.78 (s, 1H), 10.76 (s, 1H), 8.92 (s, 1H), 8.50 (d, J=5.2 Hz, 1H), 8.18 (s, 1H), 8.07 (d, J=8.8 Hz, 2H), 7.96 (d, J=8.4 Hz, 1H), 7.75 (dd, J=4.8 Hz, 1.6 Hz, 1H), 7.66 (d, J=8.8 Hz, 1H), 7.05 (d, J=8.8 Hz, 2H), 3.85 (s, 3H).

Example 9—Synthesis of (S)—N-((1-(5-((4-chloro-1H-indazol-5-yl)amino)-1,2,4-thiadiazol-3-yl)pyrrolidin-2-yl)methyl)-1-methyl-1H-pyrazole-5-carboxamide 2,2,2-trifluoroacetic acid solvate

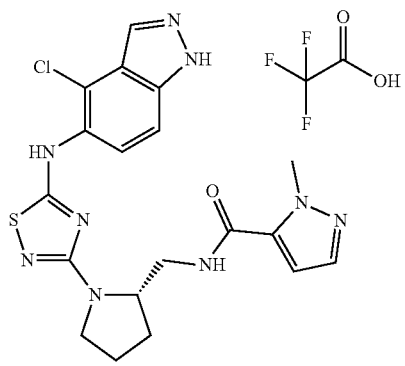

Part 1—Synthesis of tert-butyl N-[[(2S)-1-carbamimidoylpyrrolidin-2-yl]methyl]carbamate hydrochloride

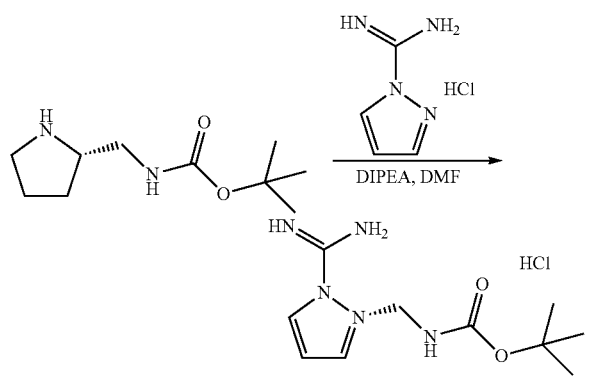

A 100 mL round-bottom flask was charged with a solution of tert-butyl N-[[(2S)-pyrrolidin-2-yl]methyl]carbamate (1 g, 4.993 mmol) in DMF (3 mL), then was added pyrazole-1-carboxamidine hydrochloride (0.7319 g, 4.993 mmol) and N,N-diisopropylethylamine (0.6453 g, 4.993 mmol). The reaction was stirred at ambient temperature for 4 days, then diluted with 50 mL of diethyl ether. The mixture was stirred for 2 h, then the solvents were decanted to leave an oil. This was taken up in 2 mL of ethanol, then the solution was diluted with 25 mL of ethyl acetate and 10 mL of hexanes. The solvents were decanted, and the residue was dried in vacuo to give tert-butyl N-[[(2S)-1-carbamimidoylpyrrolidin-2-yl]methyl]carbamate hydrochloride (1.058 g, 76% yield) as an off-white foam.

Part 2—Synthesis of tert-butyl N-[[(2S)-1-[5-[(4-chloro-1H-indazol-5-yl)amino]-1,2,4-thiadiazol-3-yl]pyrrolidin-2-yl]methyl]carbamate

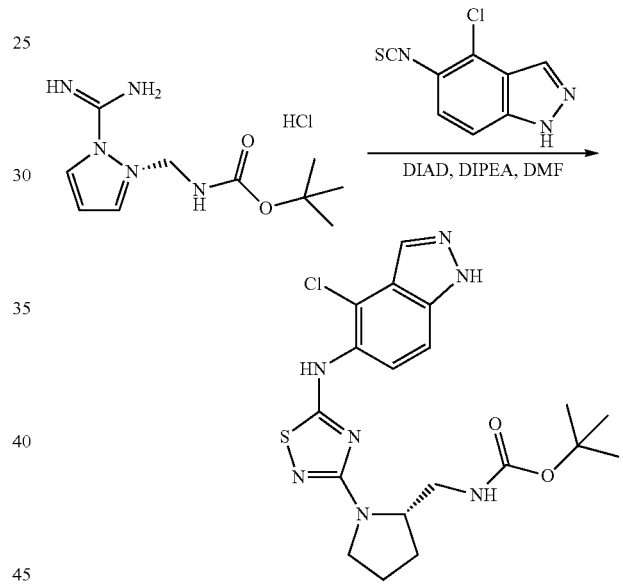

A 35 mL screw cap vial was charged with a solution of 4-chloro-5-isothiocyanato-1H-indazole (0.3000 g, 1.4309 mmol) in DMF (10 mL) was added tert-butyl N-[[(2S)-1-carbamimidoylpyrrolidin-2-yl]methyl]carbamate hydrochloride (0.3989 g, 1.4309 mmol) and N,N-diisopropylethylamine (0.4623 g, 3.5772 mmol). Stirred at room temperature for 18 hours. Afterwards was added DIAD (0.3183 g, 1.574 mmol) dropwise. Stirred resulting mixture at room temperature for 2 hours. The mixture was concentrated onto silica and purified by silica gel chromatography (40 g, HP 15-40 uM 60 A flash cartridge from Silicycle) eluting with 0 to 50% ethyl acetate in hexanes to yield tert-butyl N-[[(2S)-1-[5-[(4-chloro-1H-indazol-5-yl)amino]-1,2,4-thiadiazol-3-yl]pyrrolidin-2-yl]methyl]carbamate (0.0640 g, 9.94% yield) as a yellow foam.

Part 3—Synthesis of 3-[(2S)-2-(aminomethyl)pyrrolidin-1-yl]-N-(4-chloro-1H-indazol-5-yl)-1,2,4-thiadiazol-5-amine

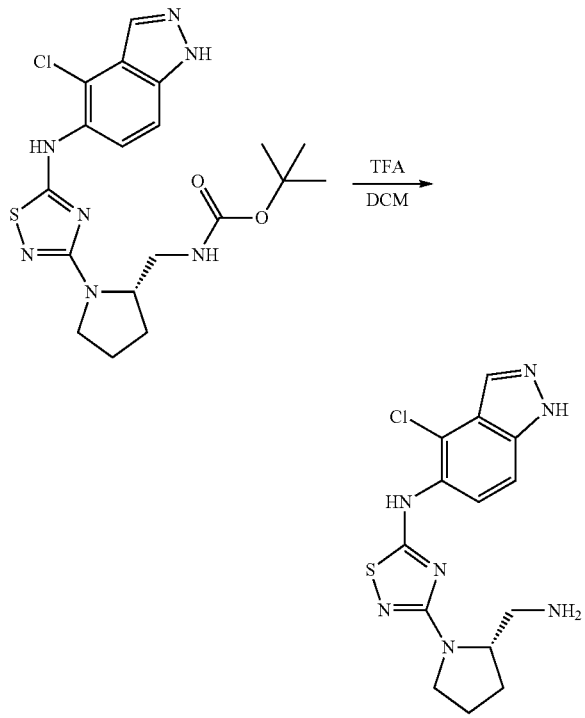

A 50 mL round-bottom flask was charged with a solution of tert-butyl N-[[(2S)-1-[5-[(4-chloro-1H-indazol-5-yl)amino]-1,2,4-thiadiazol-3-yl]pyrrolidin-2-yl]methyl]carbamate (0.0640 g, 0.1422 mmol) in DCM (3 mL) and then was treated with trifluoroacetic acid (1.6218 g, 14.223 mmol) and the mixture was stirred at room temperature for 2 hours. The mixture was concentrated, the residue dissolved in DCM containing few drops of methanol, and purified by silica gel chromatography (25 g, HP 15-40 uM 60 A flash cartridge from Silicycle) eluting with 0 to 10% DCM/(MeOH containing 10% NH₄OH) to yield 3-[(2S)-2-(aminomethyl)pyrrolidin-1-yl]-N-(4-chloro-1H-indazol-5-yl)-1,2,4-thiadiazol-5-amine (0.0470 g, 94.4% yield) as an off-white solid.

Part 4—Synthesis of (S)—N-((1-(5-((4-chloro-1H-indazol-5-yl)amino)-1,2,4-thiadiazol-3-yl)pyrrolidin-2-yl)methyl)-1-methyl-1H-pyrazole-5-carboxamide 2,2,2-trifluoroacetic acid solvate

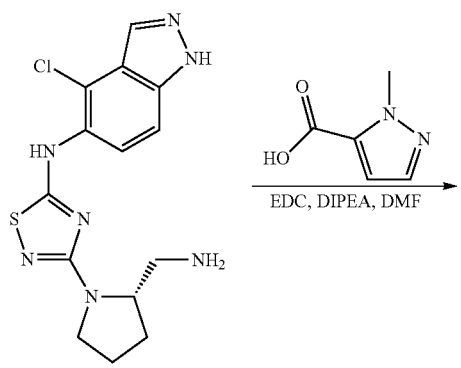

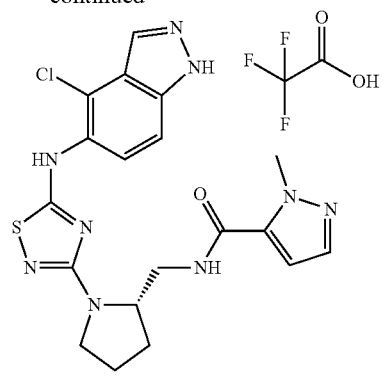

A 25 mL round-bottom flask was charged with a solution of 2-methylpyrazole-3-carboxylic acid (0.0099 g, 0.0786 mmol), EDC.HCl (0.0168 g, 0.0858 mmol), 1-hydroxybenzotriazole (0.0116 g, 0.0858 mmol) and N,N-diisopropylethylamine (0.0277 g, 0.2144 mmol) in DMF (1 mL) and the mixture stirred at room temperature for 10 min. Then the mixture was transferred to a 25 mL flask containing 3-[(2S)-2-(aminomethyl)pyrrolidin-1-yl]-N-(4-chloro-1H-indazol-5-yl)-1,2,4-thiadiazol-5-amine (0.0250 g, 0.0715 mmol) and the mixture was stirred at room temperature for 18 hours. The mixture was purified directly by preparative HPLC to yield (S)—N-((1-(5-((4-chloro-1H-indazol-5-yl)amino)-1,2,4-thiadiazol-3-yl)pyrrolidin-2-yl)methyl)-1-methyl-1H-pyrazole-5-carboxamide 2,2,2-trifluoroacetic acid solvate (0.0148 g, 35.4% yield) as an off-white solid. (ES, m/z): [M+H]⁺ 458.03, 460.02. ¹H NMR (DMSO-d6, 400 MHz): δ=13.24-13.60 (m, 1H), 10.23 (s, 1H), 8.46-8.60 (m, 1H), 8.11 (br d, J=0.8 Hz, 1H), 7.95 (br d, J=9.0 Hz, 1H), 7.57 (d, J=8.8 Hz, 1H), 7.39 (d, J=2.2 Hz, 1H), 6.75 (d, J=2.0 Hz, 1H), 4.08-4.24 (m, 1H), 4.02 (s, 3H), 3.50-3.35 (m, 4H), 1.72-2.03 ppm (m, 4H).

Example 10—Synthesis of 3-[3-[5-[(4-chloro-1H-indazol-5-yl)amino]-1,2,4-thiadiazol-3-yl]phenyl]-2-methyl-quinazolin-4-one

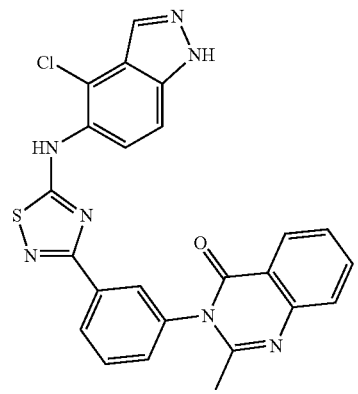 [SMILES: Cc1nc2ccccc2c(=O)n1-c1cccc(-c2nsc(Nc3ccc4[nH]ncc4c3Cl)n2)c1]

Part 1—Synthesis of tert-butyl 5-[tert-butoxycarbonyl-[3-[3-[(2-nitrobenzoyl)amino]phenyl]-1,2,4-thiadiazol-5-yl]amino]-4-chloro-indazole-1-carboxylate

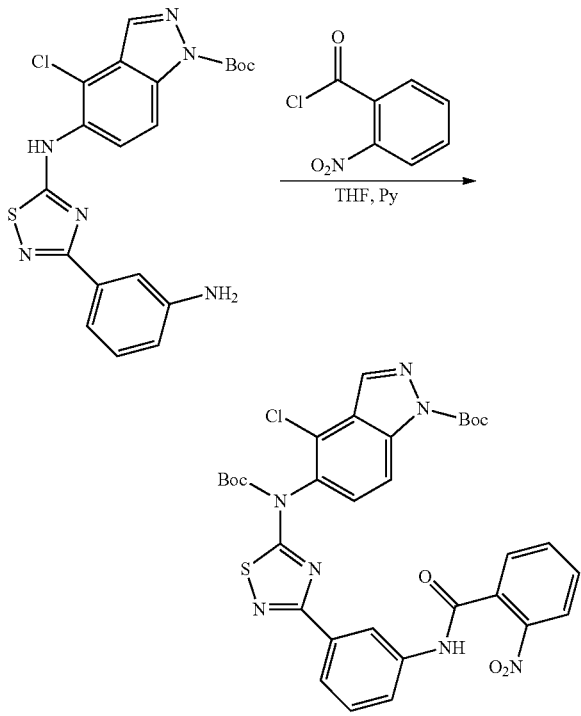

2—Nitrobenzoyl chloride (0.0683 g, 0.3683 mmol) in dry THF (6 mL) was slowly added to a stirred solution at 0° C. of tert-butyl 5-[[3-(3-aminophenyl)-1,2,4-thiadiazol-5-yl]-tert-butoxycarbonyl-amino]-4-chloro-indazole-1-carboxylate (0.2 g, 0.3683 mmol) and pyridine (0.0291 g, 0.3683 mmol) in dry THF (15 mL) under a nitrogen atmosphere. The mixture was maintained with stirring for 3 h at room temperature and then partitioned between EtOAc (100 mL) and saturated solution of NaHCO₃ in water (20 mL). The aqueous solution was extracted with ethyl acetate (2×50 mL) and the organic layers dried over MgSO₄. Concentration of the solvent in vacuo afforded crude tert-butyl 5-[tert-butoxycarbonyl-[3-[3-[(2-nitrobenzoyl)amino]phenyl]-1,2,4-thiadiazol-5-yl]amino]-4-chloro-indazole-1-carboxylate (0.2550 g, 100% yield), as an off-white foam which was used into the next step without further purification.

Part 2—Synthesis of tert-butyl 5-[[3-[3-[(2-aminobenzoyl)amino]phenyl]-1,2,4-thiadiazol-5-yl]-tert-butoxycarbonyl-amino]-4-chloro-indazole-1-carboxylate

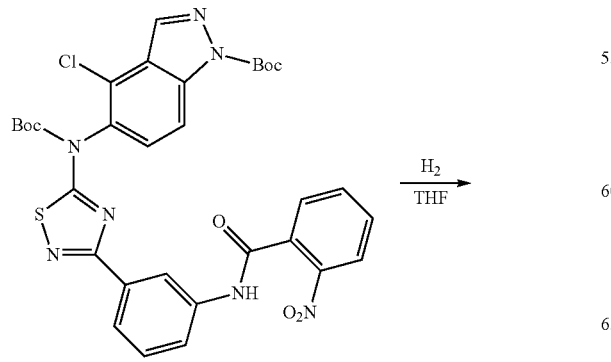

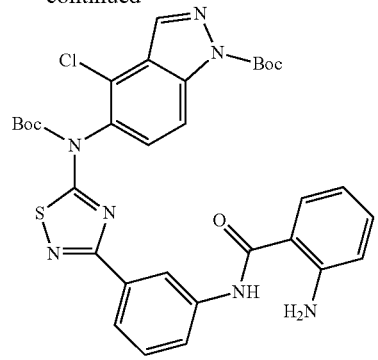

A 100 mL round-bottom flask was charged with a solution of tert-butyl 5-[tert-butoxycarbonyl-[3-[3-[(2-nitrobenzoyl)amino]phenyl]-1,2,4-thiadiazol-5-yl]amino]-4-chloro-indazole-1-carboxylate (0.2550 g, 0.3684 mmol) in dry THF (6 mL), then was added 5% Rhodium on carbon (0.0758 g, 0.0368 mmol) (pre-suspended under nitrogen with 5 mL of THF) and the suspension was evacuated and back filled with hydrogen. Then was stirred under a hydrogen filled balloon for 18 hours. Catalyst was removed by filtration over celite, rinsed with THF and the solvent evaporated to yield tert-butyl 5-[[3-[3-[(2-aminobenzoyl)amino]phenyl]-1,2,4-thiadiazol-5-yl]-tert-butoxycarbonyl-amino]-4-chloro-indazole-1-carboxylate (0.24 g, 99.9% yield) as a beige foam, which was used directly in the next step without further purification.

Part 3—Synthesis of 3-[3-[5-[(4-chloro-1H-indazol-5-yl)amino]-1,2,4-thiadiazol-3-yl]phenyl]-2-methyl-quinazolin-4-one

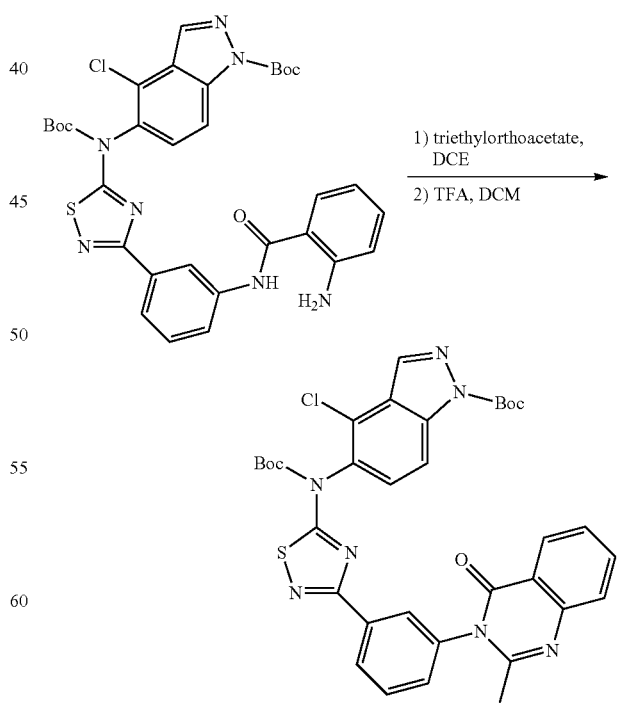

A 100 mL round-bottom flask was charged with a solution of tert-butyl 5-[[3-[3-[(2-aminobenzoyl)amino]phenyl]-1,2, 4-thiadiazol-5-yl]-tert-butoxycarbonyl-amino]-4-chloro-indazole-1-carboxylate (0.1220 g, 0.1842 mmol) in DCE (15 mL), then was added triethylorthoacetate (4.4835 g, 27.637 mmol) and the solution was heated to 100° C. for 12 hours. The solvents were evaporated and the residue was dissolved in DCM (10 mL) and treated with trifluoroacetic acid (4.2015 g, 36.849 mmol) and the mixture stirred at room temperature for 2 h. Solvents were removed under vacuum and the residue purified by silica gel chromatography (40 g, HP 15-40 uM 60 A flash cartridge from Silicycle) eluting with 0 to 5% DCM/(MeOH containing 10% NH$_4$OH) to yield 34345-[(4-chloro-1H-indazol-5-yl)amino]-1,2,4-thiadiazol-3-yl]phenyl]-2-methyl-quinazolin-4-one (0.0570 g, 62.39% yield) as a beige solid. (ES, m/z): [M+H]$^+$ 486.05, 488.01. $^1$H NMR (DMSO-d6, 400 MHz): δ=13.48 (s, 1H), 10.62 (s, 1H), 8.21 (br d, J=8.0 Hz, 1H), 8.14 (s, 1H), 8.04-8.12 (m, 2H), 7.99 (br d, J=8.8 Hz, 1H), 7.76-7.90 (m, 1H), 7.46-7.72 (m, 5H), 2.15 ppm (s, 3H).

Example 11—Preparation of Additional Indazol-5-yl-amino-1,2,4-thiadiazol-3-yl Compounds Compounds in Table 3-1 below were prepared based on procedures described in the examples above and detailed description.

TABLE 3-1

| No. | Chemical Structure | NMR Physical Characterization Data | MS |
|---|---|---|---|
| IV-1 | 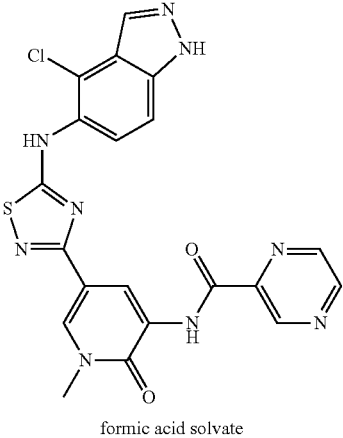 [SMILES: Cn1cc(-c2nsc(Nc3ccc4[nH]ncc4c3Cl)n2)cc(NC(=O)c2cnccn2)c1=O] formic acid solvate | $^1$H NMR (400 MHz, DMSO-d$_6$, ppm) δ 13.53 (s, 1H), 10.64 (s, 1H), 10.55 (s, 1H), 9.36 (d, J = 1.5 Hz, 1H), 9.18 (d, J = 2.3 Hz, 1H), 9.00 (d, J = 2.5 Hz, 1H), 8.87 (dd, J = 2.5,1.5 Hz, 1H), 8.25 (d, J = 2.3 Hz, 1H), 8.18 (s, 1H), 8.00 (d, J = 8.9 Hz, 1H), 7.66 (d, J = 8.9 Hz, 1H), 7.13 (s, 1H), 3.68 (s, 3H) | 480 |
| IV-2 | 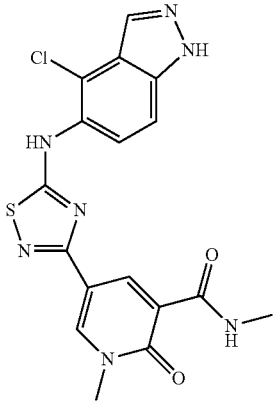 [SMILES: CNC(=O)c1cc(-c2nsc(Nc3ccc4[nH]ncc4c3Cl)n2)cn(C)c1=O] | $^1$H NMR (300 MHz, DMSO-d$_6$, ppm) δ 13.67(s, 1H), 9.48(s, 1H), 8.96(s, 1H), 8.68(s, 1H), 8.16(s, 1H), 7.95(d, J = 8.8 Hz, 1H), 7.63(d, J = 8.8 Hz, 1H), 3.67(s, 3H), 2.85(s, 3H) | 416 |
| IV-3 | 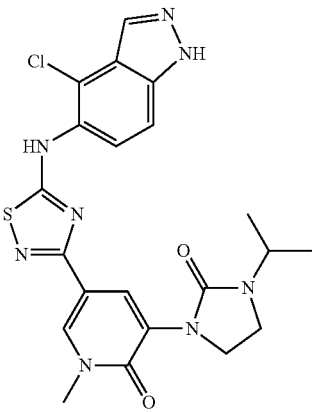 [SMILES: CC(C)N1CCN(c2cc(-c3nsc(Nc4ccc5[nH]ncc5c4Cl)n3)cn(C)c2=O)C1=O] | $^1$H NMR (300 MHz, DMSO-d$_6$, ppm) δ 13.51 (s, 1H), 10.56 (s, 1H), 8.29 (d, J = 2.4 Hz, 1H), 8.20-8.15 (m, 2H), 7.97 (d, J = 8.8 Hz, 1H), 7.63 (d, J = 8.9 Hz, 1H), 4.03-3.98 (m, 1H), 3.83 (dd, J = 9.1, 6.8 Hz, 2H), 3.57 (s, 3H), 3.39 (s, 2H), 1.11 (d, J = 6.8 Hz, 6H) | 485 |

TABLE 3-1-continued

| No. | Chemical Structure | NMR Physical Characterization Data | MS |
|---|---|---|---|
| IV-4 | 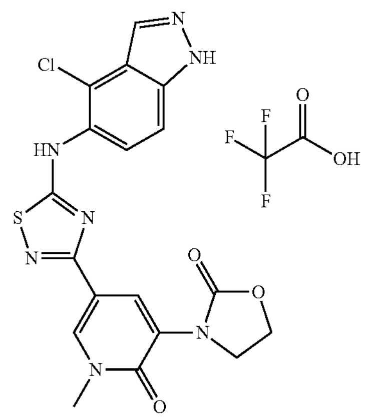 [SMILES: Cn1cc(-c2nsc(Nc3ccc4[nH]ncc4c3Cl)n2)cc(N2CCOC2=O)c1=O ; O=C(O)C(F)(F)F] | $^1$H NMR (400 MHz, DMSO-d$_6$, ppm) δ 13.51 (s, 1H), 10.58 (s, 1H), 8.41 (d, J = 2.4 Hz, 1H), 8.22 (d, J = 2.4 Hz, 1H), 8.17 (s, 1H), 7.98 (d, J = 8.9 Hz, 1H), 7.64 (dd, J = 8.8, 1.0 Hz, 1H), 4.43 (dd, J = 8.9, 7.0 Hz, 2H), 4.11-3.95 (m, 2H), 3.60 (s, 3H) | 444 |
| IV-5 | 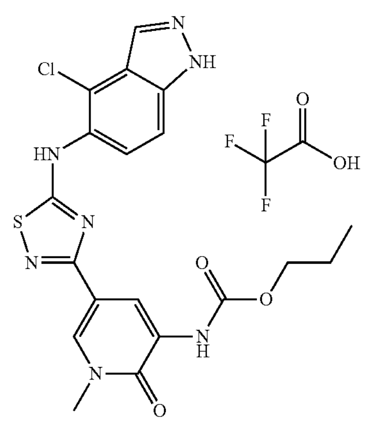 [SMILES: CCCOC(=O)Nc1cc(-c2nsc(Nc3ccc4[nH]ncc4c3Cl)n2)cn(C)c1=O ; O=C(O)C(F)(F)F] | $^1$H NMR (300 MHz, DMSO-d$_6$, ppm) δ 13.51 (s, 1H), 10.57 (s, 1H), 8.58 (d, J = 2.3 Hz, 1H), 8.27 (s, 1H), 8.19-8.15 (m, 1H), 8.11 (d, J = 2.3 Hz, 1H), 7.98 (d, J = 8.8 Hz, 1H), 7.64 (dd, J = 8.8, 1.0 Hz, 1H), 4.08 (t, J = 6.6 Hz, 2H), 3.61 (s, 3H), 1.64 (q, J = 7.0 Hz, 2H), 0.93 (t, J = 7.4 Hz, 3H) | 460 |
| IV-6 | 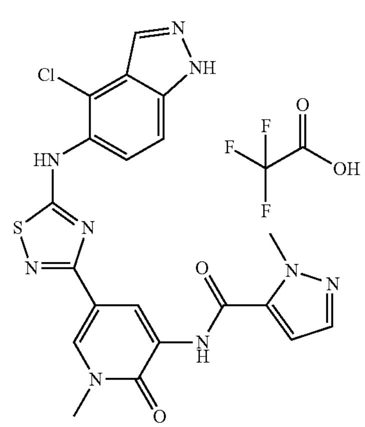 | $^1$H NMR (400 MHz, DMSO-d$_6$, ppm) δ 13.53 (s, 1H), 10.62 (s, 1H), 9.27 (s, 1H), 8.93 (d, J = 2.3 Hz, 1H), 8.24 (d, J = 2.3 Hz, 1H), 8.18 (s, 1H), 7.98 (d, J = 9.0 Hz, 1H), 7.65 (d, J = 8.8 Hz, 1H), 7.56 (d, J = 2.1 Hz, 2H), 7.14-7.02 (m, 2H), 6.97 (d, J = 9.0 Hz, 1H), 4.11 (s, 3H), 3.65 (s, 3H), 1.25-0.96 (m, 5H) | 482.92 |

TABLE 3-1-continued

| No. | Chemical Structure | NMR Physical Characterization Data | MS |
|---|---|---|---|
| IV-7 | 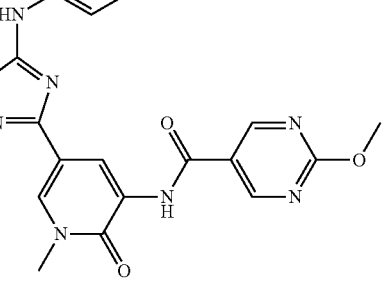 formic acid solvate | $^1$H NMR (400 MHz, DMSO-d$_6$, ppm) δ 13.53 (s, 1H), 10.61 (s, 1H), 9.84 (s, 1H), 9.07 (s, 2H), 8.99 (d, J = 2.3 Hz, 1H), 8.25 (d, J = 2.3 Hz, 1H), 8.18 (s, 1H), 7.99 (d, J = 8.9 Hz, 1H), 7.65 (dd, J = 8.8, 1.0 Hz, 1H), 4.02 (s, 3H), 3.66 (s, 3H) | 510 |
| IV-8 | 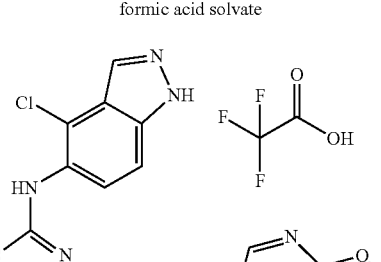 | $^1$H NMR (400 MHz, DMSO-d$_6$, ppm): δ 13.54 (s, 1H), 10.76 (d, J = 8.8 Hz, 2H), 9.16 (s, 2H), 9.04 (dd, J = 11.0, 2.1 Hz, 2H), 8.87 (t, J = 2.2 Hz, 1H), 8.17 (d, J = 15.3 Hz, 1H), 8.00 (d, J = 8.9 Hz, 1H), 7.67 (d, J = 8.9 Hz, 1H), 4.03 (s, 3H) | 480 |
| IV-9 | 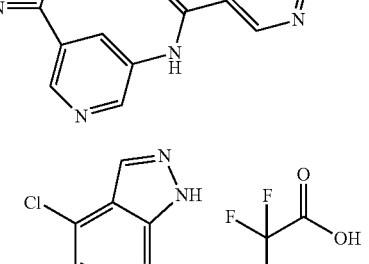 | $^1$H NMR (300 MHz, DMSO-d$_6$, ppm) δ 113.53 (d, J = 7.2 Hz, 1H), 10.60 (s, 1H), 8.18 (s, 1H), 8.05 (d, J = 8.8 Hz, 1H), 7.95 (d, J = 8.0 Hz, 1H), 7.78-7.63 (m, 3H), 7.42 (t, J = 8.0 Hz, 1H), 7.07 (dd, J = 8.4, 2.6 Hz, 1H), 4.51 (s, 2H), 3.97 (h, J = 6.9 Hz, 1H), 1.09 (d, J = 6.6 Hz, 6H) | 443 |
| IV-10 | 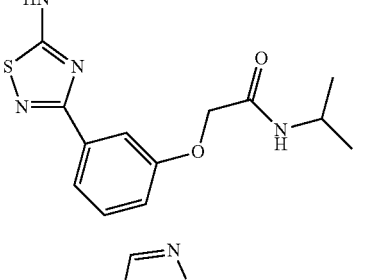 | $^1$H NMR (300 MHz, DMSO-d$_6$, ppm) δ 13.52 (s, 1H), 10.60 (s, 1H), 9.63 (s, 1H), 9.05 (d, J = 2.3 Hz, 1H), 8.17 (d, J = 2.2 Hz, 2H), 8.03-7.88 (m, 2H), 7.65 (d, J = 9.1 Hz, 1H), 6.79 (d, J = 2.3 Hz, 1H), 3.98 (s, 3H), 3.66 (s, 3H) | 482.3 |

TABLE 3-1-continued

| No. | Chemical Structure | NMR Physical Characterization Data | MS |
|---|---|---|---|
| IV-11 | 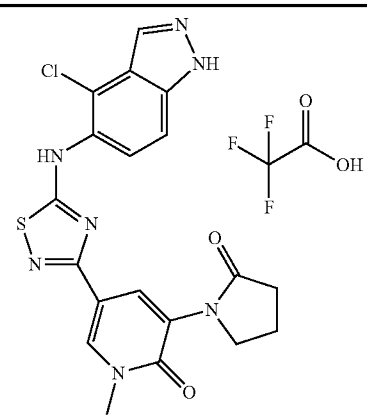 | $^1$H NMR (400 MHz, DMSO-d$_6$, ppm) δ 13.53 (d, J = 14.7 Hz, 1H), 10.57 (s, 1H), 8.40 (d, J = 2.4 Hz, 1H), 8.21-8.11 (m, 2H), 7.97 (d, J = 8.9 Hz, 1H), 7.64 (dd, J = 8.9, 1.0 Hz, 1H), 3.79 (t, J = 7.0 Hz, 2H), 3.59 (s, 3H), 2.40 (t, J = 8.0 Hz, 2H), 2.06 (p, J = 7.5 Hz, 2H) | 442 |
| IV-12 | 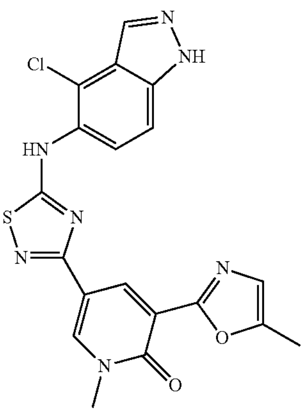 [SMILES: Cc1cnc(-c2cc(-c3nsc(Nc4ccc5[nH]ncc5c4Cl)n3)cn(C)c2=O)o1] | $^1$H NMR (400 MHz, DMSO-d$_6$, ppm) δ 13.53 (s, 1H), 10.63 (s, 1H), 8.68 (d, J = 2.5 Hz, 1H), 8.60 (d, J = 2.4 Hz, 1H), 8.18 (s, 1H), 7.97 (d, J = 8.8 Hz, 1H), 7.65 (dd, J = 8.9, 1.0 Hz, 1H), 6.99 (s, 1H), 3.63 (s, 3H), 2.38 (s, 3H) | 440 |
| IV-13 | 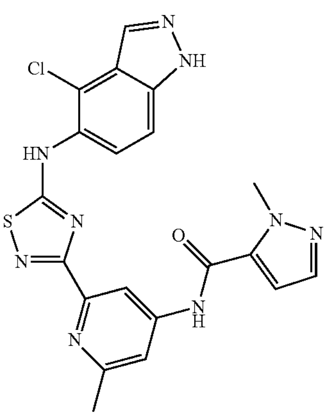 [SMILES: Cc1cc(NC(=O)c2ccnn2C)cc(-c2nsc(Nc3ccc4[nH]ncc4c3Cl)n2)n1] | $^1$H NMR (400 MHz, DMSO-d$_6$, ppm) δ 13.55 (s, 1H), 10.58 (s, 2H), 8.37 (d, J = 1.9 Hz, 1H), 8.19 (s, 1H), 7.92 (d, J = 8.8 Hz, 1H), 7.78 (d, J = 1.9 Hz, 1H), 7.66 (dd, J = 8.8, 1.0 Hz, 1H), 7.57 (d, J = 2.1 Hz, 1H), 7.16 (d, J = 2.1 Hz, 1H), 4.11 (s, 4H), 3.17 (d, J = 5.2 Hz, 1H), 2.00 (s, 1H), 1.24 (s, 1H), 1.18 (t, J = 7.1 Hz, 1H) | 466.1 |
| IV-14 | 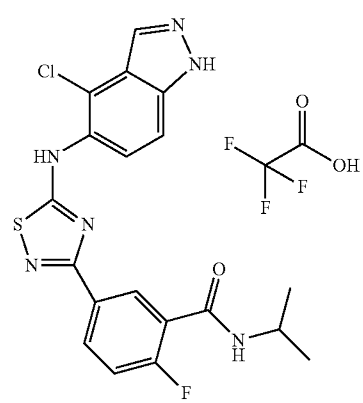 [SMILES: CC(C)NC(=O)c1cc(-c2nsc(Nc3ccc4[nH]ncc4c3Cl)n2)ccc1F ; O=C(O)C(F)(F)F] | $^1$H NMR (300 MHz, DMSO-d$_6$, ppm) δ 13.52 (s, 1H), 10.66 (s, 1H), 8.36-8.10 (m, 4H), 7.97 (d, J = 8.8 Hz, 1H), 7.70-7.61 (m, 1H), 7.39 (dd, J = 10.0, 8.6 Hz, 1H), 4.08 (dq, J = 13.6, 6.8 Hz, 1H), 1.17 (d, J = 6.6 Hz, 6H) | 545.91 |

TABLE 3-1-continued

| No. | Chemical Structure | NMR Physical Characterization Data | MS |
| --- | --- | --- | --- |
| IV-15 | 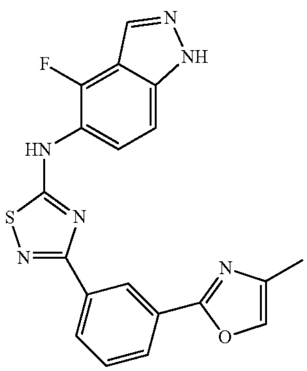 [SMILES: Cc1coc(-c2cccc(-c3nsc(Nc4ccc5[nH]ncc5c4F)n3)c2)n1] | $^1$H NMR (300 MHz, DMSO-d$_6$, ppm) δ 13.54-13.47 (m, 1H), 10.73 (s, 1H), 8.71 (d, J = 1.8 Hz, 1H), 8.31-8.19 (m, 2H), 8.11-7.92 (m, 3H), 7.66 (t, J = 7.8 Hz, 1H), 7.52 (d, J = 8.9 Hz, 1H), 2.20 (d, J = 1.3 Hz, 3H) | 393 |
| IV-16 | 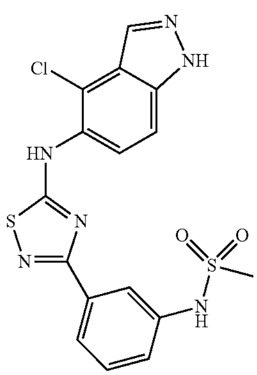 [SMILES: CS(=O)(=O)Nc1cccc(-c2nsc(Nc3ccc4[nH]ncc4c3Cl)n2)c1] | $^1$H NMR (300 MHz, DMSO-d$_6$, ppm) δ 13.53(s, 1H), 10.62(s, 1H), 9.91(s, 1H), 8.17(s, 1H), 8.01-7.98(m, 2H), 7.83(d, J = 7.8 Hz, 1H), 7.64(d, J = 8.7 Hz, 1H), 7.44(t, J = 7.8 Hz, 1H), 7.32(d, J = 6.9 Hz, 1H), 3.01(s, 3H) | 421.02 |
| IV-17 | 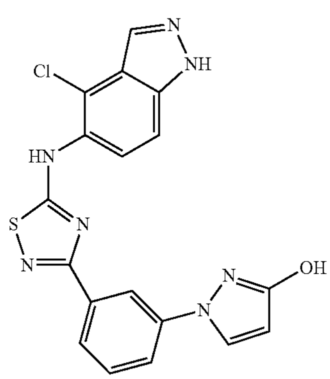 [SMILES: Oc1ccn(-c2cccc(-c3nsc(Nc4ccc5[nH]ncc5c4Cl)n3)c2)n1] | $^1$H NMR (400 MHz, DMSO-d$_6$, ppm) δ 13.52 (s, 1H), 10.63 (s, 1H), 10.30 (s, 1H), 8.41 (t, J = 1.9 Hz, 1H), 8.28 (d, J = 2.6 Hz, 1H), 8.17 (t, J = 1.3 Hz, 1H), 7.97 (d, J = 8.9 Hz, 1H), 7.89 (dt, J = 7.7, 1.2 Hz, 1H), 7.77 (ddd, J = 8.2, 2.3, 1.0 Hz, 1H), 7.66 (dd, J = 8.9, 1.0 Hz, 1H), 7.53 (t, J = 7.9 Hz, 1H), 5.84 (d, J = 2.5 Hz, 1H) | 410 |
| IV-18 | 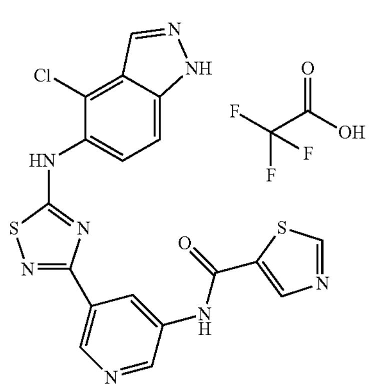 | $^1$H NMR (300 MHz, DMSO-d$_6$, ppm) δ 13.52 (s, 1H), 10.80 (s, 1H), 10.71 (s, 1H), 9.33 (s, 1H), 9.01 (dd, J = 9.1, 2.2 Hz, 1H), 8.82-8.69 (m, 2H), 8.17 (s, 1H), 7.97 (d, J = 8.8 Hz, 1H), 7.65 (d, J = 8.9 Hz, 1H), 7.27-6.91 (m, 2H) | 454.95 |

TABLE 3-1-continued

| No. | Chemical Structure | NMR Physical Characterization Data | MS |
|---|---|---|---|
| IV-19 | 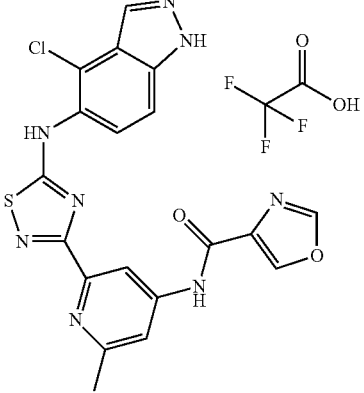 | ¹H NMR (400 MHz, DMSO-d₆, ppm) δ 13.55 (s, 1H), 10.76 (s, 1H), 8.91 (d, J = 26.1 Hz, 1H), 8.69 (s, 1H), 8.60 (s, 1H), 8.20 (s, 1H), 7.95 (d, J = 9.0 Hz, 2H), 7.67 (d, J = 8.9 Hz, 1H), 2.59 (s, 3H) | 453 |
| IV-20 | 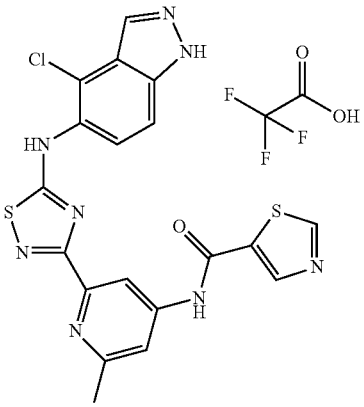 | ¹H NMR (400 MHz, DMSO-d₆, ppm) δ 13.56 (s, 1H), 10.74 (s, 1H), 9.39 (s, 1H), 8.77 (s, 1H), 8.38 (s, 1H), 8.20 (s, 1H), 7.91 (d, J = 8.9 Hz, 2H), 7.67 (d, J = 8.8 Hz, 1H), 2.60 (s, 3H) | 469 |
| IV-21 | 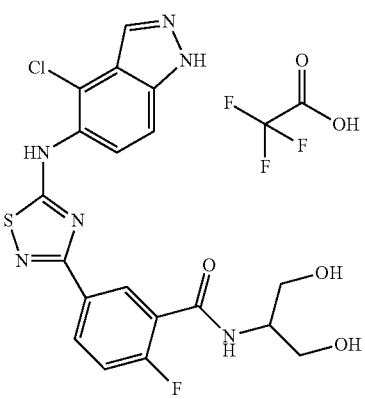 [SMILES: O=C(NC(CO)CO)c1cc(-c2nsc(Nc3ccc4[nH]ncc4c3Cl)n2)ccc1F ; O=C(O)C(F)(F)F] | ¹H NMR (300 MHz, DMSO-d₆, ppm) δ 13.55 (s, 1H), 10.70 (s, 1H), 8.67 (dd, J = 7.1, 2.3 Hz, 1H), 8.36 (ddd, J = 8.7, 4.7, 2.4 Hz, 1H), 8.19 (s, 1H), 8.10 (s, 2H), 7.97 (d, J = 8.9 Hz, 1H), 7.67 (d, J = 8.8 Hz, 1H), 7.51 (dd, J = 10.7, 8.7 Hz, 1H), 5.46 (s, 1H), 4.48 (qd, J = 11.9, 5.5 Hz, 2H), 3.69 (d, J = 12.7 Hz, 2H), 3.56 (s, 2H) | 463 |
| IV-22 | 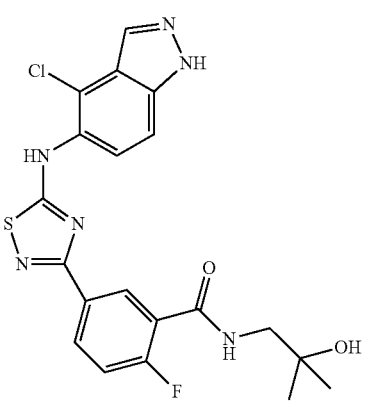 [SMILES: CC(C)(O)CNC(=O)c1cc(-c2nsc(Nc3ccc4[nH]ncc4c3Cl)n2)ccc1F] | ¹H NMR (300 MHz, DMSO-d₆, ppm) δ 13.53 (s, 1H), 10.66 (s, 1H), 8.33 (dd, J = 7.0, 2.3 Hz, 1H), 8.28-8.14 (m, 3H), 7.99 (d, J = 9.0 Hz, 1H), 7.65 (d, J = 8.9 Hz, 1H), 7.41 (dd, J = 10.2, 8.6 Hz, 1H), 4.57 (s, 1H), 3.26 (d, J = 6.0 Hz, 2H), 1.24 (s, 1H), 1.14 (s, 6H) | 461 |

TABLE 3-1-continued

| No. | Chemical Structure | NMR Physical Characterization Data | MS |
|---|---|---|---|
| IV-23 | 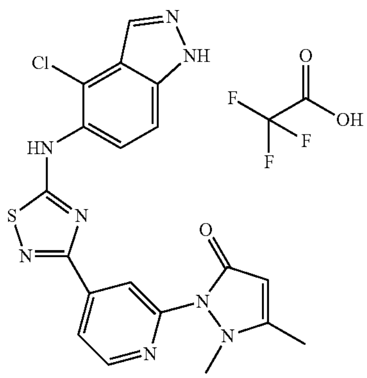 [SMILES: Cc1cc(=O)n(-c2cc(-c3nsc(Nc4ccc5[nH]ncc5c4Cl)n3)ccn2)n1C ; O=C(O)C(F)(F)F] | $^1$H NMR (400 MHz, DMSO-d$_6$, ppm) δ 8.54 (d, J = 5.2 Hz, 1H), 8.36 (s, 1H), 8.14 (d, J = 1.0 Hz, 1H), 7.80 (t, J = 9.5 Hz, 2H), 7.60 (d, J = 8.5 Hz, 1H), 6.04 (s, 1H), 3.28 (s, 3H), 2.23 (s, 3H) | 439.25 |
| IV-24 | 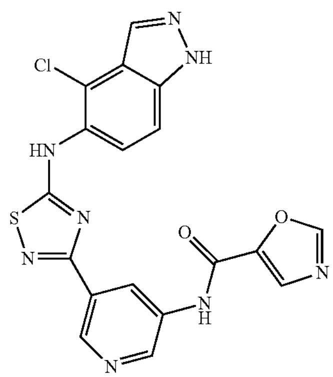 [SMILES: O=C(Nc1cncc(-c2nsc(Nc3ccc4[nH]ncc4c3Cl)n2)c1)c1cnco1] | $^1$H NMR (300 MHz, DMSO-d$_6$, ppm): δ 9.02 (dd, J = 4.6, 2.2 Hz, 2H), 8.84 (t, J = 2.2 Hz, 1H), 8.72 (s, 1H), 8.18 (s, 1H), 8.06 (s, 1H), 7.99 (d, J = 8.8 Hz, 1H), 7.67 (dd, J = 8.8, 1.0 Hz, 1H) | 439/2 |
| IV-25 | 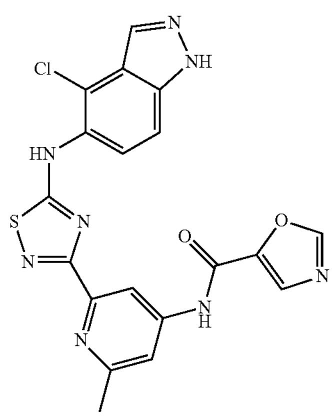 [SMILES: Cc1cc(NC(=O)c2cnco2)cc(-c2nsc(Nc3ccc4[nH]ncc4c3Cl)n2)n1] | $^1$H NMR (300 MHz, DMSO-d$_6$, ppm) δ 13.53 (s, 1H), 10.82 (s, 1H), 10.65 (s, 1H), 8.71 (s, 1H), 8.34 (d, J = 1.8 Hz, 1H), 8.18 (s, 1H), 8.09 (s, 1H), 7.93 (d, J = 8.8 Hz, 1H), 7.77 (d, J = 1.9 Hz, 1H), 7.65 (d, J = 8.8 Hz, 1H), 1.28-1.13 (m, 3H) | 453 |
| IV-26 | 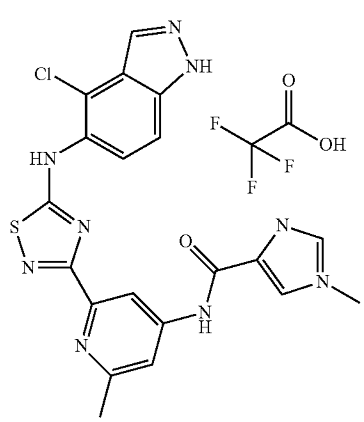 | $^1$H NMR (400 MHz, DMSO-d$_6$, ppm) δ 13.55 (s, 1H), 11.09 (s, 1H), 10.87 (s, 1H), 8.82 (d, J = 21.7 Hz, 1H), 8.18 (d, J = 6.6 Hz, 2H), 8.02 (d, J = 1.3 Hz, 1H), 7.96-7.86 (m, 2H), 7.66 (d, J = 8.8 Hz, 1H), 3.75 (s, 3H), 2.65 (s, 3H) | 466.05 |

TABLE 3-1-continued

| No. | Chemical Structure | NMR Physical Characterization Data | MS |
|---|---|---|---|
| IV-27 | 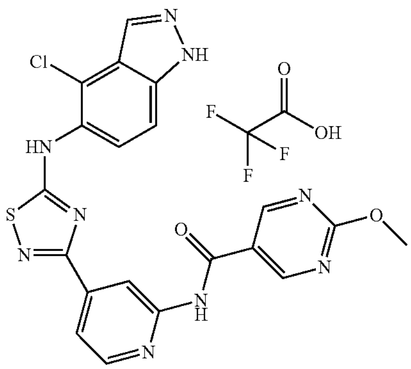 | $^1$H NMR (400 MHz, DMSO-d$_6$, ppm) δ 13.53(s, 1H), 11.23(s, 1H), 10.79(s, 1H), 9.17(s, 2H), 8.92(s, 1H), 8.52(d, J = 5.2 Hz, 1H), 8.19(s, 1H), 7.95(d, J = 8.4 Hz, 1H), 7.79(dd, J = 5.2Hz, 1.2 Hz, 1H), 7.66(d, J = 8.8 Hz, 1H), 4.02(s, 3H) | 480 |
| IV-28 | 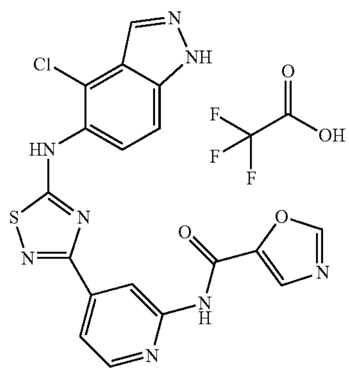 | $^1$H NMR (400 MHz, DMSO-d$_6$, ppm) δ 13.57(s, 1H), 11.17(s, 1H), 10.78(s, 1H), 8.85(s, 1H), 8.67(s, 1H), 8.52(d, J = 4.8 Hz, 1H), 8.26(s, 1H), 8.19(s, 1H), 7.97(d, J = 8.8 Hz, 1H), 7.79(dd, J = 5.2 Hz, 1.2 Hz, 1H), 7.66(d, J = 8.8 Hz, 1H) | 439 |
| IV-29 | 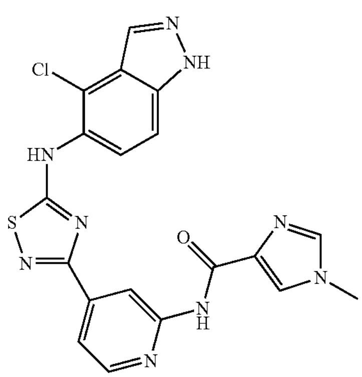 [SMILES: Cn1cnc(C(=O)Nc2cc(-c3nsc(Nc4ccc5[nH]ncc5c4Cl)n3)ccn2)c1] | $^1$H NMR (400 MHz, DMSO-d$_6$, ppm) δ 13.54(s, 1H), 10.78(s, 1H), 10.11(s, 1H), 8.90(s, 1H), 8.51 (d, J = 4.8 Hz, 1H), 8.19-8.11(m, 3H), 7.97(d, J = 8.8 Hz, 1H), 7.77(dd, J = 5.2 Hz, 1.2 Hz, 1H), 7.66(d, J = 8.8 Hz, 1H), 3.79(s, 3H) | 452 |
| IV-30 | 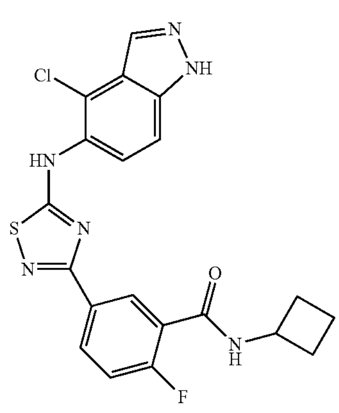 [SMILES: O=C(NC1CCC1)c1cc(-c2nsc(Nc3ccc4[nH]ncc4c3Cl)n2)ccc1F] | $^1$H NMR (300 MHz, DMSO-d$_6$, ppm) δ 13.52 (s, 1H), 10.65 (s, 1H), 8.69 (d, J = 7.5 Hz, 1H), 8.29-8.13 (m, 3H), 7.97 (d, J = 8.9 Hz, 1H), 7.66 (d, J = 8.9 Hz, 1H), 7.39 (dd, J = 10.0, 8.6 Hz, 1H), 4.40 (q, J = 8.1 Hz, 1H), 2.23 (dt, J = 10.9, 5.2 Hz, 2H), 2.04 (qd, J = 11.6, 10.7, 7.5 Hz, 2H), 1.77-1.59 (m, 2H), 1.25 (d, J = 4.6 Hz, 1H) | 443 |

TABLE 3-1-continued

| No. | Chemical Structure | NMR Physical Characterization Data | MS |
|---|---|---|---|
| IV-31 | 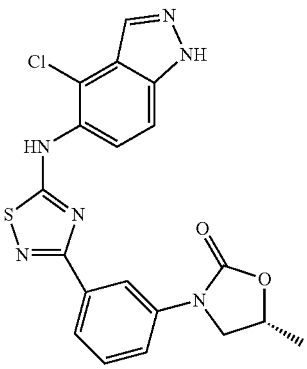 [SMILES: C[C@@H]1CN(c2cccc(-c3nsc(Nc4ccc5[nH]ncc5c4Cl)n3)c2)C(=O)O1] | $^1$H-NMR (400 MHz, DMSO-d$_6$, ppm) δ 12.5 (s, 1H), 10.62 (s, 1H), 8.38 (m, 1H), 8.08 (m, 1H), 7.98 (m, 1H), 7.82 (m, 1H), 7.61 (m, 2H), 7.44 (m, 1H), 3.8 (m, 1H), 4.21 (m, 1H), 3.72 (m, 1H), 1.42 (d, 3H). | 427.02, 429.05 |
| IV-32 | 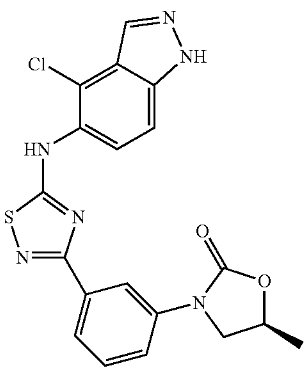 [SMILES: C[C@H]1CN(c2cccc(-c3nsc(Nc4ccc5[nH]ncc5c4Cl)n3)c2)C(=O)O1] | $^1$H-NMR (400 MHz, DMSO-d$_6$, ppm) δ 12.5 (s, 1H), 10.62 (s, 1H), 8.38 (m, 1H), 8.08 (m, 1H), 7.98 (m, 1H), 7.82 (m, 1H), 7.61 (m, 2H), 7.44 (m, 1H), 3.8 (m, 1H), 4.21 (m, 1H), 3.72 (m, 1H), 1.42 (d, 3H). | 427.06, 429.09 |
| IV-33 | 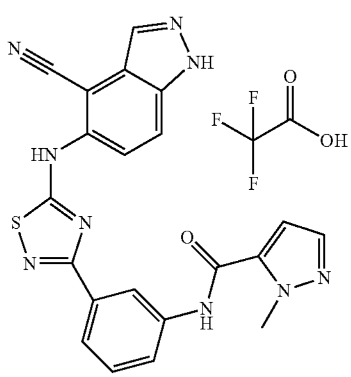 | $^1$H-NMR (400 MHz, DMSO-d$_6$, ppm) δ 13.74 (s, 1H), 11.2 (s, 1H), 10.36 (s, 1H), 8.52 (s, 1H), 8.1 (m, 2H), 8.02 (m, 1H), 7.88 (m, 2H), 7.55 (s, 1H), 7.45 (m, 1H), 7.1 (m, 1H), 4.1 (s, 3H). | 442.13 |
| IV-34 | 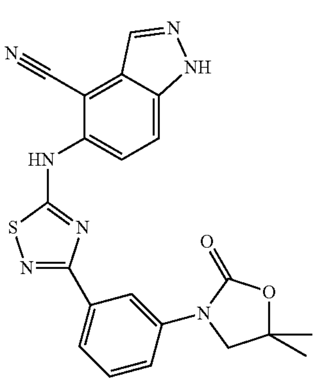 [SMILES: CC1(C)CN(c2cccc(-c3nsc(Nc4ccc5[nH]ncc5c4C#N)n3)c2)C(=O)O1] | $^1$H-NMR (400 MHz, DMSO-d$_6$, ppm) δ 13.74 (s, 1H), 11.2 (s, 1H), 8.39 (m, 1H), 8.2 (m, 2H), 8.0 (m, 1H), 7.85 (m, 1H), 7.6 (m, 1H), 7.5 (m, 1H), 3.94 (s, 2H), 1.48 (s, 6H). | 454.08 (M + Na) |

TABLE 3-1-continued

| No. | Chemical Structure | NMR Physical Characterization Data | MS |
| --- | --- | --- | --- |
| IV-35 | 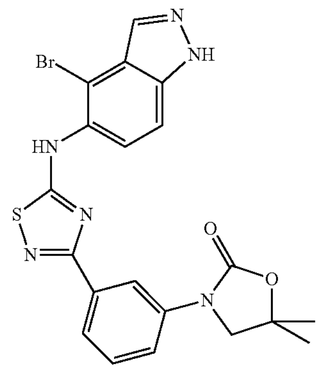 [SMILES: CC1(C)CN(c2cccc(-c3nsc(Nc4ccc5[nH]ncc5c4Br)n3)c2)C(=O)O1] | ¹H-NMR (400 MHz, DMSO-d₆, ppm) δ 13.55 (s, 1H), 10.58 (s, 1H), 8.37 (m, 1H), 8.08 (m, 1H), 7.82 (m, 2H), 7.66 (m, 1H), 7.58 (m, 1H), 7.46 (m, 1H), 3.92 (s, 2H), 1.48 (s, 6H). | 485.10, 487 |
| IV-36 | 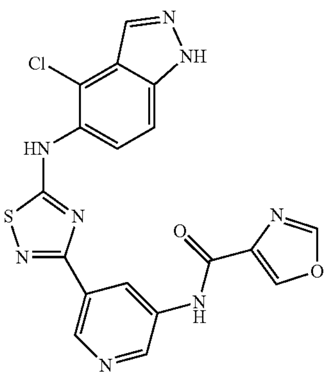 [SMILES: O=C(Nc1cncc(-c2nsc(Nc3ccc4[nH]ncc4c3Cl)n2)c1)c1cocn1] | ¹H NMR (400 MHz, DMSO-d₆, ppm) δ 13.55 (s, 1H), 10.74 (s, 1H), 10.70 (s, 1H), 9.08 (d, J = 2.4 Hz, 1H), 9.00 (dd, J = 7.1, 2.0 Hz, 2H), 8.89 (d, J = 1.0 Hz, 1H), 8.68 (d, J = 1.0 Hz, 1H), 8.19 (d, J = 1.0 Hz, 1H), 8.02 (d, J = 8.8 Hz, 1H), 7.68 (dd, J = 8.9.1.0 Hz, 1H) | 439 |
| IV-37 | 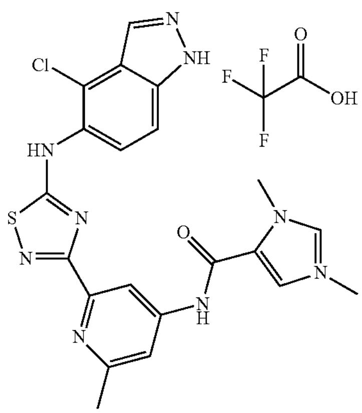 | ¹H NMR (300 MHz, DMSO-d₆) δ 13.55 (s, 1H), 10.80 (s, 2H), 8.48 (s, 1H), 8.21 (s, 1H), 7.92 (d, J = 8.9 Hz, 1H), 7.67 (d, J = 8.8 Hz, 1H), 6.96 (s, 1H), 4.03 (s, 3H), 2.62 (s, 3H), 2.23 (s, 3H) | 480 |
| IV-38 | 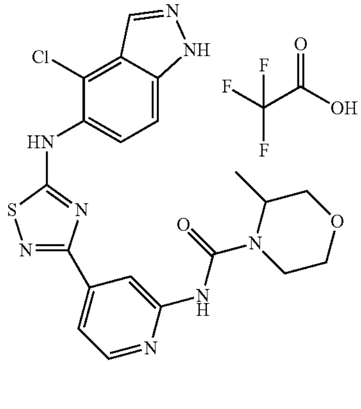 | ¹H NMR (400 MHz, DMSO-d₆, ppm) δ 13.53(s, 1H), 10.78(s, 1H), 9.72(s, 1H), 8.43(s, 1H), 8.37(d, J = 5.6 Hz, 1H), 8.19(d, J = 0.8 Hz, 1H), 7.93(d, J = 8.8 Hz, 1H), 7.70-7.64(m, 2H), 4.26-4.24(m, 1H), 3.88-3.81(m, 2H), 3.67-3.64(m, 1H), 3.56-3.52(m, 1H), 3.42-3.36(m, 1H), 3.22-3.16(m, 1H), 1.23(d, J = 6.8 Hz, 3H) | 471 |

TABLE 3-1-continued

| No. | Chemical Structure | NMR Physical Characterization Data | MS |
|---|---|---|---|
| IV-39 | 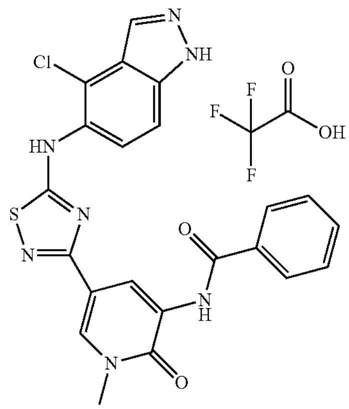 | $^1$H NMR (400 MHz, DMSO-d$_6$, ppm) δ 13.51 (s, 1H), 10.60 (s, 1H), 9.36 (s, 1H), 9.01 (d, J = 2.3 Hz, 1H), 8.20 (d, J = 2.3 Hz, 1H), 8.16 (s, 1H), 7.99-7.91 (m, 3H), 7.66-7.54 (m, 4H), 3.65 (s, 3H) | 478.05 |
| IV-40 | 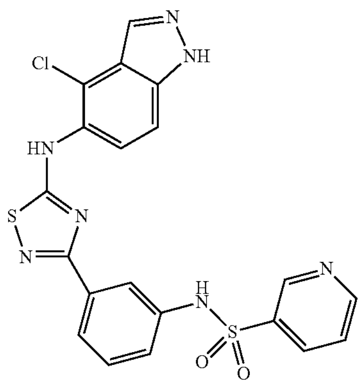 [SMILES: O=S(=O)(Nc1cccc(-c2nsc(Nc3ccc4[nH]ncc4c3Cl)n2)c1)c1cccnc1] | $^1$H NMR (400 MHz, DMSO-d$_6$, ppm): δ = 13.41-13.56 (m, 1H), 10.38-10.81 (m, 2H), 8.88 (d, J = 1.8 Hz, 1H), 8.75 (dd, J = 4.8, 1.5 Hz, 1H), 8.15 (s, 1H), 8.02-8.11 (m, 1H), 7.90-7.99 (m, 1H), 7.82-7.90 (m, 1H), 7.71-7.79 (m, 1H), 7.60-7.68 (m, 1H), 7.48-7.58 (m, 1H), 7.29-7.39 (m, 1H), 7.12-7.24 (m, 1H) | 483.97, 485.99 |
| IV-41 | 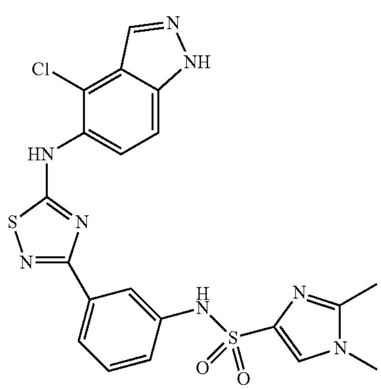 [SMILES: Cc1nc(S(=O)(=O)Nc2cccc(-c3nsc(Nc4ccc5[nH]ncc5c4Cl)n3)c2)cn1C] | $^1$H NMR (400 MHz, DMSO-d$_6$, ppm): δ = 13.26-13.74 (m, 1H), 9.91-10.75 (m, 2H), 8.06-8.26 (m, 1H), 7.80-8.06 (m, 2H), 7.54-7.78 (m, 3H), 7.09-7.40 (m, 2H), 3.49 (s, 3H), 2.21 ppm (s, 3H) | 501.0 |
| IV-42 | 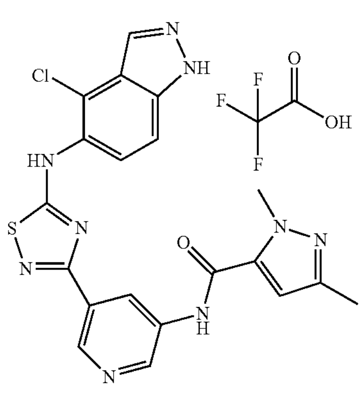 | $^1$H NMR (300 MHz, DMSO-d$_6$, ppm): δ 13.56 (s, 1H), 10.75 (s, 1H), 10.55-10.50 (m, 1H), 9.02 (d, J = 6.1 Hz, 2H), 8.89 (t, J = 2.0 Hz, 1H), 8.19 (d, J = 1.0 Hz, 1H), 8.00 (d, J = 8.9 Hz, 1H), 7.67 (dd, J = 8.9, 1.0 Hz, 1H), 6.91 (s, 1H), 4.03 (s, 3H), 2.22 (s, 3H) | 466 |

TABLE 3-1-continued

| No. | Chemical Structure | NMR Physical Characterization Data | MS |
|---|---|---|---|
| IV-43 | 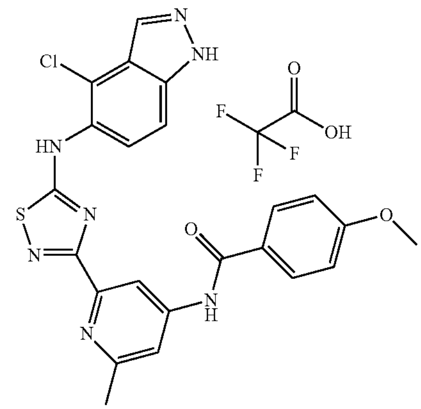 | $^1$H NMR (400 MHz, DMSO-d$_6$, ppm) δ 13.55 (s, 1H), 10.94 (s, 1H), 10.80 (s, 1H), 8.55-8.49 (m, 1H), 8.18 (d, J = 1.0 Hz, 1H), 8.08-7.96 (m, 3H), 7.91 (d, J = 8.8 Hz, 1H), 7.65 (dd, J = 8.8, 1.0 Hz, 1H), 7.14-7.05 (m, 2H), 3.84 (s, 3H), 2.62 (s, 3H) | 492 |
| IV-44 | 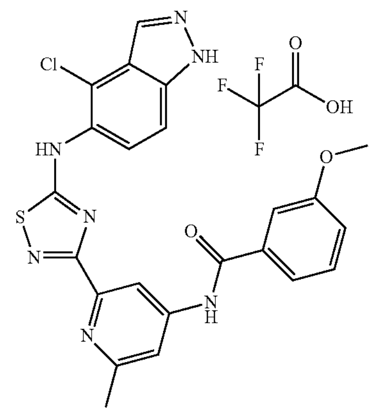 | $^1$H NMR (400 MHz, DMSO-d$_6$, ppm) δ 13.53 (s, 1H), 10.96 (s, 1H), 10.77 (s, 1H), 18.50 (d, J = 1.9 Hz, 1H), 8.18 (s, 1H), 8.01 (d, J = 7.8 Hz, 1H), 7.91 (d, J = 8.8 Hz, 1H), 7.64 (dd, J = 8.8, 1.0 Hz, 1H), 7.60-7.44 (m, 3H), 7.26-7.18 (m, 1H), 3.84 (s, 3H), 2.60 (s, 3H) | 492 |
| IV-45 | 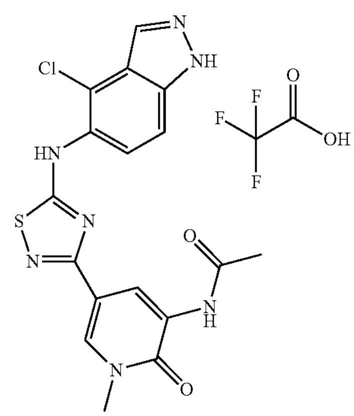 | $^1$H NMR (400 MHz, DMSO-d$_6$, ppm) δ 13.49 (s, 1H), 10.55 (s, 1H), 9.34 (s, 1H), 8.93 (d, J = 2.3 Hz, 1H), 8.15 (s, 1H), 8.10 (d, J = 2.3 Hz, 1H), 7.95 (d, J = 8.9 Hz, 1H), 7.64-7.59 (m, 1H), 7.29-6.86 (m, 1H), 3.59 (s, 3H), 2.14 (s, 3H) | 416.25 |
| IV-46 | 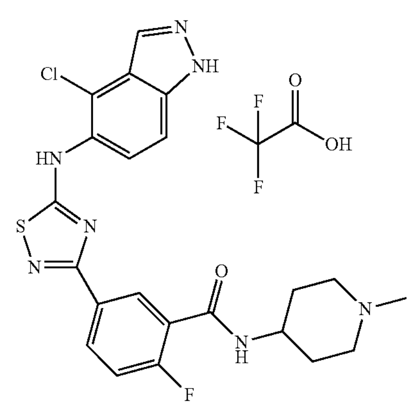 | $^1$H NMR (300 MHz, DMSO-d$_6$, ppm) δ 13.55 (s, 1H), 10.67 (s, 1H), 9.31 (s, 2H), 8.60 (dd, J = 17.9, 7.3 Hz, 1H), 8.30-8.20 (m, 2H), 8.19 (s, 1H), 7.96 (dd, J = 9.0, 3.3 Hz, 1H), 7.74-7.38 (m, 2H), 4.07-3.95 (m, 2H), 2.88 (q, J = 12.1, 11.6 Hz, 2H), 2.10 (dd, J = 4.7, 2.4 Hz, 2H), 1.95 (p, J = 1.9 Hz, 1H), 1.78(m, 2H), 1.32 (q, J = 11.7 Hz, 2H), 0.85 (m, 1H) | 600.99 |

TABLE 3-1-continued

| No. | Chemical Structure | NMR Physical Characterization Data | MS |
|---|---|---|---|
| IV-47 | 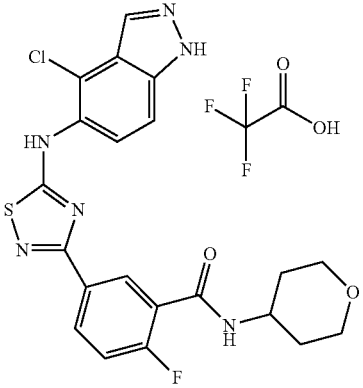 | $^{1}$H NMR (300 MHz, DMSO-d$_{6}$, ppm) δ 13.53 (s, 1H), 10.67 (s, 1H), 8.47 (d, J = 7.7 Hz, 1H), 8.30-8.14 (m, 3H), 7.98 (d, J = 8.9 Hz, 1H), 7.70-7.60 (m, 1H), 7.40 (dd, J = 9.9, 8.7 Hz, 1H), 4.05-3.74 (m, 3H), 3.47-3.32 (m, 2H), 1.80 (d, J = 12.5 Hz, 2H), 1.56 (td, J = 11.8, 4.2 Hz, 2H) | 587.95 |
| IV-48 | 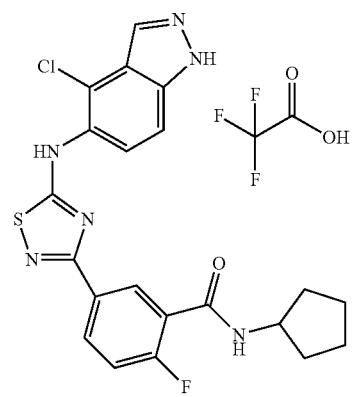 | $^{1}$H NMR (300 MHz, DMSO-d$_{6}$, ppm) δ 13.53 (s, 1H), 10.66 (s, 1H), 8.43 (d, J = 7.2 Hz, 1H), 8.27-8.12 (m, 3H), 7.98 (d, J = 8.9 Hz, 1H), 7.65 (dd, J = 8.9, 1.0 Hz, 1H), 7.38 (dd, J = 9.9, 8.6 Hz, 1H), 4.21 (q, J = 6.7 Hz, 1H), 1.96-1.81 (m, 2H), 1.75-1.43 (m, 6H) | 457 |
| IV-49 | 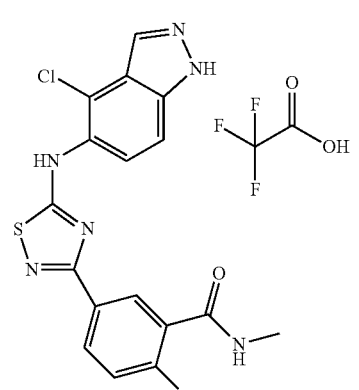 | $^{1}$H NMR (300 MHz, DMSO-d$_{6}$, ppm) δ 13.55 (s, 1H), 10.66 (s, 1H), 8.41-8.28 (m, 2H), 8.26-8.15 (m, 2H), 7.97 (d, J = 8.8 Hz, 1H), 7.66 (dd, J = 8.8, 1.0 Hz, 1H), 7.41 (dd, J = 10.3, 8.7 Hz, 1H), 2.80 (d, J = 4.5 Hz, 3H) | 403 |
| IV-50 | 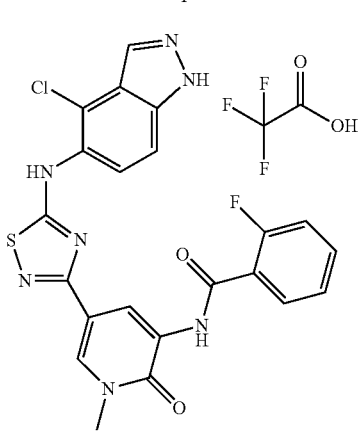 | $^{1}$H NMR (400 MHz, DMSO-d$_{6}$, ppm) δ 13.50 (s, 1H), 10.60 (s, 1H), 9.71 (d, J = 11.5 Hz, 1H), 9.12 (d, J = 2.3 Hz, 1H), 8.31-8.10 (m, 2H), 7.98 (td, J = 7.9, 1.7 Hz, 2H), 7.66 (dt, J = 14.7, 8.1 Hz, 2H), 7.49-7.33 (m, 2H), 3.64 (s, 3H) | 496.1 |

TABLE 3-1-continued

| No. | Chemical Structure | NMR Physical Characterization Data | MS |
|---|---|---|---|
| IV-51 | 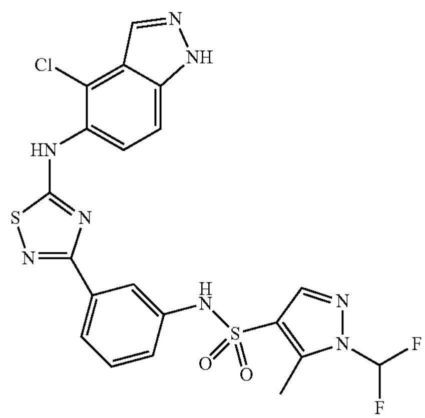 [SMILES: Cc1c(S(=O)(=O)Nc2cccc(-c3nsc(Nc4ccc5[nH]ncc5c4Cl)n3)c2)cnn1C(F)F] | $^1$H NMR (DMSO-d$_6$, 400 MHz, ppm): δ = 13.43-13.56 (m, 1H), 10.30-10.71 (m, 2H), 8.15 (s, 1H), 7.94-8.00 (m, 1H), 7.86-7.93 (m, 1H), 7.91 (t, J = 60.0 Hz, 1H), 7.76-7.82 (m, 1H), 7.63 (d, J = 8.8 Hz, 1H), 7.33-7.41 (m, 1H), 7.19 (s, 1H), 2.43 ppm (s, 3H) | 536.95, 538.97 |
| IV-52 | 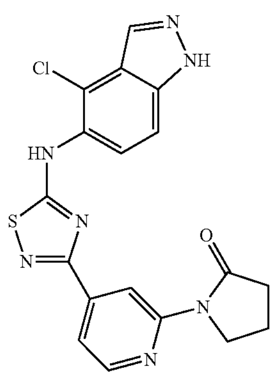 [SMILES: O=C1CCCN1c1cc(-c2nsc(Nc3ccc4[nH]ncc4c3Cl)n2)ccn1] | $^1$H-NMR (400 MHz, DMSO-d$_6$, ppm) δ 13.5 (br s, 1H), 10.6 (br s, 1H), 9.02 (m, 1H), 8.5 (m, 1H), 8.18 (m, 1H), 7.95 (m, 1H), 7.74 (m, 1H), 7.62 (m, 1H), 4.02 (m, 2H), 2.6 (m, 2H), 2.1 (m, 2H). | 412.04, 414.02 |
| IV-53 | 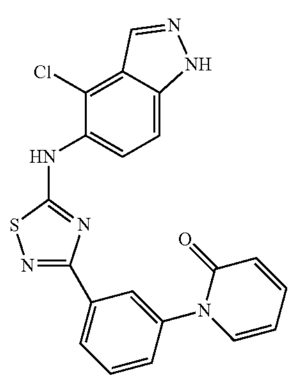 [SMILES: O=c1ccccn1-c1cccc(-c2nsc(Nc3ccc4[nH]ncc4c3Cl)n2)c1] | $^1$H-NMR (400 MHz, DMSO-d$_6$, ppm) δ 13.5 (s, 1H), 10.64 (s, 1H), 8.16 (m, 2H), 8.0 (m, 2H), 7.72 (m, 1H), 7.64 (m, 2H), 7.55 (m, 2H), 6.5 (m, 1H), 6.35 (m, 1H). | 421.08, 423 |
| IV-54 | 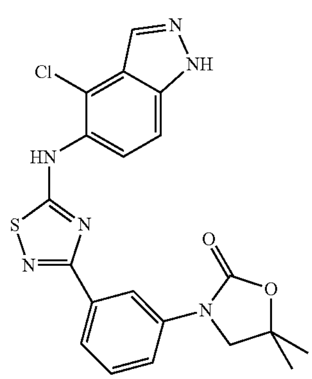 [SMILES: CC1(C)CN(c2cccc(-c3nsc(Nc4ccc5[nH]ncc5c4Cl)n3)c2)C(=O)O1] | $^1$H-NMR (400 MHz, DMSO-d$_6$, ppm) δ 13.52 (s, 1H), 10.62 (s, 1H), 8.38 (m, 1H), 8.18 (m, 1H), 7.98 (m, 1H), 7.84 (m, 1H), 7.64-7.56 (m, 2H), 7.48 (m, 1H), 3.92 (s, 2H), 1.5 (s, 6H). | 441, 443 |

TABLE 3-1-continued

| No. | Chemical Structure | NMR Physical Characterization Data | MS |
|---|---|---|---|
| IV-55 | 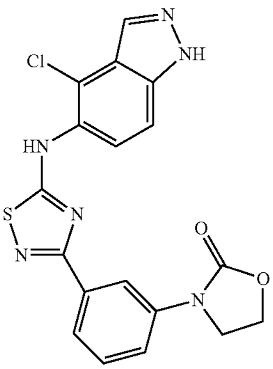 [SMILES: O=C1OCCN1c1cccc(-c2nsc(Nc3ccc4[nH]ncc4c3Cl)n2)c1] | $^1$H-NMR (400 MHz, DMSO-d$_6$, ppm) δ 13.52 (s, 1H), 10.64 (s, 1H), 8.4 (m, 1H), 8.16 (m, 1H), 7.98 (m, 1H), 7.84 (m, 1H), 7.62 (m, 2H), 7.5 (m, 1H), 4.44 (m, 2H), 4.12 (s, 2H). | 413.02, 415 |
| IV-56 | 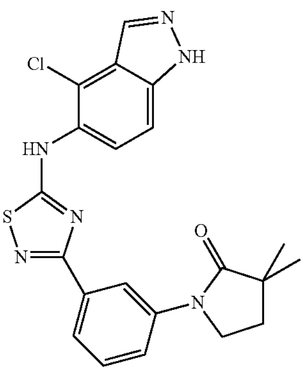 [SMILES: CC1(C)CCN(c2cccc(-c3nsc(Nc4ccc5[nH]ncc5c4Cl)n3)c2)C1=O] | $^1$H-NMR (400 MHz, DMSO-d$_6$, ppm) δ 13.52 (s, 1H), 10.64 (s, 1H), 8.48 (m, 1H), 8.16 (m, 1H), 7.98 (m, 1H), 7.84 (m, 1H), 7.74 (m, 1H), 7.64 (m, 1H), 7.48 (m, 1H), 3.82 (t, 2H), 1.96 (t, 2H), 1.18 (s, 6H). | 439.07, 441 |
| IV-57 | 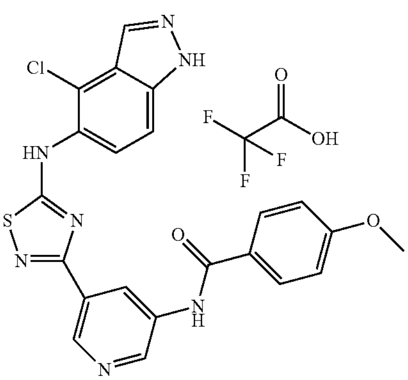 | $^1$H NMR (300 MHz, DMSO-d$_6$, ppm) δ 13.52 (s, 1H), 10.93 (s, 1H), 10.71 (s, 1H), 8.92-8.83 (m, 1H), 8.48 (dd, J = 5.2, 0.9 Hz, 1H), 8.16 (s, 1H), 7.91 (d, J = 8.9 Hz, 1H), 7.75 (dd, J = 5.2, 1.5 Hz, 1H), 7.63 (dd, J = 8.9, 1.0 Hz, 1H), 7.50 (d, J = 2.1 Hz, 1H), 7.29 (d, J = 2.1 Hz, 1H), 4.10 (s, 3H) | 452 |
| IV-58 | 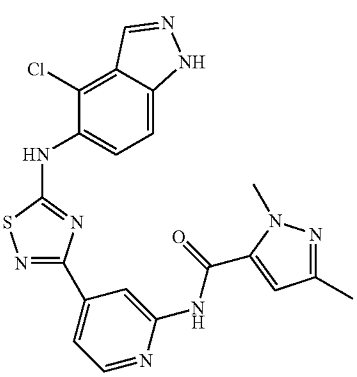 [SMILES: Cc1cc(C(=O)Nc2cc(-c3nsc(Nc4ccc5[nH]ncc5c4Cl)n3)ccn2)n(C)n1] | $^1$H NMR (400 MHz, DMSO-d$_6$, ppm) δ 13.54(s, 1H), 10.84(s, 1H), 8.88(s, 1H), 8.51(d, J = 4.8 Hz, 1H), 8.19(s, 1H), 7.95(d, J = 8.8 Hz, 1H), 7.77(d, J = 5.2 Hz, 1H), 7.66(d, J = 8.8 Hz, 1H), 7.08(d, J = 8.8 Hz, 1H), 4.04(s, 3H), 2.12(s, 3H) | 466 |

TABLE 3-1-continued

| No. | Chemical Structure | NMR Physical Characterization Data | MS |
|---|---|---|---|
| IV-59 | 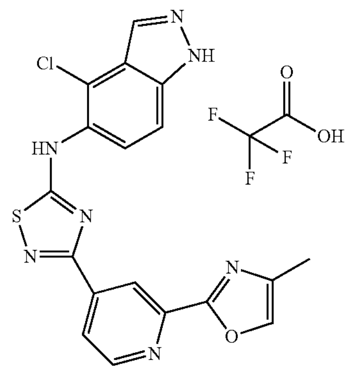 | $^1$H NMR (300 MHz, DMSO-d$_6$, ppm) δ 13.56 (s, 1H), 10.80 (s, 1H), 8.65 (dd, J = 1.6, 0.9 Hz, 1H), 8.20 (d, J = 1.0 Hz, 1H), 8.07 (dd, J = 5.1, 1.6 Hz, 1H), 8.04 (q, J = 1.1 Hz, 1H), 7.96 (d, J = 8.9 Hz, 1H), 7.68 (dd, J = 8.8, 1.0 Hz, 1H), 2.21 (d, J = 1.2 Hz, 3H) | 409.85 |
| IV-60 | 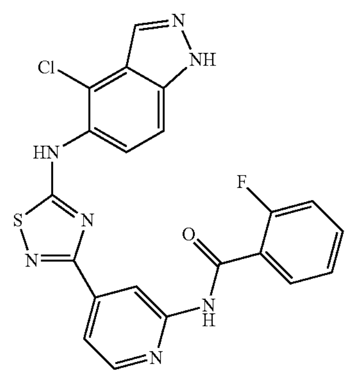 [SMILES: O=C(Nc1cc(-c2nsc(Nc3ccc4[nH]ncc4c3Cl)n2)ccn1)c1ccccc1F] | $^1$H NMR (400 MHz, DMSO-d$_6$, ppm) δ 13.53(s, 1H), 10.94(s, 1H), 10.79(s, 1H), 8.92(s, 1H), 8.49(d, J = 4.8 Hz, 1H), 8.18(s, 1H), 7.96-7.83(m, 1H), 7.78-7.64(m, 4H), 7.35-7.33(m, 2H) | 466 |
| IV-61 | 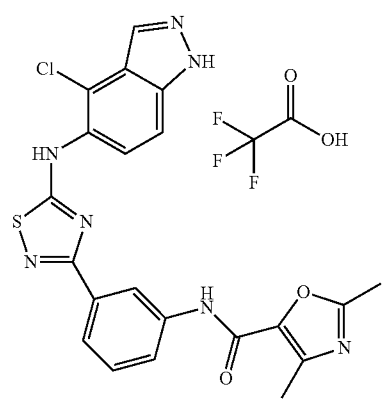 | $^1$H NMR (DMSO-d$_6$, 400 MHz, ppm): δ = 13.50 (br s, 1H), 10.60 (s, 1H), 10.28 (s, 1H), 8.57 (br t, J = 1.8 Hz, 1H), 8.15 (s, 1H), 7.98 (br d, J = 8.8 Hz, 1H), 7.79-7.84 (m, 2H), 7.63 (br d, J = 8.8 Hz, 1H), 7.42 (br t, J = 7.9 Hz, 1H), 2.48 (s, 3H), 2.37 ppm (s, 3H) | 466.02, 467.98 |
| IV-62 | 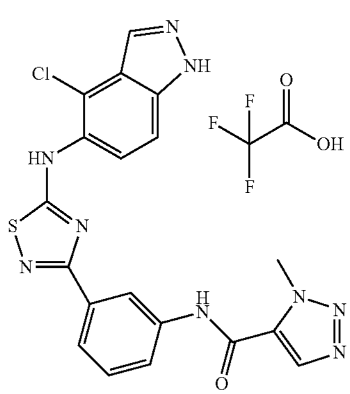 | $^1$H NMR (DMSO-d$_6$, 400 MHz, ppm): δ = 13.51 (s, 1H), 10.63 (s, 1H), 10.61 (s, 1H), 8.50 (s, 1H), 8.41 (s, 1H), 8.16 (s, 1H), 7.97 (br d, J = 9.0 Hz, 1H), 7.81-7.88 (m, 2H), 7.64 (br d, J = 8.8 Hz, 1H), 7.47 (br t, J = 8.0 Hz, 1H), 4.25 ppm (s, 3H) | 451.98 |

| No. | Chemical Structure | NMR Physical Characterization Data | MS |
|---|---|---|---|
| IV-63 | 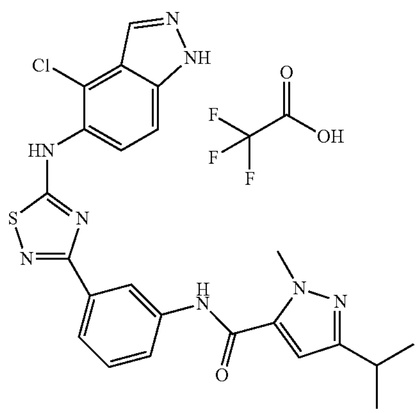 | ¹H NMR (DMSO-d₆, 400 MHz, ppm): δ = 13.51 (s, 1H), 10.60 (s, 1H), 10.26 (s, 1H), 8.48-8.56 (m, 1H), 8.16 (s, 1H), 7.97 (br d, J = 8.8 Hz, 1H), 7.83 (dt, J = 7.9, 2.2 Hz, 2H), 7.64 (br d, J = 9.0 Hz, 1H), 7.40-7.49 (m, 1H), 6.94 (s, 1H), 4.01 (s, 3H), 2.89 (s, 2H), 2.52-2.70 (m, 2H), 1.21 ppm (d, J = 6.8 Hz, 6H) | 493.5, 495.06 |
| IV-64 | 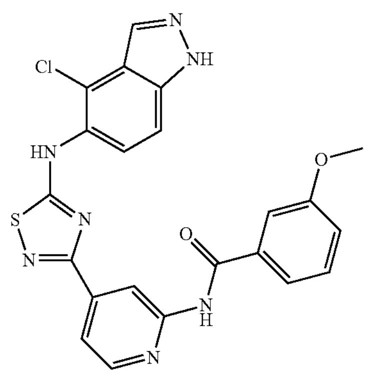 [SMILES: COc1cccc(C(=O)Nc2cc(-c3nsc(Nc4ccc5[nH]ncc5c4Cl)n3)ccn2)c1] | ¹H NMR (400 MHz, DMSO-d₆, ppm) δ 10.95(s, 1H), 8.93(s, 1H), 8.51(d, J = 5.2 Hz, 1H), 8.19(s, 1H), 7.96(d, J = 9.2 Hz, 1H), 7.77(dd, J = 5.2 Hz, 1.2 Hz, 1H), 7.67-7.62(m, 3H), 7.43(t, J = 8.0 Hz, 1H), 7.18-7.16(m, 1H), 3.85(s, 3H) | 478 |
| IV-65 | 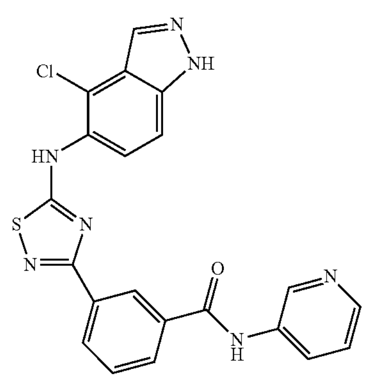 [SMILES: O=C(Nc1cccnc1)c1cccc(-c2nsc(Nc3ccc4[nH]ncc4c3Cl)n2)c1] | ¹H NMR (400 MHz, DMSO-d₆, ppm) δ 13.54(s, 1H), 10.69(s, 1H), 10.66(s, 1H), 8.96(s, 1H), 8.69(s, 1H), 8.34-8.31 (m, 2H), 8.24-8.18 (m, 2H), 8.09-7.97 (m, 2H), 7.70-7.66(m, 2H), 7.43-7.41(m, 1H) | 448/2 |
| IV-66 | 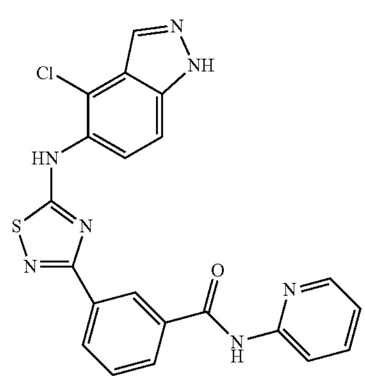 [SMILES: O=C(Nc1ccccn1)c1cccc(-c2nsc(Nc3ccc4[nH]ncc4c3Cl)n2)c1] | ¹H NMR (400 MHz, DMSO-d₆, ppm) δ 13.54(s, 1H), 10.97(s, 1H), 10.65(s, 1H), 8.69(s, 1H), 8.40(d, J = 3.6 Hz, 1H), 8.29(d, J = 8.6 Hz, 1H), 8.21-8.11 (m, 3H), 7.99(d, J = 8.8 Hz, 1H), 7.88-7.84(m, 1H), 7.67-7.61(m, 2H), 7.17(d, J = 6.4 Hz, 1H) | 448/2 |

TABLE 3-1-continued

| No. | Chemical Structure | NMR Physical Characterization Data | MS |
|---|---|---|---|
| IV-67 | 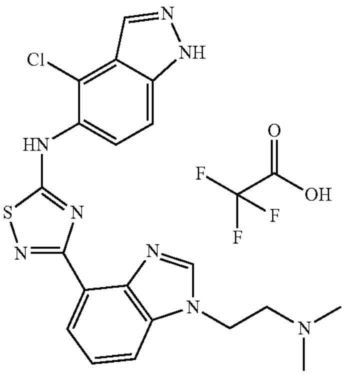 | ¹H NMR (400 MHz, DMSO-d₆, ppm) δ 13.60 (s, 1H), 10.81 (s, 1H), 10.07 (s, 1H), 9.48 (s, 1H), 8.25-8.12 (m, 3H), 8.05 (d, J = 8.9 Hz, 1H), 7.76-7.65 (m, 2H), 7.38-6.95 (m, 0H), 4.91 (t, J = 6.4 Hz, 2H), 3.73 (t, J = 6.5 Hz, 2H), 2.92 (s, 6H) | 439.15 |
| IV-68 | 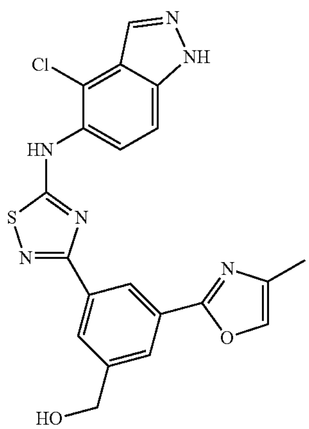 [SMILES: Cc1coc(-c2cc(CO)cc(-c3nsc(Nc4ccc5[nH]ncc5c4Cl)n3)c2)n1] | ¹H NMR (400 MHz, DMSO-d₆, ppm) δ 13.56 (s, 1H), 10.67 (s, 1H), 8.55 (t, J = 1.7 Hz, 1H), 8.23-8.15 (m, 2H), 8.05-7.99 (m, 1H), 7.99-7.90 (m, 2H), 7.67 (dd, J = 8.8, 1.0 Hz, 1H), 5.47 (t, J = 5.8 Hz, 1H), 4.65 (d, J = 5.8 Hz, 2H), 2.19 (d, J = 1.3 Hz, 3H) | 439 |
| IV-69 | 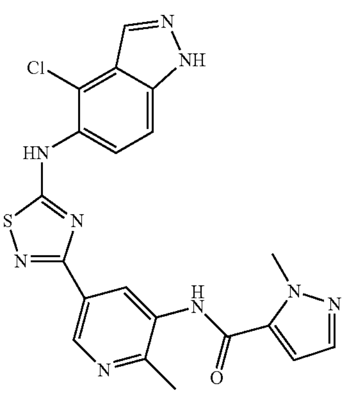 [SMILES: Cc1ncc(-c2nsc(Nc3ccc4[nH]ncc4c3Cl)n2)cc1NC(=O)c1ccnn1C] | ¹H NMR (400 MHz, DMSO-d₆, ppm) δ 13.53 (s, 1H), 10.72 (d, J = 4.5 Hz, 1H), 10.16 (d, J = 4.7 Hz, 1H), 9.04 (d, J = 4.6 Hz, 1H), 8.40 (d, J = 4.3 Hz, 1H), 8.19 (d, J = 4.2 Hz, 1H), 7.99 (t, J = 6.1 Hz, 1H), 7.71-7.62 (m, 1H), 7.60-7.54 (m, 1H), 7.10 (d, J = 4.8 Hz, 1H), 4.14-4.07 (m, 3H), 2.54 (s, 3H) | 466.92 |
| IV-70 | 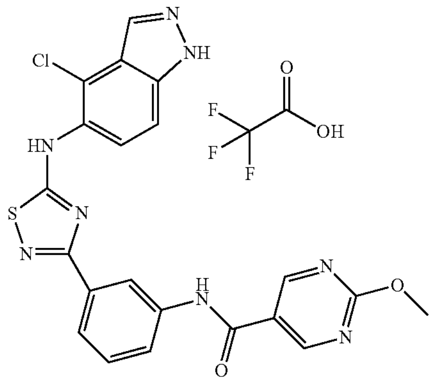 | ¹H NMR (DMSO-d₆, 400 MHz, ppm): δ = 13.44-13.57 (m, 1H), 10.56-10.63 (m, 1H), 10.50-10.55 (m, 1H), 9.12 (s, 2H), 8.47-8.55 (m, 1H), 8.15 (s, 1H), 7.92-8.05 (m, 1H), 7.79-7.93 (m, 2H), 7.59-7.68 (m, 1H), 7.46 (br t, J = 7.9 Hz, 1H), 3.92-4.03 ppm (m, 3H) | 479.04, 480.99 |

TABLE 3-1-continued

| No. | Chemical Structure | NMR Physical Characterization Data | MS |
|---|---|---|---|
| IV-71 | 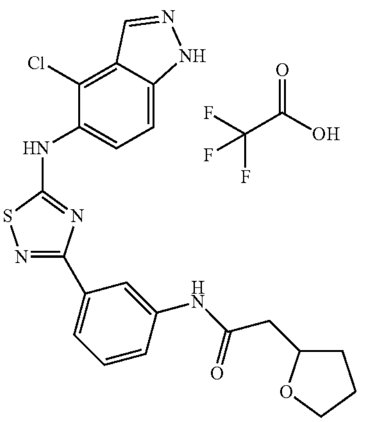 | $^1$H NMR (DMSO-d6, 400 MHz, ppm): δ = 13.36-13.63 (m, 1H), 10.54-10.64 (m, 1H), 10.05 (s, 1H), 8.35 (d, J = 1.6 Hz, 1H), 8.16 (s, 1H), 7.96 (d, J = 8.8 Hz, 1H), 7.73-7.79 (m, 1H), 7.70 (dd, J = 8.2, 1.0 Hz, 1H), 7.60-7.66 (m, 1H), 7.37 (t, J = 7.9 Hz, 1H), 4.06-4.26 (m, 1H), 3.69-3.81 (m, 1H), 3.55-3.63 (m, 1H), 2.39-2.58 (m, 2H), 1.91-2.06 (m, 1H), 1.73-1.88 (m, 2H), 1.45-1.63 ppm (m, 1H) | 455.06, 457.08 |
| IV-72 | trifluoroacetic acid solvate | $^1$H NMR (DMSO-d$_6$, 400 MHz, ppm): δ = 13.45-13.55 (m, 1H), 10.56-10.66 (m, 1H), 10.22-10.31 (m, 1H), 8.54 (s, 1H), 8.47 (t, J = 1.7 Hz, 1H), 8.15 (s, 1H), 7.97 (brd, J = 8.8 Hz, 1H), 7.76-7.84 (m, 2H), 7.63 (br d, J = 8.8 Hz, 1H), 7.43 (br t, J = 7.9 Hz, 1H), 3.97 ppm (s, 3H) | 519.01, 520.99 |
| IV-73 | 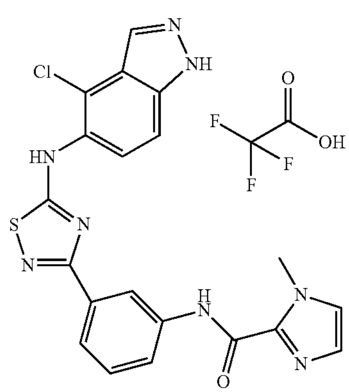 | $^1$H NMR (DMSO-d$_6$, 400 MHz, ppm): δ = 13.50 (br s, 1H), 10.62 (s, 1H), 10.47 (s, 1H), 8.71-8.74 (m, 1H), 8.16 (s, 1H), 7.97-8.02 (m, 1H), 7.76-7.84 (m, 2H), 7.64 (br d, J = 8.8 Hz, 1H), 7.44 (s, 1H), 7.41 (t, J = 7.9 Hz, 1H), 7.08 (d, J = 1.0 Hz, 1H), 3.99 ppm (s, 3H) | 451.03, 453.04 |

TABLE 3-1-continued

| No. | Chemical Structure | NMR Physical Characterization Data | MS |
| --- | --- | --- | --- |
| IV-74 | 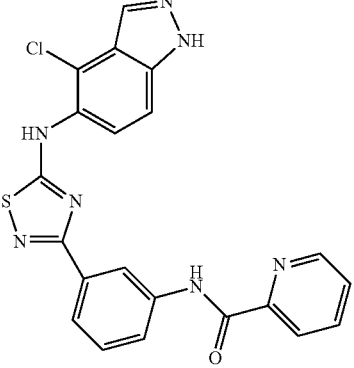 | ¹H NMR (DMSO-d₆, 400 MHz, ppm): δ = 13.50 (br s, 1H), 10.78 (s, 1H), 10.61 (s, 1H), 8.76-8.79 (m, 1H), 8.72-8.76 (m, 1H), 8.11-8.22 (m, 2H), 8.07 (td, J = 7.7, 1.7 Hz, 1H), 8.00 (br d, 9.0 Hz, 1H), 7.87-7.94 (m, 1H), 7.85 (br dd, J = 7.7, 1.3 Hz, 1H), 7.67-7.71 (m, 1H), 7.61-7.66 (m, 1H), 7.45 ppm (br t, J = 7.9 Hz, 1H) | 448.04, 448.06 |
| IV-75 | 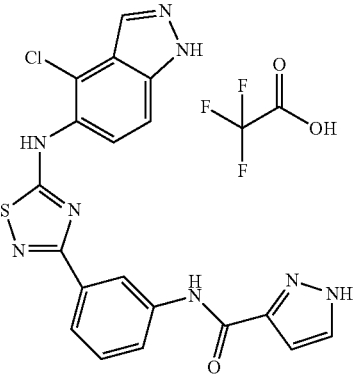 | ¹H NMR (DMSO-d₆, 400 MHz, ppm): δ = 13.43-13.57 (m, 1H), 10.59 (s, 1H), 10.20 (s, 1H), 8.61 (br s, 1H), 8.16 (s, 1H), 8.00 (br d, J = 8.8 Hz, 1H), 7.86 (m, 2H), 7.80 (br d, J = 7.6 Hz, 1H), 7.64 (d, J = 8.8 Hz, 1H), 7.41 (br t, J = 7.9 Hz, 1H), 6.83 ppm (br s, 1H), 6.55 ppm (br s, 1H) | 436.99, 438.94 |
| IV-76 | 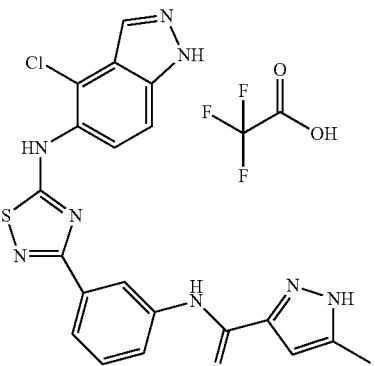 | ¹H NMR (DMSO-d₆, 400 MHz, ppm): δ = 13.50 (br d, J = 2.2 Hz, 1H), 13.02-13.21 (m, 1H), 10.59 (s, 1H), 10.10 (s, 1H), 8.62 (br s, 1H), 8.12-8.20 (m, 1H), 8.00 (br d, J = 9.0 Hz, 1H), 7.81-7.87 (m, 1H), 7.79 (br d, J = 7.6 Hz, 1H), 7.64 (d, J = 8.8 Hz, 1H), 7.40 (br t, J = 7.9 Hz, 1H), 6.55 (br s, 1H), 2.28 ppm (s, 3H) | 451.03, 453.01 |
| IV-77 | 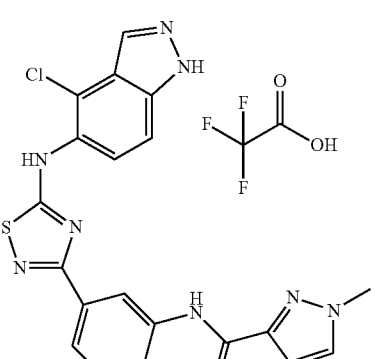 | ¹H NMR (DMSO-d₆, 400 MHz, ppm): δ = 13.45-13.53 (m, 1H), 10.59 (s, 1H), 10.16 (s, 1H), 8.63 (br t, J = 1.8 Hz, 1H), 8.15 (s, 1H), 8.00 (br d, J = 8.8 Hz, 1H), 7.74-7.89 (m, 3H), 7.64 (br d, J = 8.8 Hz, 1H), 7.40 (br t, J = 7.9 Hz, 1H), 6.77 (d, J = 2.2 Hz, 1H), 3.95 ppm (s, 3H) | 451.03, 453.05 |

TABLE 3-1-continued

| No. | Chemical Structure | NMR Physical Characterization Data | MS |
|---|---|---|---|
| IV-78 | 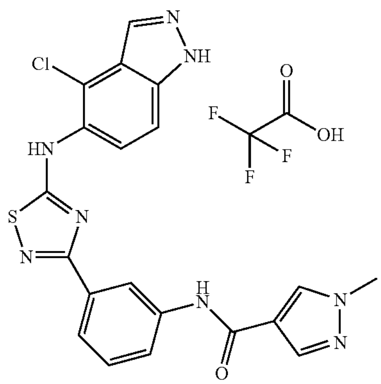 | $^1$H NMR (DMSO-d$_6$, 400 MHz, ppm): δ = 13.51 (br d, J = 1.4 Hz, 1H), 10.58 (s, 1H), 9.95 (s, 1H), 8.42 (br t, J = 1.7 Hz, 1H), 8.31 (s, 1H), 8.16 (s, 1H), 8.02 (s, 1H), 7.97 (br d, J = 8.8 Hz, 1H), 7.89 (br dd, J = 8.1, 1.1 Hz, 1H), 7.78 (br d, J = 7.8 Hz, 1H), 7.64 (br d, J = 8.8 Hz, 1H), 7.41 (br t, J = 8.0 Hz, 1H), 3.88 ppm (s, 3H) | 451.03, 453.05 |
| IV-79 | 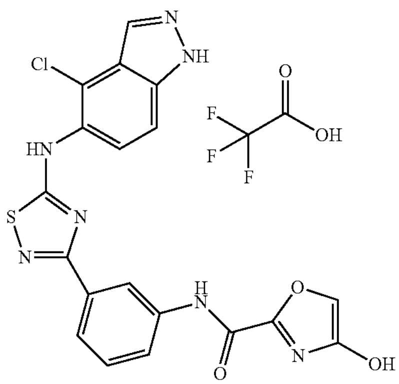 | $^1$H NMR (DMSO-d$_6$, 400 MHz, ppm): δ = 13.45-13.53 (m, 1H), 11.78 (s, 1H), 10.71 (s, 1H), 10.59 (s, 1H), 8.51 (s, 1H), 8.15 (s, 1H), 7.98 (br d, J = 8.8 Hz, 1H), 7.80-7.90 (m, 2H), 7.64 (br d, J = 8.4 Hz, 1H), 7.46 (br t, J = 7.9 Hz, 1H), 6.79 (s, 1H), 6.50 ppm (s, 1H) | 454.02, 455.97 |
| IV-80 | 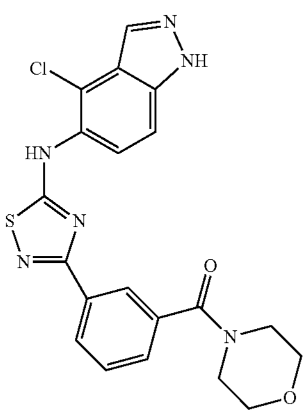 [SMILES: O=C(c1cccc(-c2nsc(Nc3ccc4[nH]ncc4c3Cl)n2)c1)N1CCOCC1] | $^1$H NMR (400 MHz, DMSO-d$_6$, ppm) δ 13.45(s, 1H), 10.54(s, 1H), 8.16-8.14(m, 2H), 8.06 (s, 1H), 7.98(d, J = 8.7 Hz, 1H), 7.64(d, J = 9.0 Hz, 1H), 7.58-7.48(m, 2H), 3.60-3.25(m, 8H) | 441 |
| IV-81 | 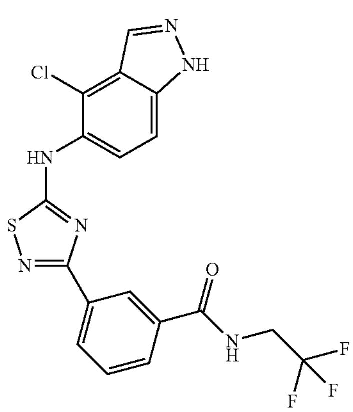 [SMILES: O=C(NCC(F)(F)F)c1cccc(-c2nsc(Nc3ccc4[nH]ncc4c3Cl)n2)c1] | $^1$H NMR (400 MHz, DMSO-d$_6$, ppm) δ 13.51 (s, 1H), 10.65 (s, 1H), 9.27 (t, J = 6.2 Hz, 1H), 8.60 (t, J = 1.7 Hz, 1H), 8.26 (dt, J = 7.7, 1.4 Hz, 1H), 8.16 (s, 1H), 8.02-7.91 (m, 2H), 7.67-7.56 (m, 2H), 4.09 (qd, J = 9.7, 6.2 Hz, 2H) | 453 |

TABLE 3-1-continued

| No. | Chemical Structure | NMR Physical Characterization Data | MS |
|---|---|---|---|
| IV-82 | 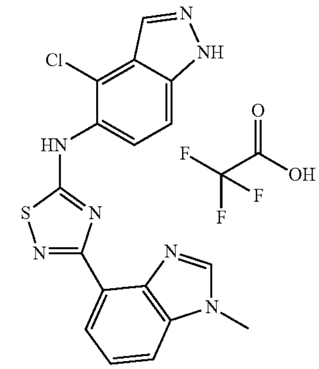 | $^1$H NMR (400 MHz, DMSO-d$_6$, ppm) δ 13.57 (s, 1H), 10.81 (s, 1H), 9.58 (s, 1H), 8.27 (d, J = 7.6 Hz, 1H), 8.21 (s, 1H), 8.11 (d, J = 8.4 Hz, 1H), 8.02 (d, J = 9.0 Hz, 1H), 7.76 (t, J = 8.0 Hz, 1H), 7.69 (d, J = 8.9 Hz, 1H), 7.25-6.98 (m, 1H), 4.11 (s, 3H) | 381.95 |
| IV-83 | 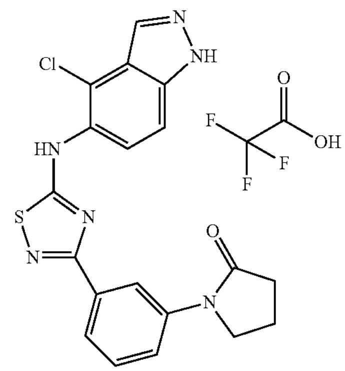 | $^1$H-NMR (400 MHz, DMSO-d$_6$, ppm) δ 13.52 (s, 1H), 10.62 (s, 1H), 8.46 (m, 1H), 8.16 (m, 1H), 7.98 (m, 1H), 7.84 (m, 1H), 7.70 (m, 1H), 7.62 (m, 1H), 7.46 (m, 1H), 3.84 (t, 2H), 3.3 (m, 2H), 2.08 (t, 2H). | 411.10, 413.08 |
| IV-84 | 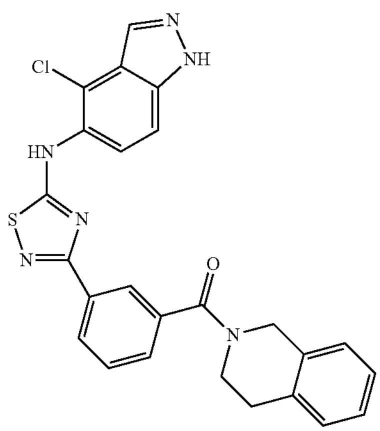 [SMILES: O=C(c1cccc(-c2nsc(Nc3ccc4[nH]ncc4c3Cl)n2)c1)N1CCc2ccccc2C1] | $^1$H NMR (400 MHz, DMSO-d$_6$, ppm) δ 13.52(s, 1H), 10.58(s, 1H), 8.21-8.12 (m, 3H), 7.98(d, J = 8.0 Hz, 1H), 7.65-7.58 (m, 3H), 7.26-7.08(m, 4H), 4.79-4.60(m, 2H), 3.87-3.53(m, 2H), 2.86(s, 2H) | 487 |
| IV-85 | 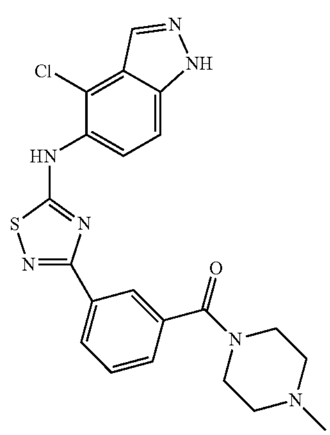 [SMILES: CN1CCN(C(=O)c2cccc(-c3nsc(Nc4ccc5[nH]ncc5c4Cl)n3)c2)CC1] | $^1$H NMR (400 MHz, DMSO-d$_6$, ppm) δ 13.53 (s, 1H), 10.64 (s, 1H), 8.21-8.14 (m, 2H), 8.11-8.04 (m, 1H), 8.01 (d, J = 8.8 Hz, 1H), 7.67 (d, J = 8.9 Hz, 1H), 7.58 (t, J = 7.7 Hz, 1H), 7.50 (dt, J = 7.6, 1.4 Hz, 1H), 3.64 (s, 2H), 3.41 (d, J = 4.2 Hz, 2H), 2.43-2.30 (m, 4H), 2.22 (s, 3H) | 454.1 |

TABLE 3-1-continued

| No. | Chemical Structure | NMR Physical Characterization Data | MS |
|---|---|---|---|
| IV-86 | 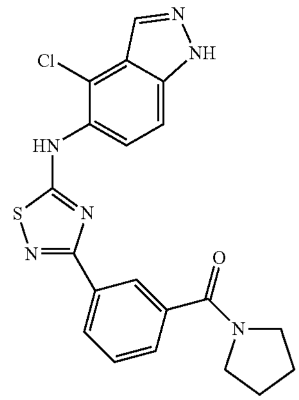 [SMILES: O=C(c1cccc(-c2nsc(Nc3ccc4[nH]ncc4c3Cl)n2)c1)N1CCCC1] | $^1$H NMR (400 MHz, DMSO-d$_6$, ppm) δ 13.52 (s, 1H), 10.63 (s, 1H), 8.23-8.14 (m, 3H), 8.00 (d, J = 8.9 Hz, 1H), 7.70-7.61 (m, 2H), 7.56 (t, J = 7.6 Hz, 1H), 3.50 (t, J = 6.9 Hz, 2H), 3.42 (d, J = 6.7 Hz, 2H), 1.91-1.82 (m, 4H) | 425.1 |
| IV-87 | 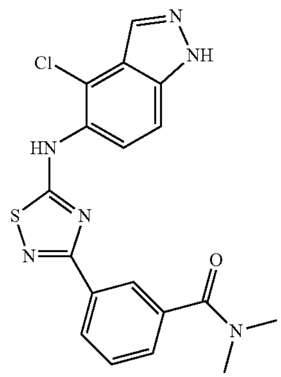 [SMILES: CN(C)C(=O)c1cccc(-c2nsc(Nc3ccc4[nH]ncc4c3Cl)n2)c1] | $^1$H NMR (400 MHz, DMSO-d$_6$, ppm) δ 13.53 (s, 1H), 10.64 (s, 1H), 8.20-8.12 (m, 2H), 8.07 (t, J = 1.6 Hz, 1H), 8.00 (d, J = 8.8 Hz, 1H), 7.67 (d, J = 8.9 Hz, 1H), 7.60-7.47 (m, 2H), 3.01 (s, 3H), 2.93 (s, 3H), 1.24 (s, 1H) | 399 |
| IV-88 | 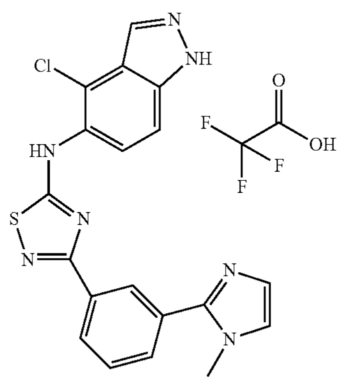 | $^1$H NMR (300 MHz, DMSO-d$_6$, ppm) δ 13.56 (s, 1H), 10.70 (s, 1H), 8.50-8.32 (m, 2H), 8.23-8.00 (m, 2H), 7.97-7.73 (m, 4H), 7.66 (dd, J = 8.9, 1.0 Hz, 1H), 3.89 (s, 3H), 1.27-1.07 (m, 1H). | 408 |
| IV-89 | formic acid solvate | $^1$H NMR (300 MHz, DMSO-d$_6$, ppm): δ 13.53 (s, 1H), 10.64 (s, 1H), 8.57 (d, J = 6.6 Hz, 1H), 8.23 (s, 1H), 8.19-8.10 (m, 2H), 7.85-7.76 (m, 2H), 7.64 (d, J = 8.9 Hz, 1H), 6.93 (t, J = 6.9 Hz, 1H), 2.38 (s, 3H). | 382 |

TABLE 3-1-continued

| No. | Chemical Structure | NMR Physical Characterization Data | MS |
|---|---|---|---|
| IV-90 | 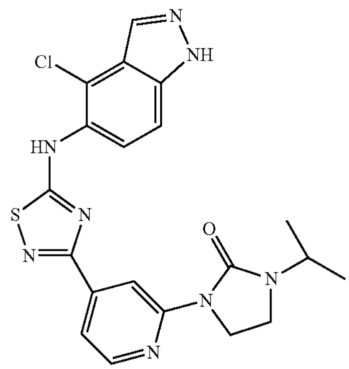 [SMILES: CC(C)N1CCN(c2cc(-c3nsc(Nc4ccc5[nH]ncc5c4Cl)n3)ccn2)C1=O] | $^1$H NMR (400 MHz, DMSO-d$_6$, ppm) δ 13.54 (s, 1H), 10.70 (s, 1H), 8.96-8.91 (m, 1H), 8.39 (d, J = 5.2 Hz, 1H), 8.19 (d, J = 1.0 Hz, 1H), 7.96 (d, J = 8.9 Hz, 1H), 7.65 (dd, J = 8.9, 1.0 Hz, 1H), 7.58 (dd, J = 5.2, 1.5 Hz, 1H), 4.08 (hept, J = 6.6 Hz, 1H), 3.97 (dd, J = 9.0, 7.0 Hz, 2H), 3.43 (t, J = 8.0 Hz, 2H), 1.15 (d, J = 6.8 Hz, 6H) | 455 |
| IV-91 | 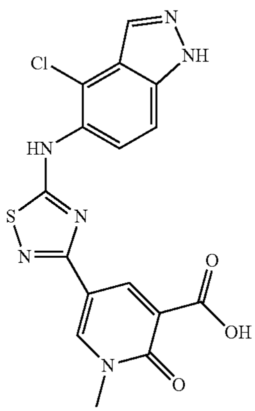 [SMILES: Cn1cc(-c2nsc(Nc3ccc4[nH]ncc4c3Cl)n2)cc(C(=O)O)c1=O] | $^1$H NMR (300 MHz, DMSO-d$_6$, ppm) δ 14.28(s, 1H), 13.52(s, 1H), 10.68(s, 1H), 8.89-8.87(m, 2H), 8.17(s, 1H), 7.96(d, J = 8.8 Hz, 1H), 7.65(d, J = 8.8 Hz, 1H), 3.75(s, 3H) | 403 |
| IV-92 | 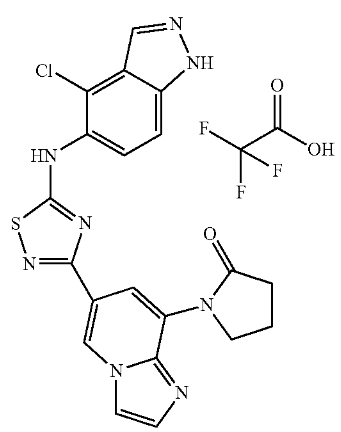 | $^1$H NMR (400 MHz, DMSO-d$_6$, ppm) δ 13.87 (s, 1H), 13.58 (s, 1H), 11.00 (s, 1H), 9.31 (d, J = 2.0 Hz, 1H), 9.14 (s, 1H), 8.46 (d, J = 2.0 Hz, 1H), 8.22 (s, 1H), 8.12 (d, J = 2.1 Hz, 1H), 7.98-7.90 (m, 1H), 7.68 (d, J = 8.8 Hz, 1H), 3.96 (t, J = 7.0 Hz, 2H), 2.62 (t, J = 8.1 Hz, 2H), 2.19 (p, J = 7.6 Hz, 2H) | 451 |
| IV-93 | 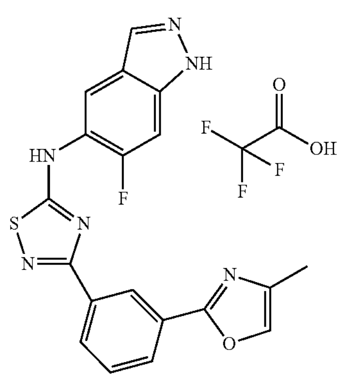 | $^1$H NMR (300 MHz, DMSO-d$_6$, ppm) δ 10.79 (s, 1H), 8.78 (s, 1H), 8.68 (d, J = 7.7 Hz, 1H), 8.32 (d, J = 7.9 Hz, 1H), 8.18 (s, 1H), 8.07 (d, J = 7.9 Hz, 1H), 7.99 (s, 1H), 7.70 (t, J = 7.8 Hz, 1H), 7.57 (d, J = 11.0 Hz, 1H), 2.22 (s, 3H) | 393 |

TABLE 3-1-continued

| No. | Chemical Structure | NMR Physical Characterization Data | MS |
|---|---|---|---|
| IV-94 | 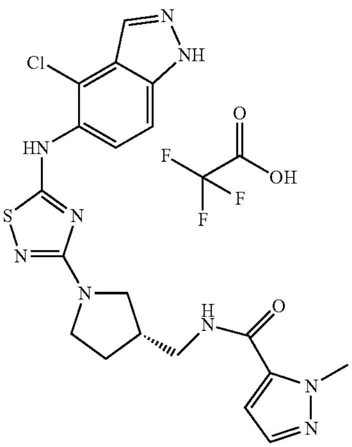 | $^1$H NMR (DMSO-d$_6$, 400 MHz, ppm): δ = 13.34-13.58 (m, 1H), 10.16-10.26 (m, 1H), 8.57 (br t, J = 5.8 Hz, 1H), 8.12 (s, 1H), 7.76 (d, J = 8.8 Hz, 1H), 7.55 (d, J = 9.4 Hz, 1H), 7.43 (d, J = 2.0 Hz, 1H), 6.82 (d, J = 2.0 Hz, 1H), 4.02 (s, 3H), 3.48-3.60 (m, 3H), 3.36-3.46 (m, 1H), 3.15-3.32 (m, 3H), 1.92-2.04 (m, 1H), 1.64-1.76 ppm (m, 1H) | 457.99, 460.02 |
| IV-95 | 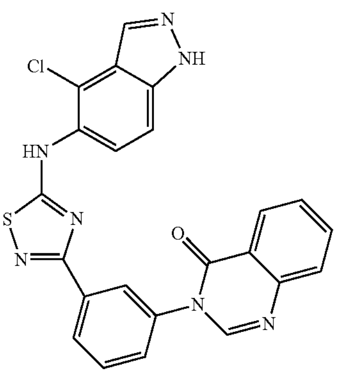 [SMILES: O=c1c2ccccc2ncn1-c1cccc(-c2nsc(Nc3ccc4[nH]ncc4c3Cl)n2)c1] | $^1$H NMR (DMSO-d$_6$, 400 MHz, ppm): δ = 13.48 (br s, 1H), 10.63 (s, 1H), 8.41 (s, 1H), 8.21 (m, 3H), 8.07-8.17 (m, 1H), 7.98 (br d, J = 9.0 Hz, 1H), 7.81-7.93 (m, 1H), 7.71-7.81 (m, 1H), 7.51-7.71 ppm (m, 4H) | 472.02, 474.03 |
| IV-96 | 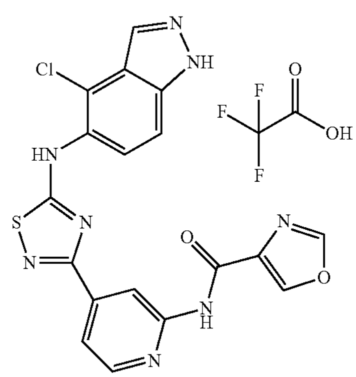 | $^1$H NMR (400 MHz, DMSO-d$_6$, ppm) δ 13.54(s, 1H), 10.78(s, 1H), 10.01(s, 1H), 8.97(s, 1H), 8.87(s, 1H), 8.64(s, 1H), 8.50(d, J = 5.2 Hz, 1H), 8.19(s, 1H), 7.97(d, J = 8.8 Hz, 1H), 7.79(dd, J = 5.2 Hz, 1.2 Hz, 1H), 7.66(d, J = 9.6 Hz, 1H) | 439 |
| IV-97 | 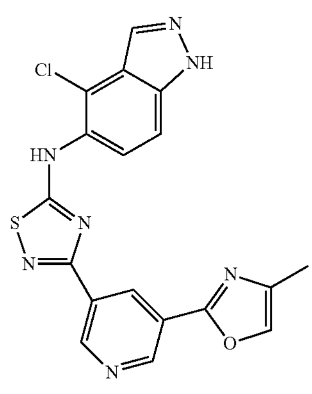 [SMILES: Cc1coc(-c2cncc(-c3nsc(Nc4ccc5[nH]ncc5c4Cl)n3)c2)n1] | $^1$H NMR (400 MHz, DMSO-d$_6$, ppm) δ 13.56 (s, 1H), 10.80 (s, 1H), 9.34 (d, J = 2.0 Hz, 1H), 9.20 (d, J = 2.1 Hz, 1H), 8.84 (t, J = 2.1 Hz, 1H), 8.19 (d, J = 1.6 Hz, 1H), 8.05 (d, J = 1.4 Hz, 1H), 8.00 (d, J = 8.9 Hz, 1H), 7.69 (d, J = 8.9 Hz, 1H), 2.21 (d, J = 1.2 Hz, 3H) | 410 |

TABLE 3-1-continued
| No. | Chemical Structure | NMR Physical Characterization Data | MS |
|---|---|---|---|
| IV-98 | 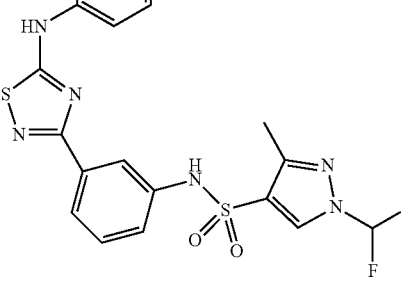 | ¹H NMR (DMSO-d₆, 400 MHz, ppm): δ = 13.49 (br s, 1H), 10.41-10.71 (m, 2H), 8.61 (s, 1H), 8.15 (s, 1H), 7.93-8.01 (m, 1H), 7.89 (s, 1H), 7.73-7.82 (m, 1H), 7.58-7.68 (m, 1H), 7.65 (t, J = 58.0 Hz, 1H), 7.36 (br t, J = 7.9 Hz, 1H), 7.16-7.24 (m, 1H), 2.25 ppm (s, 3H) | 536.89, 538.90 |
| IV-99 | 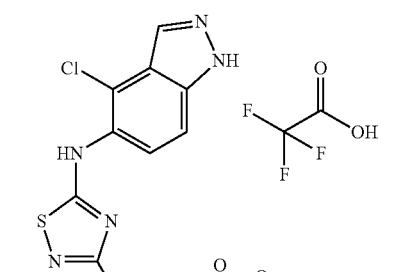 | N/A | 406.11, 408.02 |
| IV-100 | 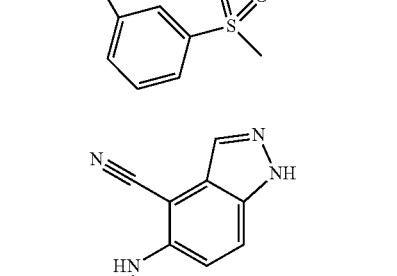 | N/A | 364.12 |
| IV-101 | 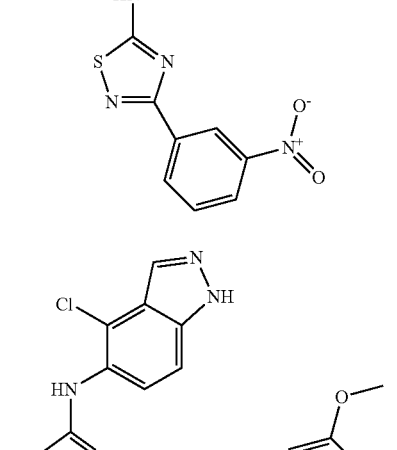<br>trifluoroacetic acid solvate | ¹H NMR (300 MHz, DMSO-d₆, ppm): δ 13.54 (s, 1H), 10.73 (s, 1H), 10.59 (s, 1H), 9.10-8.89 (m, 3H), 8.18 (d, J = 0.9 Hz, 1H), 8.00 (d, J = 8.8 Hz, 1H), 7.70-7.43 (m, 4H), 7.23-7.17 (m, 1H), 3.85 (s, 3H) | 478 |

TABLE 3-1-continued

| No. | Chemical Structure | NMR Physical Characterization Data | MS |
|---|---|---|---|
| IV-102 | 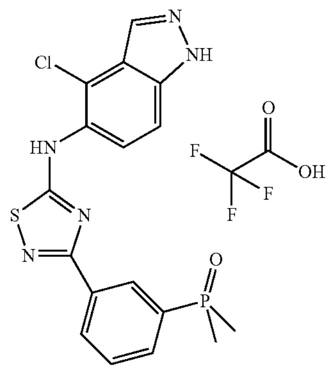 | $^1$H-NMR (400 MHz, DMSO-d$_6$, ppm) δ 13.52 (br s, 1H), 10.64 (s, 1H), 8.46 (m, 1H), 8.22 (m, 1H), 8.18 (m, 1H), 7.96 (m, 1H), 7.84 (m, 1H), 7.62 (m, 2H), 1.72 (s, 3H), 1.68 (s, 3H). | 404.06, 406.07 |
| IV-103 | 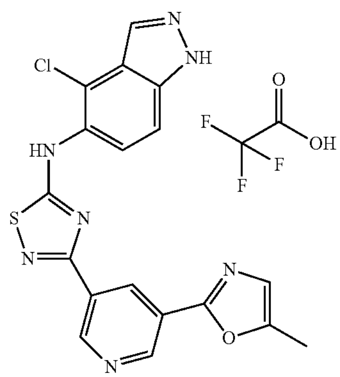 | $^1$H NMR (400 MHz, DMSO-d$_6$, ppm) δ 13.55-13.50 (m, 1H), 10.77 (s, 1H), 9.30 (s, 1H), 9.17 (s, 1H), 8.80 (t, J = 2.0 Hz, 1H), 8.17 (s, 1H), 7.97 (d, J = 8.9 Hz, 1H), 7.66 (d, J = 8.8 Hz, 1H), 7.20 (s, 0H), 7.12-7.05 (m, 1H), 6.95 (s, 0H), 4.77 (s, 0H), 2.41 (d, J = 1.2 Hz, 3H), 1.20 (d, J = 12.6 Hz, 11H) | 524.88 |
| IV-104 | 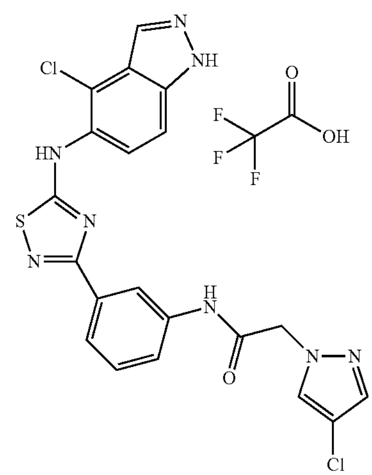 | $^1$H NMR (DMSO-d$_6$, 400 MHz, ppm): δ = 13.46-13.55 (m, 1H), 10.55-10.64 (m, 1H), 10.44-10.52 (m, 1H), 8.28-8.36 (m, 1H), 8.12-8.19 (m, 1H), 8.00 (s, 1H), 7.90-7.97 (m, 1H), 7.76-7.85 (m, 1H), 7.66-7.75 (m, 1H), 7.59-7.65 (m, 1H), 7.52-7.60 (m, 1H), 7.36-7.46 (m, 1H), 5.00 ppm (s, 2H) | 484.95, 486.96 |
| IV-105 | 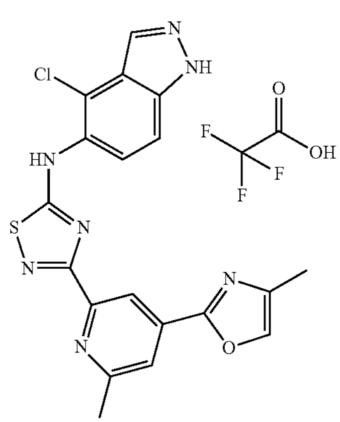 | $^1$H NMR (400 MHz, DMSO-d$_6$, ppm) δ 13.56 (s, 1H), 10.74 (s, 1H), 8.41 (d, J = 1.5 Hz, 1H), 8.20 (d, J = 1.0 Hz, 1H), 8.07 (d, J = 1.5 Hz, 1H), 7.89 (d, J = 8.8 Hz, 2H), 7.84 (d, J = 1.5 Hz, 1H), 7.67 (dd, J = 8.8, 1.1 Hz, 1H), 2.64 (s, 3H), 2.21 (d, J = 1.3 Hz, 3H) | 424.1 |

TABLE 3-1-continued

| No. | Chemical Structure | NMR Physical Characterization Data | MS |
|---|---|---|---|
| IV-106 | 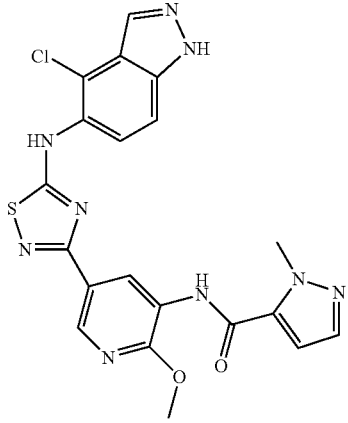 [SMILES: COc1ncc(-c2nsc(Nc3ccc4[nH]ncc4c3Cl)n2)cc1NC(=O)c1ccnn1C] | $^1$H NMR (400 MHz, DMSO-$d_6$, ppm) δ 13.53 (s, 1H), 10.71 (s, 1H), 9.76 (s, 1H), 8.73 (t, J = 1.6 Hz, 2H), 8.18 (s, 1H), 8.01 (d, J = 8.9 Hz, 1H), 7.70-7.63 (m, 1H), 7.55 (d, J = 2.1 Hz, 1H), 7.13 (d, J = 2.1 Hz, 1H), 4.09 (s, 3H), 4.01 (s, 3H). | 482 |

Example 12—Biological Assays for Inhibition of Rho-Associated Protein Kinase

Exemplary compounds were tested for ability to inhibit Rho-associated protein kinase isoform 1 (ROCK1) and Rho-associated protein kinase isoform 2 (ROCK2). Assay procedures and results are described below.

Part I—Procedure for Determining ROCK Inhibition Ability of Test Compounds Using an Isolated Enzyme Assay The Isolated Enzyme Assay for evaluating ROCK inhibition by a test compound was performed using the following protein constructs: glutathione S-transferase (GST)-tagged human ROCK1 catalytic domain 1-477 from Carna Biosciences (cat #01-109; apparent $K_m$ value for ATP is 10 μM) and GST-tagged human ROCK2 catalytic domain 1-553 from Carna Biosciences (Cat #01-110; apparent $K_m$ value for ATP is 15 μM). Protein constructs were purified from a baculovirus expression system. The peptide substrate was fluorescent LANCE® Ultra ULight-CREBtide: CKRREILSRRP$\underline{S}$YRK (PerkinElmer, # TRF0107-D). Kinase reactions were carried out in a 10 μL volume in 384-well plates: 50 nM ULight-CREBtide substrate, 2 nM constitutively active ROCK1 or ROCK2 kinase, and test compound in DMSO (or DMSO only for controls) were diluted into assay buffer containing 50 mM Tris-HCl (pH=7.5), 10 mM MgCl$_2$, 1 mM EGTA, 0.01% Tween-20, and 2 mM DTT such that the final concentration of DMSO was 0.5%. After a 90 minute incubation at room temperature on a shaker table, the kinase reaction was stopped by addition of 10 mM EDTA, and phosphorylation of the substrate was detected by adding 1 nM LANCE® Ultra Europium-anti-phospho-CREB (ser133) antibody (PerkinElmer, # TRF0200-D) and incubating for 60 minutes on a shaker at room temperature. The fluorescence resonance energy transfer (FRET) signals were read and analyzed on an Envision™ 2103 Multilabel Reader (Perkin Elmer). The concentration of test compound required to inhibit substrate phosphorylation by 50% (the IC$_{50}$) was calculated by non-linear regression using GraphPad PRIZM.

Part II—Procedure for Determining ROCK Inhibition Ability of Test Compounds Using a Cell-Base Assay The Cell-Based Assay for determining ROCK inhibition ability of test compounds utilized a genetically modified HAP1 cell line engineered to eliminate expression of either ROCK1 or ROCK2. In the procedure, HAP1 knockout cells are grown in Iscove's Modified Dulbecco's Medium that is additionally supplemented with 10% fetal bovine and 1x antibiotic-antimycotic mixture. Cells are plated in 96 well tissue culture plates at 1×10$^5$ cells/well (100 μL, of cells at 1×10$^6$/mL). Test compounds are solubilized in DMSO and diluted into the same media used to grow the cells. A 100 μL, aliquot of each compound dilution in media is added to each well containing the HAP1 cells and incubated at 37° C. for 30 minutes. Following compound incubation, the cells are pelleted by centrifugation at 1800 rpm for 5 minutes at 4° C. Media is removed from the cell pellet and the cells lysed and de-salted. An 80 μL, aliquot of each cell lysate is added to a single well of a 96-well high binding ELISA plate which has been pre-coated with a MYPT1 capture antibody and incubated at 4° C. overnight. The following day the ELISA plate is washed 4× with 0.05% Tween-20 in PBS. After washing, an anti-phospho-MYPT1 (Thr853) antibody is added and allowed to bind for 1 hour at room temperature. The wash step is repeated, and then an anti-rabbit HRP detection antibody is added and allowed to incubate at room temperature for 1 hour. The wash step is then repeated and 100 μL/well 1-Step™ Ultra TMB substrate is added to the ELISA plate and allowed to develop for approximately 5 minutes. The reaction is stopped by addition of H$_2$SO$_4$. Absorbance is read at 450 OD. Data is analyzed using GraphPad Prism software to calculate the 50% inhibitory concentration of test compound (IC$_{50}$).

Part III—Results

Experimental results from the Isolated Enzyme Assay and the Cell-Based Assay described above are provided in Tables 4 and 5 below. The symbol "++++" indicates an IC$_{50}$ less than 1 μM. The symbol "+++" indicates an IC$_{50}$ in the range of 1 μM to 15 μM. The symbol "++" indicates an IC$_{50}$ in the range of greater than 15 μM to 30 μM. The symbol "+" indicates an IC$_{50}$ greater than 30 μM. In this assay, 30 μM was the highest concentration of test compound analyzed.

TABLE 4

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| A-1 | (1H-indazol-5-yl-amino-1,2,4-thiadiazole with phenyl-NH-C(O)-imidazole; TFA salt) | +++ | ++++ | N/A | N/A |
| A-2 | (1H-indazol-5-yl-amino-1,2,4-thiadiazole with phenyl-NH-C(O)-pyridine; TFA salt) | + | ++++ | N/A | N/A |
| A-3 | (4-chloro-1H-indazol-5-yl-amino-1,2,4-thiadiazole with phenyl-NH-C(O)-1-methylpyrazole; TFA salt) | ++++ | ++++ | +++ | ++++ |

TABLE 4-continued
| | | Results from Isolated Enzyme Assay | | Results from Cell-Based Assay | |
|---|---|---|---|---|---|
| | | IC$_{50}$ (μM) | | IC$_{50}$ (μM) | |
| No. | Compound Structure | ROCK1 | ROCK2 | ROCK1 | ROCK2 |
| A-4 | 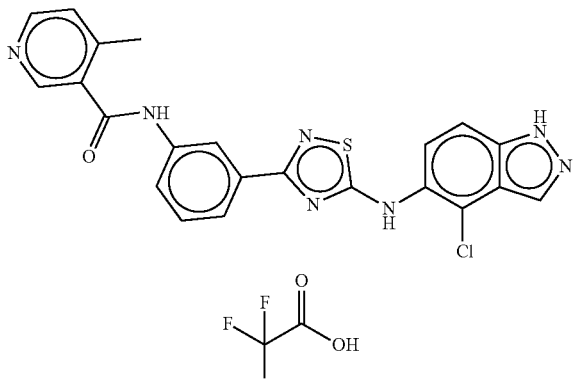 | + | ++++ | +++ | ++++ |
| A-5 | 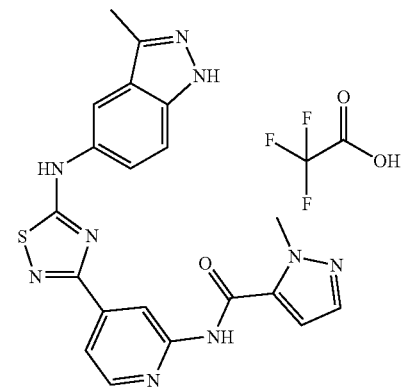 | + | + | N/A | N/A |
| A-6 | 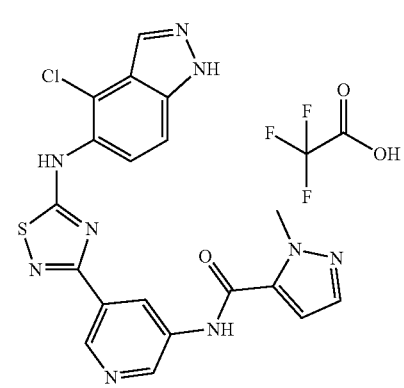 | + | ++++ | N/A | N/A |

TABLE 4-continued
| No. | Compound Structure | Results from Isolated Enzyme Assay IC$_{50}$ (μM) | | Results from Cell-Based Assay IC$_{50}$ (μM) | |
| --- | --- | --- | --- | --- | --- |
| | | ROCK1 | ROCK2 | ROCK1 | ROCK2 |
| A-7 | 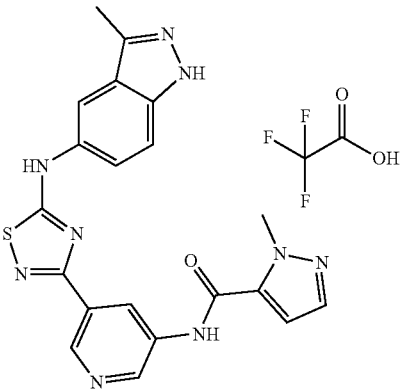 | + | + | N/A | N/A |
| A-8 | 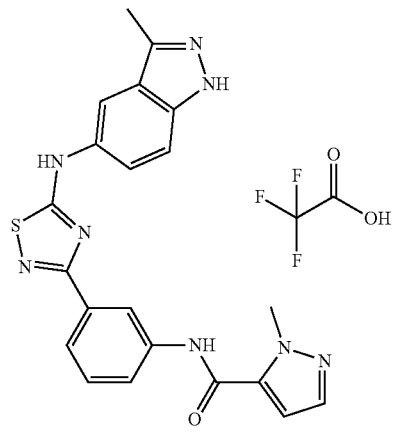 | + | ++++ | N/A | N/A |
| A-9 | 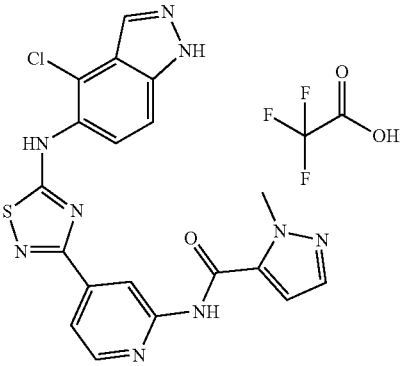 | + | ++++ | N/A | ++++ |

TABLE 4-continued
| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| A-10 | 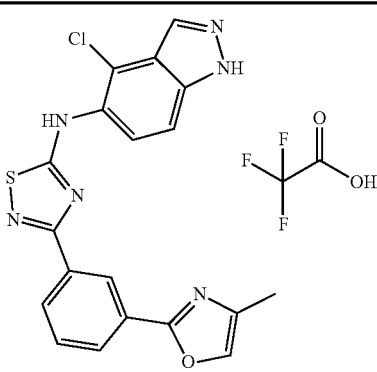 | ++++ | ++++ | N/A | ++++ |
| A-11 | 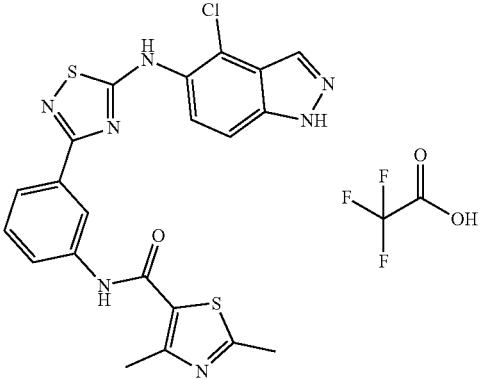 [SMILES: Cc1nc(C)c(C(=O)Nc2cccc(-c3nsc(Nc4ccc5[nH]ncc5c4Cl)n3)c2)s1 ; O=C(O)C(F)(F)F] | ++++ | ++++ | N/A | ++++ |
| A-12 | 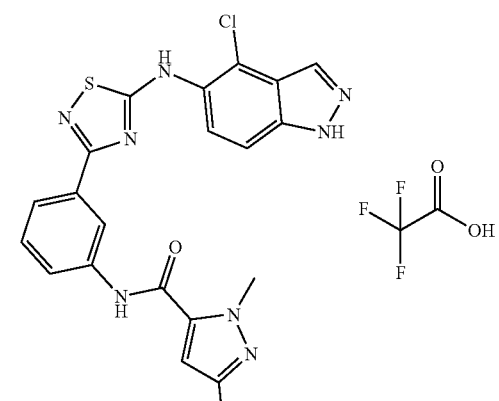 | ++++ | ++++ | N/A | ++++ |

TABLE 4-continued
| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| A-13 | 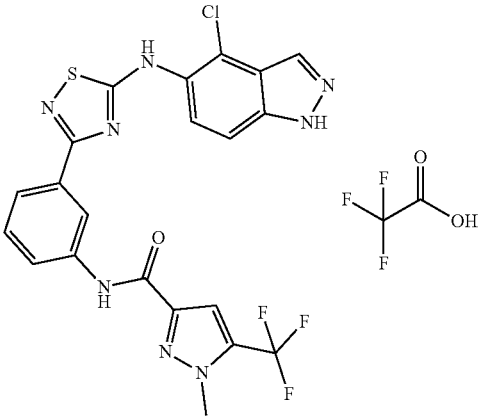 [SMILES: Cn1nc(C(=O)Nc2cccc(-c3nsc(Nc4ccc5[nH]ncc5c4Cl)n3)c2)cc1C(F)(F)F ; O=C(O)C(F)(F)F] | ++++ | ++++ | N/A | ++++ |
| A-14 | 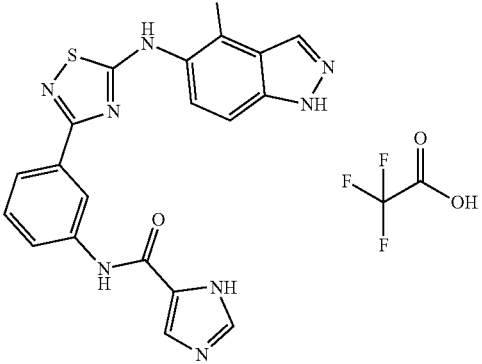 | ++++ | ++++ | N/A | ++++ |
| A-15 | 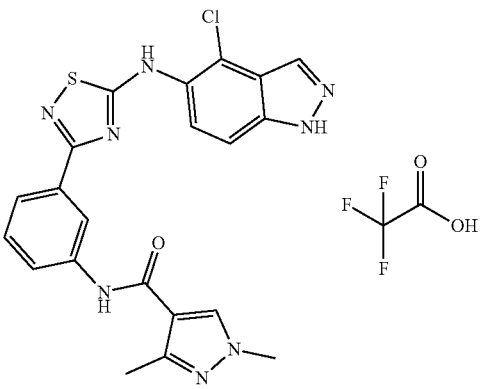 [SMILES: Cc1nn(C)cc1C(=O)Nc1cccc(-c2nsc(Nc3ccc4[nH]ncc4c3Cl)n2)c1 ; O=C(O)C(F)(F)F] | ++++ | ++++ | N/A | ++++ |

TABLE 4-continued
| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| A-16 | 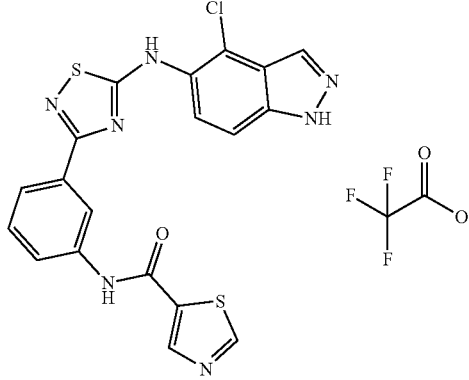 | ++++ | ++++ | N/A | ++++ |
| A-17 | 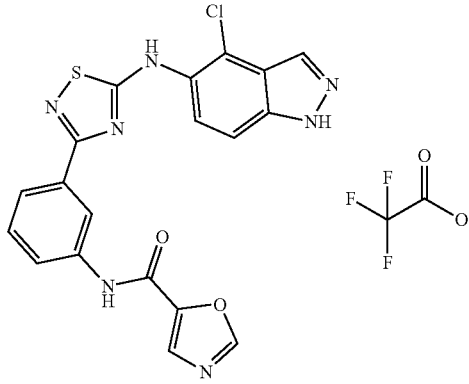 | ++++ | ++++ | N/A | ++++ |
| A-18 | 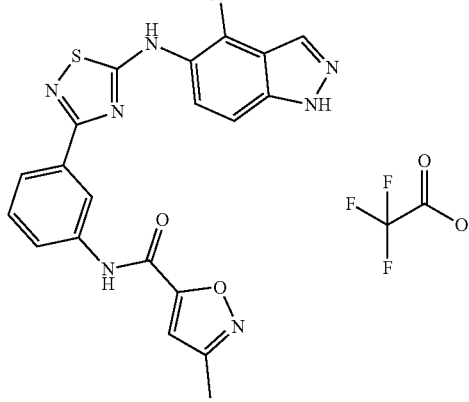 | ++++ | ++++ | N/A | ++++ |

TABLE 4-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| A-19 | 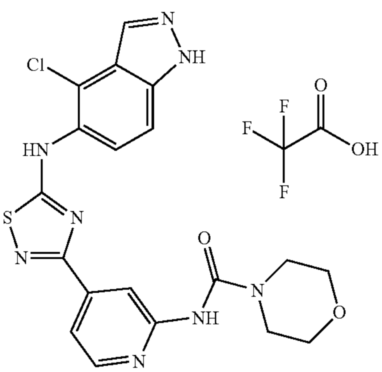 [SMILES: O=C(Nc1cc(-c2nsc(Nc3ccc4[nH]ncc4c3Cl)n2)ccn1)N1CCOCC1 ; O=C(O)C(F)(F)F] | ++++ | ++++ | N/A | ++++ |
| A-20 | 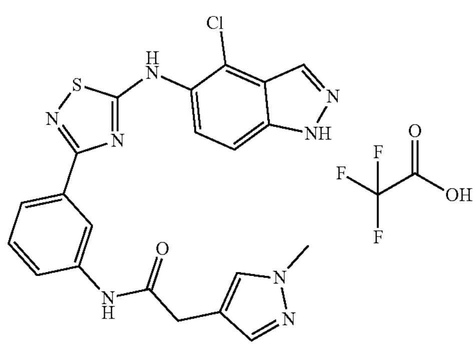 | ++++ | ++++ | N/A | ++++ |
| A-21 | 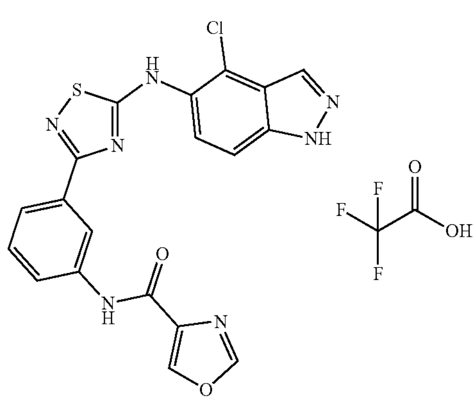 [SMILES: O=C(Nc1cccc(-c2nsc(Nc3ccc4[nH]ncc4c3Cl)n2)c1)c1cocn1 ; O=C(O)C(F)(F)F] | ++++ | ++++ | N/A | ++++ |

TABLE 4-continued
| No. | Compound Structure | Results from Isolated Enzyme Assay IC$_{50}$ (µM) | | Results from Cell-Based Assay IC$_{50}$ (µM) | |
|---|---|---|---|---|---|
| | | ROCK1 | ROCK2 | ROCK1 | ROCK2 |
| A-22 | 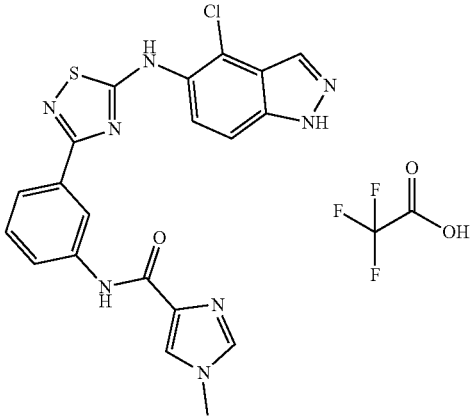 [SMILES: Cn1cnc(C(=O)Nc2cccc(-c3nsc(Nc4ccc5[nH]ncc5c4Cl)n3)c2)c1 ; O=C(O)C(F)(F)F] | ++++ | ++++ | N/A | ++++ |
| A-23 | 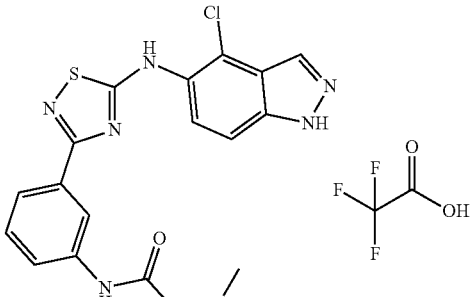 | ++++ | ++++ | N/A | ++++ |
TABLE 5
| No. | Compound Structure | Results from Isolated Enzyme Assay IC$_{50}$ (µM) | | Results from Cell-Based Assay IC$_{50}$ (µM) | |
|---|---|---|---|---|---|
| | | ROCK1 | ROCK2 | ROCK1 | ROCK2 |
| IV-1 | 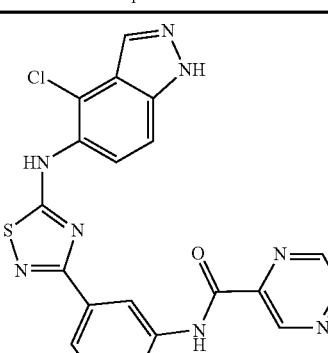 formic acid solvate | + | ++++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-2 | 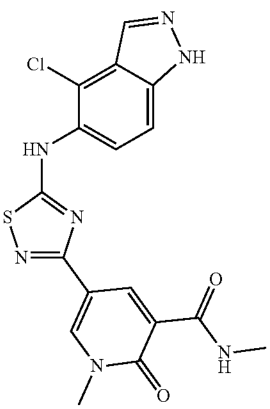 [SMILES: CNC(=O)c1cc(-c2nsc(Nc3ccc4[nH]ncc4c3Cl)n2)cn(C)c1=O] | ++++ | ++++ | >10 | ++++ |
| IV-3 | 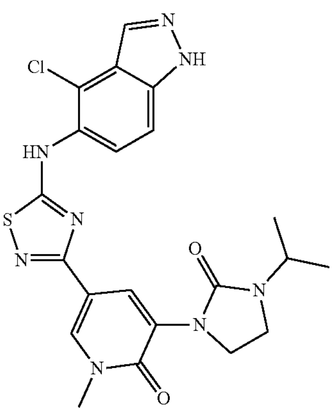 [SMILES: CC(C)N1CCN(c2cc(-c3nsc(Nc4ccc5[nH]ncc5c4Cl)n3)cn(C)c2=O)C1=O] | +++ | ++++ | N/A | N/A |
| IV-4 | 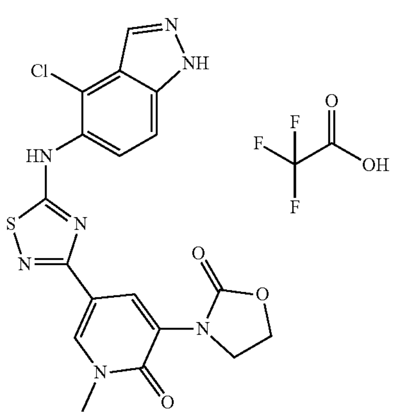 [SMILES: Cn1cc(-c2nsc(Nc3ccc4[nH]ncc4c3Cl)n2)cc(N2CCOC2=O)c1=O ; O=C(O)C(F)(F)F] | + | ++++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-5 | 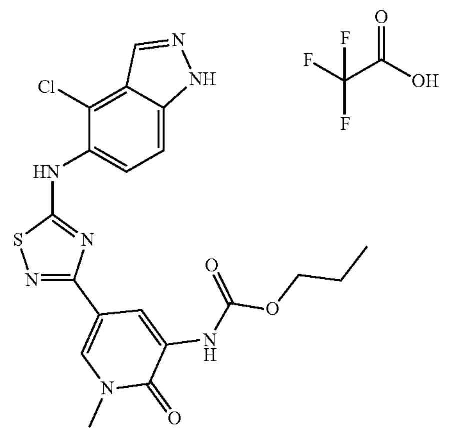 [SMILES: CCCOC(=O)Nc1cc(-c2nsc(Nc3ccc4[nH]ncc4c3Cl)n2)cn(C)c1=O ; O=C(O)C(F)(F)F] | ++++ | ++++ | +++ | ++++ |
| IV-6 | 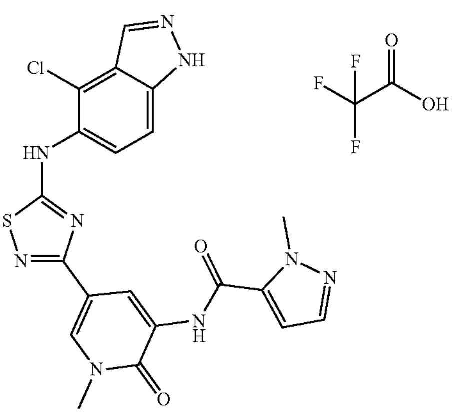 [SMILES: Cn1nccc1C(=O)Nc1cc(-c2nsc(Nc3ccc4[nH]ncc4c3Cl)n2)cn(C)c1=O ; O=C(O)C(F)(F)F] | ++++ | ++++ | >10 | ++++ |
| IV-7 | (formic acid solvate) | + | ++++ | >10 | >10 |

TABLE 5-continued

| | | Results from Isolated Enzyme Assay | | Results from Cell-Based Assay | |
|---|---|---|---|---|---|
| | | IC$_{50}$ (μM) | | IC$_{50}$ (μM) | |
| No. | Compound Structure | ROCK1 | ROCK2 | ROCK1 | ROCK2 |
| IV-8 | | + | ++++ | >10 | >10 |
| IV-9 | | ++++ | ++++ | +++ | ++++ |
| IV-10 | | + | ++++ | >10 | >10 |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-11 | 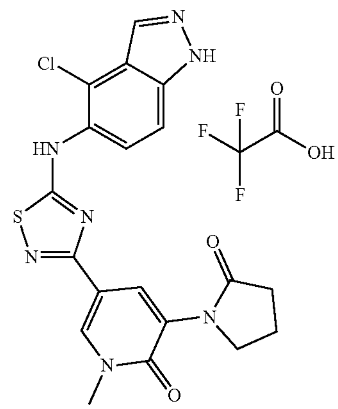 | + | +++ | N/A | N/A |
| IV-12 | 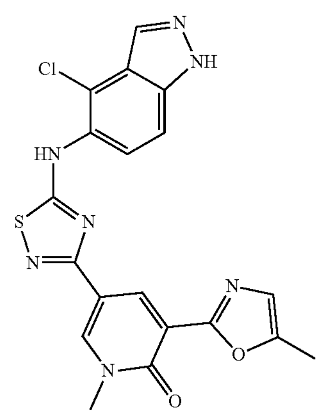 [SMILES: Cc1cnc(-c2cc(-c3nsc(Nc4ccc5[nH]ncc5c4Cl)n3)cn(C)c2=O)o1] | ++++ | ++++ | >10 | ++++ |
| IV-13 | 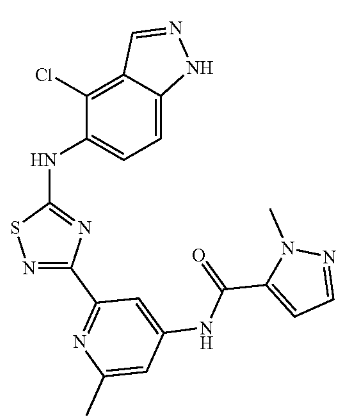 [SMILES: Cc1cc(NC(=O)c2ccnn2C)cc(-c2nsc(Nc3ccc4[nH]ncc4c3Cl)n2)n1] | ++++ | ++++ | >10 | >10 |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-14 | 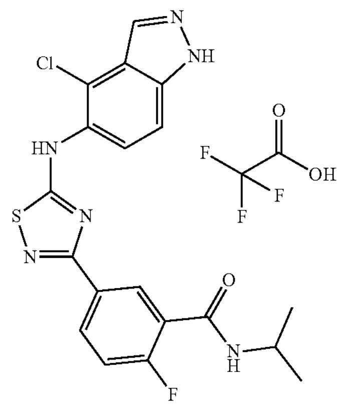 | ++++ | ++++ | +++ | ++++ |
| IV-15 | 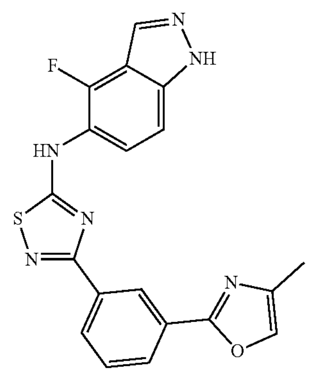 [SMILES: Cc1coc(-c2cccc(-c3nsc(Nc4ccc5[nH]ncc5c4F)n3)c2)n1] | ++++ | ++++ | >10 | ++++ |
| IV-16 | 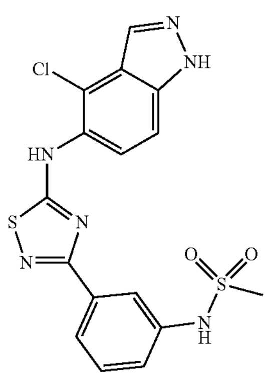 [SMILES: CS(=O)(=O)Nc1cccc(-c2nsc(Nc3ccc4[nH]ncc4c3Cl)n2)c1] | +++ | ++++ | N/A | N/A |
| IV-17 | 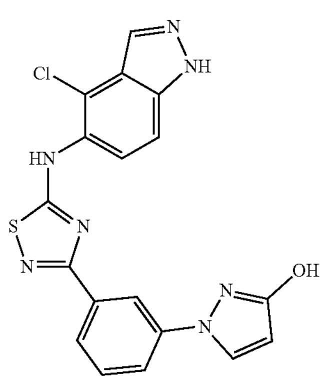 [SMILES: Oc1ccn(-c2cccc(-c3nsc(Nc4ccc5[nH]ncc5c4Cl)n3)c2)n1] | ++++ | ++++ | >10 | +++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-18 | 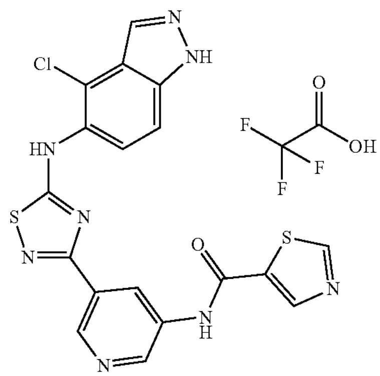 | + | ++++ | N/A | N/A |
| IV-19 | 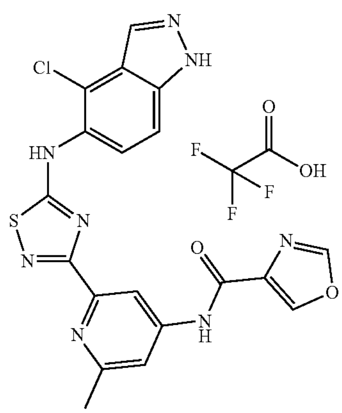 | ++++ | ++++ | >10 | ++++ |
| IV-20 | 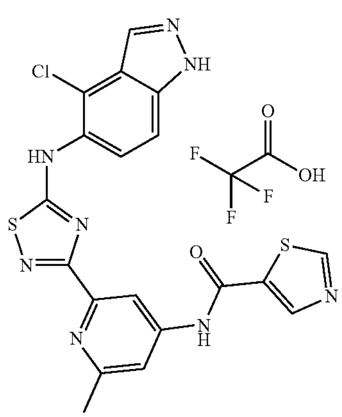 | ++++ | ++++ | N/A | >10 |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-21 | 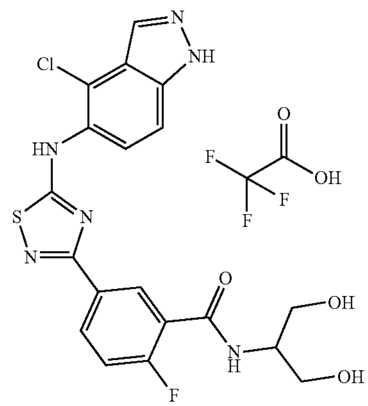 | ++++ | ++++ | N/A | +++ |
| IV-22 | 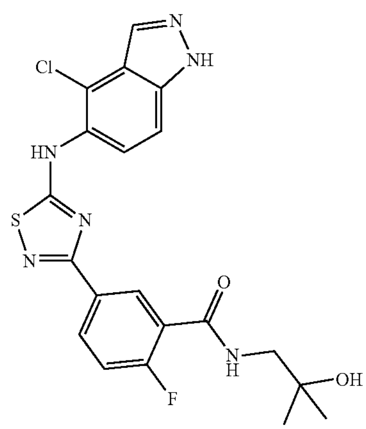 [SMILES: CC(C)(O)CNC(=O)c1cc(-c2nsc(Nc3ccc4[nH]ncc4c3Cl)n2)ccc1F] | ++++ | ++++ | +++ | ++++ |
| IV-23 | 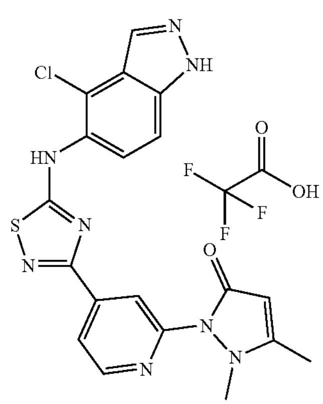 | ++++ | ++++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-24 | | + | ++++ | N/A | >10 |
| IV-25 | | ++++ | ++++ | N/A | >10 |
| IV-26 | | ++++ | ++++ | >10 | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-27 | 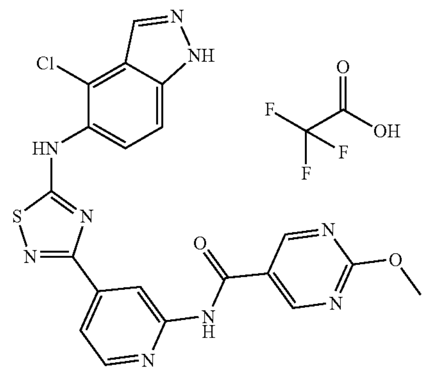 [SMILES: COc1ncc(C(=O)Nc2cc(-c3nsc(Nc4ccc5[nH]ncc5c4Cl)n3)ccn2)cn1 ; O=C(O)C(F)(F)F] | + | ++++ | N/A | >10 |
| IV-28 | 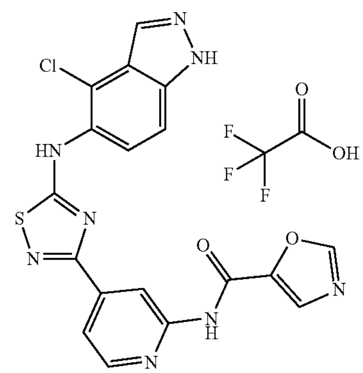 | + | ++++ | N/A | >10 |
| IV-29 | 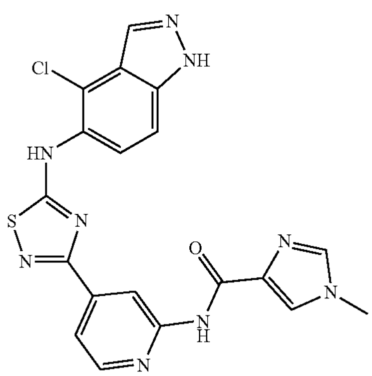 [SMILES: Cn1cnc(C(=O)Nc2cc(-c3nsc(Nc4ccc5[nH]ncc5c4Cl)n3)ccn2)c1] | + | ++++ | N/A | >10 |
| IV-30 | 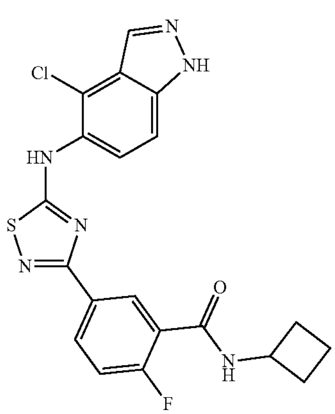 [SMILES: O=C(NC1CCC1)c1cc(-c2nsc(Nc3ccc4[nH]ncc4c3Cl)n2)ccc1F] | ++++ | ++++ | N/A | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-31 | 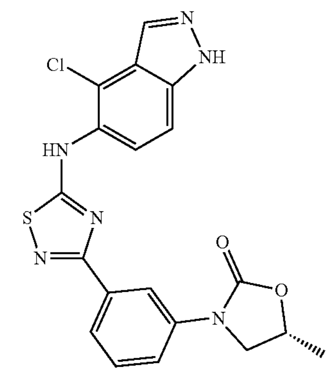 [SMILES: C[C@@H]1CN(c2cccc(-c3nsc(Nc4ccc5[nH]ncc5c4Cl)n3)c2)C(=O)O1] | ++++ | ++++ | +++ | ++++ |
| IV-32 | 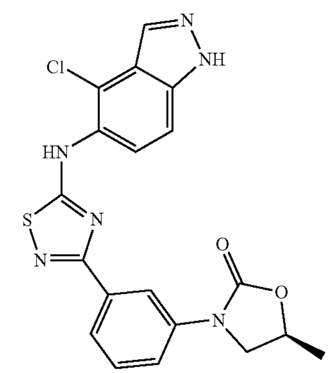 [SMILES: C[C@H]1CN(c2cccc(-c3nsc(Nc4ccc5[nH]ncc5c4Cl)n3)c2)C(=O)O1] | ++++ | ++++ | +++ | ++++ |
| IV-33 | 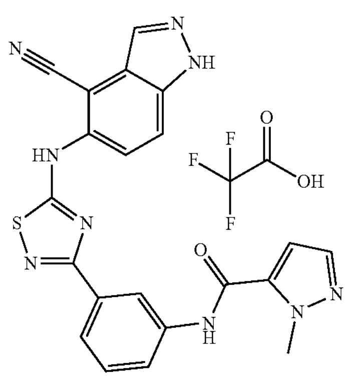 | ++++ | ++++ | N/A | >10 |
| IV-34 | 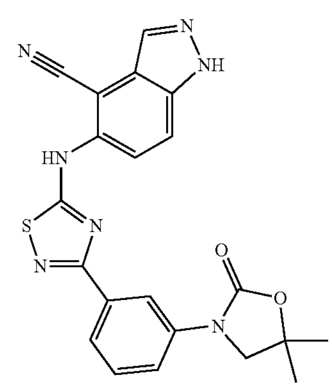 [SMILES: CC1(C)CN(c2cccc(-c3nsc(Nc4ccc5[nH]ncc5c4C#N)n3)c2)C(=O)O1] | ++++ | ++++ | N/A | +++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-35 | 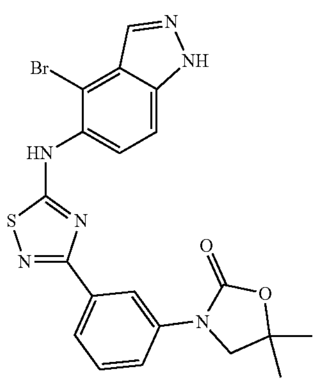 [SMILES: CC1(C)CN(c2cccc(-c3nsc(Nc4ccc5[nH]ncc5c4Br)n3)c2)C(=O)O1] | ++++ | ++++ | +++ | ++++ |
| IV-36 | 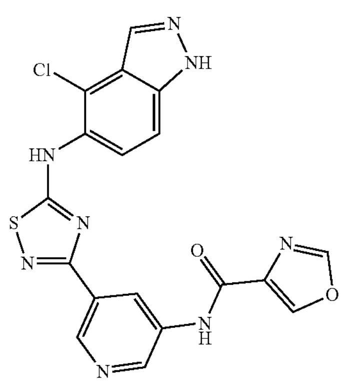 | + | ++++ | N/A | N/A |
| IV-37 | 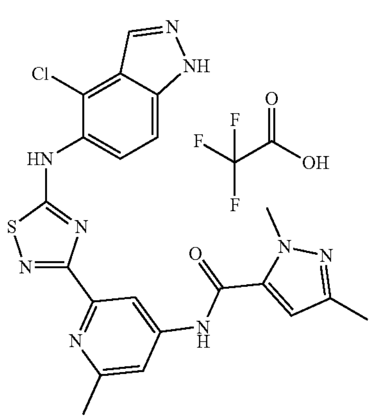 | + | ++++ | N/A | N/A |

TABLE 5-continued

| | | Results from Isolated Enzyme Assay IC$_{50}$ (µM) | | Results from Cell-Based Assay IC$_{50}$ (µM) | |
|---|---|---|---|---|---|
| No. | Compound Structure | ROCK1 | ROCK2 | ROCK1 | ROCK2 |
| IV-38 | | ++++ | ++++ | +++ | ++++ |
| IV-39 | | +++ | ++++ | N/A | ++++ |
| IV-40 | | + | +++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
| --- | --- | --- | --- | --- | --- |
| | | ROCK1 | ROCK2 | ROCK1 | ROCK2 |
| IV-41 | | ++++ | +++ | N/A | N/A |
| IV-42 | | + | + | >10 | ++++ |
| IV-43 | | + | + | N/A | +++ |

TABLE 5-continued

| No. | Compound Structure | Results from Isolated Enzyme Assay IC$_{50}$ (μM) | | Results from Cell-Based Assay IC$_{50}$ (μM) | |
| --- | --- | --- | --- | --- | --- |
| | | ROCK1 | ROCK2 | ROCK1 | ROCK2 |
| IV-44 | 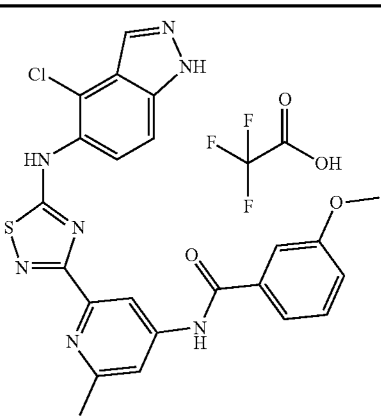 | + | + | N/A | +++ |
| IV-45 | 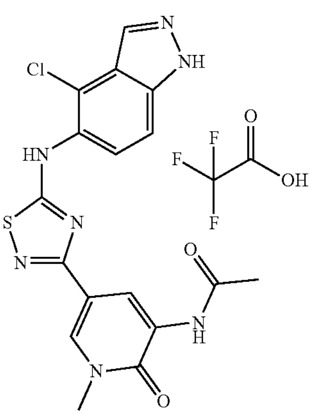 | ++++ | ++++ | N/A | >10 |
| IV-46 | 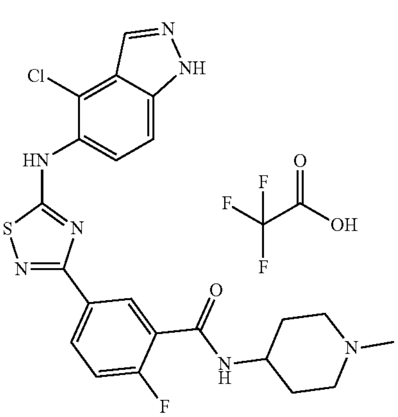 | ++++ | ++++ | >10 | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-47 | 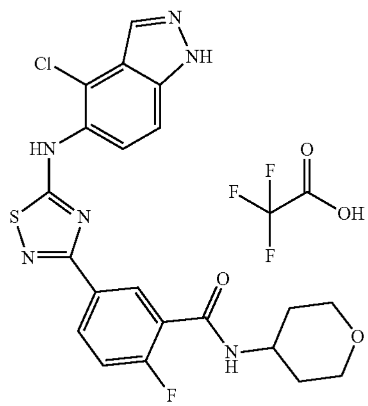 | ++++ | ++++ | +++ | ++++ |
| IV-48 | 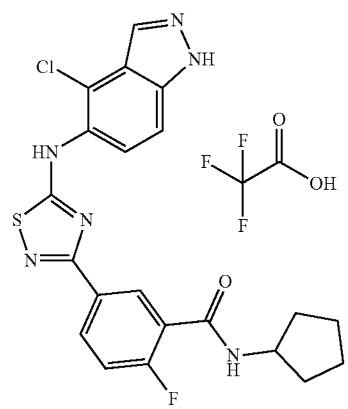 | ++++ | ++++ | +++ | ++++ |
| IV-49 | 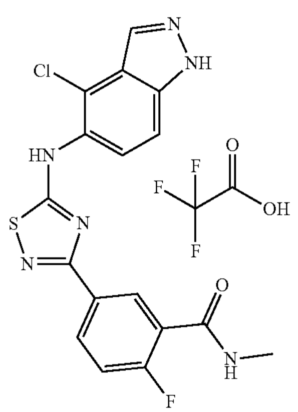 | ++++ | ++++ | >10 | ++++ |

TABLE 5-continued

| No. | Compound Structure | Results from Isolated Enzyme Assay IC$_{50}$ (μM) ROCK1 | ROCK2 | Results from Cell-Based Assay IC$_{50}$ (μM) ROCK1 | ROCK2 |
|---|---|---|---|---|---|
| IV-50 | 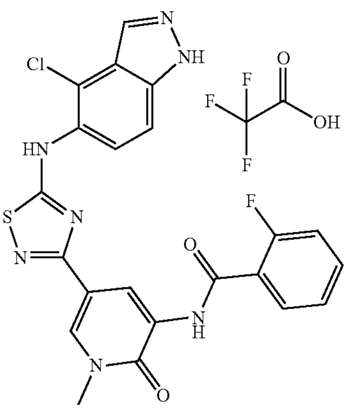 | + | ++++ | >10 | ++++ |
| IV-51 | 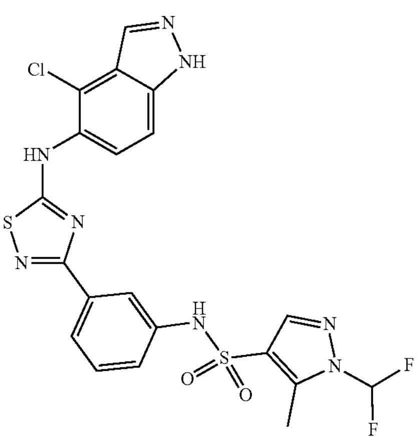 [SMILES: Cc1c(S(=O)(=O)Nc2cccc(-c3nsc(Nc4ccc5[nH]ncc5c4Cl)n3)c2)cnn1C(F)F] | ++ | +++ | N/A | N/A |
| IV-52 | 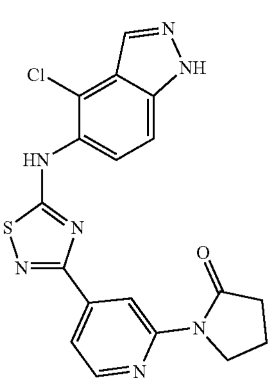 [SMILES: O=C1CCCN1c1cc(-c2nsc(Nc3ccc4[nH]ncc4c3Cl)n2)ccn1] | ++++ | ++++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-53 | 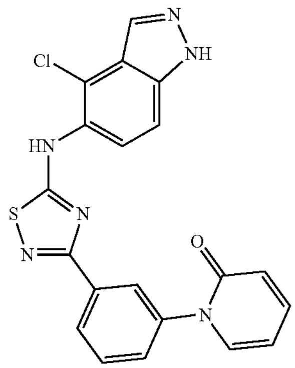 [SMILES: O=c1ccccn1-c1cccc(-c2nsc(Nc3ccc4[nH]ncc4c3Cl)n2)c1] | +++ | +++ | N/A | N/A |
| IV-54 | 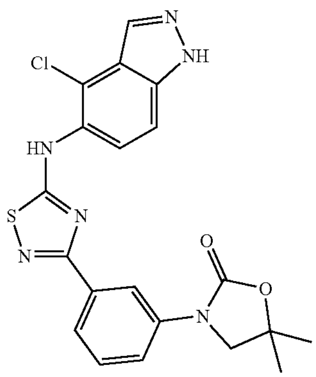 [SMILES: CC1(C)CN(c2cccc(-c3nsc(Nc4ccc5[nH]ncc5c4Cl)n3)c2)C(=O)O1] | ++++ | ++++ | +++ | ++++ |
| IV-55 | 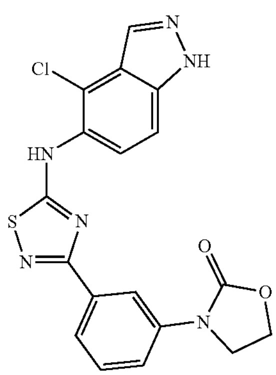 [SMILES: O=C1OCCN1c1cccc(-c2nsc(Nc3ccc4[nH]ncc4c3Cl)n2)c1] | ++++ | ++++ | +++ | ++++ |
| IV-56 | 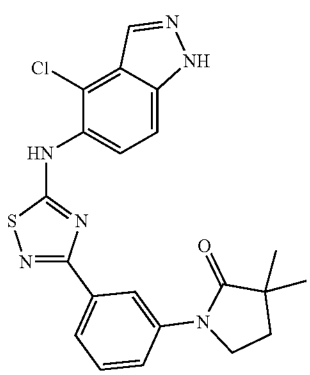 [SMILES: CC1(C)CCN(c2cccc(-c3nsc(Nc4ccc5[nH]ncc5c4Cl)n3)c2)C1=O] | ++++ | ++++ | +++ | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-57 | | + | + | >10 | ++++ |
| IV-58 | | + | ++++ | >10 | ++++ |
| IV-59 | | + | ++++ | >10 | ++++ |
| IV-60 | | + | + | N/A | +++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-61 | 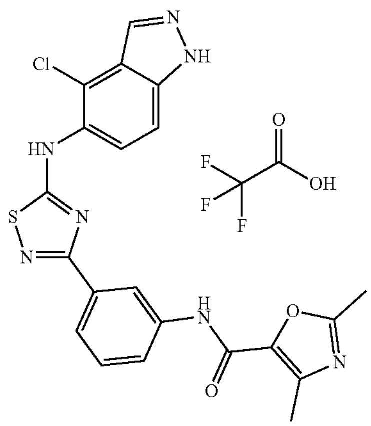 | ++++ | ++++ | >10 | ++++ |
| IV-62 | 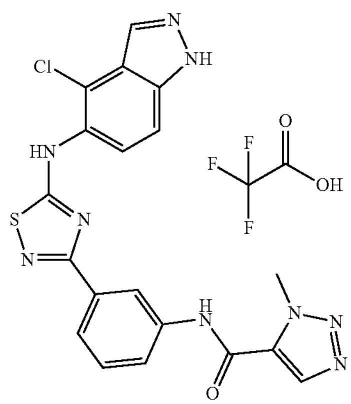 | ++++ | ++++ | >10 | ++++ |
| IV-63 | 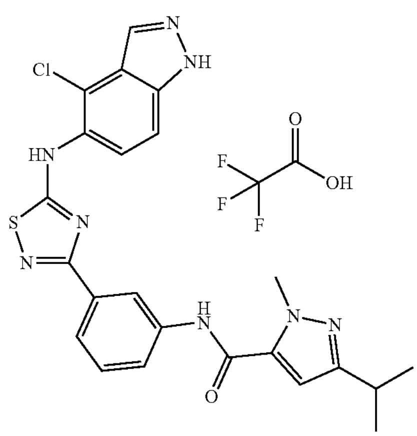 | ++++ | ++++ | +++ | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-64 | | + | + | N/A | ++++ |
| IV-65 | | ++++ | ++++ | >10 | ++++ |
| IV-66 | | ++++ | ++++ | +++ | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-67 | | +++ | +++ | N/A | N/A |
| IV-68 | | ++++ | ++++ | N/A | ++++ |
| IV-69 | | +++ | ++++ | N/A | >10 |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-70 | | ++++ | ++++ | >10 | ++++ |
| IV-71 | | ++++ | ++++ | +++ | ++++ |
| IV-72 | | ++++ | ++++ | +++ | ++++ | trifluoroacetic acid solvate

TABLE 5-continued

| No. | Compound Structure | Results from Isolated Enzyme Assay IC$_{50}$ (μM) | | Results from Cell-Based Assay IC$_{50}$ (μM) | |
| --- | --- | --- | --- | --- | --- |
| | | ROCK1 | ROCK2 | ROCK1 | ROCK2 |
| IV-73 | 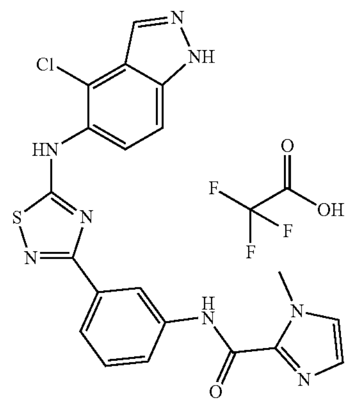 | ++++ | ++++ | >10 | ++++ |
| IV-74 | 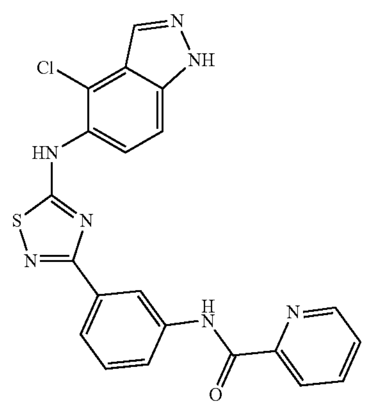 [SMILES: O=C(Nc1cccc(-c2nsc(Nc3ccc4[nH]ncc4c3Cl)n2)c1)c1ccccn1] | ++++ | ++++ | +++ | ++++ |
| IV-75 | 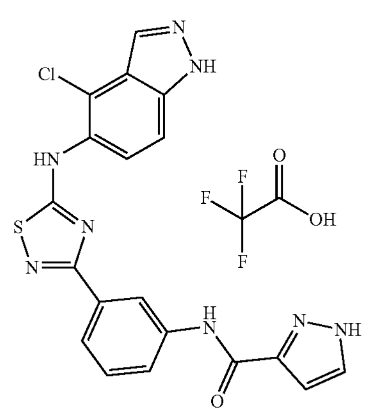 [SMILES: O=C(Nc1cccc(-c2nsc(Nc3ccc4[nH]ncc4c3Cl)n2)c1)c1cc[nH]n1 ; O=C(O)C(F)(F)F] | ++++ | ++++ | >10 | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-76 | | ++++ | ++++ | >10 | ++++ |
| IV-77 | | ++++ | ++++ | >10 | ++++ |
| IV-78 | | ++++ | ++++ | >10 | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-79 | 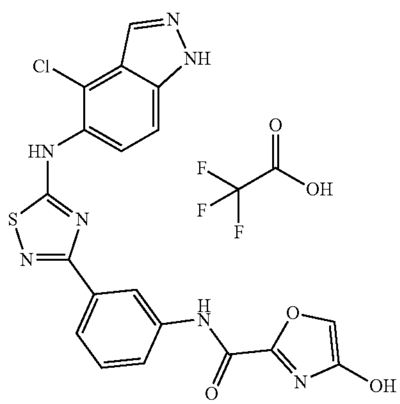 | ++++ | ++++ | N/A | >10 |
| IV-80 | 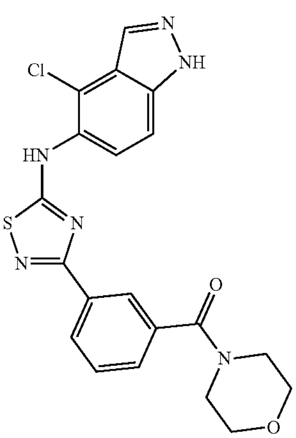 [SMILES: O=C(c1cccc(-c2nsc(Nc3ccc4[nH]ncc4c3Cl)n2)c1)N1CCOCC1] | +++ | +++ | N/A | N/A |
| IV-81 | 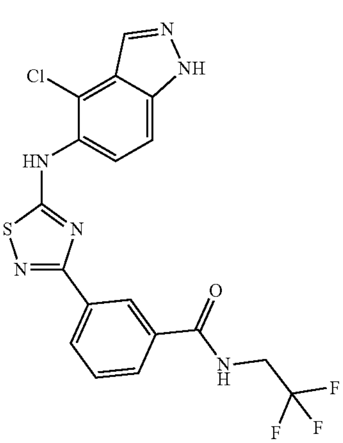 [SMILES: O=C(NCC(F)(F)F)c1cccc(-c2nsc(Nc3ccc4[nH]ncc4c3Cl)n2)c1] | ++++ | ++++ | >10 | ++++ |

TABLE 5-continued

| | | Results from Isolated Enzyme Assay | | Results from Cell-Based Assay | |
| | | IC$_{50}$ (μM) | | IC$_{50}$ (μM) | |
| No. | Compound Structure | ROCK1 | ROCK2 | ROCK1 | ROCK2 |

IV-82 ++++ +++ +++ ++++

IV-83 ++++ ++++ +++ ++++

IV-84 + ++++ N/A N/A

TABLE 5-continued
| No. | Compound Structure | Results from Isolated Enzyme Assay IC$_{50}$ (µM) | | Results from Cell-Based Assay IC$_{50}$ (µM) | |
|---|---|---|---|---|---|
| | | ROCK1 | ROCK2 | ROCK1 | ROCK2 |
| IV-85 | 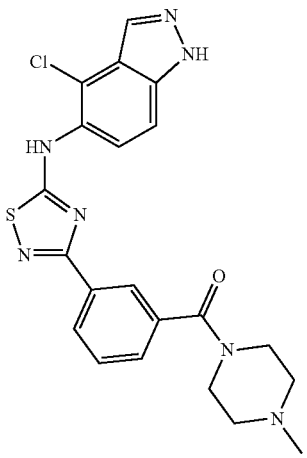 [SMILES: CN1CCN(C(=O)c2cccc(-c3nsc(Nc4ccc5[nH]ncc5c4Cl)n3)c2)CC1] | +++ | +++ | N/A | N/A |
| IV-86 | 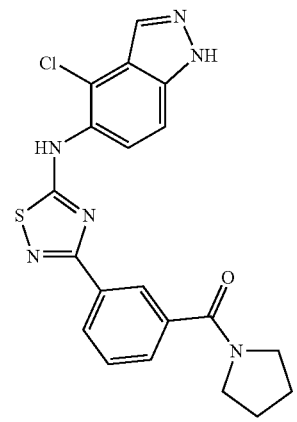 [SMILES: O=C(c1cccc(-c2nsc(Nc3ccc4[nH]ncc4c3Cl)n2)c1)N1CCCC1] | +++ | +++ | N/A | N/A |
| IV-87 | 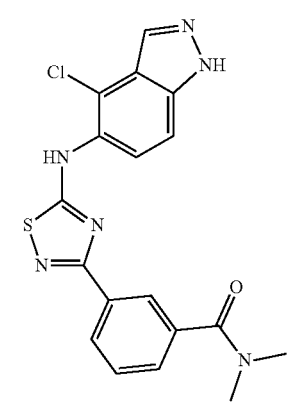 [SMILES: CN(C)C(=O)c1cccc(-c2nsc(Nc3ccc4[nH]ncc4c3Cl)n2)c1] | + | +++ | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-88 | 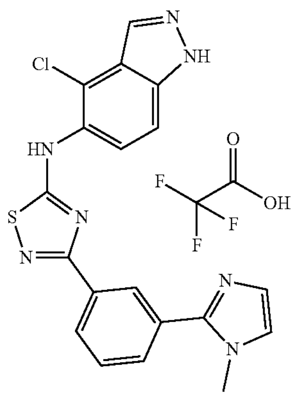 | ++++ | ++++ | N/A | +++ |
| IV-89 | formic acid solvate | ++++ | ++++ | N/A | >10 |
| IV-90 | 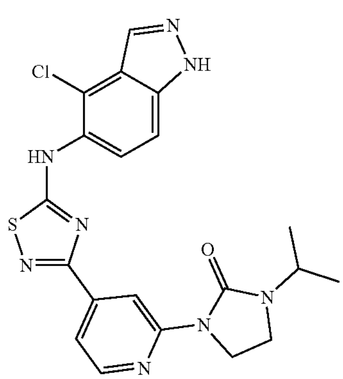 [SMILES: CC(C)N1CCN(c2cc(-c3nsc(Nc4ccc5[nH]ncc5c4Cl)n3)ccn2)C1=O] | ++++ | ++++ | +++ | ++++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-91 | 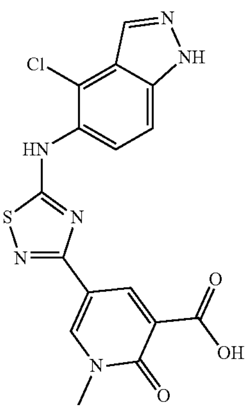 [SMILES: Cn1cc(-c2nsc(Nc3ccc4[nH]ncc4c3Cl)n2)cc(C(=O)O)c1=O] | + | + | N/A | N/A |
| IV-92 | 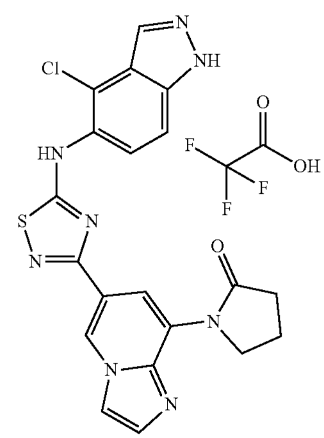 | + | + | N/A | N/A |
| IV-93 | 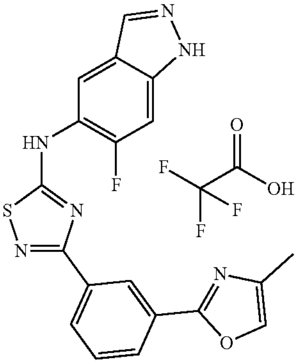 | + | + | N/A | N/A |

US 10,556,898 B2
TABLE 5-continued
| | | Results from Isolated Enzyme Assay | | Results from Cell-Based Assay | |
| | | IC$_{50}$ (µM) | | IC$_{50}$ (µM) | |
| No. | Compound Structure | ROCK1 | ROCK2 | ROCK1 | ROCK2 |
| IV-94 | 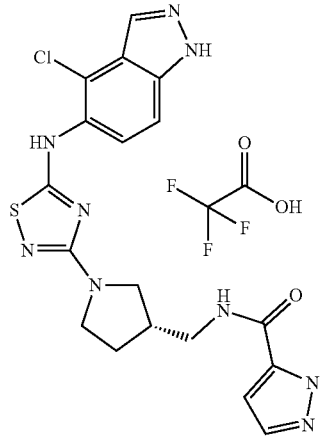 | + | + | N/A | N/A |
| IV-95 | 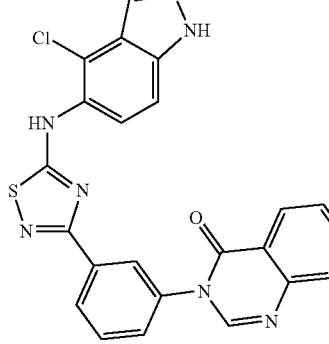 | + | + | N/A | N/A |
| IV-96 | 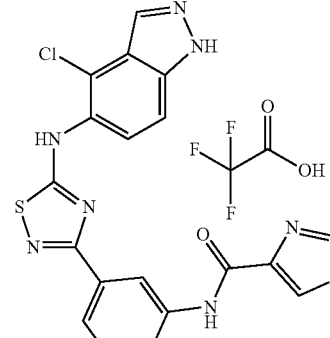 | + | + | N/A | N/A |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-97 | 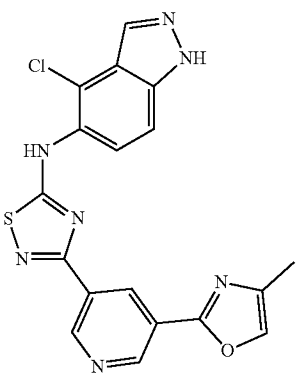 [SMILES: Cc1coc(-c2cncc(-c3nsc(Nc4ccc5[nH]ncc5c4Cl)n3)c2)n1] | + | + | N/A | >10 |
| IV-98 | 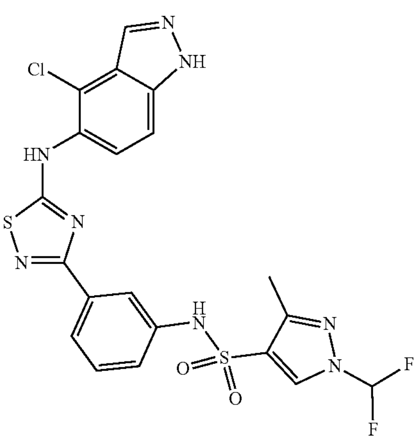 [SMILES: Cc1nn(C(F)F)cc1S(=O)(=O)Nc1cccc(-c2nsc(Nc3ccc4[nH]ncc4c3Cl)n2)c1] | + | + | N/A | N/A |
| IV-99 | 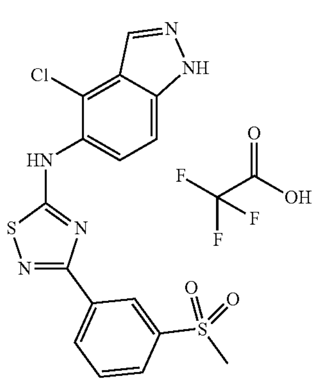 | + | + | N/A | N/A |

TABLE 5-continued

| No. | Compound Structure | Results from Isolated Enzyme Assay IC$_{50}$ (μM) | | Results from Cell-Based Assay IC$_{50}$ (μM) | |
| --- | --- | --- | --- | --- | --- |
| | | ROCK1 | ROCK2 | ROCK1 | ROCK2 |
| IV-100 | 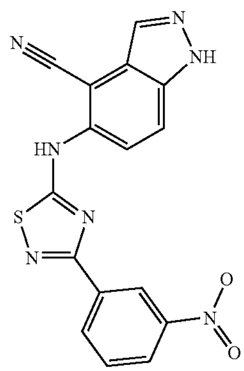 | + | + | N/A | N/A |
| IV-101 | trifluoroacetic acid solvate | + | + | N/A | >10 |
| IV-102 | 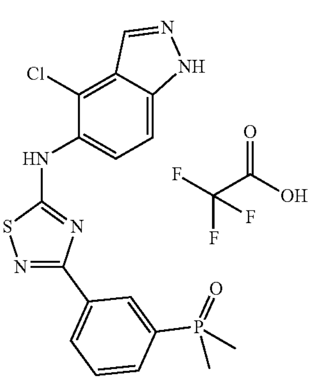 | + | + | N/A | N/A |

TABLE 5-continued

| No. | Compound Structure | Results from Isolated Enzyme Assay IC$_{50}$ (µM) ROCK1 | ROCK2 | Results from Cell-Based Assay IC$_{50}$ (µM) ROCK1 | ROCK2 |
|---|---|---|---|---|---|
| IV-103 | 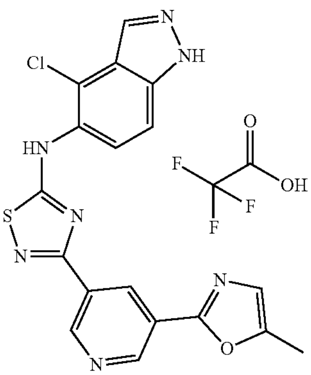 | + | + | N/A | >10 |
| IV-104 | 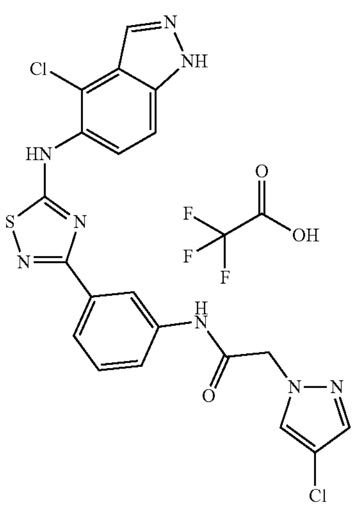 | + | + | N/A | N/A |
| IV-105 | 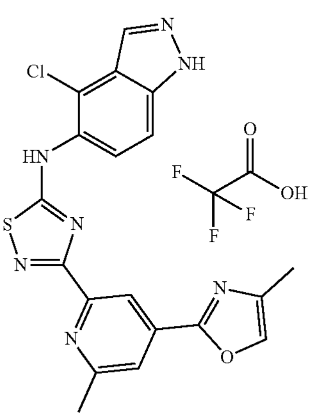 | + | + | N/A | >10 |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-106 | 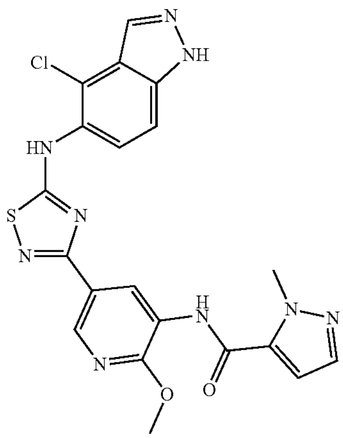 [SMILES: COc1ncc(-c2nsc(Nc3ccc4[nH]ncc4c3Cl)n2)cc1NC(=O)c1ccnn1C] | + | + | N/A | >10 |
| IV-107 | 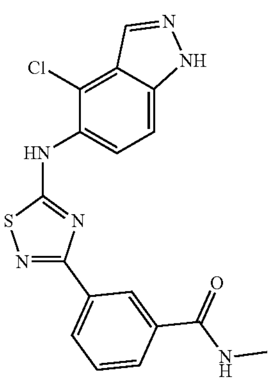 [SMILES: CNC(=O)c1cccc(-c2nsc(Nc3ccc4[nH]ncc4c3Cl)n2)c1] | ++++ | ++++ | >10 | ++++ |
| IV-108 | 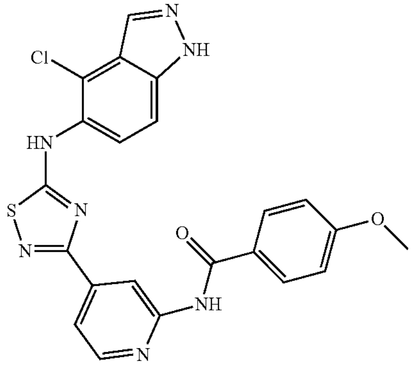 [SMILES: COc1ccc(C(=O)Nc2cc(-c3nsc(Nc4ccc5[nH]ncc5c4Cl)n3)ccn2)cc1] | + | ++++ | N/A | +++ |

TABLE 5-continued

| No. | Compound Structure | Results from Isolated Enzyme Assay IC$_{50}$ (μM) | | Results from Cell-Based Assay IC$_{50}$ (μM) | |
|---|---|---|---|---|---|
| | | ROCK1 | ROCK2 | ROCK1 | ROCK2 |
| IV-109 | 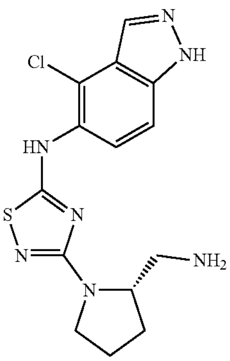 [SMILES: NC[C@@H]1CCCN1c1nsc(Nc2ccc3[nH]ncc3c2Cl)n1] | ++ | + | N/A | N/A |
| IV-110 | 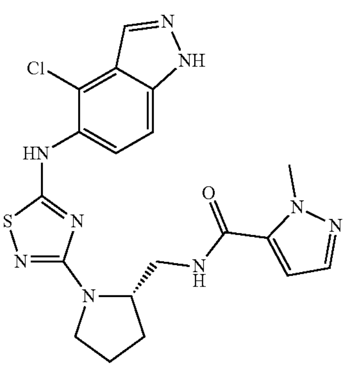 [SMILES: Cn1nccc1C(=O)NC[C@@H]1CCCN1c1nsc(Nc2ccc3[nH]ncc3c2Cl)n1] | + | ++ | N/A | N/A |
| IV-111 | 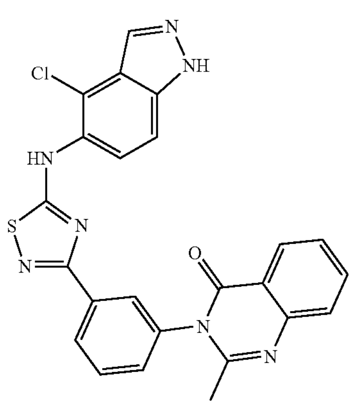 [SMILES: Cc1nc2ccccc2c(=O)n1-c1cccc(-c2nsc(Nc3ccc4[nH]ncc4c3Cl)n2)c1] | + | +++ | N/A | N/A |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be

The invention claimed is:

1. A compound represented by Formula I:

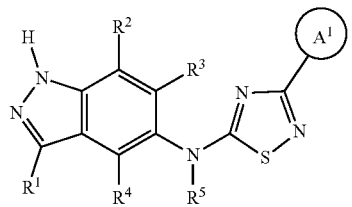

(I)

or a pharmaceutically acceptable salt thereof, or a solvate of the foregoing; wherein:

$R^1$ is hydrogen, halogen, $C_1$-$C_3$ alkyl, $C_1$-$C_3$ haloalkyl, cyclopropyl, $C_2$-$C_4$ alkenyl, cyano, or —N($R^6$)($R^7$);

$R^2$, $R^3$, and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;

$R^5$ is hydrogen, $C_1$-$C_6$ alkyl, $C_1$-$C_6$ hydroxyalkyl, or —$CO_2R^{12}$;

$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 occurrences of $R^{12}$;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, 3-7 membered heterocycloalkyl, —($C_1$-$C_6$ alkylene)-O—($C_1$-$C_6$ alkyl), or —($C_1$-$C_6$ alkylene)-N($R^6$)($R^7$); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;

$R^{10}$ represents independently for each occurrence $C_1$-$C_6$ alkyl, $C_1$-$C_6$ haloalkyl, $C_3$-$C_6$ cycloalkyl, —($C_1$-$C_6$ alkylene)-($C_3$-$C_6$ cycloalkyl), $C_1$-$C_6$ hydroxyalkyl, —($C_1$-$C_6$ alkylene)-O—($C_1$-$C_6$ alkyl), —($C_1$-$C_6$ alkylene)-N($R^8$)($R^9$), —($C_1$-$C_6$ alkylene)-$CO_2R^6$, —($C_1$-$C_6$ alkylene)-(3-7 membered heterocycloalkyl), 3-7 membered heterocyclyl, phenyl, or aralkyl; wherein said cycloalkyl, heterocyclyl, phenyl, and aralkyl are optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, and hydroxyl;

$R^{11}$ represents independently for each occurrence a 5-6 membered heteroaryl, 3-7 membered heterocycloalkyl, or phenyl, each of which is optionally substituted with 1 or 2 occurrences of $Y^1$;

$R^{12}$ represents independently for each occurrence $C_1$-$C_6$ alkyl or $C_3$-$C_6$ cycloalkyl;

$R^{13}$ represents independently for each occurrence $C_1$-$C_6$ alkyl, $C_3$-$C_6$ cycloalkyl, —($C_1$-$C_6$ alkylene)-($C_3$-$C_6$ cycloalkyl), or aralkyl;

$A^1$ is a cyclic group selected from:
(a) phenyl, $C_3$-$C_7$ cycloalkyl, $C_3$-$C_7$ oxocycloalkyl, 5-10 membered heterocyclyl, 5-10 membered oxo-heterocyclyl, aralkyl, or heteroaralkyl, each being substituted by $X^1$ and 0, 1, 2, or 3 occurrences of $Y^1$; and
(b) 8-10 membered bicyclic heterocyclyl optionally substituted by $C_6$ aryl and 0, 1, 2, or 3 occurrences of $Y^1$;

$X^1$ represents independently for each occurrence:
—N($R^6$)C(O)-(3-7 membered heterocyclyl), —N($R^6$)C(O)-(3-7 membered oxo-heterocyclyl), —N($R^6$)C(O)-phenyl, —N($R^6$)C(O)-aralkyl, or —N($R^6$)C(O)-heteroaralkyl; each of which is optionally substituted by 1, 2, or 3 occurrences of $Y^1$;
—$CO_2R^8$, —C(O)N($R^8$)($R^9$), —C(O)$R^{11}$, —C(O)$R^{12}$, —C(O)-(3-7 membered heterocyclyl), —C(O)N($R^8$)($R^{10}$), —N($R^6$)C(O)$R^{10}$, —N($R^{10}$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), —N($R^6$)C(O)N($R^6$)($R^7$), —N($R^6$)C(O)N($R^6$)($R^{10}$), —N($R^6$)($R^7$), or —$NO_2$;
—O—($C_1$-$C_6$ alkylene)-$CO_2R^8$, —OC(O)$R^{12}$, —O—($C_1$-$C_6$ alkylene)-C(O)N($R^8$)($R^9$), —O—($C_1$-$C_6$ alkylene)-N($R^8$)($R^9$), —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;
—$SO_2R^{10}$, —$SO_2N(R^8)$-heteroaryl, cyano, —P(O)(O$R^8$)$_2$, or —P(O)($R^{12}$)($R^{13}$);
5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl); or
—($C_1$-$C_6$ alkylene)-aryl, —($C_1$-$C_6$ alkylene)-heterocyclyl, —($C_1$-$C_6$ alkylene)-COR$^{12}$, —($C_1$-$C_6$ alkylene)-N($R^6$)C(O)$R^{10}$, or —($C_1$-$C_6$ alkylene)-C(O)N($R^8$)($R^{10}$); and $Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —C(O)N($R^8$)($R^9$), —N($R^6$)C(O)$R^{10}$, —N($R^6$)C(O)N($R^6$)($R^7$), —N($R^6$)($R^7$), —($C_1$-$C_6$ alkylene)-$CO_2R^8$, —($C_1$-$C_6$ alkylene)-O—($C_1$-$C_6$ alkyl), —($C_1$-$C_6$ alkylene)-N($R^6$)($R^7$), —($C_1$-$C_6$ alkylene)-N($R^6$)S(O)$_2R^{12}$, —($C_1$-$C_6$ alkylene)-S—C(O)$R^{12}$, —S—$R^{12}$, 3-7 membered heterocycloalkyl, or —($C_1$-$C_6$ alkylene)-(3-7 membered heterocycloalkyl).

2. The compound of claim 1, wherein $R^4$ is chloro.

3. The compound of claim 1, wherein $A^1$ is phenyl or a 5-6 membered heteroaryl, each being substituted by $X^1$ and 0, 1, 2, or 3 occurrences of $Y^1$.

4. The compound of claim 2, wherein $A^1$ is phenyl substituted by $X^1$ and 0, 1, 2, or 3 occurrences of $Y^1$.

5. The compound of claim 1, wherein $X^1$ is —N($R^6$)C(O)-(5-6 membered heteroaryl) substituted by 1, 2, or 3 occurrences of $Y^1$.

6. The compound of claim 1, wherein $X^1$ is —$CO_2R^8$, —C(O)N($R^8$)($R^9$), —C(O)$R^{11}$, —C(O)$R^{12}$, —C(O)-(3-7 membered heterocyclyl), —C(O)N($R^8$)($R^{10}$), —N($R^6$)C(O)$R^{10}$, —N($R^{10}$)C(O)$R^{10}$, —N($R^6$)$CO_2R^{10}$, —N($R^8$)$SO_2R^{10}$, —N(R⁶)—(C₁-C₆ alkylene)-C(O)N(R⁸)(R⁹), —N(R⁶)—C(O)—(C₁-C₆ hydroxyalkylene)-N(R⁸)(R⁹), —N(R⁶)—C(O)-(2-6 membered heteroalkyl), —N(R⁶)C(O)N(R⁶)(R⁷), or —NO₂.

7. The compound of claim 1, wherein $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl).

8. The compound of claim 1, wherein the compound is represented by Formula I-A:

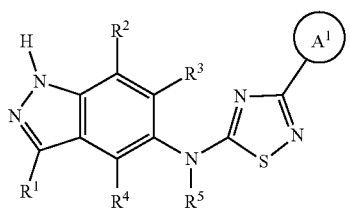

(I-A)

or a pharmaceutically acceptable salt thereof, or a solvate of the foregoing; wherein:
$R^1$ is hydrogen or $C_1$-$C_3$ alkyl;
$R^2$, $R^3$, and $R^5$ are hydrogen;
$R^4$ is hydrogen, chloro, or fluoro;
$R^6$ and $R^7$ each represent independently for each occurrence hydrogen or $C_1$-$C_3$ alkyl;
$R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, —CO₂R⁶, —N(R⁶)₂, and hydroxyl;
$R^{10}$ is $C_1$-$C_6$ alkyl, $C_1$-$C_6$ haloalkyl, $C_3$-$C_6$ cycloalkyl, or $C_1$-$C_6$ hydroxyalkyl;
$A^1$ is phenyl or a 6-membered heteroaryl, each being substituted by $X^1$ and 0, 1, 2, or 3 occurrences of $Y^1$;
$X^1$ represents independently for each occurrence:
 —N(R⁶)C(O)-(3-7 membered heterocyclyl) or —N(R⁶)C(O)-phenyl, each of which is optionally substituted by 1, 2, or 3 occurrences of $Y^1$;
 —C(O)N(R⁸)(R⁹), —N(R⁶)C(O)R¹⁰, —N(R¹⁰)C(O)R¹⁰, —N(R⁶)CO₂R¹⁰, or —N(R⁸)SO₂R¹⁰; or
 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl); and
$Y^1$ represents independently for each occurrence halogen, $C_1$-$C_6$ alkyl, $C_1$-$C_6$ haloalkyl, $C_1$-$C_6$ hydroxyalkyl, —CO₂R⁸, hydroxyl, or —(C₁-C₆ alkylene)-N(R⁶)(R⁷).

9. The compound of claim 8, wherein the compound is a compound of Formula I-A or a pharmaceutically acceptable salt thereof.

10. The compound of claim 9 wherein $R^4$ is chloro.

11. The compound of claim 10, wherein $A^1$ is phenyl substituted by $X^1$ and 0, 1, 2, or 3 occurrences of Y1.

12. The compound of claim 10, wherein $A^1$ is a 6-membered heteroaryl substituted by $X^1$ and 0, 1, 2, or 3 occurrences of $Y^1$.

13. The compound of claim 10, wherein $A^1$ is

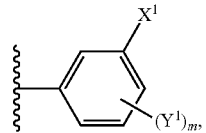

wherein m is 0, 1, 2, or 3.

14. The compound of claim 10, wherein $X^1$ is —N(R⁶)C(O)-(3-7 membered heterocyclyl) optionally substituted by 1, 2, or 3 occurrences of $Y^1$.

15. The compound of claim 10, wherein $X^1$ is —N(R⁶)C(O)-(5-6 membered heteroaryl) substituted by 1, 2, or 3 occurrences of $Y^1$.

16. The compound of claim 13, wherein $X^1$ is —N(R⁶)C(O)-(5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl) substituted by 1, 2, or 3 occurrences of $Y^1$.

17. The compound of claim 10, wherein $X^1$ is —N(R⁶)C(O)R¹⁰, —N(R¹⁰)C(O)R¹⁰, —N(R⁶)CO₂R¹⁰, or —N(R⁸)SO₂R¹⁰.

18. The compound of claim 10, wherein $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, $C_6$ aryl, and —C(O)—($C_6$ aryl).

19. The compound of claim 13, wherein $X^1$ is a 5-6 membered heteroaryl optionally substituted with 1, 2, or 3 occurrences of $Y^1$.

20. The compound of claim 10, wherein $Y^1$ represents independently for each occurrence halogen, $C_1$-$C_6$ alkyl, $C_1$-$C_6$ haloalkyl, $C_1$-$C_6$ hydroxyalkyl, —CO₂R⁸, or hydroxyl.

21. The compound of claim 16, wherein $Y^1$ represents independently for each occurrence halogen or $C_1$-$C_6$ alkyl.

22. A compound represented by Formula II:

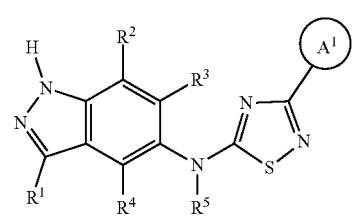

(II)

or a pharmaceutically acceptable salt thereof, or a solvate of the foregoing; wherein:
$R^1$ is hydrogen, halogen, $C_1$-$C_3$ alkyl, $C_1$-$C_3$ haloalkyl, cyclopropyl, $C_2$-$C_4$ alkenyl, cyano, or —N(R⁶)(R⁷);
$R^2$, $R^3$, and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;
$R^5$ is hydrogen, $C_1$-$C_6$ alkyl, or $C_1$-$C_6$ hydroxyalkyl;
$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 substituents selected from the group consisting of $C_1$-$C_6$ alkyl and $C_3$-$C_6$ cycloalkyl;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, 3-7 membered heterocycloalkyl, —($C_1$-$C_6$ alkylene)-O—($C_1$-$C_6$ alkyl), or —($C_1$-$C_6$ alkylene)-N($R^6$)($R^7$); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;

$A^1$ is a cyclic group selected from:
(a) phenyl, $C_3$-$C_7$ cycloalkyl, $C_3$-$C_7$ oxocycloalkyl, 5-10 membered heterocyclyl, 5-10 membered oxo-heterocyclyl, aralkyl, or heteroaralkyl, each being substituted by $X^1$ and 0, 1, 2, or 3 occurrences of $Y^1$; and
(b) 3-7 membered heterocycloalkyl substituted by —($C_1$-$C_6$alkylene)-N($R^6$)($R^7$) and 0, 1, 2, or 3 occurrences of $Y^1$;

$X^1$ represents independently for each occurrence:
—C(O)-(8-10 membered heterocyclyl containing a ring nitrogen atom bonded to the carbon atom of the attached —C(O)— group); or
5-10 membered oxo-heterocyclyl that is partially unsaturated and optionally substituted with 1, 2, or 3 occurrences of $Y^1$; and $Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —C(O)N($R^8$)($R^9$), —N($R^6$)C(O)N($R^6$)($R^7$), —N($R^6$)($R^7$), —($C_1$-$C_6$ alkylene)-$CO_2R^8$, —($C_1$-$C_6$ alkylene)-O—($C_1$-$C_6$ alkyl), or —($C_1$-$C_6$alkylene)-N($R^6$)($R^7$).

23. A compound in any one of Tables 1, 2, 3, or 4 below, wherein the compound is in solvated form, non-solvated form, or a pharmaceutically acceptable salt of any of the foregoing:

TABLE 1

| No. | $R^I$ | $R^{II}$ | $R^{III}$ | $A^1$ |
|---|---|---|---|---|
| I-1 | H | Cl | H | 3-acetamidophenyl |
| I-2 | CH₃ | Cl | H | 3-(2-aminopropanamido)phenyl |
| I-3 | CH₃ | H | H | 5-(cyclohexanecarboxamido)pyridin-3-yl |
| I-4 | H | Cl | H | 2-(tetrahydro-2H-pyran-2-carboxamido)pyridin-4-yl |

TABLE 1-continued

| No. | $R^I$ | $R^{II}$ | $R^{III}$ | $A^1$ |
|---|---|---|---|---|
| I-5 | CH₃ | H | H | 3-(1-methylpiperidine-4-carboxamido)phenyl |
| I-6 | H | Cl | H | 3-(2-(isopropylamino)acetamido)phenyl |
| I-7 | H | Cl | H | 5-(morpholine-4-carboxamido)pyridin-3-yl |
| I-8 | H | Cl | H | 3-(3-(pyridin-3-yl)ureido)phenyl |
| I-9 | H | Cl | H | 2-(3-methylpyrrolidine-1-carboxamido)pyridin-4-yl |
| I-10 | H | Cl | H | 3-((ethoxycarbonyl)amino)phenyl |

TABLE 1-continued
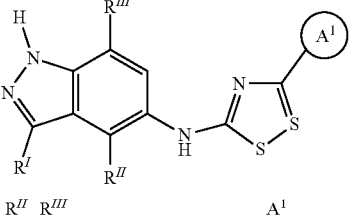
| No. | R$^I$ | R$^{II}$ | R$^{III}$ | A$^1$ |
|---|---|---|---|---|
| I-11 | H | Cl | H |  |
| I-12 | CH$_3$ | H | H | 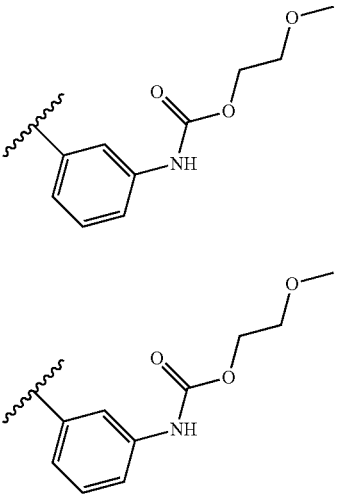 |
| I-13 | H | Cl | H |  |
| I-14 | H | Cl | H | 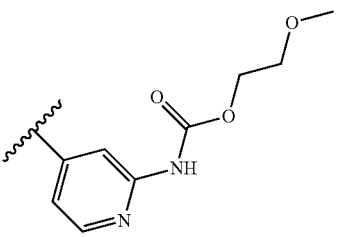 [SMILES: *c1ccnc(NC(=O)OCCOC)c1] |
| I-15 | H | Cl | H |  |
| I-16 | H | Cl | H | 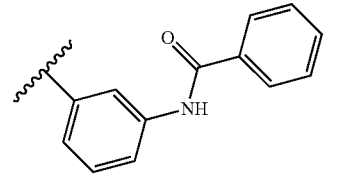 [SMILES: *c1cccc(NC(=O)c2ccccc2)c1] |

TABLE 1-continued
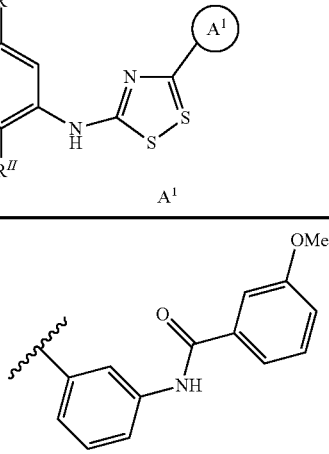
| No. | R$^I$ | R$^{II}$ | R$^{III}$ | A$^1$ |
|---|---|---|---|---|
| I-17 | H | Cl | H | 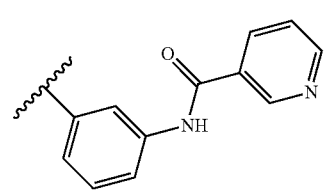 [SMILES: *c1cccc(NC(=O)c2cccnc2)c1] |
| I-18 | CH$_3$ | Cl | H | 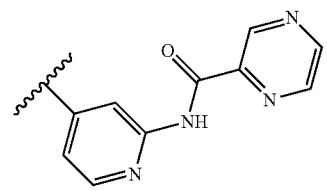 [SMILES: *c1ccnc(NC(=O)c2cnccn2)c1] |
| I-19 | H | Cl | H | 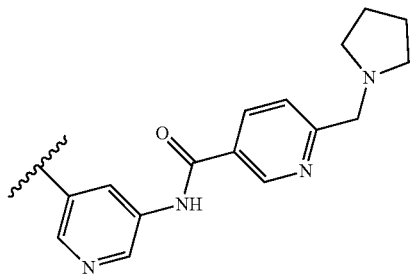 [SMILES: *c1cncc(NC(=O)c2ccc(CN3CCCC3)nc2)c1] |
| I-20 | H | Cl | H | 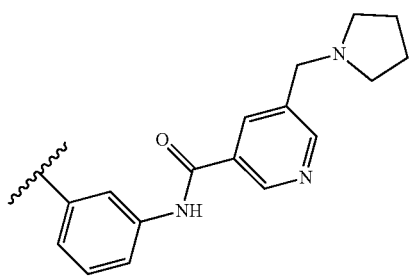 [SMILES: *c1cccc(NC(=O)c2cncc(CN3CCCC3)c2)c1] |
| I-21 | H | Cl | H | 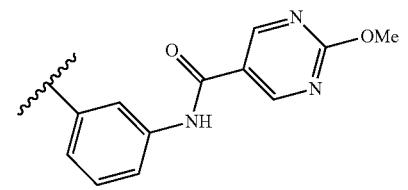 [SMILES: *c1cccc(NC(=O)c2cnc(OC)nc2)c1] |
| I-22 | CH$_3$ | H | H | |

TABLE 1-continued
| No. | R<sup>I</sup> | R<sup>II</sup> | R<sup>III</sup> | A<sup>1</sup> |
|---|---|---|---|---|
| I-23 | H | Cl | H | 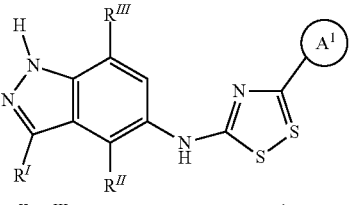 |
| I-24 | H | Cl | H | 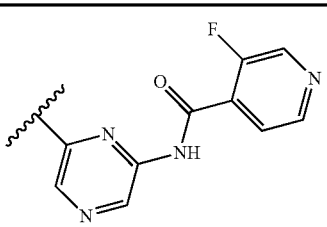 |
| I-25 | H | Cl | H | 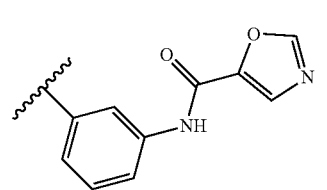 [SMILES: *c1cccc(NC(=O)c2cnco2)c1] |
| I-26 | H | Cl | H | 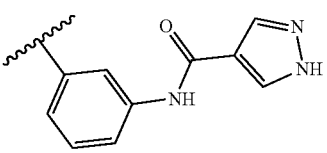 [SMILES: *c1cccc(NC(=O)c2cn[nH]c2)c1] |
| I-27 | H | Cl | H | 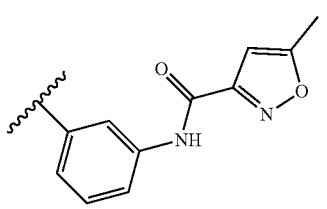 [SMILES: *c1cccc(NC(=O)c2cc(C)on2)c1] |
| I-28 | CH$_3$ | Cl | H | 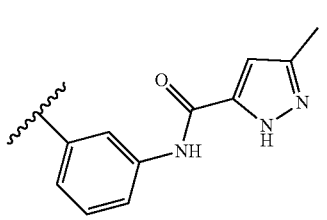 [SMILES: *c1cccc(NC(=O)c2cc(C)n[nH]2)c1] |
| I-29 | H | Cl | H | 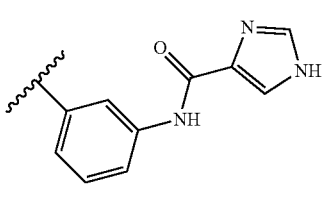 [SMILES: *c1cccc(NC(=O)c2c[nH]cn2)c1] |

TABLE 1-continued

| No. | R^I | R^II | R^III | A^1 |
|---|---|---|---|---|
| I-30 | CH$_3$ | H | H | 5-(pyridin-3-yl) linked to NH-C(O)-(1-methyl-1H-pyrazol-4-yl) |
| I-31 | H | Cl | H | 3-phenyl linked to NH-C(O)-(2-oxo-2,3-dihydro-1H-imidazol-4-yl) |
| I-32 | H | Cl | H | 3-phenyl linked to NH-C(O)-(3-methyl-1H-pyrazol-4-yl) |
| I-33 | H | Cl | H | 3-phenyl linked to NH-C(O)-(1,3-dimethyl-1H-pyrazol-4-yl) |
| I-34 | H | Cl | H | 3-phenyl linked to NH-C(O)-(4-methylisoxazol-5-yl) |
| I-35 | H | Cl | H | 3-phenyl linked to NH-C(O)-(isoxazol-3-yl) |
| I-36 | H | Cl | H | 4-(pyridin-2-yl) linked to NH-C(O)-(1-methyl-1H-pyrazol-3-yl) |

TABLE 1-continued
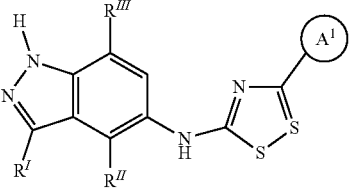
| No. | R$^I$ | R$^{II}$ | R$^{III}$ | A$^1$ |
|---|---|---|---|---|
| I-37 | H | Cl | H | 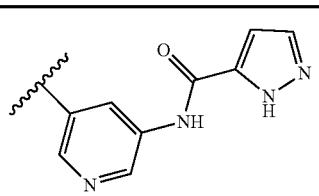 |
| I-38 | H | Cl | H | 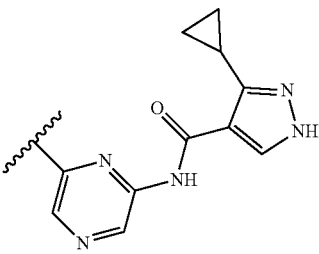 [SMILES: *c1cncc(NC(=O)c2c[nH]nc2C2CC2)n1] |
| I-39 | CH$_3$ | H | H | 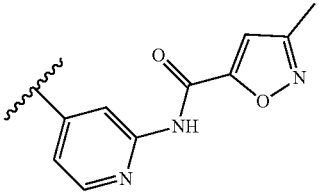 [SMILES: *c1ccnc(NC(=O)c2cc(C)no2)c1] |
| I-40 | H | Cl | H | 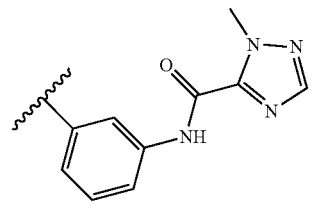 [SMILES: *c1cccc(NC(=O)c2ncnn2C)c1] |
| I-41 | H | Cl | H | 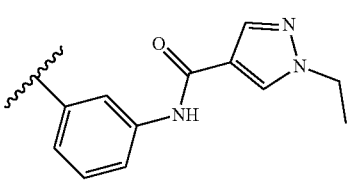 [SMILES: *c1cccc(NC(=O)c2cnn(CC)c2)c1] |
| I-42 | H | Cl | H | 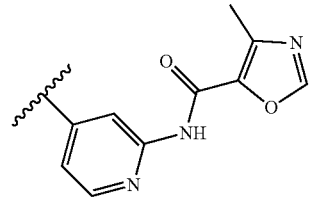 [SMILES: *c1ccnc(NC(=O)c2ocnc2C)c1] |

TABLE 1-continued

| No. | R$^I$ | R$^{II}$ | R$^{III}$ | A$^1$ |
|---|---|---|---|---|
| I-43 | H | Cl | H | pyridine-N-linked isoxazole-5-carboxamide |
| I-44 | H | Cl | H | phenyl-NH-C(O)-(5-methyl-1,3,4-oxadiazol-2-yl) |
| I-45 | H | Cl | H | phenyl-NH-C(O)-(1-methyl-1,2,4-triazol-5-yl) |
| I-46 | CH$_3$ | Cl | H | phenyl-NH-C(O)-(2-methyl-1H-imidazol-5-yl) |
| I-47 | H | Cl | H | phenyl-NH-C(O)-CH$_2$CH$_3$ |
| I-48 | H | Cl | H | phenyl-NH-C(O)-CH$_2$-(4-fluorophenyl) |

TABLE 1-continued

| No. | R$^I$ | R$^{II}$ | R$^{III}$ | A$^1$ |
|---|---|---|---|---|
| I-49 | H | Cl | H | (N-methylpyrazol-4-yl)acetamide-pyridin-4-yl |
| I-50 | CH$_3$ | H | H | (isoxazol-3-yl)acetamide-phenyl |
| I-51 | H | Cl | H | isobutyramide-phenyl |
| I-52 | H | Cl | Cl | (5-methylpyridin-2-yl)acetamide-phenyl |
| I-53 | H | Cl | H | 2-(4-fluorophenyl)propanamide-(6-methylpyridin-4-yl) |

TABLE 1-continued

| No. | R$^I$ | R$^{II}$ | R$^{III}$ | A$^1$ |
|---|---|---|---|---|
| I-54 | H | Cl | H | 3-methylisoxazol-5-yl-CH$_2$-C(O)-NH-(3-phenyl) |
| I-55 | H | H | H | 1-methyl-1H-pyrazol-5-yl-C(O)-NH-(3-phenyl) |
| I-56 | CH$_3$ | H | H | 1-methyl-1H-pyrazol-5-yl-C(O)-NH-(3-phenyl) |
| I-57 | H | H | Cl | 1-methyl-1H-pyrazol-5-yl-C(O)-NH-(3-phenyl) |
| I-58 | CH$_3$ | Cl | H | 1-methyl-1H-pyrazol-5-yl-C(O)-NH-(3-phenyl) |
| I-59 | H | Cl | Cl | 1-methyl-1H-pyrazol-5-yl-C(O)-NH-(3-phenyl) |

TABLE 1-continued
| No. | R$^I$ | R$^{II}$ | R$^{III}$ | A$^1$ |
|---|---|---|---|---|
| I-60 | CH$_3$ | H | Cl | 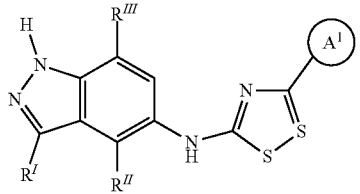 |
| I-61 | H | Cl | H | 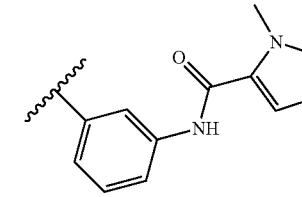 |
| I-62 | H | Cl | H | 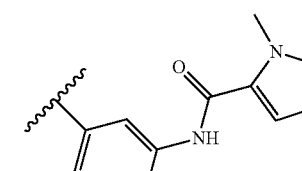 |
| I-63 | H | Cl | H | 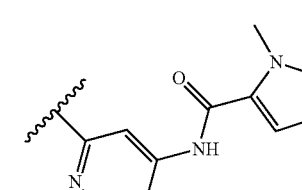 |
| I-64 | H | Cl | H | 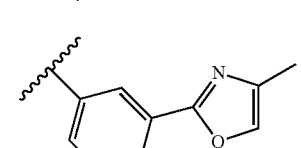 |
| I-65 | H | Cl | H | 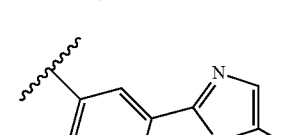 |
| I-66 | CH$_3$ | H | H | 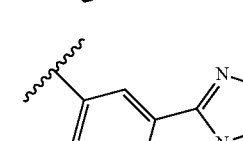 |

TABLE 1-continued
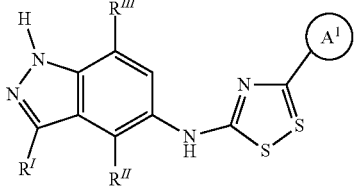
| No. | R<sup>I</sup> | R<sup>II</sup> | R<sup>III</sup> | A<sup>1</sup> |
|---|---|---|---|---|
| I-67 | H | Cl | H | 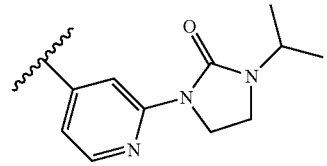 [SMILES: *c1ccnc(N2CCN(C(C)C)C2=O)c1] |
| I-68 | H | Cl | Cl | 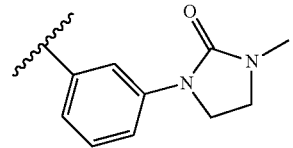 [SMILES: *c1cccc(N2CCN(C)C2=O)c1] |
| I-69 | H | Cl | H | 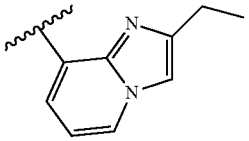 [SMILES: *c1cccn2cc(CC)nc12] |
| I-70 | CH₃ | H | H | 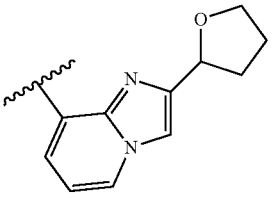 [SMILES: *c1cccn2cc(C3CCCO3)nc12] |
| I-71 | CH₃ | Cl | H | 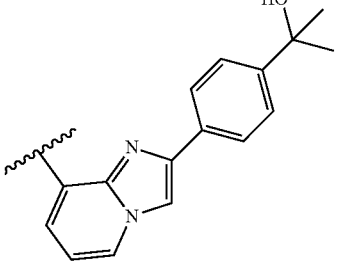 |
| I-72 | H | Cl | H | 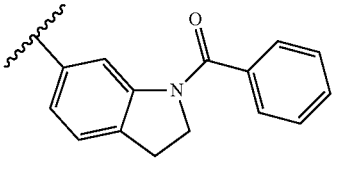 [SMILES: *c1ccc2c(c1)N(C(=O)c1ccccc1)CC2] |
| I-73 | H | Cl | H | 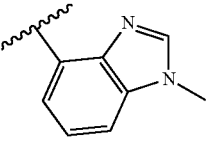 [SMILES: *c1cccc2c1ncn2C] |

TABLE 1-continued
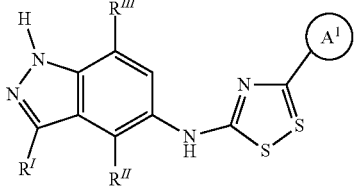
| No. | R$^I$ | R$^{II}$ | R$^{III}$ | A$^1$ |
|---|---|---|---|---|
| I-74 | CH$_3$ | Cl | H | 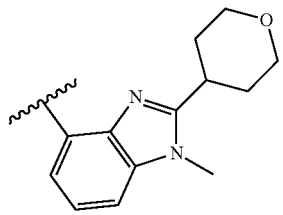 [SMILES: *c1cccc2c1nc(C1CCOCC1)n2C] |
| I-75 | H | H | Cl | 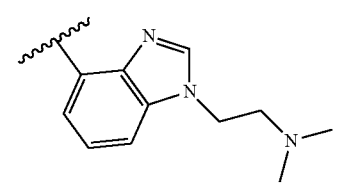 [SMILES: *c1cccc2c1ncn2CCN(C)C] |
| I-76 | H | Cl | H | 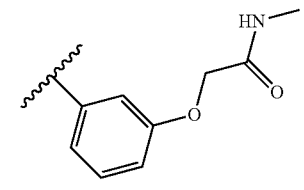 [SMILES: *c1cccc(OCC(=O)NC)c1] |
| I-77 | CH$_3$ | H | H | 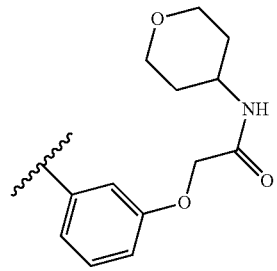 [SMILES: *c1cccc(OCC(=O)NC2CCOCC2)c1] |
| I-78 | H | Cl | H | 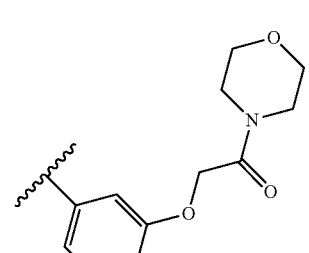 |
| I-79 | CH$_3$ | Cl | H | 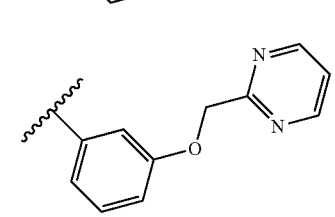 |

TABLE 1-continued
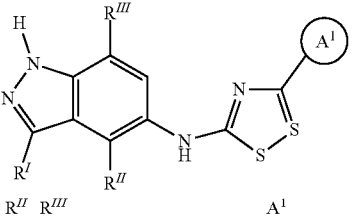
| No. | R^I | R^II | R^III | A^1 |
|---|---|---|---|---|
| I-80 | H | Cl | H | 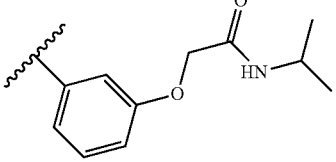 |
| I-81 | H | Cl | H | 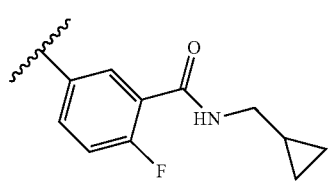 [SMILES: *c1ccc(F)c(C(=O)NCC2CC2)c1] |
| I-82 | H | Cl | H | 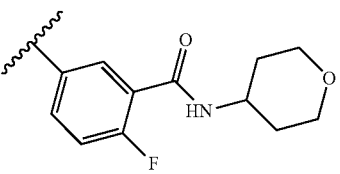 [SMILES: *c1ccc(F)c(C(=O)NC2CCOCC2)c1] |
| I-83 | H | Cl | H | 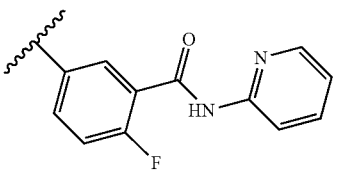 [SMILES: *c1ccc(F)c(C(=O)Nc2ccccn2)c1] |
| I-84 | H | Cl | H | 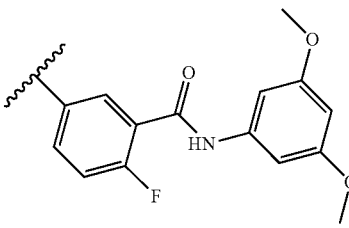 |
| I-85 | —NH$_2$ | H | H | 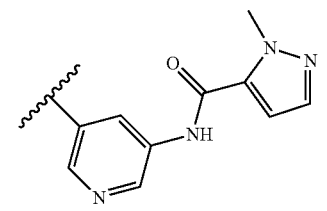 [SMILES: *c1cncc(NC(=O)c2ccnn2C)c1] |
| I-86 | H | Cl | H | 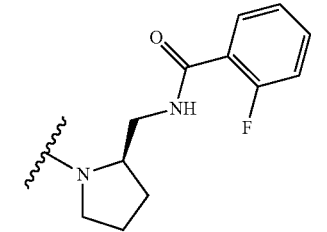 [SMILES: *N1CCC[C@@H]1CNC(=O)c1ccccc1F] |

TABLE 1-continued

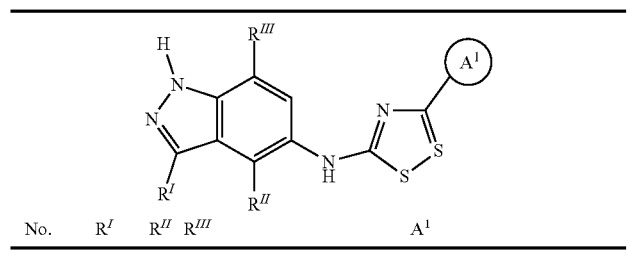

| No. | $R^I$ | $R^{II}$ | $R^{III}$ | $A^1$ |
|---|---|---|---|---|
| I-87 | H | Cl | H | 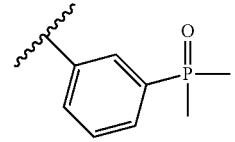 [SMILES: *c1cccc(P(C)(C)=O)c1] |
| I-88 | H | Cl | H | 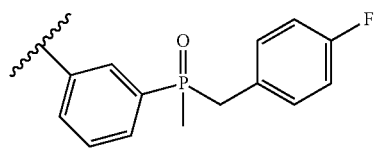 [SMILES: *c1cccc(P(C)(=O)Cc2ccc(F)cc2)c1] |

TABLE 2

| No. | Chemical Structure [name] |
|---|---|
| II-1 | 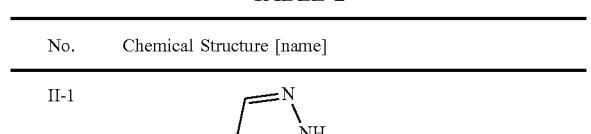<br>[N-(4-(5-((4-chloro-1H-indazol-5-yl)amino)-1,2,4-thiadiazol-3-yl)pyridin-2-yl)morpholine-4-carboxamide 2,2,2-trifluoroacetic acid solvate] |
| II-2 | 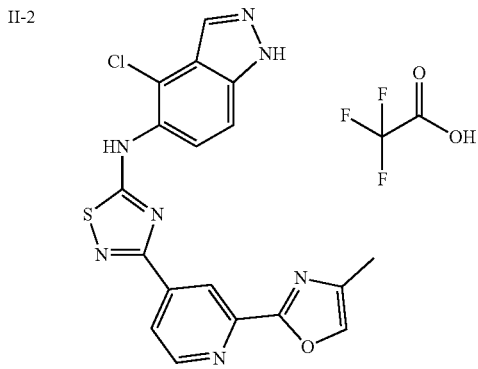<br>[N-(4-chloro-1H-indazol-5-yl)amino)-3-(3-(4-methyloxazol-2-yl)phenyl)-1,2,4-thiadiazol-5-amine 2,2,2-trifluoroacetic acid solvate] |
| II-3 | 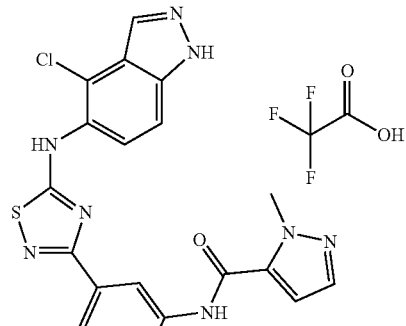<br>[N-(4-(5-((4-chloro-1H-indazol-5-yl)amino)-1,2,4-thiadiazol-3-yl)pyridin-2-yl)-1-methyl-1H-pyrazole-5-carboxamide 2,2,2-trifluoroacetic acid solvate] |
| II-4 | 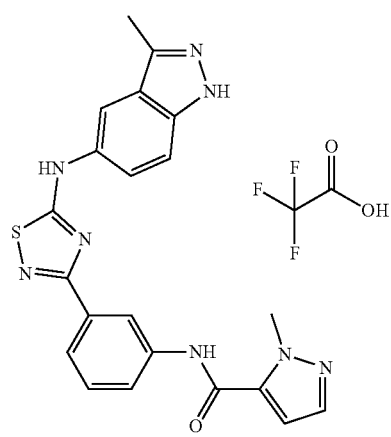 [SMILES: Cc1n[nH]c2ccc(Nc3nc(-c4cccc(NC(=O)c5ccnn5C)c4)ns3)cc12 ; O=C(O)C(F)(F)F]<br>[1-methyl-N-(3-(5-((3-methyl-1H-indazol-5-yl)amino)-1,2,4-thiadiazol-3-yl)phenyl)-1H-pyrazole-5-carboxamide 2,2,2-trifluoroacetic acid solvate] |

TABLE 2-continued

| No. | Chemical Structure [name] |
|---|---|
| II-5 | 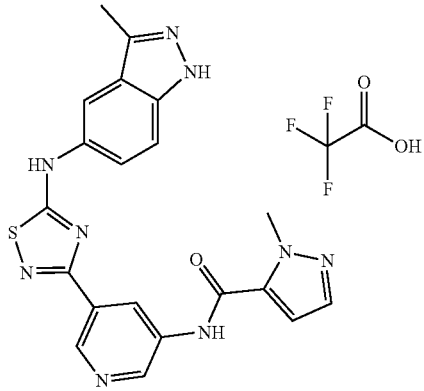 [SMILES: Cc1n[nH]c2ccc(Nc3nc(-c4cncc(NC(=O)c5ccnn5C)c4)ns3)cc12 ; O=C(O)C(F)(F)F] [1-methyl-N-(5-(5-((3-methyl-1H-indazol-5-yl)amino)-1,2,4-thiadiazol-3-yl)pyridin-3-yl)-1H-pyrazole-5-carboxamide 2,2,2-trifluoroacetic acid solvate] |
| II-6 | 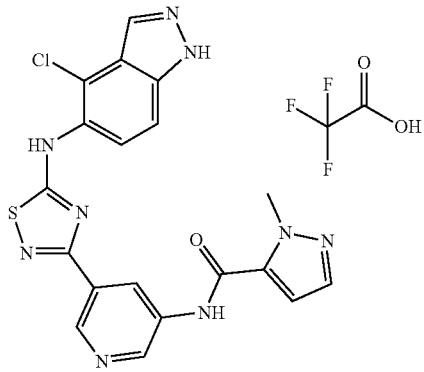 [SMILES: Cn1nccc1C(=O)Nc1cncc(-c2nsc(Nc3ccc4[nH]ncc4c3Cl)n2)c1 ; O=C(O)C(F)(F)F] [N-(5-(5-((4-chloro-1H-indazol-5-yl)amino)-1,2,4-thiadiazol-3-yl)pyridin-3-yl)-1-methyl-1H-pyrazole-5-carboxamide 2,2,2-trifluoroacetic acid solvate] |
| II-7 | 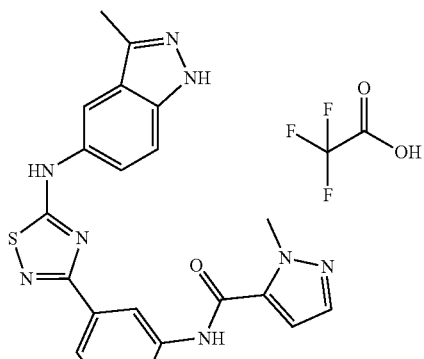 [1-methyl-N-(4-(5-((3-methyl-1H-indazol-5-yl)amino)-1,2,4-thiadiazol-3-yl)pyridin-2-yl)-1H-pyraole-5-carboxamide 2,2,2-trifluoroacetic acid solvate] |

TABLE 3

| No. | Chemical Structure [name] |
|---|---|
| III-1 | 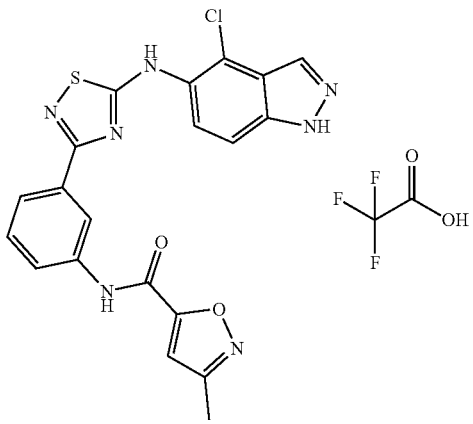 [SMILES: Cc1cc(C(=O)Nc2cccc(-c3nsc(Nc4ccc5[nH]ncc5c4Cl)n3)c2)on1 ; O=C(O)C(F)(F)F] [N-(3-(5-((4-Chloro-1H-indazol-5-yl)amino)-1,2,4-thiadiazol-3-yl)phenyl)-3-methylisoxazole-5-carboxamide 2,2,2-trifluoroacetic acid solvate] |
| III-2 | 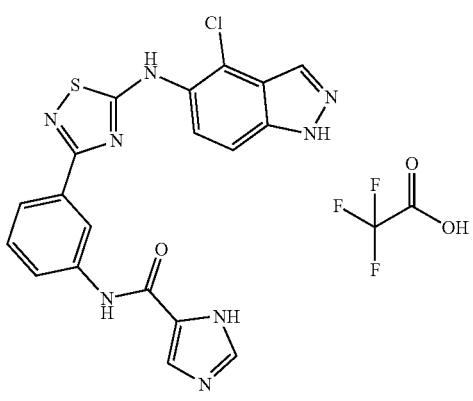 [SMILES: O=C(Nc1cccc(-c2nsc(Nc3ccc4[nH]ncc4c3Cl)n2)c1)c1cnc[nH]1 ; O=C(O)C(F)(F)F] [N-(3-(5-((4-Chloro-1H-indazol-5-yl)amino)-1,2,4-thiadiazol-3-yl)phenyl)-1H-imidazole-5-carboxamide 2,2,2-trifluoroacetic acid solvate] |
| III-3 | 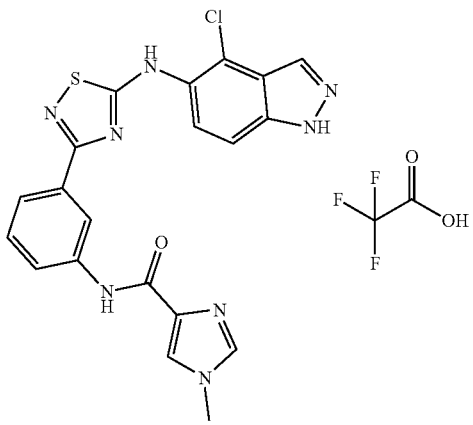 [SMILES: Cn1cnc(C(=O)Nc2cccc(-c3nsc(Nc4ccc5[nH]ncc5c4Cl)n3)c2)c1 ; O=C(O)C(F)(F)F] [N-[3-[5-[(4-chloro-1H-indazol-5-yl)amino]-1,2,4-thiadiazol-3-yl]phenyl]-1-methyl-imidazole-4-carboxamide 2,2,2-trifluoroacetic acid solvate] |

TABLE 3-continued

| No. | Chemical Structure [name] |
|---|---|
| III-4 | 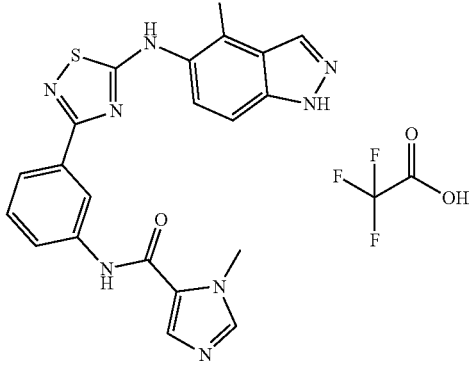<br>[of N-(3-(5-((4-Chloro-1H-indazol-5-yl)amino)-1,2,4-thiadiazol-3-yl)phenyl)-1-methyl-1H-imidazole-4-carboxamide 2,2,2-trifluoroacetic acide solvate] |
| III-5 | 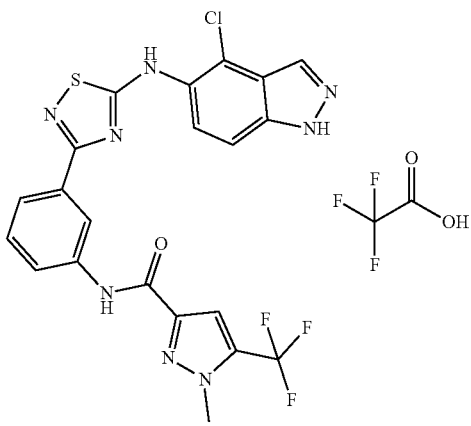 [SMILES: Cn1nc(C(=O)Nc2cccc(-c3nsc(Nc4ccc5[nH]ncc5c4Cl)n3)c2)cc1C(F)(F)F ; O=C(O)C(F)(F)F]<br>[N-(3-(5-((4-Chloro-1H-indazol-5-yl)amino)-1,2,4-thiadiazol-3-yl)phenyl)-1-methyl-5-(trifluoromethyl)-1H-pyrazole-3-carboxamide 2,2,2-trifluoroacetic acid solvate] |
| III-6 | 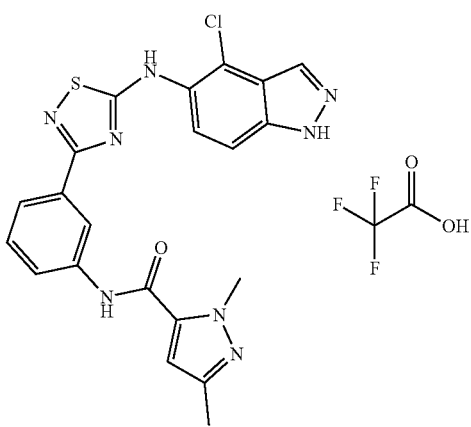 [SMILES: Cc1cc(C(=O)Nc2cccc(-c3nsc(Nc4ccc5[nH]ncc5c4Cl)n3)c2)n(C)n1 ; O=C(O)C(F)(F)F]<br>[N-(3-(5-((4-Chloro-1H-indazol-5-yl)amino)-1,2,4-thiadiazol-3-yl)phenyl)-1,3-dimethyl-1H-pyrazole-5-carboxamide 2,2,2-triflioroacetic acid solvate] |
| III-7 | 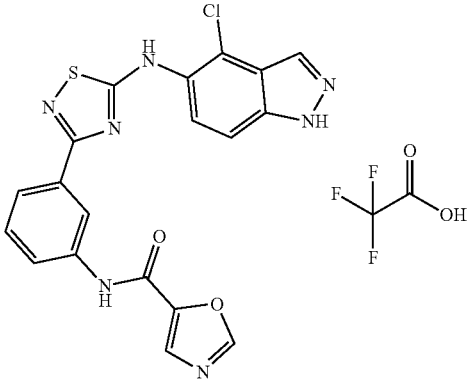 [SMILES: O=C(Nc1cccc(-c2nsc(Nc3ccc4[nH]ncc4c3Cl)n2)c1)c1cnco1 ; O=C(O)C(F)(F)F]<br>[N-(3-(5-((4-Chloro-1H-indazol-5-yl)amino)-1,2,4-thiadiazol-3-yl)phenyl)oxazole-5-carboxamide 2,2,2,-trifluoroacetic acid solvate] |
| III-8 | 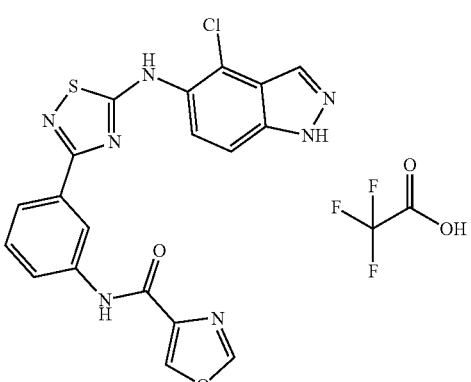<br>[N-(3-(5-((4-Chloro-1H-indazol-5-yl)amino)-1,2,4-thiadiazol-3-yl)phenyl)oxazole-5-carboxamide 2,2,2-trifluoroacetic acid solvate] |
| III-9 | 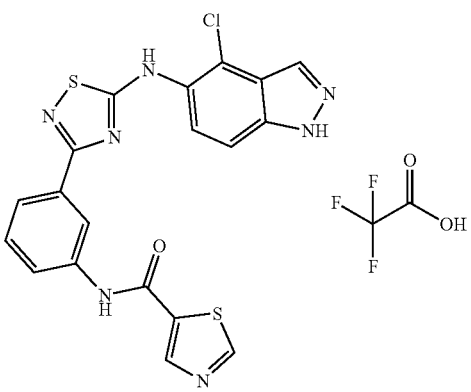<br>[N-(3-(5-((4-Chloro-1H-indazol-5-yl)amino)-1,2,4-thiadiazol-3-yl)phenyl)thiazole-5-carboxamide 2,2,2,-trifluoroacetic acid solvate] |

TABLE 3-continued

| No. | Chemical Structure [name] |
|---|---|
| III-10 | 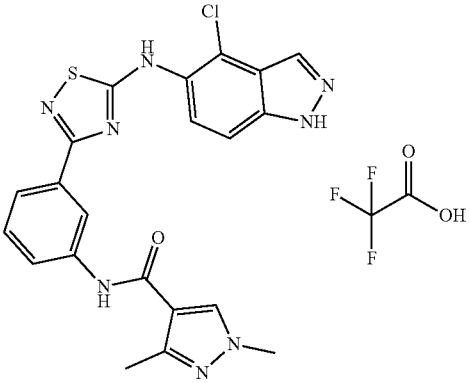 [SMILES: Cc1nn(C)cc1C(=O)Nc1cccc(-c2nsc(Nc3ccc4[nH]ncc4c3Cl)n2)c1 ; O=C(O)C(F)(F)F] [N-(3-(5-((4-Chloro-1H-indazol-5-yl)amino)-1,2,4-thiadiazol-3-yl)phenyl)-1,3-dimethyl-1H-pyrazole-4-carboxamide 2,2,2-trifluoroacetic acid solvate] |
| III-11 | 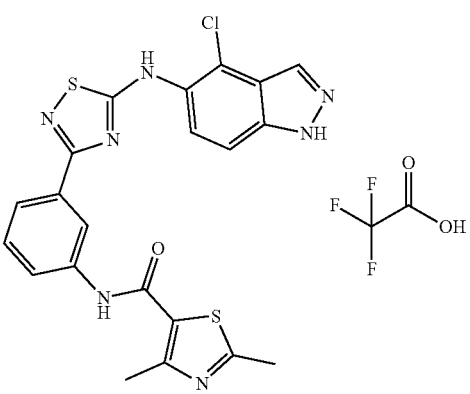 [SMILES: Cc1nc(C)c(C(=O)Nc2cccc(-c3nsc(Nc4ccc5[nH]ncc5c4Cl)n3)c2)s1 ; O=C(O)C(F)(F)F] [N-(3-(5-((4-Chloro-1H-indazol-5-yl)amino)-1,2,4-thiadiazol-3-yl)phenyl)-2,4-dimethylthiazole-5-carboxamide 2,2,2-trifluoroacetic acid solvate] |
| III-12 | 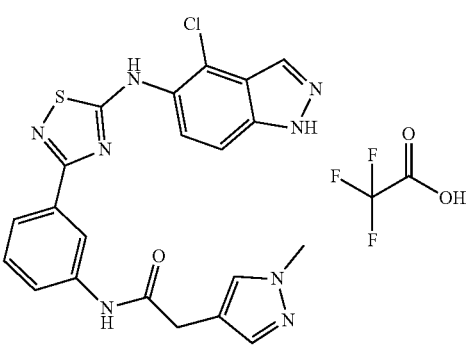 [SMILES: Cn1cc(CC(=O)Nc2cccc(-c3nsc(Nc4ccc5[nH]ncc5c4Cl)n3)c2)cn1 ; O=C(O)C(F)(F)F] [N-(3-(5-((4-Chloro-1H-indazol-5-yl)amino)-1,2,4-thiadiazol-3-yl)phenyl)-2-(1-methyl-1H-pyrazol-4-yl)acetamide 2,2,2-trifluoroactic acid solvate] |

TABLE 4

| No. | Compound Structure |
|---|---|
| A-1 | 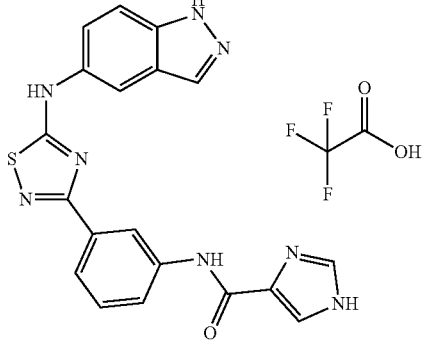 |
| A-2 | 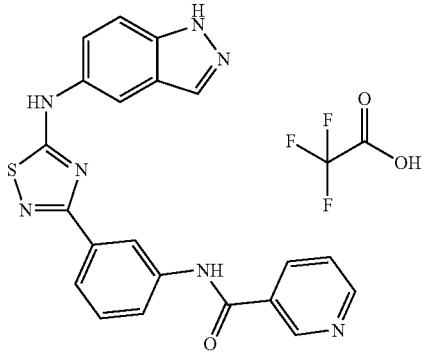 |
| A-3 | 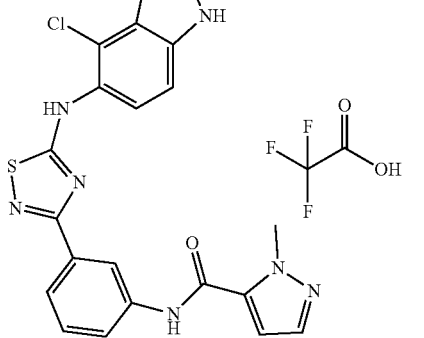 |
| A-4 | 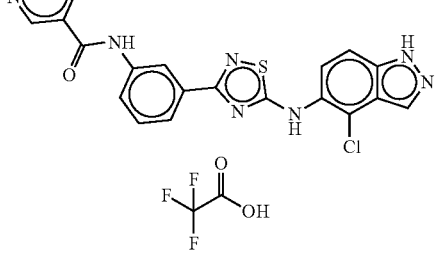 |

TABLE 4-continued

| No. | Compound Structure |
|---|---|
| A-5 | 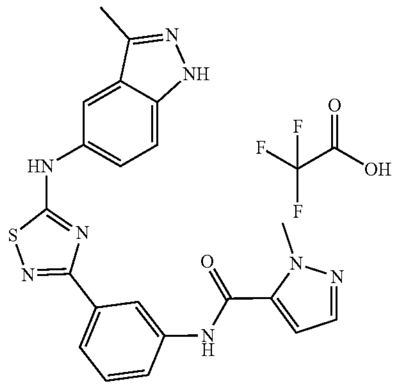 |
| A-6 | 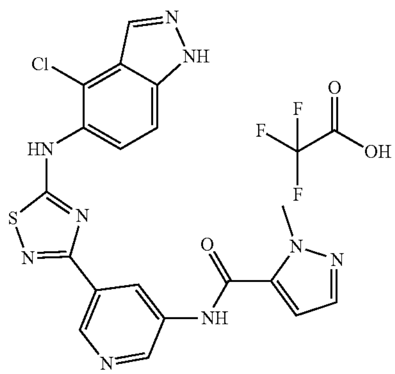 |
| A-7 | 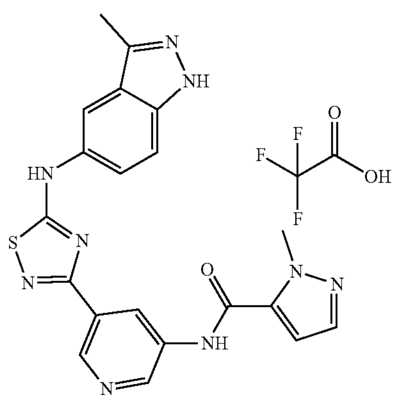 |
| A-8 | 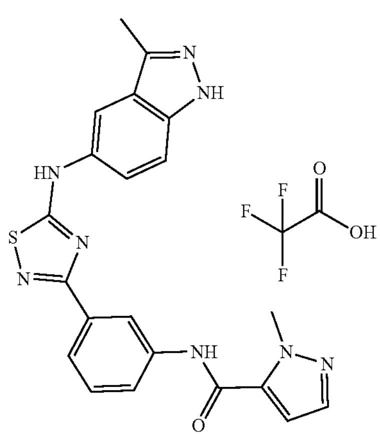 |
| A-9 | |
| A-10 | |
| A-11 | |
| A-12 | |

TABLE 4-continued

| No. | Compound Structure |
|---|---|
| A-13 | (structure) |
| A-14 | (structure) |
| A-15 | (structure) |
| A-16 | (structure) |
| A-17 | (structure) |
| A-18 | (structure) |
| A-19 | (structure) |
| A-20 | (structure) |

TABLE 4-continued

| No. | Compound Structure |
|---|---|
| A-21 | 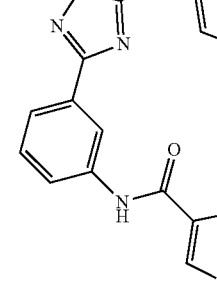 |
| A-22 | 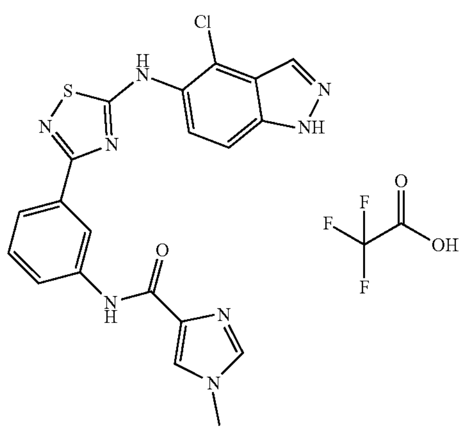 [SMILES: Cn1cnc(C(=O)Nc2cccc(-c3nsc(Nc4ccc5[nH]ncc5c4Cl)n3)c2)c1 ; O=C(O)C(F)(F)F] |
| A-23 | 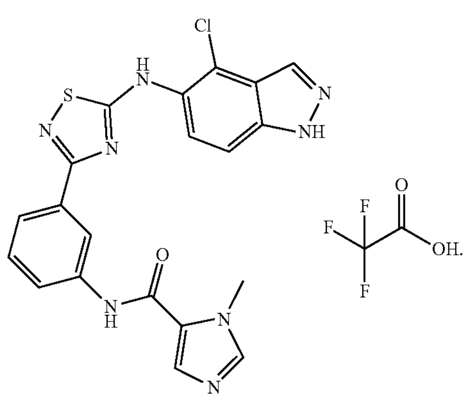 [SMILES: Cn1cncc1C(=O)Nc1cccc(-c2nsc(Nc3ccc4[nH]ncc4c3Cl)n2)c1 ; O=C(O)C(F)(F)F] |

24. The compound of claim 23, wherein the compound is in non-solvated form, or a pharmaceutically acceptable salt thereof.

25. A compound in Table 5 below, wherein the compound is in solvated form, non-solvated form, or a pharmaceutically acceptable salt of any of the foregoing:

TABLE 5

| No. | Compound Structure |
|---|---|
| IV-1 | 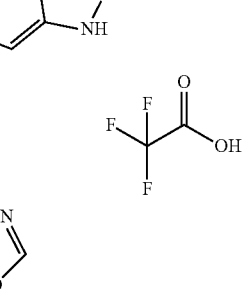<br>formic acid solvate |
| IV-2 | 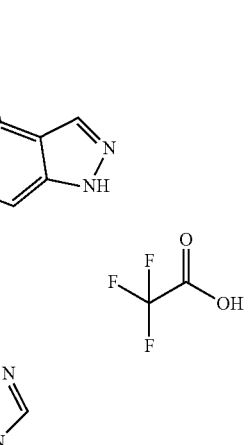 |
| IV-3 | 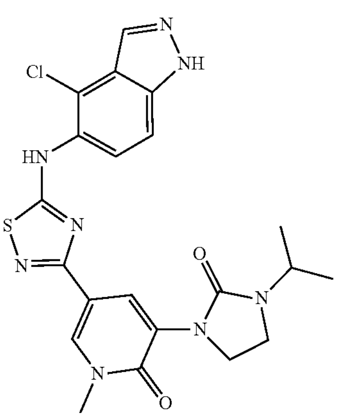 [SMILES: CC(C)N1CCN(c2cc(-c3nsc(Nc4ccc5[nH]ncc5c4Cl)n3)cn(C)c2=O)C1=O] |

TABLE 5-continued

| No. | Compound Structure |
|---|---|
| IV-4 | 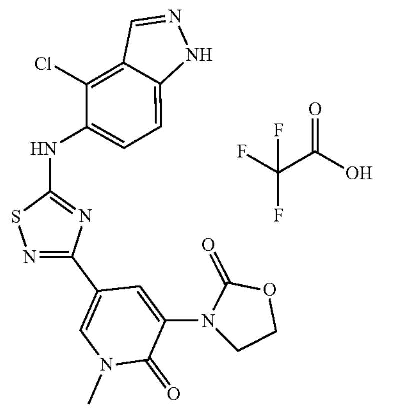 [SMILES: Cn1cc(-c2nsc(Nc3ccc4[nH]ncc4c3Cl)n2)cc(N2CCOC2=O)c1=O ; O=C(O)C(F)(F)F] |
| IV-5 | 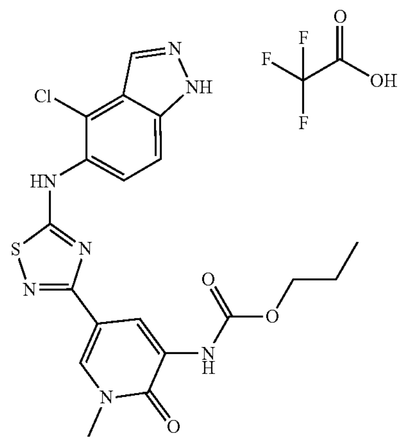 [SMILES: CCCOC(=O)Nc1cc(-c2nsc(Nc3ccc4[nH]ncc4c3Cl)n2)cn(C)c1=O ; O=C(O)C(F)(F)F] |
| IV-6 | 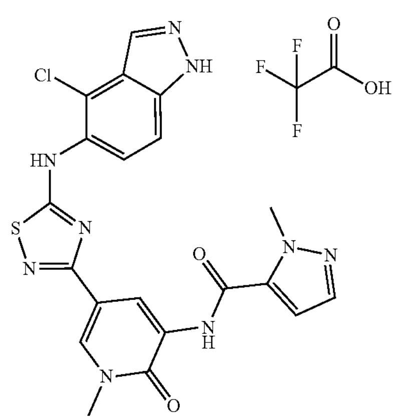 [SMILES: Cn1nccc1C(=O)Nc1cc(-c2nsc(Nc3ccc4[nH]ncc4c3Cl)n2)cn(C)c1=O ; O=C(O)C(F)(F)F] |
| IV-7 | formic acid solvate |
| IV-8 | 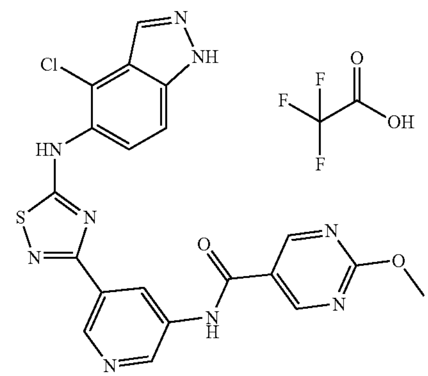 [SMILES: COc1ncc(C(=O)Nc2cncc(-c3nsc(Nc4ccc5[nH]ncc5c4Cl)n3)c2)cn1 ; O=C(O)C(F)(F)F] |
| IV-9 | 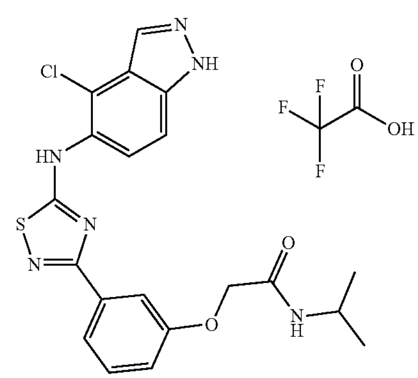 [SMILES: CC(C)NC(=O)COc1cccc(-c2nsc(Nc3ccc4[nH]ncc4c3Cl)n2)c1 ; O=C(O)C(F)(F)F] |
| IV-10 | 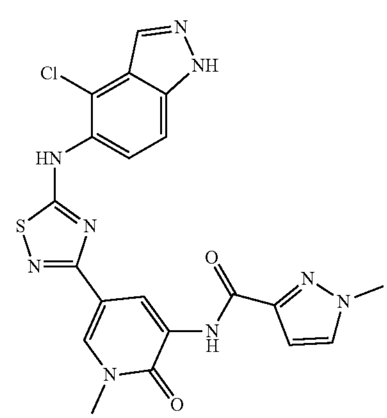 [SMILES: Cn1ccc(C(=O)Nc2cc(-c3nsc(Nc4ccc5[nH]ncc5c4Cl)n3)cn(C)c2=O)n1] |

TABLE 5-continued

| No. | Compound Structure |
|-----|-------------------|
| IV-11 | [chemical structure with chloro-indazole, thiadiazole, methylpyridine-pyrrolidinone; trifluoroacetic acid] |
| IV-12 | [chemical structure with chloro-indazole, thiadiazole, methylpyridinone-methylisoxazole] |
| IV-13 | [chemical structure with chloro-indazole, thiadiazole, methylpyridine, methylpyrazole carboxamide] |
| IV-14 | [chemical structure with chloro-indazole, thiadiazole, fluorophenyl isopropylcarboxamide; trifluoroacetic acid] |
| IV-15 | [chemical structure with fluoro-indazole, thiadiazole, phenyl, methyloxazole] |
| IV-16 | [chemical structure with chloro-indazole, thiadiazole, phenyl, methanesulfonamide] |
| IV-17 | [chemical structure with chloro-indazole, thiadiazole, phenyl, hydroxypyrazole] |
| IV-18 | [chemical structure with chloro-indazole, thiadiazole, pyridine, thiazole carboxamide; trifluoroacetic acid] |

TABLE 5-continued

| No. | Compound Structure |
|---|---|
| IV-19 | 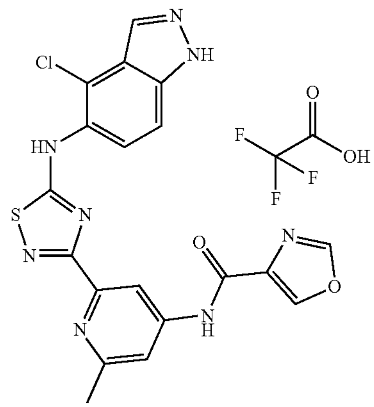 |
| IV-20 | 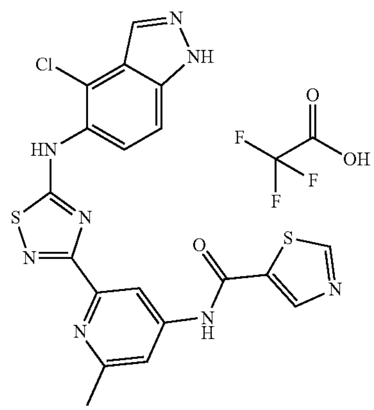 |
| IV-21 | 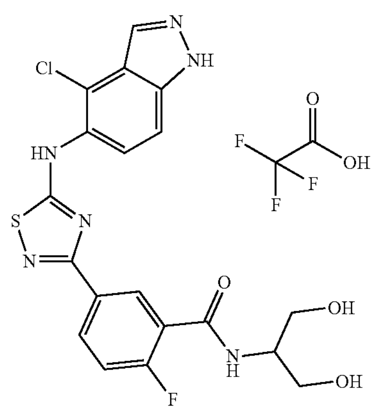 [SMILES: O=C(NC(CO)CO)c1cc(-c2nsc(Nc3ccc4[nH]ncc4c3Cl)n2)ccc1F ; O=C(O)C(F)(F)F] |
| IV-22 | 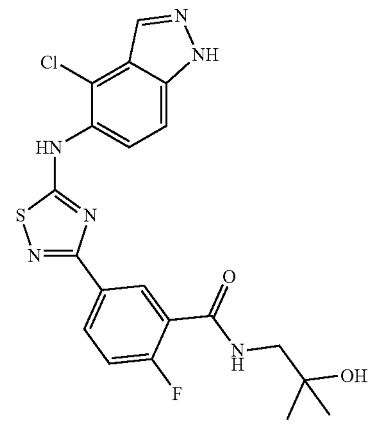 [SMILES: CC(C)(O)CNC(=O)c1cc(-c2nsc(Nc3ccc4[nH]ncc4c3Cl)n2)ccc1F] |
| IV-23 | 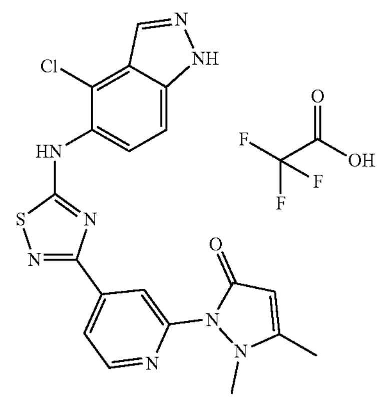 [SMILES: Cc1cc(=O)n(-c2cc(-c3nsc(Nc4ccc5[nH]ncc5c4Cl)n3)ccn2)n1C ; O=C(O)C(F)(F)F] |
| IV-24 | 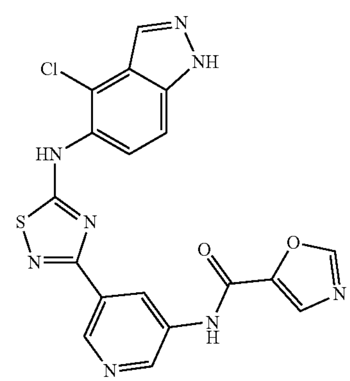 [SMILES: O=C(Nc1cncc(-c2nsc(Nc3ccc4[nH]ncc4c3Cl)n2)c1)c1cnco1] |
| IV-25 | 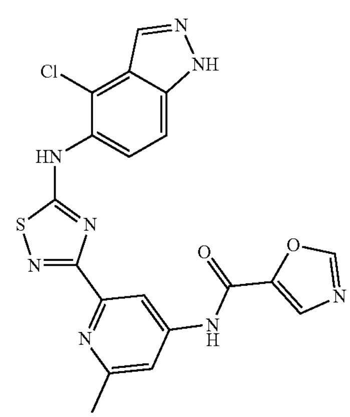 [SMILES: Cc1cc(NC(=O)c2cnco2)cc(-c2nsc(Nc3ccc4[nH]ncc4c3Cl)n2)n1] |

TABLE 5-continued
| No. | Compound Structure |
|---|---|
| IV-26 | 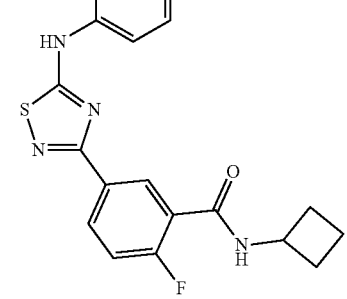 |
| IV-27 | 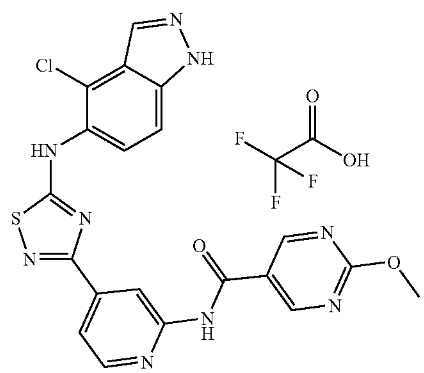 |
| IV-28 | 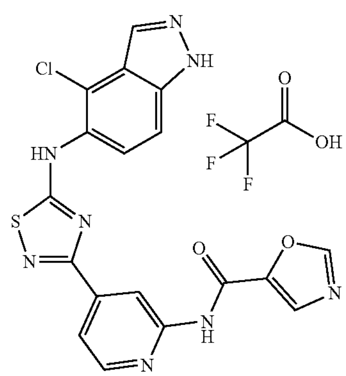 |
| IV-29 | 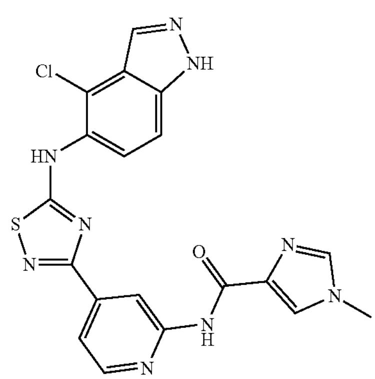 [SMILES: Cn1cnc(C(=O)Nc2cc(-c3nsc(Nc4ccc5[nH]ncc5c4Cl)n3)ccn2)c1] |
TABLE 5-continued
| No. | Compound Structure |
|---|---|
| IV-30 | 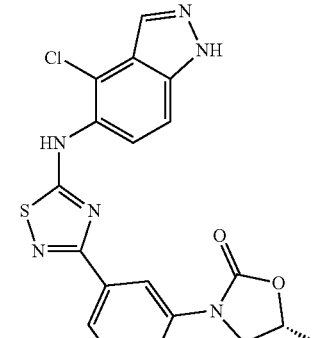 |
| IV-31 | 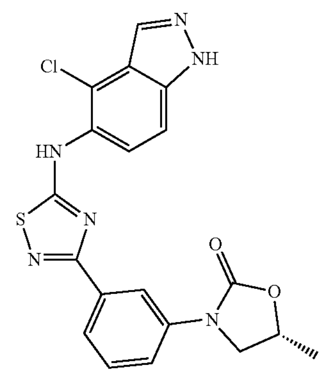 [SMILES: C[C@@H]1CN(c2cccc(-c3nsc(Nc4ccc5[nH]ncc5c4Cl)n3)c2)C(=O)O1] |
| IV-32 | 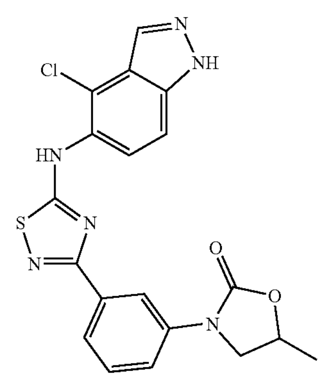 [SMILES: CC1CN(c2cccc(-c3nsc(Nc4ccc5[nH]ncc5c4Cl)n3)c2)C(=O)O1] |
| IV-33 | 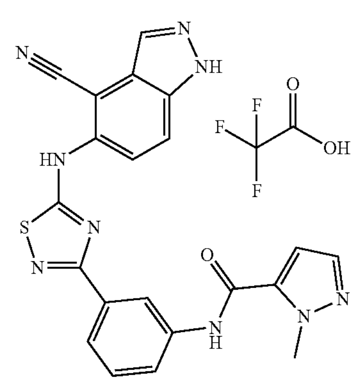 |

TABLE 5-continued

| No. | Compound Structure |
|---|---|
| IV-34 | 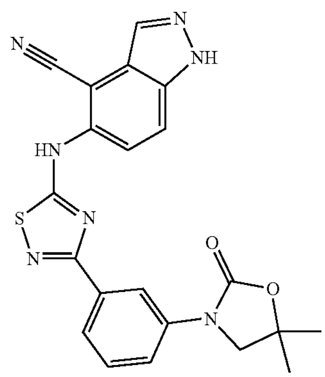 [SMILES: CC1(C)CN(c2cccc(-c3nsc(Nc4ccc5[nH]ncc5c4C#N)n3)c2)C(=O)O1] |
| IV-35 | 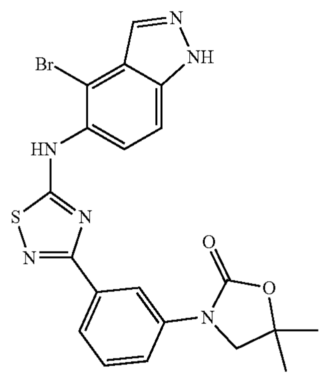 [SMILES: CC1(C)CN(c2cccc(-c3nsc(Nc4ccc5[nH]ncc5c4Br)n3)c2)C(=O)O1] |
| IV-36 | 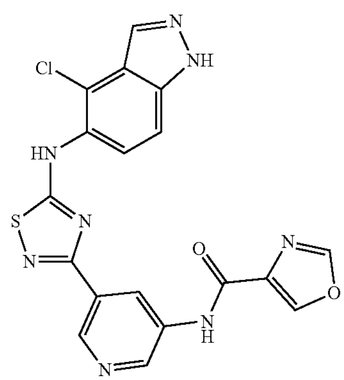 [SMILES: O=C(Nc1cncc(-c2nsc(Nc3ccc4[nH]ncc4c3Cl)n2)c1)c1cocn1] |
| IV-37 | 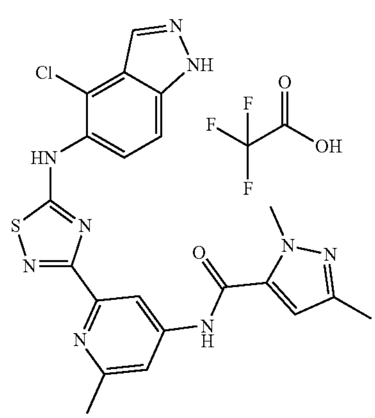 |
| IV-38 | |
| IV-39 | |
| IV-40 | |
| IV-41 | |

TABLE 5-continued

| No. | Compound Structure |
|---|---|
| IV-42 | 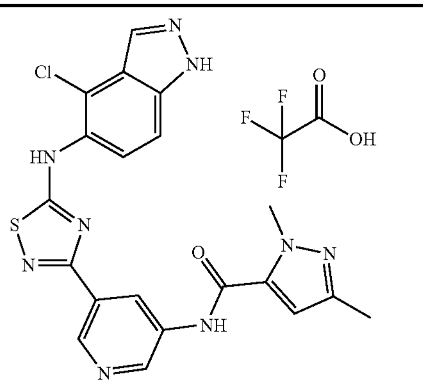 |
| IV-43 | 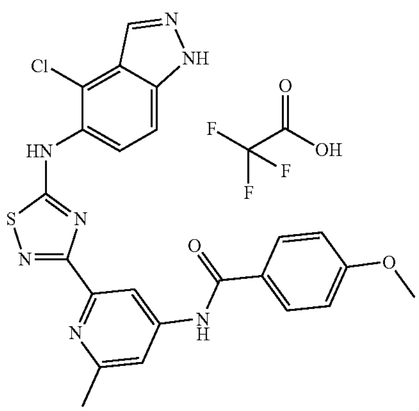 |
| IV-44 | 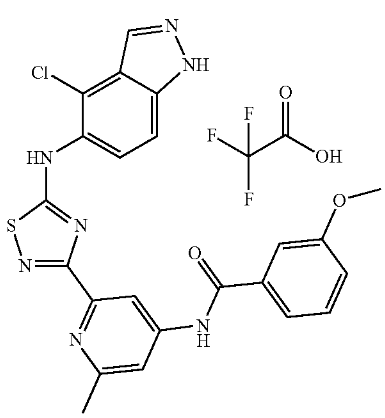 |
| IV-45 | 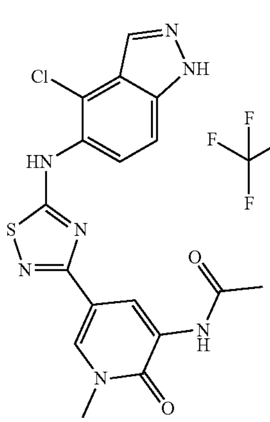 |
| IV-46 | |
| IV-47 | |
| IV-48 | |
| IV-49 | |

TABLE 5-continued

| No. | Compound Structure |
|---|---|
| IV-50 | 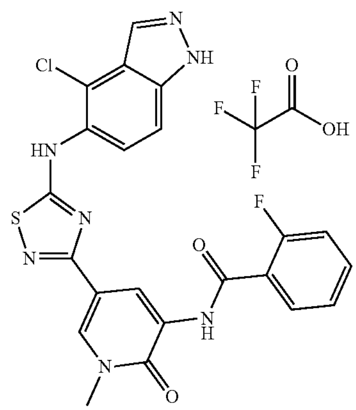 |
| IV-51 | 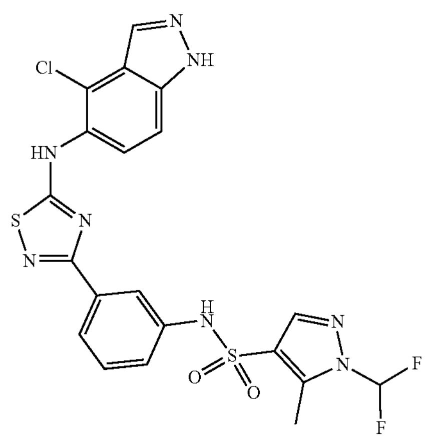 [SMILES: Cc1c(S(=O)(=O)Nc2cccc(-c3nsc(Nc4ccc5[nH]ncc5c4Cl)n3)c2)cnn1C(F)F] |
| IV-52 | 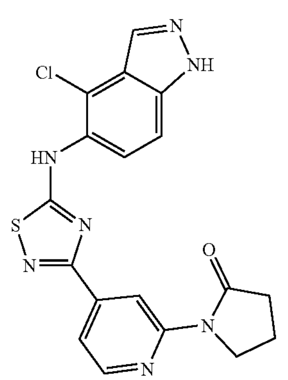 [SMILES: O=C1CCCN1c1cc(-c2nsc(Nc3ccc4[nH]ncc4c3Cl)n2)ccn1] |
| IV-53 | 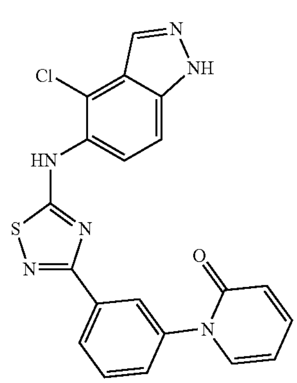 [SMILES: O=c1ccccn1-c1cccc(-c2nsc(Nc3ccc4[nH]ncc4c3Cl)n2)c1] |
| IV-54 | |
| IV-55 | |
| IV-56 | |
| IV-57 | |

TABLE 5-continued

| No. | Compound Structure |
|---|---|
| IV-58 | 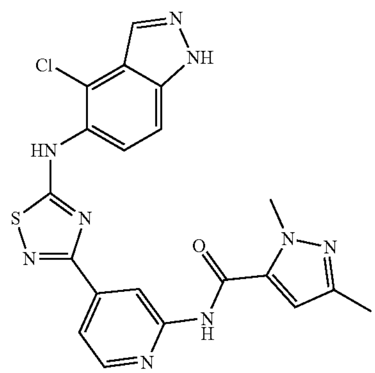 [SMILES: Cc1cc(C(=O)Nc2cc(-c3nsc(Nc4ccc5[nH]ncc5c4Cl)n3)ccn2)n(C)n1] |
| IV-59 | 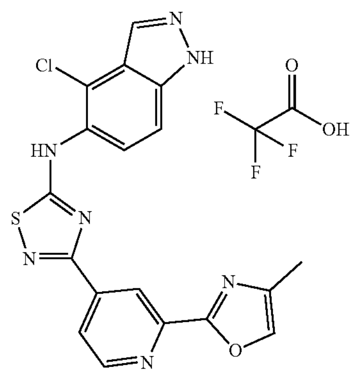 |
| IV-60 | 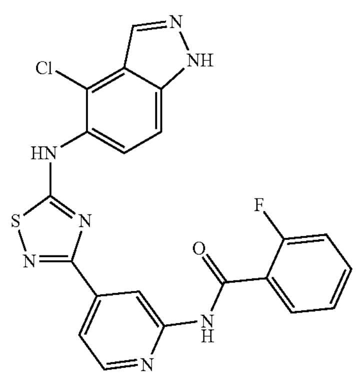 [SMILES: O=C(Nc1cc(-c2nsc(Nc3ccc4[nH]ncc4c3Cl)n2)ccn1)c1ccccc1F] |
| IV-61 | 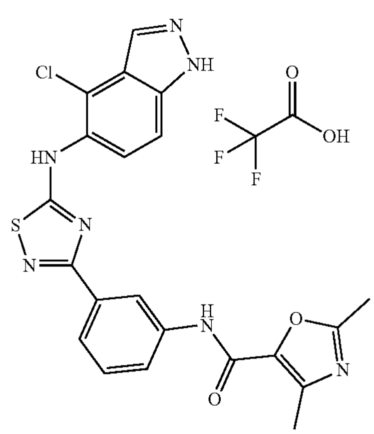 |
| IV-62 | |
| IV-63 | |
| IV-64 | |
| IV-65 | |

TABLE 5-continued
| No. | Compound Structure |
|---|---|
| IV-66 | 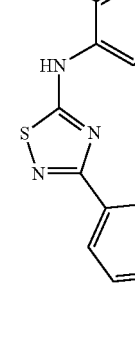 |
| IV-67 | 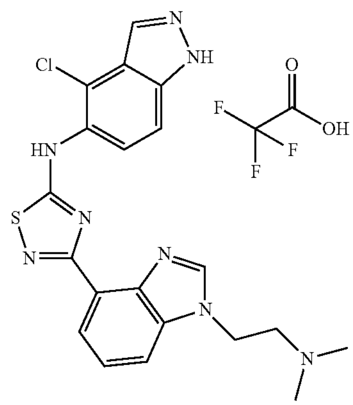 |
| IV-68 | 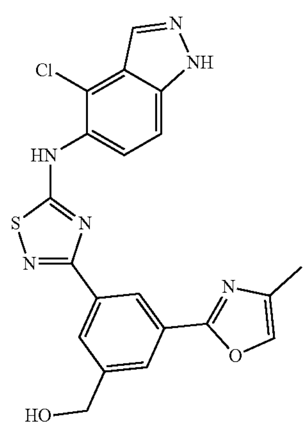 [SMILES: Cc1coc(-c2cc(CO)cc(-c3nsc(Nc4ccc5[nH]ncc5c4Cl)n3)c2)n1] |
| IV-69 | 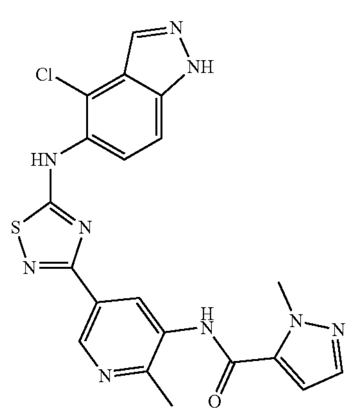 [SMILES: Cc1ncc(-c2nsc(Nc3ccc4[nH]ncc4c3Cl)n2)cc1NC(=O)c1ccnn1C] |
| IV-70 | 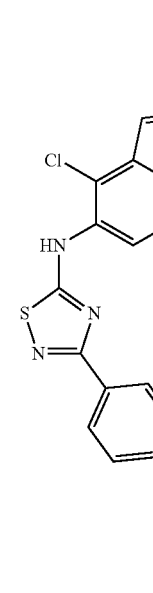 |
| IV-71 | 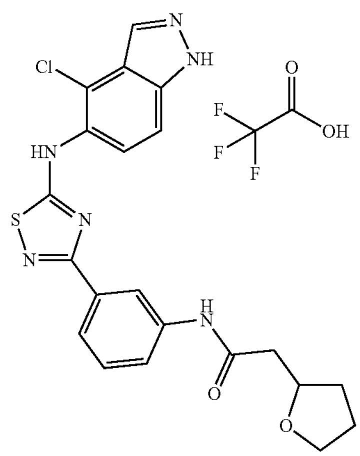 |
| IV-72 | 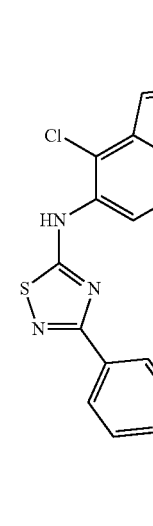
trifluoroacetic acid solvate |

TABLE 5-continued

| No. | Compound Structure |
|---|---|
| IV-73 | (4-chloro-1H-indazol-5-yl)amino-1,2,4-thiadiazole with phenyl-N-(1-methyl-1H-imidazole-2-carboxamide); trifluoroacetic acid |
| IV-74 | (4-chloro-1H-indazol-5-yl)amino-1,2,4-thiadiazole with phenyl-N-(pyridine-2-carboxamide) |
| IV-75 | (4-chloro-1H-indazol-5-yl)amino-1,2,4-thiadiazole with phenyl-N-(1H-pyrazole-3-carboxamide); trifluoroacetic acid |
| IV-76 | (4-chloro-1H-indazol-5-yl)amino-1,2,4-thiadiazole with phenyl-N-(5-methyl-1H-pyrazole-3-carboxamide); trifluoroacetic acid |
| IV-77 | (4-chloro-1H-indazol-5-yl)amino-1,2,4-thiadiazole with phenyl-N-(1-methyl-1H-pyrazole-3-carboxamide); trifluoroacetic acid |
| IV-78 | (4-chloro-1H-indazol-5-yl)amino-1,2,4-thiadiazole with phenyl-N-(1-methyl-1H-pyrazole-4-carboxamide); trifluoroacetic acid |
| IV-79 | (4-chloro-1H-indazol-5-yl)amino-1,2,4-thiadiazole with phenyl-N-(4-hydroxyoxazole-2-carboxamide); trifluoroacetic acid |

TABLE 5-continued

| No. | Compound Structure |
|---|---|
| IV-80 | 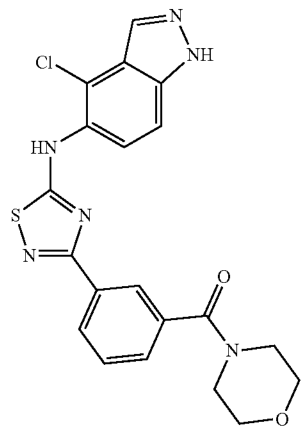 [SMILES: O=C(c1cccc(-c2nsc(Nc3ccc4[nH]ncc4c3Cl)n2)c1)N1CCOCC1] |
| IV-81 | 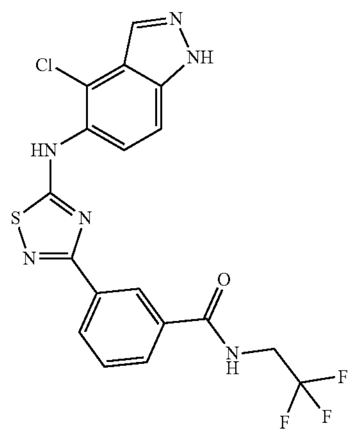 [SMILES: O=C(NCC(F)(F)F)c1cccc(-c2nsc(Nc3ccc4[nH]ncc4c3Cl)n2)c1] |
| IV-82 | 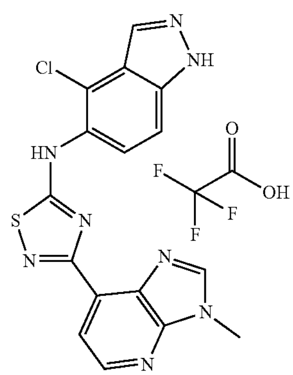 |
| IV-83 | 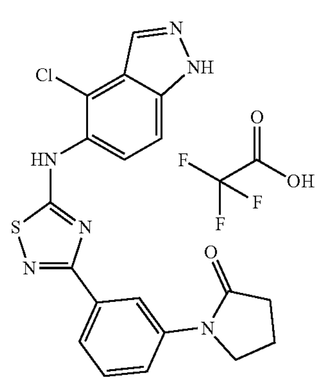 |
| IV-84 | |
| IV-85 | |
| IV-86 | |

TABLE 5-continued

| No. | Compound Structure |
|---|---|
| IV-87 | (4-chloro-1H-indazol-5-yl)amino-thiadiazole linked to phenyl-C(=O)N(CH3)2 |
| IV-88 | (4-chloro-1H-indazol-5-yl)amino-thiadiazole linked to phenyl-(1-methylimidazol-2-yl); trifluoroacetic acid |
| IV-89 | (4-chloro-1H-indazol-5-yl)amino-thiadiazole linked to 2-methylimidazo[1,2-a]pyridin-8-yl; formic acid solvate |
| IV-90 | (4-chloro-1H-indazol-5-yl)amino-thiadiazole linked to pyridinyl-(3-isopropyl-2-oxoimidazolidin-1-yl) |
| IV-91 | (4-chloro-1H-indazol-5-yl)amino-thiadiazole linked to 1-methyl-2-oxo-1,2-dihydropyridine-3-carboxylic acid |
| IV-92 | (4-chloro-1H-indazol-5-yl)amino-thiadiazole linked to 8-(2-oxopyrrolidin-1-yl)imidazo[1,2-a]pyridin-6-yl; trifluoroacetic acid |
| IV-93 | (6-fluoro-1H-indazol-5-yl)amino-thiadiazole linked to phenyl-(4-methyloxazol-2-yl); trifluoroacetic acid |

TABLE 5-continued

| No. | Compound Structure |
|---|---|
| IV-94 | 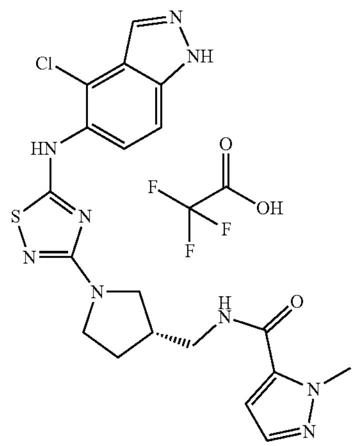 |
| IV-95 | 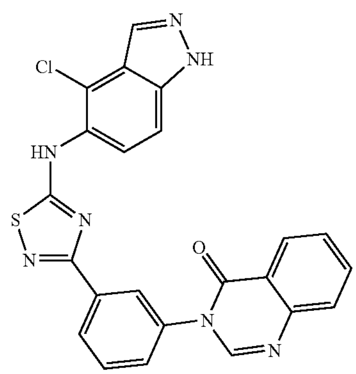 [SMILES: O=c1c2ccccc2ncn1-c1cccc(-c2nsc(Nc3ccc4[nH]ncc4c3Cl)n2)c1] |
| IV-96 | 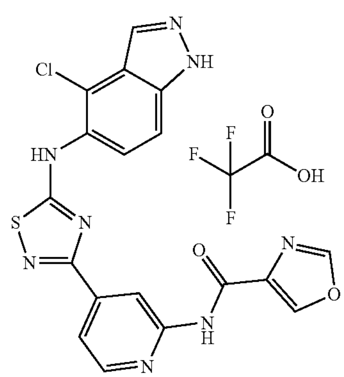 |
| IV-97 | 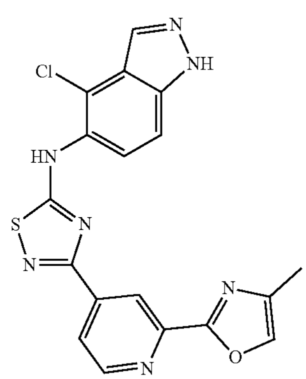 [SMILES: Cc1coc(-c2cc(-c3nsc(Nc4ccc5[nH]ncc5c4Cl)n3)ccn2)n1] |
| IV-98 | 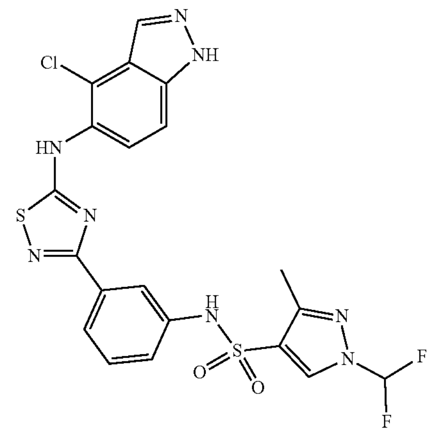 [SMILES: Cc1nn(C(F)F)cc1S(=O)(=O)Nc1cccc(-c2nsc(Nc3ccc4[nH]ncc4c3Cl)n2)c1] |
| IV-99 | 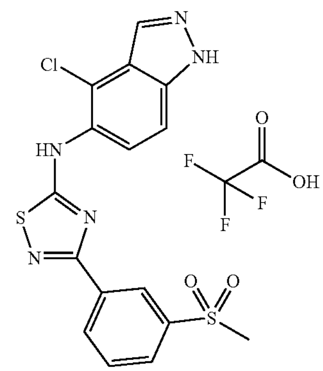 |
| IV-100 | 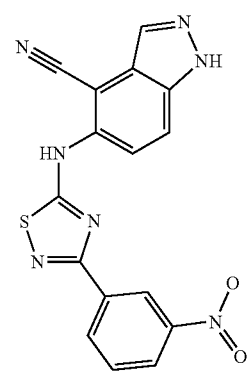 |
| IV-101 | | trifluoroacetic acid solvate

TABLE 5-continued
| No. | Compound Structure |
|---|---|
| IV-102 | 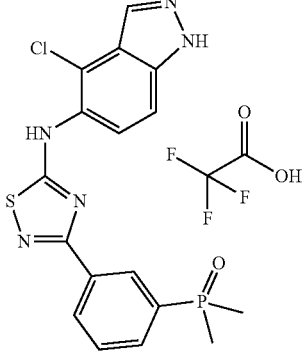 |
| IV-103 | 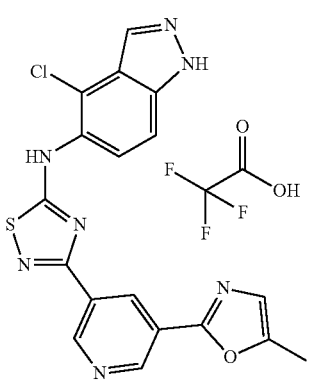 |
| IV-104 | 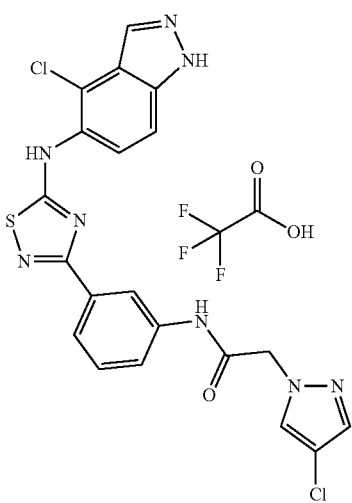 |
| IV-105 | 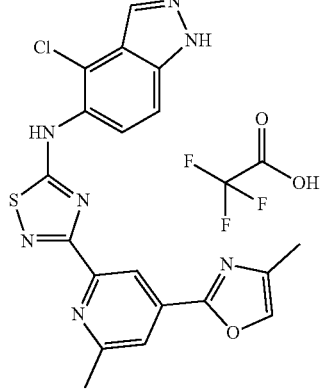 |
| IV-106 | 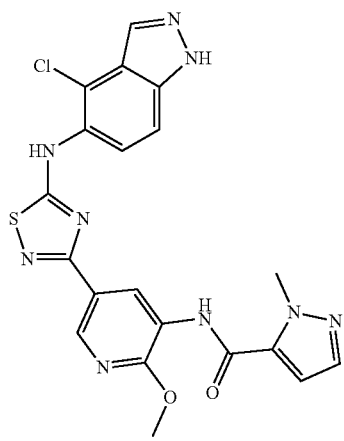 [SMILES: COc1ncc(-c2nsc(Nc3ccc4[nH]ncc4c3Cl)n2)cc1NC(=O)c1ccnn1C] |
| IV-107 | 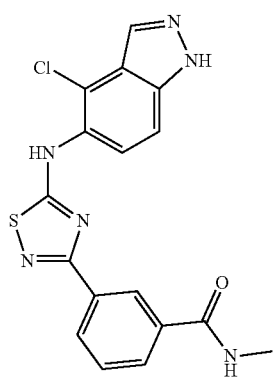 [SMILES: CNC(=O)c1cccc(-c2nsc(Nc3ccc4[nH]ncc4c3Cl)n2)c1] |

TABLE 5-continued

| No. | Compound Structure |
|-----|-------------------|
| IV-108 | [structure: 4-chloro-1H-indazol-5-yl amino-1,2,4-thiadiazole linked to pyridine with 4-methoxybenzamide] |
| IV-109 | [structure: 4-chloro-1H-indazol-5-yl amino-1,2,4-thiadiazole linked to pyrrolidine bearing aminomethyl] |
| IV-110 | [structure: 4-chloro-1H-indazol-5-yl amino-1,2,4-thiadiazole linked to pyrrolidine with methylaminocarbonyl-1-methylpyrazole] |
| IV-111 | [structure: 4-chloro-1H-indazol-5-yl amino-1,2,4-thiadiazole linked to phenyl-2-methylquinazolin-4(3H)-one] |

26. The compound of claim 25, wherein the compound is in non-solvated form, or a pharmaceutically acceptable salt thereof.

27. A pharmaceutical composition comprising a compound of claim 1 and a pharmaceutically acceptable carrier.

28. A pharmaceutical composition comprising a compound of claim 22 and a pharmaceutically acceptable carrier.

29. A method of treating a disorder selected from the group consisting of scleroderma, psoriasis, nonalcoholic steatohepatitis, giant cell arteritis, Crohn's disease, inflammatory bowel disease, multiple sclerosis, systemic lupus erythematosus, ulcerative colitis, asthma, and rheumatoid arthritis, comprising administering to a patient in need thereof a therapeutically effective amount of a compound of claim 1 to treat the disorder.

30. The method of claim 29, wherein the disorder is psoriasis, nonalcoholic steatohepatitis, inflammatory bowel disease, systemic lupus erythematosus, or asthma.

31. A method of inhibiting a Rho-associated protein kinase isoform 2, comprising exposing a Rho-associated protein kinase isoform 2 to a compound of claim 1 to inhibit said Rho-associated protein kinase isoform 2.

* * * * *